United States Patent
Kim et al.

[11] Patent Number: 6,040,321
[45] Date of Patent: Mar. 21, 2000

[54] AMINOTHIAZOLE INHIBITORS OF CYCLIN DEPENDENT KINASES

[75] Inventors: Kyoung S. Kim, North Brunswick; S. David Kimball, East Windsor; Zhen-wei Cai, Somerville, all of N.J.; David B. Rawlins, Morrisville, Pa.; Raj N. Misra, Hopewell; Michael A. Poss, Lawrenceville, both of N.J.; Kevin R. Webster, Yardley, Pa.; John T. Hunt, Princeton, N.J.; Wen-Ching Han, Newtown, Pa.

[73] Assignee: Bristol-Myers Squibb Company, Princeton, N.J.

[21] Appl. No.: 09/176,239

[22] Filed: Oct. 21, 1998

Related U.S. Application Data

[60] Provisional application No. 60/065,195, Nov. 12, 1997.

[51] Int. Cl.[7] .................... A61K 31/425; C07D 417/12
[52] U.S. Cl. ..................... 514/369; 548/184; 548/185
[58] Field of Search .................... 548/184, 185; 514/369

[56] References Cited

U.S. PATENT DOCUMENTS 4,254,260  3/1981  Takaya ........................ 544/27

*Primary Examiner*—Robert Gerstl
*Attorney, Agent, or Firm*—Barry J. Marenberg

[57] ABSTRACT

Compounds of the formula

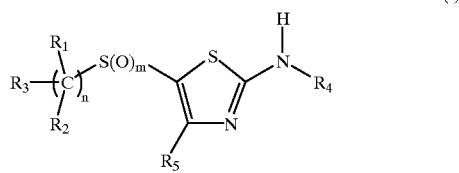

(I)

and pharmaceuticaly acceptable salts thereof. As used in formula I, and throughout the specification, the symbols have the following meanings:

$R_1$ and $R_2$ are independently hydrogen, fluorine or alkyl;

$R_3$ is aryl or heteroaryl $R_4$ is hydrogen, alkyl, cycloalkyl, aryl, cycloalkylalkyl, arylalkyl, heteroaryl, heteroarylalkyl, heterocycloalkyl, heterocycloalkylalkyl; or CO-alkyl, CONH-alkyl, COO-alkyl, $SO_2$-alkyl, C(NCN)NH-alkyl, $C(NNO_2)$NH-alkyl, C(NH)NH-alkyl, C(NH)NHCO-alkyl, $C(NOR_6)$NH-alkyl, $R_5$ is hydrogen or alkyl;

$R_6$ is hydrogen, alkyl, cycloalkyl, aryl, cycloalkylakyl, arylalkyl, heteroaryl, heteroarylalkyl, heterocycloalkyl or heterocycloalkylalkyl;

m is an integer of 0 to 2; and n is an integer of 1 to 3.

The compounds of formula I are protein kinase inhibitors and are useful in the treatment and prevention of proliferative diseases, for example, cancer, inflammation and arthritis. They may also be useful in the treatment of neurodegenerative diseases such as Alzheimer's disease, cardiovascular diseases, viral diseases and fungal diseases.

45 Claims, No Drawings

AMINOTHIAZOLE INHIBITORS OF CYCLIN DEPENDENT KINASES

This application claims benefit of Provisional Appl. No. 60/065,195 filed Nov. 12, 1997.

BRIEF DESCRIPTION OF THE INVENTION

The present invention is directed to compounds of the formula

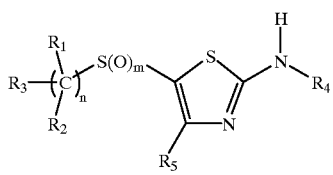

(I)

and pharmaceutically acceptable salts thereof. As used in formula I, and throughout the specification, the symbols have the following meanings:

$R_1$ and $R_2$ are independently hydrogen, fluorine or alkyl;
$R_3$ is aryl or heteroaryl
$R_4$ is hydrogen, alkyl, cycloalkyl, aryl, cycloalkylalkyl, arylalkyl, heteroaryl, heteroarylalkyl, heterocycloalkyl, heterocycloalkylalkyl; or CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or $SO_2$-alkyl, $SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or C(NCN)NH-alkyl, C(NCN)NH-cycloalkyl, C(NCN)NH-aryl, C(NCNNH)-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocylcoalkyl; or $C(NNO_2)$NH-alkyl, $C(NNO_2)$NH-cycloalkyl, $C(NNO_2)$NH-aryl, $C(NNO_2)$NH-alkyl-cycloalkyl, $C(NNO_2)$NH-alkyl-aryl, $C(NNO_2)$NH-heteroaryl, $C(NNO_2)$NH-alkyl-heteroaryl, $C(NNO_2)$NH-heterocyloalkyl, $C(NNO_2)$NH-alkyl-heterocycloalkyl; or C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocylcloalkyl, C(NH)NHCO-alkyl-heterocycloalkyl; or $C(NOR_6)$NH-alkyl, $C(NOR_6)$NH-cycloalkyl, $C(NOR_6)$NH-aryl, $C(NOR_6)$NH-alkyl-cycloalkyl, $C(NOR_6)$NH-alkyl-aryl, $C(NOR_6)$NH-heteroaryl, $C(NOR_6)$NH-alkyl-heteroaryl, $C(NOR_6)$NH-heterocylcoalkyl, $C(NOR_6)$NH-alkyl-heterocycloalkyl;

$R_5$ is hydrogen or alkyl;
$R_6$ is hydrogen, alkyl, cycloalkyl, aryl, cycloalkylakyl, arylalkyl, heteroaryl, heteroarylalkyl, heterocycloalkyl or heterocycloalkylalkyl;

m is an integer of 0 to 2; and
n is an integer of 1 to 3.

The compounds of formula I are protein kinase inhibitors and are useful in the treatment and prevention of proliferative diseases, for example, cancer, inflammation and arthritis. They may also be useful in the treatment of neurodegenerative diseases such as Alzheimer's disease, cardiovascular diseases, viral diseases and fungal diseases.

DESCRIPTION OF THE INVENTION

The present invention provides for compounds of formula I, pharmaceutical compositions employing such compounds and for methods of using such compounds.

Listed below are definitions of various terms used to describe the compounds of the instant invention. These definitions apply to the terms as they are used throughout the specification (unless they are otherwise limited in specific instances) either individually or as part of a larger group.

It should be noted that any heteroatom with unsatisfied valances is assumed to have the hydrogen atom to satisfy the valances.

Carboxylate anion refers to a negatively charged group —COO⁻.

The term "alkyl" or "alk" refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). Alkyl groups as defined may also comprise one or more carbon to carbon double bonds or one or more carbon to carbon triple bonds.

The term "alkenyl" refers to a hydrocarbon radical straight, branched or cyclic containing from 2 to 12 carbon atoms and at least one carbon to carbon double bond.

The term "alkynyl" refers to a hydrocarbon radical straight, branched or cyclic containing from 2 to 12 carbon atoms and at least one carbon to carbon triple bond.

Cycloalkyl is a specie of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, adamantyl, etc. Exemplary substituents include one or more of the following groups: halogen, alkyl, alkoxy, alkyl hydroxy, amino, nitro, cyano, thiol and/or alkylthio.

The terms "alkoxy" or "alkylthio", as used herein, denote an alkyl group as described above bonded through an oxygen linkage (—O—) or a sulfur linkage (—S—), respectively.

The term "alkyloxycarbonyl", as used herein, denotes an alkoxy group bonded through a carbonyl group. An alkoxy-carbonyl radical is represented by the formula: —C(O)OR, where the R group is a straight or branched $C_{1-6}$ alkyl group.

The term "alkylcarbonyl" refers to an alkyl group bonded through a carbonyl group.

The term "alkylcarbonyloxy", as used herein, denotes an alkylcarbonyl group which is bonded through an oxygen linkage.

The term "arylalkyl", as used herein, denotes an aromatic ring bonded to an alkyl group as described above.

The term "aryl" refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkoxy, hydroxy, carboxy, carbamoyl, alkyloxycarbonyl, nitro, trifluoromethyl, amino, cycloalkyl, cyano, alkyl $S(O)_m$ (m=O, 1, 2), or thiol.

The term "heteroaryl" refers to a monocyclic aromatic hydrocarbon group having 5 or 6 ring atoms, or a bicyclic aromatic group having 8 to 10 atoms, containing at least one heteroatom, O, S, or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Exemplary heteroaryl groups include the following: thienyl, furyl, pyrrolyl, pyridinyl, imidazolyl, pyrrolidinyl, piperidinyl, thiazolyl, oxazolyl, triazolyl, pyrazolyl, isoxazolyl, isothiazolyl, pyrazinyl, pyridazinyl, pyrimidinal, triazinylazepinyl, indolyl, isoindolyl, quinolinyl, isoquinolinyl, benzothiazolyl, benzoxazolyl, benzimidazolyl, benzoxadiazolyl, benzofurazanyl and tetrahydropyranyl. Exemplary substituents include one or more of the following: halogen, alkyl, alkoxy, hydroxy, carboxy, carbamoyl, alkyloxycarbonyl, trifluoromethyl, cycloalkyl, nitro, cyano, amino, alkylS(O)$_m$ (m=0, 1, 2), or thiol.

The term "heteroarylium" refers to heteroaryl groups bearing a quaternary nitrogen atom and thus a positive charge.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by said heteroatoms.

The term "quaternary nitrogen" refers to a tetravalent positively charged nitrogen atom including, e.g. the positively charged nitrogen in a tetraalkylammonium group (e.g. tetramethylammonium, N-methylpyridinium), the positively charged nitrogen in protonated ammonium species (e.g. trimethylhydroammonium, N-hydropyridinium), the positively charged nitrogen in amine N-oxides (e.g. N-methylmorpholine-N-oxide, pyridine -N-oxide), and the positively charged nitrogen in an N-amino-ammonium group (e.g. N-aminopyridinium).

The term "heteroatom" means O, S or N, selected on an independent basis.

The term "halogen" or "halo" refers to chlorine, bromine, fluorine or iodine.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

Suitable examples of salts of the compounds according to the invention with inorganic or organic acids are hydrochloride, hydrobromide, sulfate, phosphate. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be understood that solvates (e.g., hydrates) of the compounds of formula I are also within the scope of the present invention. Methods of solvation are generally known in the art. Accordingly, the compounds of the instant invention may be in the free or hydrate form, and may be obtained by methods exemplified by the following schemes.

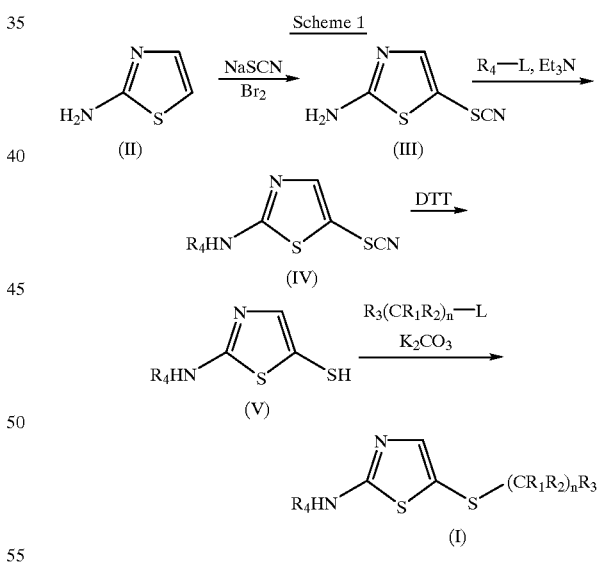

As illustrated in Scheme 1, compounds of formula I where X is S are prepared by reacting 2-aminothiazole (II) with bromine in the presence of sodium or potassium thiocyanate to obtain a thiocyanated aminothiazole, specifically 5-thiocyanatoaminothiazole (III). Compound III is then reacted with $R_4$-L, where L is a leaving group such as a halogen, in the presence of a base such as triethylamine to provide a 5-thiocyanatothiazole intermediate (IV), where $R_4$ is as defined in the specification. The intermediate (IV) is then reduced to a thiol (V) using reducing agents such as dithiothreitol (DTT), sodium borohydride, zinc or other known reducing agents. Compound (V) is then reacted with alkyl, aryl or heteroaryl halides, such as $R_3$ $(CR_1R_2)_n$-L, where L is a leaving group such as a halogen, in the presence of a base such as potassium carbonate to obtain compounds of formula I. The steps of reducing the thiocyanothiazole intermediate (IV) to the thiol (V), and the reaction of the reduced thiol (V) to provide compounds of formula I where X is S, may be carried out sequentially without purification.

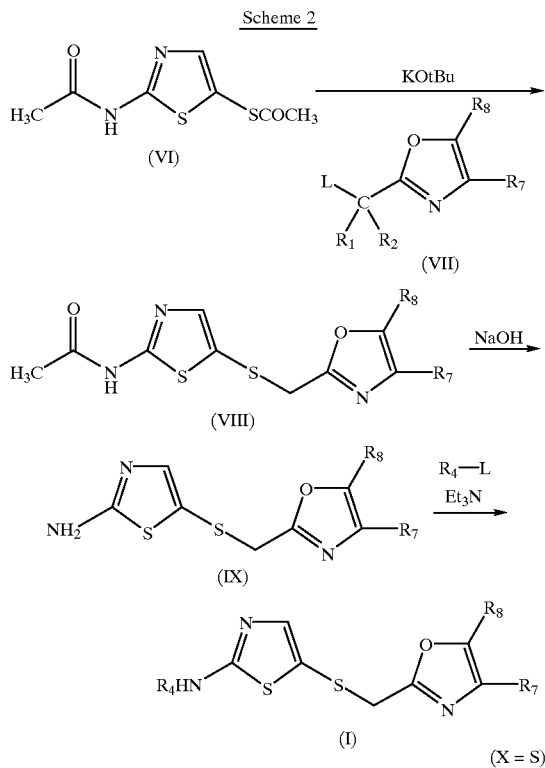

In Scheme 2, 5-thioacetyl-2-acetylaminothiazole of structure VI is reacted with an alkoxide such as potassium t-butoxide in alcohol or THF solvent and the resulting thiol is reacted in situ with a group of formula $R_3(CR_1R_2)_n$-L (where L is a leaving group, such as a halogen) such as 2-halomethyloxazole (VII) to provide a compound such as formula VIII, wherein $R_1$ and $R_2$ are hydrogen, and $R_6$ is acetyl. The 2-halomethyloxazole compounds of formula VII may be prepared using several synthetic routes known in the art. *Chem. Pharm. Bull.* 30, 1865 (1982); *Bull. Chem. Soc. Japan* (52, 3597 (1979); *JCS Chem. Comm.* 322 (1981); *Comprehensive Heterocyclic Chemistry*, vol. 6, 177, edited by A. Katritzky and C. W. Rees, Pergamon Press (1984).

Compounds of formula VIII (a compound of formula I where $R_4$ is acetyl and X is sulfur) can be hydrolyzed in the presence of a base such as sodium hydroxide to provide a compound of formula IX. A compound of formula IX may then be reacted with $R_4$-L, in the presence of a base such as triethylamine, where L is a leaving group such as a halogen, to give compounds of formula I where X is sulfur. In this manner, compounds of formula IX, which is a compound of formula I where $R_4$ is hydrogen, can be treated with agents such as isothiocyanates, halides, acyl halides, chloroformates, isocyanates or sulfonyl chlorides to provide thioureas, amines, amides, carbamates, ureas or sulfonamides. The procedures in Scheme 2 specifically illustrate a methyloxazole group, but are general for all $R_3(CR_1R_2)_n$- groups specified by formula I.

Alternatively, compounds of formula VII, where L is bromine, may be prepared by halogenation of 2-methyloxazole using N-bromosuccinimide in the presence of dibenzoylperoxide.

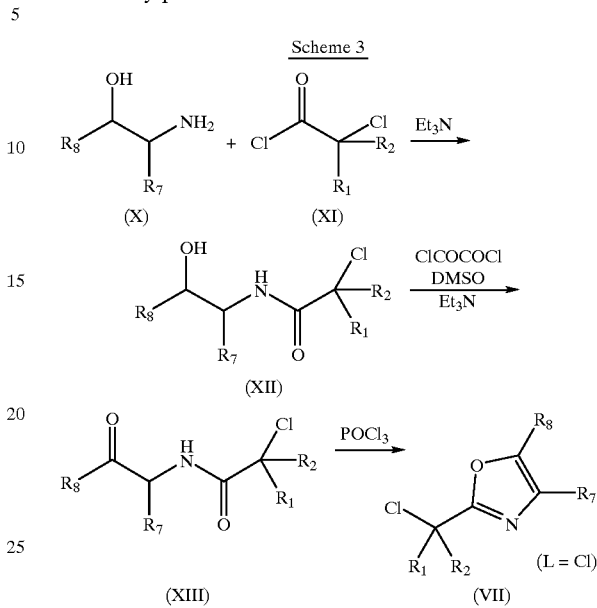

Scheme 3 lustrates an alternative method of preparing compound VII, which is a compound of formula $R_3(CR_1R_2)_n$-L where L is chlorine and n is the integer 1. In this scheme, compound VII is prepared by the reaction of a compound of formula X and formula XI in the presence of a base such as triethylamine to provide compounds of formula XII. Compound XII may be oxidized by an oxidant such as oxalylchloride/DMSO in the presence of a base such as triethylamine to provide a compound of formula XIII which may be cyclized by an agent such as phosphorous oxychloride to provide compounds of formula VII, wherein L is chlorine. Alternatively, compounds of formula XIII may be prepared by reaction of the amino ketone correponding to X with an acid chloride such as XI.

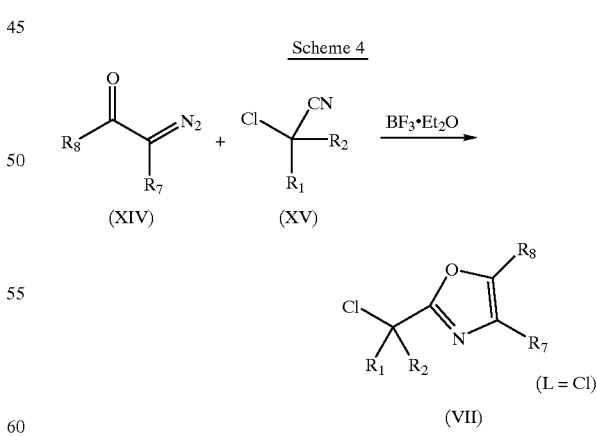

Compounds of formula VII, where L is chlorine, may also be prepared from the reaction of diazoketones as illustrated by formula XIV in Scheme 4 with chloronitriles, such as indicated by formula XV, in the presence of $BF_3$ etherate to provide compounds of formula VII, wherein L is chlorine.

Scheme 5

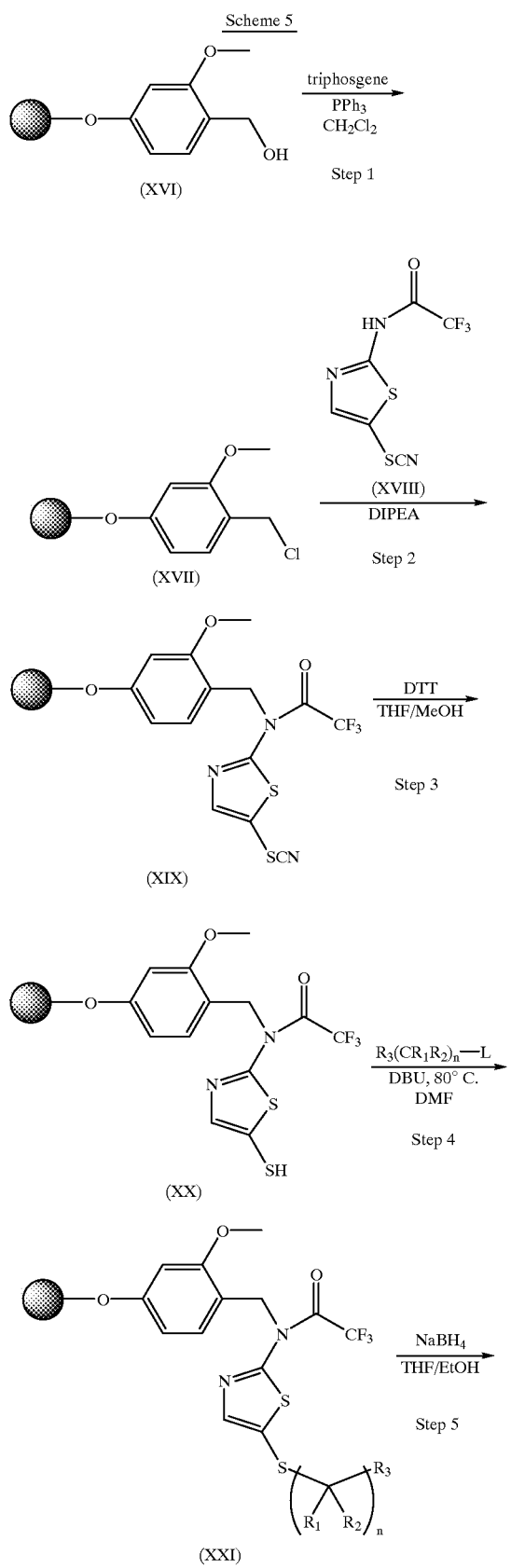

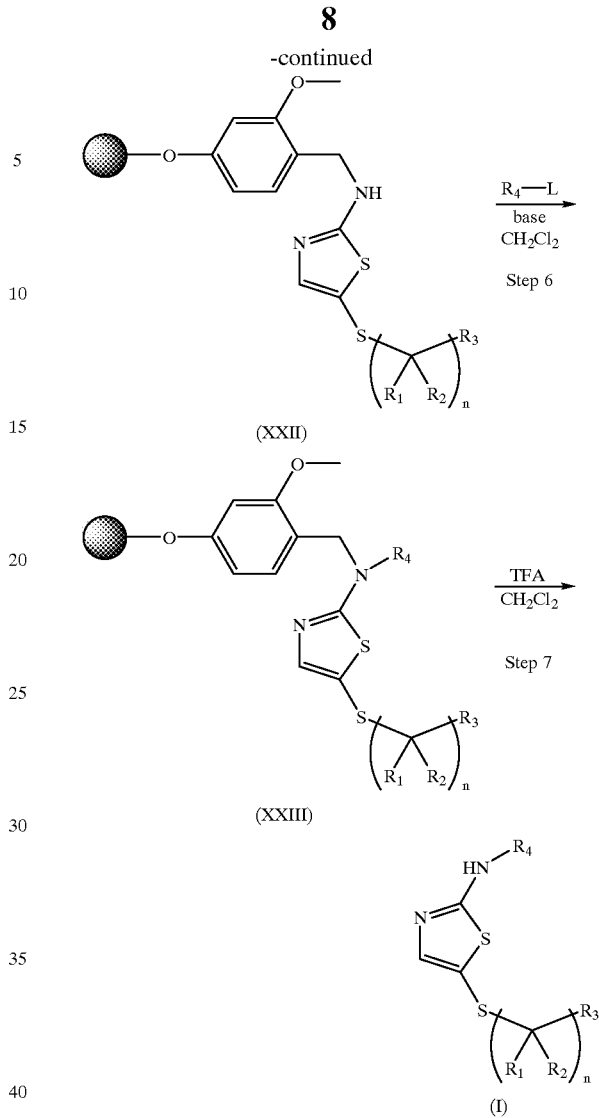

In Scheme 5, starting compound XVI denotes a resin-bound benzyl alcohol support used for solid phase synthesis which is prepared from a Merrifield resin denoted as ●, and 2-methoxy-4-hydroxybenzaldehyde, followed by reduction with reducing agents such as $NaBH_4$. In step 1, starting compound XVI is treated with triphosgene and triphenylphosphine ($PPh_3$) in dichloromethane to give the chlorobenzyl resin of formula XVII. In step 2, a thiocyanato trifluoroacetamide (XVIII) is alkylated with the resin-bound benzyl chloride (XVII) in the presence of diisopropylethylamine (DIPEA) to form a resin-bound thiocyanate (XIX). The thiocyanato trifluoroacetamide compound of formula XVII is prepared by reacting 5-thiocyanatoaminothiazole of formula III (Scheme I) with trifluoroacetic anhydride using a base such as 2,6-lutidine.

The resin-bound thiocyanate (XIX) is then reduced to a resin-bound thiol (XX) in step 3 with reducing agent such as dithiothreitol (DTT) in tetrahydrofuran (THF) and methanol. The resulting resin-bound thiol (XX) is reacted with $R_3(CR_1R_2)_n$-L, where L is a leaving group, in the presence of a base such as 1,8-diazabicyclo[5,4,0]undec-7-ene (DBU) at 80° C. in dimethylformamide (DMF) to form compounds of formula XXI (step 4). Deprotection of the trifluoroacetyl group of compound XXI is performed in step 5 using sodium borohydride to provide a compound of formula XXII. In step 6, the deprotected compound XXII is reacted with $R_6X$, where X is a leaving group, in the presence of a base such as diisopropylethylamine to provide compounds of formula XXIII. The product is then cleaved from the solid phase resin in step 7 with trifluoroacetic acid (TFA) to give compounds of formula I where X is sulfur. Compounds of formula I where X is $S(O)_m$ and m is 1 or 2 may be prepared from compounds of formula I where m is 0 by oxidation with an oxidant such as sodium periodate, meta-chloroperbenzoic acid, or oxone.

The starting compounds of Schemes 1–5 are commercially available or may be prepared by methods known to one of ordinary skill in the art.

All compounds of formula I may be prepared by modification of the procedures described herein.

The preferred compounds of formula I are those where:

$R_1$ and $R_2$ are independently hydrogen, fluorine or alkyl;

$R_3$ is 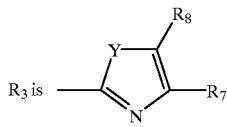

wherein Y is oxygen, sulfure or $NR_9$;

$R_4$ is hydrogen, alkyl, cycloalkyl, aryl, cycloalkylalkyl, arylalkyl, heteroaryl, heteroarylalkyl, heterocycloalkyl, heterocycloalkylalkyl; or CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or $SO_2$-alkyl, $SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or C(NCN)NH-alkyl, C(NCN)NH-cycloalkyl, C(NCN)NH-aryl, C(NCNNH)-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocylcoalkyl; or $C(NNO_2)$NH-alkyl, $C(NNO_2)$NH-cycloalkyl, $C(NNO_2)$NH-aryl, $C(NNO_2)$NH-alkyl-cycloalkyl, $C(NNO_2)$NH-alkyl-aryl, $C(NNO_2)$NH-heteroaryl, $C(NNO_2)$NH-alkyl-heteroaryl, $C(NNO_2)$NH-heterocyloalkyl, $C(NNO_2)$NH-alkyl-heterocycloalkyl; or C(NH)NH-alkyl, C(NH)NH-cycloalkyl, C(NH)NH-aryl, C(NH)NH-alkyl -cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocylcoalkyl, C(NH)NHCO-alkyl-heterocycloalkyl; or $C(NOR_6)$NH-alkyl, $C(NOR_6)$NH-cycloalkyl, $C(NOR_6)$NH-aryl, $C(NOR_6)$NH-alkyl-cycloalkyl, $C(NOR_6)$NH-alkyl-aryl, $C(NOR_6)$NH-heteroaryl, $C(NOR_6)$NH-alkyl-heteroaryl, $C(NOR_6)$NH-heterocylcoalkyl, $C(NOR_6)$NH-alkyl-heterocycloalkyl;

$R_5$ is hydrogen; and $R_6$ is hydrogen, alkyl, cycloalkyl, aryl, cycloalkylakyl, arylalkyl, heteroaryl, heteroarylalkyl, heterocycloalkyl or heterocycloalkylalkyl;

$R_7$ and $R_8$ are independently hydrogen, alkyl, cycloalkyl, aryl, alkylcycloalkyl, alkylaryl, heteroaryl, alkylheteroaryl, heterocycloalkyl, alkylheterocycloalkyl or halogen;

$R_9$ is H or alkyl;

m is the integer 0; and n is the integer 1.

The most preferred compounds of formula I are those where:

$R_1$ is hydrogen;

$R_2$ is hydrogen, fluorine or alkyl;

$R_3$ is a substituted oxazole having the configuration:

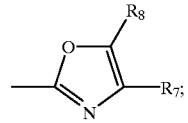

$R_4$ is CO-alkyl, CO-alkyl-aryl, CO-cycloalkyl, CO-alkyl-heteroaryl, CO-alkyl-heteroalkyl, CO-alkyl-heterocycloalkyl, CONH-alkyl, CONH-alkyl-aryl, CONH-cycloalkyl, or CONH-alkyl-heterocycloalkyl;

$R_5$ is hydrogen;

$R_7$ is hydrogen;

$R_8$ is an alkyl group, such as tert-butyl;

m is the integer 0; and n is the integer 1.

The compounds according to the invention have pharmacological properties; in particular, the compounds of formula I are inhibitors of protein kinases such as the cyclin dependent kinases (cdks), for example, cdc2 (cdk1), cdk2, and cdk4. The novel compounds of formula I are expected to be useful in the therapy of proliferative diseases such as cancer, autoimmune diseases, viral diseases, fungal diseases, neurodegenerative disorders and cardiovascular disease.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of cdks in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may also be useful in the treatment of Alzheimer's disease, as suggested by the recent finding that cdk5 is involved in the phosphorylation of tau protein (J. Biochem, 117, 741–749 (1995)).

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of formula I, as inhibitors of the cdks, can modulate the level of cellular RNA and DNA synthesis. These agents would therefore be useful in the treatment of viral infections (including but not limited to HIV, human papilloma virus, herpesvirus, poxvirus, Epstein- Barr virus, Sindbis virus and adenovirus).

Compounds of formula I may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of formula I may also be useful in inhibiting tumor angiogenesis and metastasis.

Compounds of formula I may also act as inhibitors of other protein kinases, e.g., protein kinase C, her2, raf1, MEK1, MAP kinase, EGF receptor, PDGF receptor, IGF receptor, PI3 kinase, weel kinase, Src, Abl and thus be effective in the treatment of diseases associated with other protein kinases.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methoxtrexate.

If formulated as a fixed dose, such combination products employ the compounds of this invention within the dosage range described below and the other pharmaceutically active agent or treatment within its approved dosage range. For example, the cdc2 inhibitor olomucine has been found to act synergistically with known cytotoxic agents in inducing apoptosis (J. Cell Sci., 108, 2897 (1995)). Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, 57, 3375 (1997).

The pharmacological properties of the compounds of this invention may be confirmed by a number of pharmacological assays. The exemplified pharmacological assays which follow have been carried out with the compounds according to the invention and their salts. The compounds of examples 1 to 8 exhibited cdc2/cyclin B1 kinase activity with $IC_{50}$ values less than 50 $\mu$M. The compounds of examples 1 to 8 exhibited cdk2/cyclin E kinase activity with $IC_{50}$ values less than 50 $\mu$M. The compounds of examples 1 to 8 exhibited cdk4/cyclin D1 kinase activity with $IC_{50}$ values less than 50 $\mu$M.

cdc2/cyclin B1 Kinase Assay cdc2/cyclin B1 kinase activity was determined by monitoring the incorporation of $^{32}P$ into histone H1. The reaction consisted of 50 ng baculovirus expressed GST-cdc2, 75 ng baculovirus expressed GST-cyclin B1, 1 $\mu$g histone HI (Boehringer Mannheim), 0.2 mCi of $^{32}P$ g-ATP and 25 mM ATP in kinase buffer (50 mM Tris, pH 8.0, 10 mM $MgCl_2$, 1 mM EGTA, 0.5 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Marshak, D. R., Vanderberg, M. T., Bae, Y. S., Yu, I. J., J. of Cellular Biochemistry, 45, 391–400 (1991), incorporated by reference herein).

cdk2 cyclin E Kinase Assay cdk2/cyclin E kinase activity was determined by monitoring the incorporation of $^{32}p$ into the retinoblastoma protein. The reaction consisted of 2.5 ng baculovirus expressed GST-cdk2/cyclin E, 500 ng bacterially produced GST-retinoblastoma protein (aa 776–928), 0.2 mCi $^{32}p$ g-ATP and 25 mM ATP in kinase buffer (50 mM Hepes, pH 8.0, 10 mM $MgCl_2$, 5 mM EGTA, 2 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter.

cdk 4/cyclin D1 Kinase Activity cdk4/cyclin D1 kinase activity was determined by monitoring the incorporation of $^{32}P$ in to the retinoblastoma protein. The reaction consisted of 165 ng baculovirus expressed as GST-cdk4, 282 ng bacterially expressed as S-tag cyclin D1, 500 ng bacterially produced GST-retinoblastoma protein (aa 776–928), 0.2 μCi $^{32}$P γ-ATP and 25 M ATP in kinase buffer (50 mM Hepes, pH 8.0, 10 mM MgCl$_2$, 5 mM EGTA, 2 mM DTT). The reaction was incubated at 30° C. for 1 hour and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Coleman, K. G., Wautlet, B. S., Morissey, D, Mulheron, J. G., Sedman, S., Brinkley, P., Price, S., Wedster, K. R. (1997). Identification of CDK4 Sequences involved in cyclin D, and p16 binding. *J. Biol. Chem.* 272,30:18869–18874, incorporated by reference herein).

Further subject matter of the invention also includes pharmaceuticals for use as described above including controlling cancer, inflammation and arthritis, which contain at least one compound of the formula I as defined above or at least one of its pharmacologically acceptable acid addition salts, and the use of a compound of the formula I as defined above for the preparation of a pharmaceutical having activity against proliferative diseases as described previously including against cancer, inflammation and/or arthritis.

The following examples and preparations describe the manner and process of making and using the invention and are illustrative rather than limiting. It should be understood that there may be other embodiments which fall within the spirit and scope of the invention as defined by the claims appended hereto.

Example 1
N-[5-[[(5-ethyl-2-oxazolyl)methyl]thio]-2-thiazolyl]acetamide

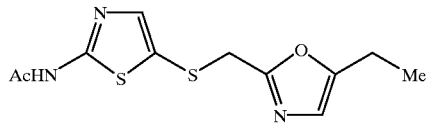

A. Preparation of 1-benzyloxycarbonylamino-2-butanol

A mixture of 1-amino-2-butanol (5.5 g, 61.8 mmol), benzyl chloroformate (11.5 g, 67.6 mmol) and sodium carbonate (7.16 g, 67.7 mmol) in water (50 mL) was stirred at 0° C. for 3 h. Water (50 mL) was added to the reaction mixture and the product was extracted with methylene chloride (3×20 mL). The methylene chloride extract was dried over Na$_2$SO$_4$ and concentrated. The residue was passed through a short column (SiO$_2$, hexanes: ethyl acetate/10:1; then ethyl acetate) to afford 1-benzyloxycarbonylamino-2-butanol (13.9 g, 100%) as a liquid.

$^1$H NMR (CDCl$_3$) δ7.30 (m, 5 H), 5.45 (s, 1 H), 5.06 (s, 2 H), 3.57 (s, 1 H), 3.31 (m, 1 H), 3.04 (m, 1 H), 2.91 (m, 1 H), 1.43 (m, 2 H), 0.91 (t, J=7.6 Hz, 3 H).

B. Preparation of 1-benzyloxycarbonylamino2-butanone

To methylene chloride (60 mL) at −78° C. under argon was added oxalyl chloride (37 mL of 2 M solution in methylene chloride, 74 mmol), followed by DMSO (7.8 g, 100 mmol). The mixture was stirred at 78° C. for 20 min. and to this mixture was added a solution of 1-benzyloxycarbonylamino-2-butanol (13.9 g, 61.8 mmol) in methylene chloride (40 mL). The mixture was stirred at −78° C. for 1 h and triethylamine (21 mL) was added to the mixture. It was warmed to room temperature (rt) and washed successively with 1 N hydrochloric acid and aqueous sodium bicarbonate solution. The methylene chloride solution was dried over MgSO$_4$ and concentrated to afford 1-benzyloxycarbonylamino-2-butanone (11.2 g, 82%) as a solid, which was enough pure for the next reaction. $^1$H NMR (CDCl$_3$) δ7.32 (m, 5 H), 5.50 (s, 1 H), 5.06 (s, 2 H), 4.07 (s, 2 H), 2.43 (q, J=7.6 Hz, 2 H), 1.06 (t, J=7.6 Hz, 3 H).

C. Preparation of 1-amino-2-butanone

A solution of 1-benzyloxycarbonylamino-2-butanone (9.30 mg, 42 mmol) in ethanol (50 mL) and 1 N hydrochloric acid (46 mL) was stirred under hydrogen atmosphere in the presence of Pd/C (1.5 g, 10%) at rt for 4 h. The mixture was filtered through a celite bed and the filtrate solution was concentrated. The residue was triturated with ethyl ether to afford 1-amino-2-butanone (5.3 g, 102%) as a hydrochloride salt. $^1$H NMR (CD$_3$OD) δ3.97 (s, 2 H), 2.60 (q, J=7.6 Hz, 2 H), 1.08 (t, J=7.6 Hz, 3 H).

D. Preparation of 2-amino-5-thiocyanatothiazole

2-Aminothiazole (41 g, 410 mM) and sodium thiocyanate (60 g, 740 mM, dried in a vacuum oven at 130° C. overnight) was dissolved in 450 mL of anhydrous methanol and the solution was cooled in a cold water bath. Here was added bromine (23 mL, 445 mM) dropwise with good stirring. After the addition it was stirred for 4 h at rt. To the mixture 500 mL of water was added and it was stirred for 5 minutes, filtered through a celite bed and washed the bed with water. The pH of the filtrate solution was about 1. Most of the methanol was removed under the reduced pressure and pH of the solution was adjusted to about 7 by adding aq. sodium carbonate slowly with stirring. The precipitated solid was filtered and washed with water to obtain 37 g (57%) of the dark brown colored desired product after drying, mp 140–143° C. $^1$H NMR (CD$_3$OD) δ7.33 (s, 1 H); MS (CI/NH$_3$) m/e 179 (M+Na)$^+$, 158 (M+H)$^+$.

E. Preparation of of 2-acetylamino-5-thiocyanatothiazole

To a mixture of 2-amino-5-thiocyanatothiazole (15.7 g, 0.1 mol) and pyridine (12 g, 0.15 mol) in methylene chloride (100 mL) was added acetic anhydride (1.2 g, 0.12 mol) at rt. The mixture was stirred at rt for 6 h. The mixture was concentrated to dryness and to the residue MeOH (50 mL) was added. The precipitates were collected and washed with water. The solid was dried and recrystallized from MeOH to afford 2-acetylamino-5-thiocyanatothiazole (15.2 g, 76%) as a solid, mp 212° C. $^1$H NMR (CD$_3$OD) δ7.79 (s, 1 H), 2.23 (s, 3 H).

F. Preparation of [[2-(acetylamino)-5-thiazolyl]thio]acetic acid 1,1-dimethylethyl ester To a mixture of 2-acetamino-5-thiocyanatothiazole (5.97 g, 30 mmol) in MeOH (360 mL) under argon was added dithiothreitol (9.26 g, 60 mmol) at rt. The mixture was stirred at rt for 2 h and it was concentrated to afford a reduced solid product. This solid product was dissolved in DMF (30 mL) and to this solution were added tert-butyl bromoacetate (5.85 g, 30 mmol) and potassium carbonate (5.0 g, 36 mmol). The mixture was stirred at rt for 2 h and water (200 mL) was added to the mixture. The precipitates were collected, washed with water and dried. The solid was dissolved in methylene chloride (100 mL) and MeOH (10 mL) and filtered through a silica gel pad. The filtrate solution was concentrated to afford the desired product (7.5 g, 87%) as a solid, mp 162–163° C. $^1$H NMR (CDCl$_3$) δ12.2 (s, 1 H), 7.48 (s, 1 H), 3.37 (s, 2 H), 2.32 (s, 3 H), 1.45 (s, 9 H); MS m/e 289 (M+H)$^+$, 287 (M−H)$^-$. HPLC (Column: YMC S3 ODS 4.6×150 mm; flow rate: 2.5 mL/min; solvent system: 0–100% B in 8 min. Solvent A: 10% MeOH-90% water-0.2% H$_3$PO$_4$; Solvent B: 90% MeOH-10% Water-0.2% H$_3$PO$_4$; UV: 220 nm): retention time 6.44 min.

G. Preparation of [[2-(acetylamino)-5-thiazolyl]thio]acetic acid

A solution of [[2-(acetylamino)-5-thiazolyl]thio]acetic acid 1,1-dimethylethyl ester (4.32 g, 15 mmol) in methylene chloride (30 mL) and trifluoroacetic acid (20 mL) was stirred at rt overnight and concentrated in vacuo. To the residue was added ethyl ether (50 mL). The precipitated solid was collected, washed with ethyl ether and dried to afford the desired product (3.38 g, 97%) as a solid, mp 210° C. $^1$H NMR (CD$_3$OD) δ7.48 (s, 1 H), 3.47 (s, 2 H), 2.20 (s, 3 H) ppm; MS m/e 231 (M–H)$^-$; HPLC (Column: Zorbax Rapid resolution C-18; flow rate: 2.5 mL/min; solvent system: 0–100% B in 8 min. Solvent A: 10% MeOH-90% water-0.2%H$_3$PO$_4$; Solvent B: 90% MeOH-10% Water-0.2% H$_3$PO$_4$; UV: 254 nm): retention time 4.32 min.

H. Preparation of [[2(acetylamino)-5-thiazolyl]thio]-N-(2-oxobutyl)acetamide

A mixture of [[2-(acetylamino)-5-thiazolyl]thio]acetic acid (9.0 g, 38.8 mmol), HOBT (5.94 g, 38.8 mmol) and ethyldimethylaminopropylcarbodiimide hydrochloride salt (11.16 g, 58.2 mmol) in DMF (50 mL) was stirred at 0° C. for 0.5 h. To this mixture was added 1-amino-2-butanone hydrochloride (5.27 g, 42.7 mmol) followed by triethylamine (15 mL, 107.5 mmol). The mixture was stirred at 0° C. for 0.5 h and at rt for 1 h. Water (200 mL) was added to the mixture and the product was extracted with methylene chloride containing 10% MeOH (5×100 mL). The methylene chloride extract was dried over Na$_2$SO$_4$ and concentrated. The residue was triturated with water and the precipitated solid product was collected by filtration. It was dried to obtain the desired product (10.5 g, 90%), mp 195–196° C.

$^1$H NMR (CDCl$_3$) δ7.53 (s, 1 H), 4.14 (s, 2 H), 3.46 (s, 2 H), 2.50 (q, J=7.6 Hz, 2 H), 2.25 (s, 3 H), 1.12 (t, J=7.6 Hz, 3 H); MS m/e 302 (M+H)$^+$. HPLC (Column: Zorbax Rapid resolution C-18; flow rate: 2.5 ml/min; solvent system: 0–100% B in 8 min. Solvent A: 10% MeOH-90% water-0.2% H$_3$PO$_4$; Solvent B: 90% MeOH-10% Water-0.2% H$_3$PO$_4$; UV: 254 nm): retention time 4.36 min.

I. Preparation of N[5-[[(5-ethyl-2-oxazolyl)methyl]thio]-2-thiazolyl]acetamide

To a solution of [[2-(acetylamino)-5-thiazolyl]thio]-N-(2-oxobutyl)acetamide (10.5 g, 34.8 mmol) in acetic anhydride (100 mL) was added conc. sulfuric acid (10 mL). The mixture was stirred at 55–60° C. for 2 h and sodium acetate (15 g, 0.18 mol) was added to the mixture. The mixture was concentrated in vacuo. To the residue was added cold water (100 mL). The precipitated solid was collected, washed with water and dried. It was purified by a flash column chromatography (SiO$_2$; methylene chloride: MeOH/100:5) to afford N-[5-[[(5-ethyl-2-oxazolyl)methyl]thio]-2-thiazolyl]acetamide (4.2 g, 43%) as a solid, mp 147–148° C. $^1$H NMR (CDCl$_3$) δ12.47 (s, 1 H), 7.29 (s, 1 H), 6.61 (s, 1 H), 3.91 (s, 2 H), 2.64 (q, J=7.6 Hz, 2 H), 2.25 (s, 3 H), 1.21 (t, J=7.6 Hz, 3 H) ppm; MS m/e 284 (M+H)$^+$;

HPLC (Column: Zorbax Rapid resolution C-18; flow rate: 2.5 mL/min; solvent system: 0–100% B in 8 min. Solvent A: 10% MeOH-90% water-0.2% H$_3$PO$_4$; Solvent B: 90% MeOH-10% Water-0.2% H$_3$PO$_4$; UV: 254 nm): retention time 6.50 min.

Example 2

N-[5-[[(5-ethyl-2-oxazolyl)methyl]thio]-2-thiazolyl]benzamide

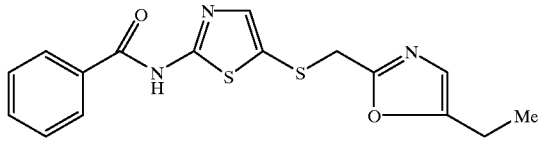

A. Preparation of 2-amino-5-[[(5-ethyl-2-oxazolyl)methyl]thio]-thiazole

A solution of N-[5-[[(5-ethyl-2-oxazolyl)methyl]thio]-2-thiazolyl]acetamide (1.3 g, 4.6 mmol) in 1 N hydrochloric acid (15 mL) was stirred at 80–90° C. for 3 h. It was cooled to rt and the pH of the solution was adjusted to 7 with sodium carbonate. The product was extracted with methylene chloride (3×10 mL). The combined extract was dried over Na$_2$SO$_4$ and concentrated. The residue was triturated with ethyl ether and the precipitated solid was collected to afford 2-amino-5-[[(5-ethyl-2-oxazolyl)methyl]thio]-thiazole (610 mg, 55%) as a solid, mp 119–120° C. $^1$H NMR (CDCl$_3$) δ6.93 (s, 1 H), 6.61 (s, 1 H), 5.41 (s, 2 H), 3.82 (s, 3 H), 2.62 (q, J=7.6 Hz, 2 H), 1.18 (t, J=7.6 Hz, 3 H); MS m/e 242 (M+H)$^+$;

HPLC (Column: Zorbax Rapid resolution C-18; flow rate: 2.5 mL/min; solvent system: 0–100% B in 8 min. Solvent A: 10% MeOH-90% water-0.2% H$_3$PO$_4$; Solvent B: 90% MeOH-10% Water-0.2% H$_3$PO$_4$; UV: 254 nm): retention time 3.96 min.

B. Preparation of N-[5-[[(5-ethyl-2oxazolyl)methyl]thio]-2-thiazolyl]benzamide

A mixture of 2-amino-5-[[(5-ethyl-2-oxazolyl)methyl]thio]-thiazole (48.2 mg, 0.2 mmol), benzoyl chloride (24.4 mg, 0.21 mmol) and triethylamine (35 mg, 0.35 mmol) in methylene chloride (0.5 mL) was stirred at rt for 10 min. The organic solution was washed with water and concentrated. The residue was purified by a flash column (SiO$_2$; hexanes: ethyl acetate/2:1) to afford N-[5-[[(5-ethyl-2-oxazolyl)methyl]thio]-2-thiazolyl]benzamide (41 mg, 59%) as a solid, mp 122–123° C. $^1$H NMR (CDCl$_3$) δ12.65 (s, 1 H), 7.96 (m, 2 H), 7.61 (m,, 1 H), 7.49 (m, 2 H), 6.88 (s, 1 H), 6.56 (s, 1 H), 3.93 (s, 2 H), 2.61 (q, J=7.6 Hz, 2 H), 1.20 (t, J=7.6 Hz, 3 H); MS m/e 346 (M+H)$^+$;

HPLC (Column: Zorbax Rapid resolution C-18; flow rate: 2.5 mL/min; solvent system: 0–100% B in 8 min. Solvent A: 10% MeOH-90% water-0.2% H$_3$PO$_4$; Solvent B: 90% MeOH-10% Water-0.2% H$_3$PO$_4$; UV: 254 nm): retention time 7.94 min.

Example 3

N-[5-[[(5-ethyl-2-oxazolyl)methyl]thio]-2-thiazolyl]benzsulfoneamide

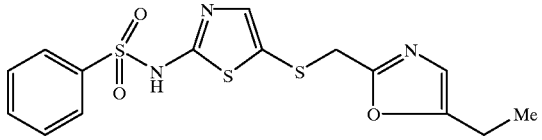

A mixture of 2-amino-6-[[(5-ethyl-2-oxazolyl)methyl]thio]-thiazole (24.1 mg, 0.1 mmol), benzenesulfonyl chloride (19.4 mg, 0.11 mmol) and triethylamine (22 mg, 0.21 mmol) in methylene chloride (0.3 mL) was stirred at rt for 10 h. The product of the reaction mixture was purified by preparative HPLC (column: YMC pack ODSA S3 20×100 mm; method: gradient from 0% B to 100% B in 20 min and flow rate 20 mL/min; Uw: 254 nm; solvent A: 10% MeOH-90% water-0.1% TFA; solvent B: 90% MeOH-10% water-0.1% TFA) to obtain N-[5-[[(5-ethyl-2-oxazolyl)methyl]thio]-2-thiazolyl]benzsulfoneamide (2.5 mg) as a solid after drying via lyophilization.

$^1$H NMR (CDCl$_3$) δ7.88 (d, J=8.0 Hz, 1 H), (s, 2 H), 7.49 (m, 3 H), 6.89 (s, 1 H), 6.64 (s, 1 H), 4.01 (s, 2 H), 2.68 (q, J=7.4 Hz, 2 H), 1.27 (t, J=7.4 Hz, 3 H); MS m/e 382 (M+H)$^+$;

HPLC (column: Zorbax Rapid resolution C-18; flow rate: 2.5 mL/min; solvent system: 0–100% B in 8 min. Solvent A: 10% MeOH-90% water-0.2% H$_3$PO$_4$; Solvent B: 90% MeOH-10% Water-0.2% H$_3$PO$_4$; UW: 254 nm): retention time 6.84 min.

Example 4
N-[5-[[(4,5-dimethyl-2-oxazolyl)methyl]thio]-2-thiazolyl]acetamide

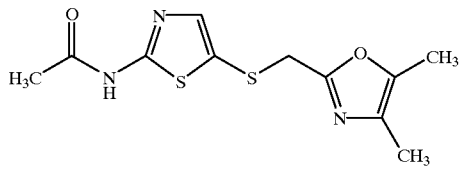

A. Preparation of 2-(bromomethyl)-4,5-dimethyloxazole

A mixture of 2,4,5-trimethyloxazole (0.50 mL, 4.3 mmol), N-bromosuccinimide (0.77 g, 4.3 mmol) and benzoyl peroxide (0.21 g, 0.86 mmol) in carbon tetrachloride (4 mL) was heated at 76° C. under nitrogen atm for 3 hrs. After cooling to rt, the solid was removed by filtration. The filtrate solution was washed with saturated aqueous NaHCO$_3$ (20 mL) and concentrated. The residue was purified by flash column chromatography (SiO$_2$; hexanes:ethyl acetate/4:1) to afford 2-(bromomethyl)-4,5-dimethyloxazole (64 mg) as an yellow oil. $^1$H NMR (CDCl$_3$) 67 4.4 (s, 2 H), 2.25 (s, 3 H), 2.05 (s, 3 H).

B. Preparation of N-[5-[[(4,5-dimethyl-2-oxazolyl)meihyl]thio]-2-thiazolyl]acetamide N-[5-(Acetylthio)-2-thiazolyl]acetamide (0.050 g, 0.23 mmol) was dissolved in dry THF (10 ml) and here potassiumtert-butoxide (1.0 M solution in THF, 0.25 ml, 0.25 mmol) was added to the mixture. The reaction mixture was stirred at rt for 15 min., and 2-(bromomethyl)-4,5-dimethyloxazole (0.064 g, 0.34 mmol) was added to this mixture. The reaction mixture was stirred at rt for 3 h and saturated aqueous NaHCO$_3$ solution (20 mL) was added to the mixture. The organic layer was separated and the aqueous layer was extracted with dichloromethane (3×20 mL). The combined organic layers was concentrated. The residue was purified by flash column chromatography (SiO$_2$; methanol:dichloromethane/1:20) to afford N-[5-[[(4,5-dimethyl-2-oxazolyl)methyl]thio]-2-thiazolyl]acetamide (15 mg, 23%) as a yellow solid.

$^1$H NMR (CDCl$_3$) δ11.78 (s, 1 H), 7.38 (s, 1 H), 3.90 (s, 2 H), 2.30 (s, 3H), 2.22 (s 3 H), 2.05 (s, 3 H); MS m/e 284 (M+H)$^+$;

HPLC (Column: Zorbax Rapid resolution C-18; flow rate: 2.5 ml/min; solvent system: 0–100% B in 8 min. Solvent A: 10% CH$_3$OH/90% H$_2$O/0.2% H$_3$PO$_4$; Solvent B: 90% CH$_3$OH/10% H$_2$O/0.2% H$_3$PO$_4$; UV: 254 nm): retention time 5.87 min.

Example 5
N-[5-[[(5-t-butyl-2-oxazolyl)methyl]thio]-2-thiazolyl]acetamide

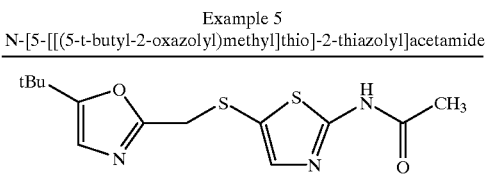

A. Preparation of diazomethane

To a mixture of 15 ml of 40% aqueous KOH solution and 50 mL of diethyl ether at 0° C. was added 5 g (68 mmol) of N-methyl-N'-nitro-N-nitrosoguanidine in portions with stirring. The resulting mixture was stirred at 0° C. for 0.5 h. The organic phase was decanted into a dry flask and dried over solid KOH pellets to give 50 mL of diazomethane solution (ca 0.5 M, by titrating with acetic acid).

B. Preparation of 1-diazo-3,3-dimethyl-2-butanone

To the diazomethane solution at 0° C. was added a solution of 1.23 mL (1.21 g, 10 mmol, Aldrich) of trimethylacetyl chloride in 1 mL of diethyl ether dropwise with stirring. The resulting mixture was kept at 0° C. for 16 h. The solution was sparged with argon to remove the excess diazomethane and diethyl ether was removed under reduced pressure to give 1.33 g (10 mmol, 100%) of crude 1-diazo-3,3-dimethyl-2-butanone as a yellow liquid.

C. Preparation of 2-chloromethyl-5-t-butyloxazole

To a solution of 2 mL (2.3 g, 16 mmol) of boron trifluoride etherate in 20 mL of chloroacetonitrile at 0° C. was added a solution of 1.33 g (10 mmol) of 1-diazo-3,3-dimethyl-2-butanone in 5 mL of chloroacetonitrile dropwise. The resulting solution was stirred at 0° C. for 0.5 h. The reaction mixture was added to saturated aqueous sodium bicarbonate solution to neutralize the acid and the product was extracted three times with dichloromethane. The combined extracts was dried (sodium sulfate), concentrated and purified by flash column chromatography (Merck silic a, 25×200 mm, dichloromethane) to give 1.1 g of 2-(chloromethyl)-5-t-butyloxazole as a yellow liquid (6.4 mmol, 64% overall from the acid chloride). $^1$H NMR δ (CDCl$_3$): 1.30 (s, 9 H), 4.58 (s, 2 H), 6.68 (s, 1 H); MS 174 (M+H)$^+$; TLC: R$_f$ (silica gel, dichloromethane)=0.33;

HPLC: t$_R$ (YMC S-3 ODS 4.6×50 mm rapid resolution; 2.5 ml/min, gradient 0–100% B over 8 min, Solvent A: 10% CH$_3$OH90% H$_2$O/0.2% H$_3$PO$_4$; Solvent B: 90% CH$_3$OH/10% H$_2$O/0.2% H$_3$PO$_4$; UV:254 nm)=6.5 min.

D. Preparation of N-[5-[[(5-t-butyl-2-oxazolyl)methyl]thio]-2-thiazolyl]acetamide To a solution of 50 mg (0.23 mmol, Applied Chemical Laboratory) of N-[5-(acetylthio)-2-thiazolyl]acetamide in 10 mL of THF was added 0.25 mL of potassium tert-butoxide solution (1 M solution, 0.25 mmol) at rt under argon. The resulting suspension was stirred for 15 min at rt, then a solution of 59 mg of 2-(chhloromethyl)-5-t-butyloxazole (0.34 mmol) in 1 mL of THF was added. The resulting mixture was stirred at ft for 16 h, concentrated under reduced pressure and purified by flash column chromatography (silica gel, 25×200 mm, 1:1 EtOAc/hexanes followed by 100% EtOAc) to give 44 mg (0.14 mmol, 61%) of N-[5-[[(5-t-butyl-2-oxazolyl)methyl]thio]-2-thiazolyl] acetamide as a white solid.

$^1$H NMR δ (CDCl$_3$) 1.27 (s, 9 H), 2.27 (s, 3 H), 3.95 (s, 2 H), 6.59 (s, 1 H), 7.31 (s, 1 H), 11.03 (broad s, 1 H); MS 312 (M+H)$^+$;

TLC: R$_f$ (silica gel, ethyl acetate)=0.53, UV;

HPLC: retention tim (YMC S-3 ODS 4.6×50 mm rapid resolution; 2.5 ml/min, gradient 0–100% B over 8 min, Solvent A: 10% CH$_3$OH/90% H$_2$O/0.2% H$_3$PO$_4$; Solvent B: 90% CH$_3$OH/10% H$_2$O/0.2% H$_3$PO$_4$; UV: 254 nm)=6.8 min.

Example 6
N-[5-[[(5-t-butyl-2-oxazolyl)methyl]thio]-2-thiazolyl]trimethylacetamide

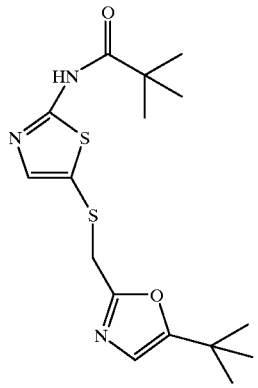

A. Preparation of N-[(5-thiocyanato)-2-thiazoy]trifluoroacetamide (XVIII)

To a mixture of 5-thiocyanato-2-aminothiazole (30 mmol) and 2,6-lutidine (35 mmol) in tetrahydrofuran (25 mL) and dichloromethane (50 mL) at −78° C. under argon was slowly added trifluoroaceticanhydride (33 mmol). After addition, the mixture was allowed to warm up to rt and stirred overnight. The mixture was diluted with dichloromethane (100 mL), and the organic solution was washed with 5% aqueous citric acid followed by brine, dried over magnesium sulfate and passed through a pad of silica gel. The product containing eluent was concentrated to afford 5.3 g of light brown solid. $^1$H -NMR (CDCl$_3$) δ12.4 (br, 1 H), 7.83 (s, 1 H).

B. Preparation of 4-hydroxymethyl-3-methoxyphenyloxy Merriffeld resin (XVI)

To the suspension of sodium hydride (11.7 g, 60% in mineral oil, 293 mmol) in dimethylformamide (30 mL) at 0° C. under argon was slowly added a solution of 4-hydroxy-3-methoxybenzyldehyde (44.5 g, 292.5 mmol) in dimethylformamide (100 mL). To the resulting mixture Merrifield resin (1% DVB, from Advanced Chemtech, loading 1.24 mmol/g, 50 g, 62 mmol) and catalytic amount of tetra-n-butylammonium iododide were added, and it was heated at 65° C. for a day. The resin was filtered, washed with water (2×), 50% dimethylformamide in water (3×), dimethylformamide (2×), and methanol (5×), and dried in vacuo. The dried resin (15 g) was treated with sodium borohydride (3.4 g, 90 mmol) in tetrahydrofuran (50 mL) and ehtanol (50 mL) overnight. The resin was filtered, washed with 50% dimethylformamide in water (3×), dimethylformamide (2×), methanol (2×), and dichloromethane (5×), and dried in vacuo.

C. Preparation of 4-chloromethyl-3-methoxyphenyloxy Merrifield resin (XVII)

To a solution of triphenylphosphine (17 g, 65 mmol) in dichloromethane (200 mL) at 0° C. was slowly added triphosgene (9.2 g, 31 mmol) portionwise over a period of 30 minutes. After addition, the reaction mixture was stirred at 0° C. for 10 minutes. The solvent was removed in vacuo and the residue was redissolved in dichloromethane (200 mL). To this mixture was added 4-hydroxymethyl-3-methoxyphenyloxy Merrifield resin (12 g). The resulting mixture was agitated for 4 h. The resin was washed with dry dichloromethane (6×) and dried in vacuo.

D. Preparation of 4-[N-[(5-thiocyanato)-2-thiazolytryfluoroacetamido]methyl]methoxyphenyloxy Merrifield resin (XIX)

A mixture of 4-chloromethyl-3-methoxyphenyloxy Merrifield resin (15 g), N-[(5-thiocyanato)-2-thiazolyl]trifluoroacetamide (14 g, 55.3 mmol) and diisopropylethylamine (7.8 mL, 45 mmol) in dimethylformamide (50 mL) and dichloromethane (100 mL) was agitated overnight. The resin was washed with dimethylformamide (2×), methanol (2×), dichloromethane (4×), and dried in uacuo.

E. Preparation of 4-[[N-[(5-mercapto)-2-thiazolyl]trifluoroacetamido]methyl]-3-methoxyphenyloxy Merrifield resin (XX)

A mixture of 4-[N-[(5-thiocyanato)-2-thiazolyltrifluoroacetamido]methyl]-3-methoxyphenyloxy Merrifield resin (XIX, 18.5 g) and dithiothreitol (12 g, 78 mmol) in tetrahydrofuran (100 mL) and methanol (100 mL) was agitated overnight. The resin was washed with dimethylformamide (2×), methanol (2×), dichloromethane (4×), and dried in vacuo and stored under argon at −20° C.

F. Preparation of 4-N-[5-[[[(5-t-butyl-2-oxazolyl)methyl]thio]-2-thiazolyl]trifloroacetamnido]methyl-3-methoxyphenyloxy Merrifield resin (XX)

A stream of argon was bubb led through a mixture 4-[[N-[(5-Mercapto)-2-thiazolyl]trifluoroacetamido]methyl]-3-methoxyphenyloxy Merrifield resin (XX, 500 mg), halide (2.0 mmol) and 1,8-diazabicyclo[5,4,0]undec-7-ene (DBU, 1.5 mmol) in dimethylformamide (3 mL) for 5 min., and the mixture was heated at 80° C. for 2 h. The resin was washed with dimethylformamide (2×), methanol (2×), dichloromethane (4×), and dried in vacuo.

G. Preparation of 4-N-[5-[[(5-t-butyl-2-oxazolyl)methyl]thio]-2-thiazolyl]methyl-3-methoxyphenyloxy Merrifield resin (XXII)

A mixture of 4-N-[5-[[[(5-t-butyl-2-oxazolyl)methyl]thio]-2-thiazolyl]trifluoroacetamido]methyl-3-methoxyphenyloxy Merrifield resin (XXI, 500 mg ) and sodium borohydride (4 mmol) in tetrahydrofuran (2 mL) and ethanol (2 mL) was agitated overnight. The resin was washed with 50% dimethylformamide in water (2×), dimethylformamide (2×), methanol (2×), dichloromethane (4×), and dried in vacuo.

H. Preparation of 4-N-[5-[[[(5-t-butyl-2-oxazolyl)methyl]thio]-2-thiazolyl]trimethylacetamido]methyl-3-methoxyphenyloxy Merrifield resin (XXIII)

A mixture of 4-N-[5-[[(5-t-butyl-2-oxazolyl)methyl]thio]-2-thiazolyl]methyl-3-methoxyphenyloxy Merrifield resin (XXII, 100 mg), diisopropylethylamine (1.2 mmol) and trimethylacetyl chloride (1 mmol) in dichloromethane (2 mL) in a polypropylene tube fitted with a polyethylene frit and a luer stopcock was agitated overnight. The resin was washed with dimethylformamide (2×), methanol (2×), dichloromethane (4×), and used in the next step without drying.

I. Preparation of N-[5-[[(5-t-butyl-2-oxazolyl)methyl]thio]-2-thiazolyl]trimethylacetamide 4-N-[5-[[[(5-t-butyl-2-oxazolyl)methyl]thio]-2-thiazolyl]trimethylacetamido]methyl-3-methoxyphenyloxy Merrifield resin (XXIII) was treated with 60% trifluoroacetic acid in dichloromethane (2 mL) in a polypropylene tube fitted with a polyethylene frit and a luer stopcock for 4 hours. The solution was decanted to a tube and the resin was washed with dichloromethane. The combined organic solution was concentrated in Speed Vac. The residue was purified by preparative-HPLC to afford 11.3 mg of the desired product.

MS m/e 354 (M+H)+.

Example 7
N-[5-[[(4-Ethyl-2-oxazolyl)methyl]thio]-2-thiazolyl]acetamide

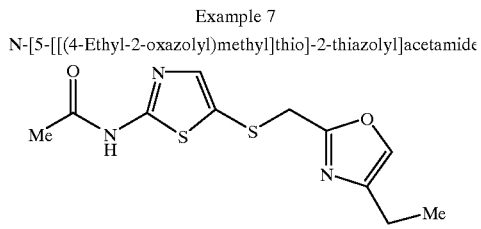

A. Preparation of 2-(2-chloroacetamido)-1-butanol

To a mixture of 2-amino-1-butanol (5.0 mL, 53 mmol) and triethyl amine (15.0 mL, 111 mmol) in dichloromethane (20 mL) at −70° C. was added chloroacetyl chloride (4.6 mL, 58 mmol) dropwise. The reaction mixture was stirred at −70° C. for 15 min. and then was allowed to warm to rt. It was diluted with EtOAc (50 mL) and the reaction was quenched by adding water (50 mL). The organic layer was separated and the aqueous layer was extracted with EtOAc (3×30 mL). The combined organic layers was concentrated to afford 2-(2-chloroacetamido)-1-butanol (8.6 g, 98%) as a brown solid. $^1$H NMR (CDCl$_3$) δ6.75 (bs, 1 H), 4.10 (s, 2 H), 4.08 (dd, 1 H), 3.90 (m, 1 H), 3.68 (m, 2 H), 2.98 (bs, 1 H), 1.60 (m, 2 H), 0.97 (t, 3 H).

B. Preparation of 2-(2-chloroacetamido)-1-butyraldehyde

To a solution of oxalyl chloride (14.5 mL, 29.0 mmol) in dichlolomethane (30 mL) at −78° C. DMSO (2.75 mL, 38.8 mmol) was added dropwise over 5 min. After stirring for 10 min. at −78° C., here was added a solution of 2-(2-chloroacetamido)-1-butanol (4.0 g, 24 mmol) in 20 mL of dichlolomethane dropwise over 15 min. The reaction mixture was stirred for 40 min. at −78° C. and here was added triethyl amine (9.4 mL, 68 mmol) dropwise over 5 min. and the reaction mixture was allowed to warm to room temperature and stirred for 2 hrs. The solid was removed by filtration and washed with EtOAc. The organic phase was washed with 1 N HCl (2×100 mL), saturated aqueous NaHCO$_3$ (1×10 mL) and concentrated to afford 2-(2-chloroacetamido)-1-butyraldehyde (3.7 g, 95%) as a brown oil.

$^1$H NMR (CDCl$_3$) δ9.60 (s, 1 H), 4.52 (q, 1 H), 4.12 (s, 2 H), 2.05 (m, 1 H), 1.80 (m, 1 H), 0.97 (t, 3 H).

C. Preparation of 2-chloromethy-4-ethyloxazole

To a solution of 2-(2-chloroacetamido)-1-butyraldehyde (3.7 g, 23 mmol) in toluene (10 mL) was added POCl$_3$ (6.3 mL, 68 mmol). The reaction mixture was heated at 90° C. for 1 h under nitrogen. After cooling the reaction mixture to room temperature it was poured into ice water (10 mL) and the pH of the solution was adjusted to 7 with 5 N NaOH. The toluene layer was separated and the aqueous layer was washed with dichloromethane (3×20 mL). The combined organic solution was concentrated and distilled to afford 2-chloromethy-4-ethyloxazole (1.1 g, 31%) as a colorless liquid.

$^1$H NMR (CDCl$_3$) δ7.30 (s, 1 H), 4.22 (s, 2 H), 2.50 (q, 2 H), 1.22 (t, 3 H).

D. Preparation of N-[5-[[(4-ethyl-2-oxazolyl)methyl]thio]-2-thiazolyl]acetamide

To a solution of 2-acetylamino-5-thiazolylthiol (0.010 g, 0.050 mmol) in dry THF (5 mL) was added potassium tert-butoxide (1.0 M solution in THF, 0.060 mL, 0.060 mmol). The reaction mixture was stirred at room temperature for 15 min. and here was added 2-chloromethyl-4-ethyloxazole (0.015 g, 0.10 mmol). After 3 h, saturated aqueous NaHCO$_3$ solution (5 mL) was added to the mixture. The organic layer was separated and the aqueous layer was washed with dichloromethane (3×10 mL). The combined organic layers was concentrated. The residue was purified by flash chromatography (SiO$_2$; methanol:dichloromethane/ 1:20) to afford N-[5-[[(4-ethyl-2-oxazolyl)methyl]thio]-2-thiazolyl]acetamide (5 mg, 36%) as a white solid.

$^1$H NMR (CDCl$_3$) δ11.25 (s, 1 H), 7.34 (s, 1 H), 7.31 (s, 1 H), 3.95 (s, 2 H), 2.50 (q, 2 H), 2.27 (s, 3 H), 1.19 (t, 3 H); MS m/e 284 (M+H)+; HPLC (Column: Zorbax Rapid resolution C-18; flow rate: 2.5 ml/min; solvent system: 0–100% B in 8 min. Solvent A: 10% CH$_3$OH/90% H$_2$O/0.2% H$_3$PO$_4$; Solvent B: 90% CH$_3$OH/10% H$_2$O/0.2% H$_3$PO$_4$; UV: 254 nm): retention time 6.14 min.

Using the procedures described herein or by modification of the procedures described herein as known to one or ordinary skill in the art, the following additional compounds have been prepared and disclosed in Table 1:

TABLE 1

| Example | Structure | Molecular Formula | (M + H)+ |
|---|---|---|---|
| 8 | 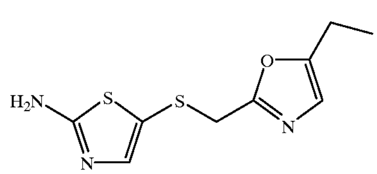 | C9H11N3OS2 | 242 |
| 9 | 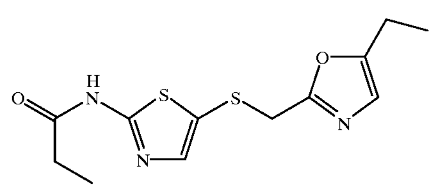 | C12H15N3O2S2 | 298 |

TABLE 1-continued

| Example | Structure | Molecular Formula | (M + H)+ |
|---|---|---|---|
| 10 | 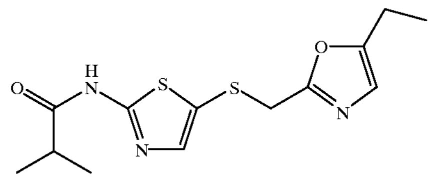 | C13H17N3O2S2 | 312 |
| 11 | 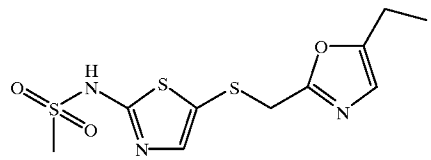 | C10H13N3O3S3 | 320 |
| 12 | 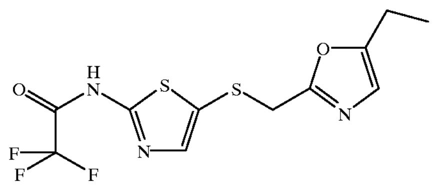 | C11H10F3N3O2S2 | 338 |
| 13 | 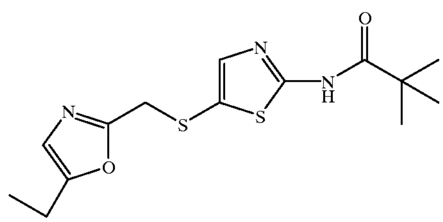 | C14H19N3O2S2 | 326 |
| 14 | 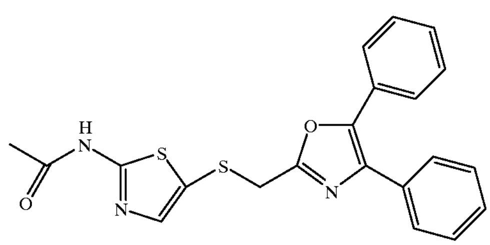 | C21H17N3O2S2 | 408 |
| 15 | 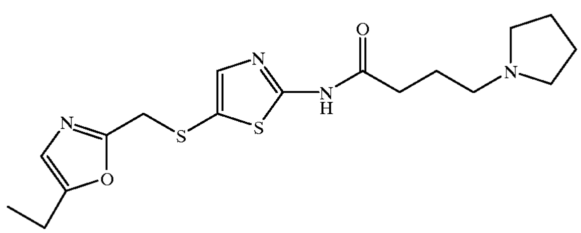 | C17H24N4O2S2 | 381 |
| 16 | 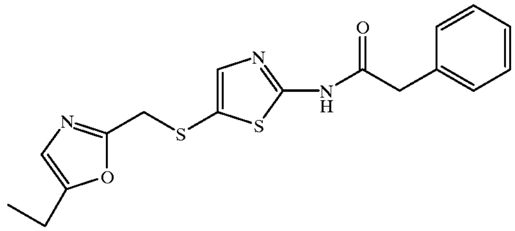 | C17H17N3O2S2 | 360 |

TABLE 1-continued

| Example | Structure | Molecular Formula | (M + H)+ |
|---|---|---|---|
| 17 | 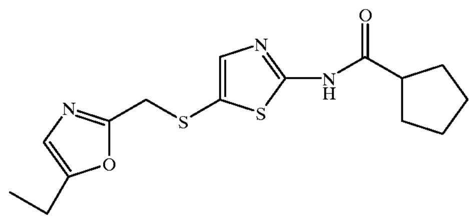 | C15H19N3O2S2 | 338 |
| 18 | 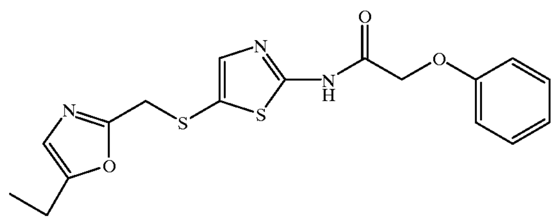 | C17H17N3O3S2 | 376 |
| 19 | 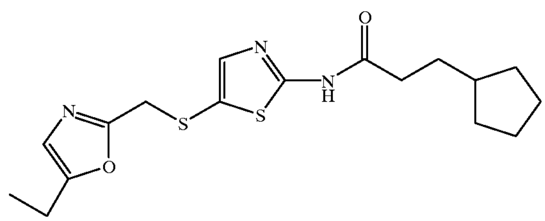 | C17H23N3O2S2 | 366 |
| 20 | 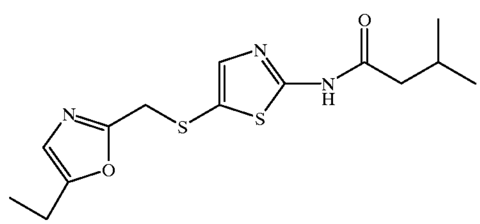 | C14H19N3O2S2 | 326 |
| 21 | 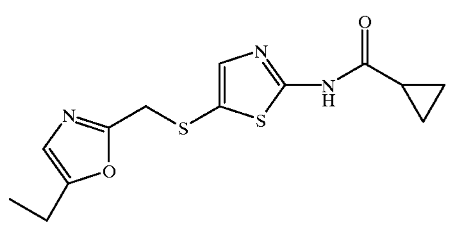 | C13H15N3O2S2 | 310 |
| 22 | 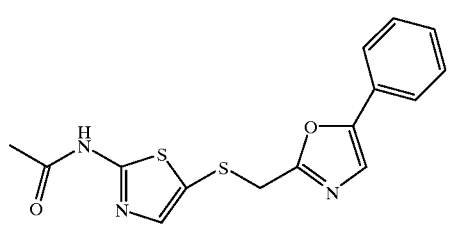 | C15H13N3O2S2 | 332 |
| 23 | 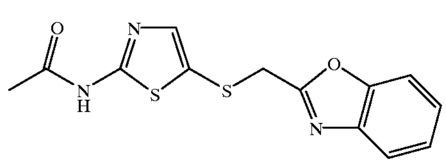 | C13H11N3O2S2 | 306 |

TABLE 1-continued

| Example | Structure | Molecular Formula | (M + H)+ |
|---|---|---|---|
| 24 | 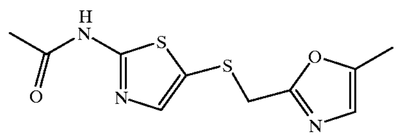 | C10H11N3O2S2 | 270 |
| 25 | 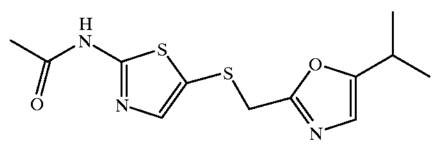 | C12H15N3O2S2 | 298 |
| 26 | 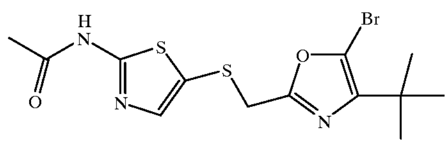 | C13H16BrN3O2S2 | 391 |
| 27 | 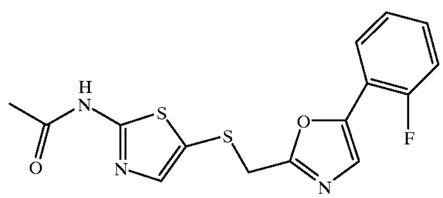 | C15H12FN3O2S2 | 350 |
| 28 | 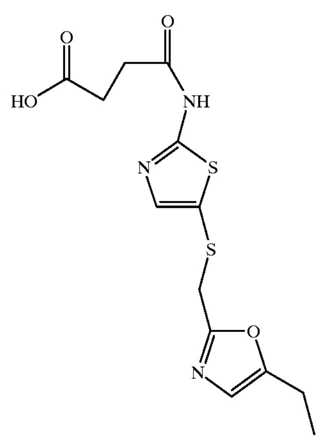 | C13H15N3O4S2 | 342 |
| 29 | 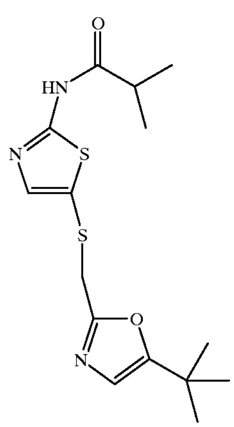 | C15H21N3O2S2 | 340 |

TABLE 1-continued

| Example | Structure | Molecular Formula | (M + H)+ |
|---|---|---|---|
| 30 | 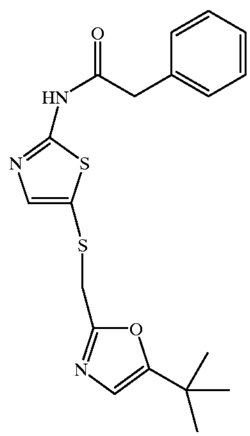 | C19H21N3O2S2 | 388 |
| 31 | 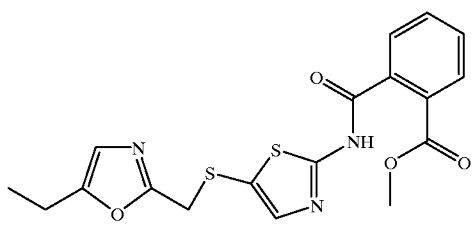 | C18H17N3O4S2 | 404 |
| 32 | 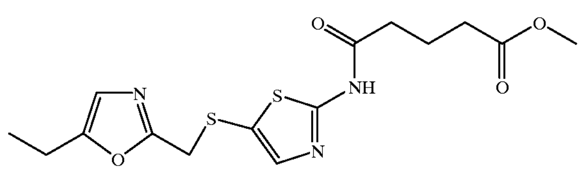 | C15H19N3O4S2 | 370 |
| 33 | 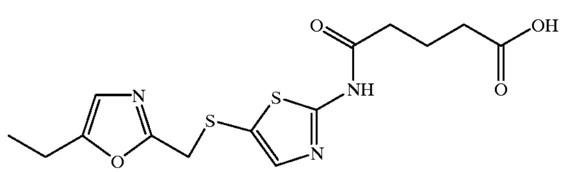 | C14H17N3O4S2 | 356 |
| 34 | 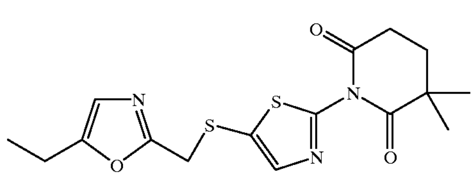 | C16H19N3O3S2 | 366 |
| 35 | 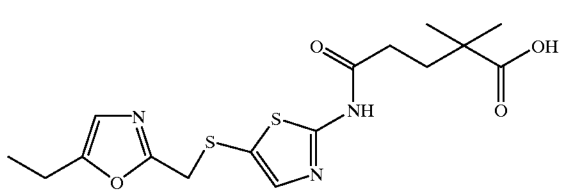 | C16H21N3O4S2 | 384 |

TABLE 1-continued

| Example | Structure | Molecular Formula | (M + H)+ |
|---|---|---|---|
| 36 | 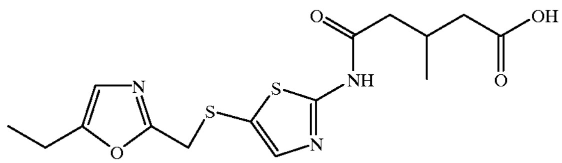 | C15H19N3O4S2 | 370 |
| 37 | 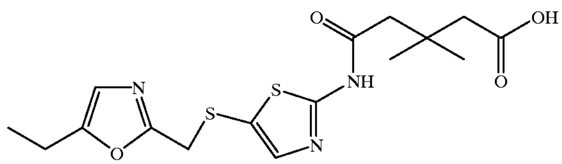 | C16H21N3O4S2 | 384 |
| 38 | 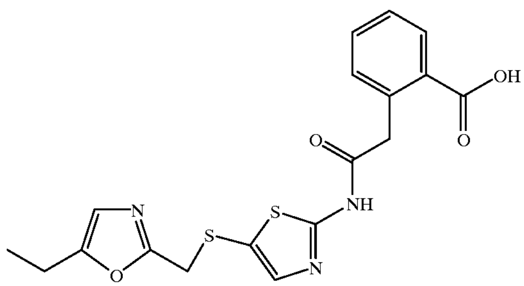 | C18H17N3O4S2 | 404 |
| 39 | 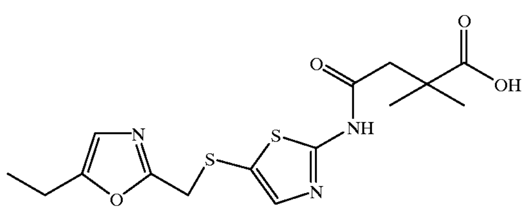 | C15H19N3O4S2 | 370 |
| 40 | 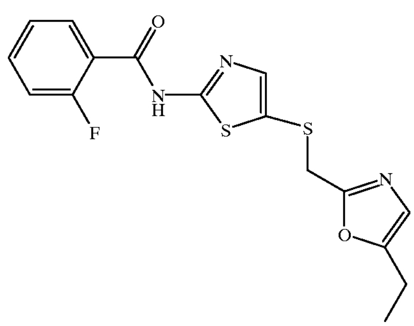 | C16H14FN3O2S2 | 364 |
| 41 | 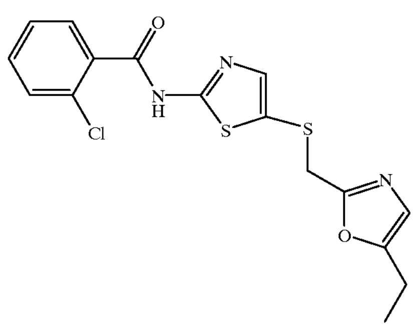 | C16H14ClN3O2S2 | 380 |

TABLE 1-continued

| Example | Structure | Molecular Formula | (M + H)+ |
|---|---|---|---|
| 42 | 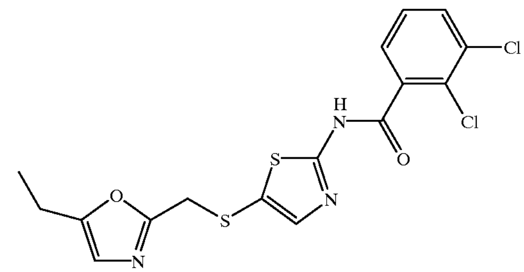 | C16H13Cl2N3O2S2 | 415 |
| 43 | 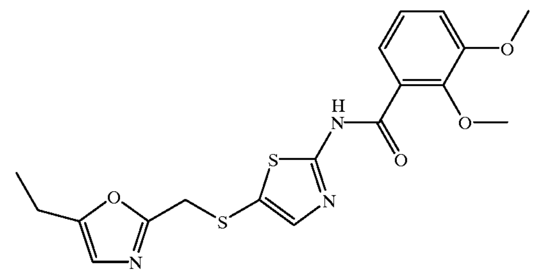 | C18H19N3O4S2 | 406 |
| 44 | 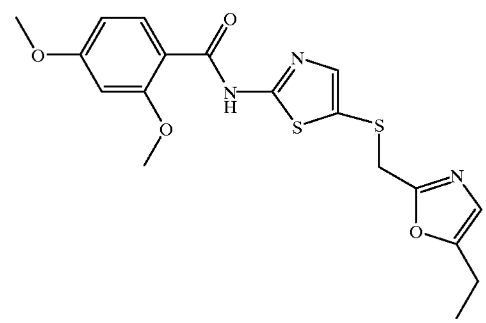 | C18H19N3O4S2 | 406 |
| 45 | 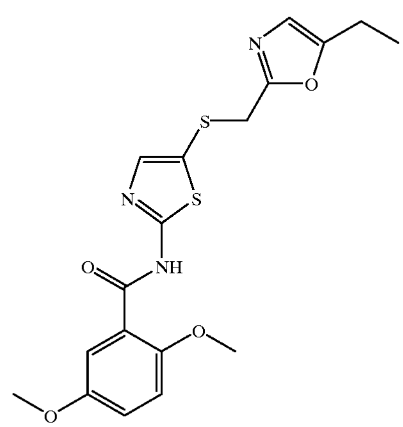 | C18H19N3O4S2 | 406 |
| 46 | 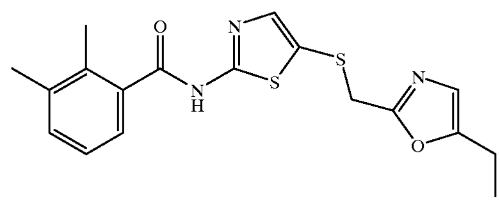 | C18H19N3O2S2 | 374 |

TABLE 1-continued

| Example | Structure | Molecular Formula | (M + H)+ |
| --- | --- | --- | --- |
| 47 | 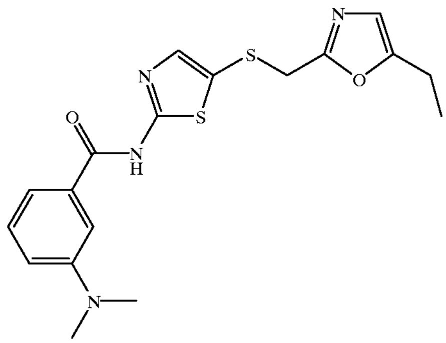 | C18H20N4O2S2 | 503 |
| 48 | 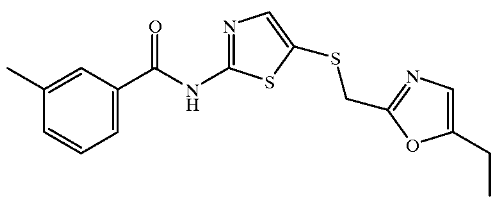 | C17H17N3O2S2 | 360 |
| 49 | 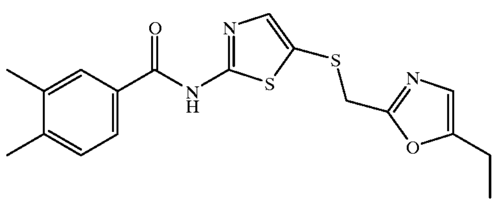 | C18H19N3O2S2 | 374 |
| 50 | 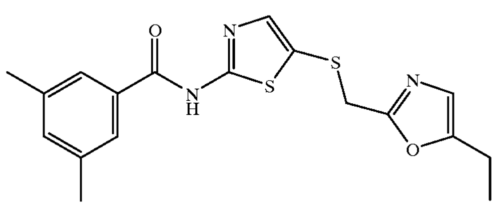 | C18H19N3O2S2 | 374 |
| 51 | 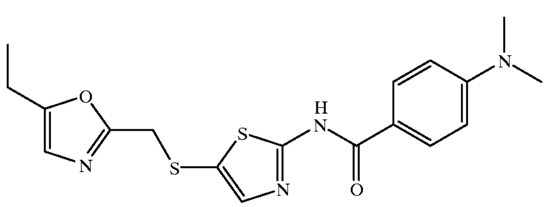 | C18H20N4O2S2 | 503 |

TABLE 1-continued

| Example | Structure | Molecular Formula | (M + H)+ |
|---|---|---|---|
| 52 | 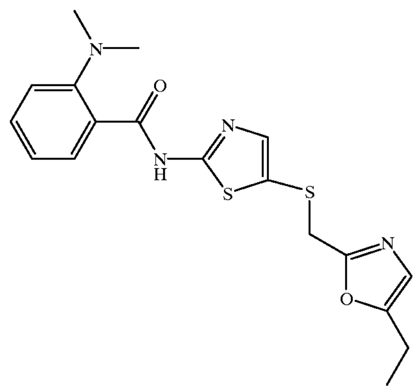 | C18H20N4O2S2 | 503 |
| 53 | 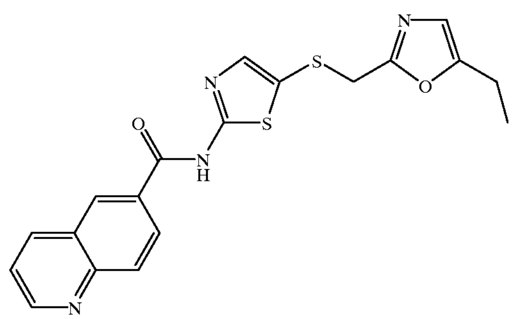 | C19H16N4O2S2 | 511 |
| 54 | 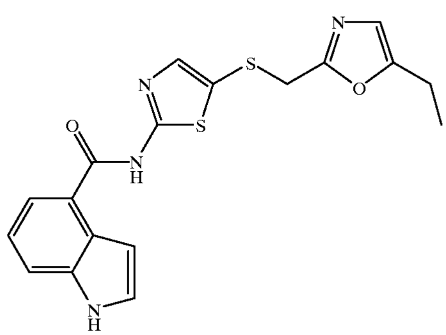 | C18H16N4O2S2 | 499 |
| 55 | 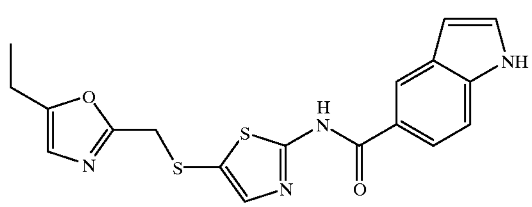 | C18H16N4O2S2 | 499 |

TABLE 1-continued
| Example | Structure | Molecular Formula | (M + H)+ |
|---|---|---|---|
| 56 | 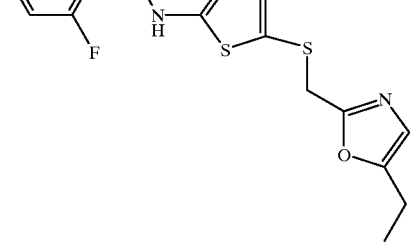 | C16H13F2N3O2S2 | 382 |
| 57 | 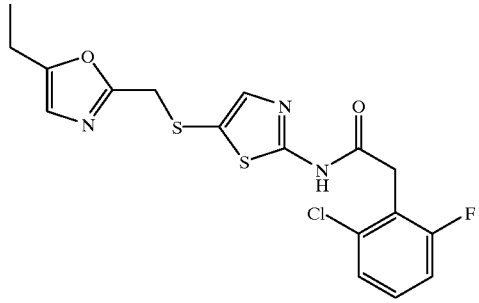 | C17H15ClFN3O2S2 | 412 |
| 58 | 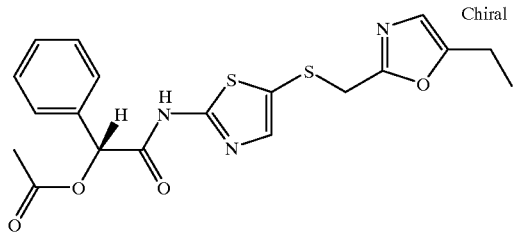 Chiral | C19H19N3O4S2 | 418 |
| 59 | 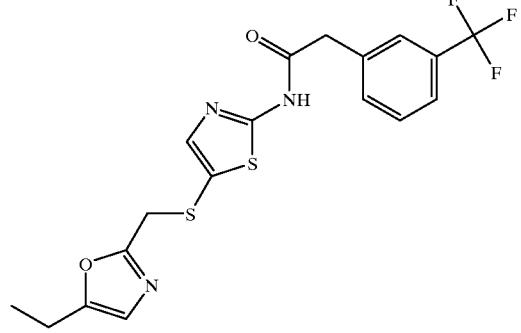 | C18H16F3N3O2S2 | 428 |
| 60 | 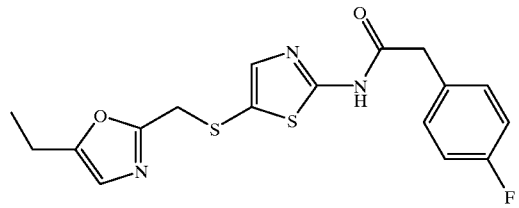 | C17H16FN3O2S2 | 378 |

TABLE 1-continued

| Example | Structure | Molecular Formula | (M + H)+ |
|---|---|---|---|
| 61 | 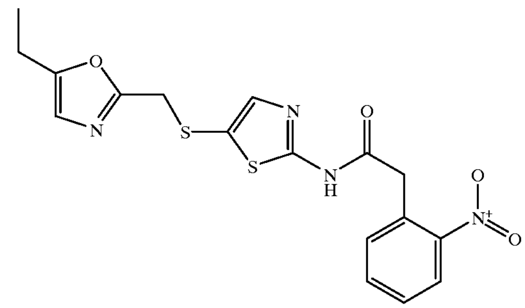 | C17H16N4O4S2 | 405 |
| 62 | 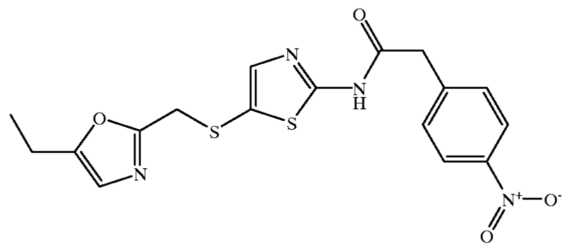 | C17H16N4O4S2 | 405 |
| 63 | 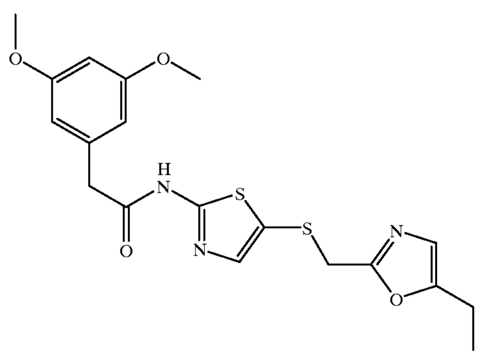 | C19H21N3O4S2 | 420 |
| 64 | 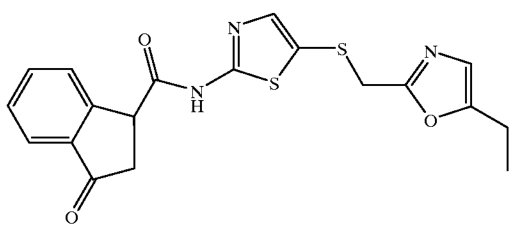 | C19H17N3O3S2 | 400 |
| 65 | 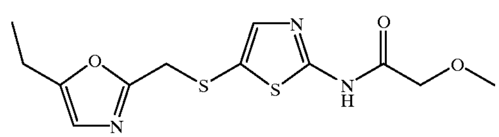 | C12H15N3O3S2 | 314 |
| 66 | 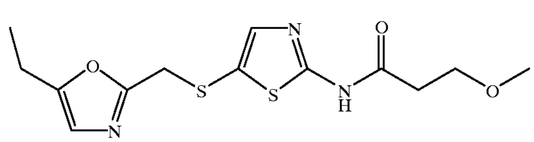 | C13H17N3O3S2 | 328 |

TABLE 1-continued

| Example | Structure | Molecular Formula | (M + H)+ |
|---|---|---|---|
| 67 | 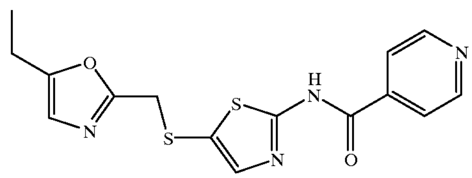 | C15H14N4O2S2 | 461 |
| 68 | 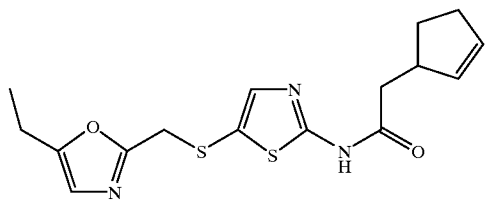 | C16H19N3O2S2 | 350 |
| 69 | 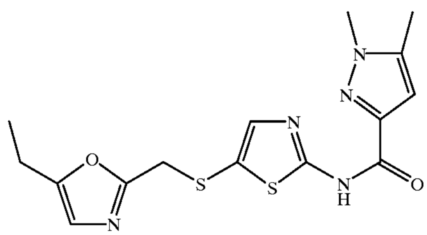 | C15H17N5O2S2 | 364 |
| 70 | 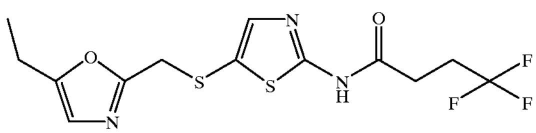 | C13H14F3N3O2S2 | 366 |
| 71 | 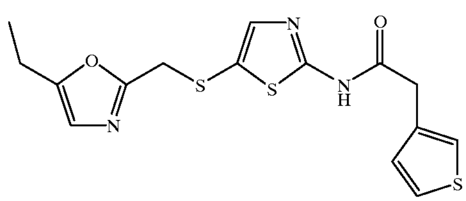 | C15H15N3O2S3 | 366 |
| 72 | 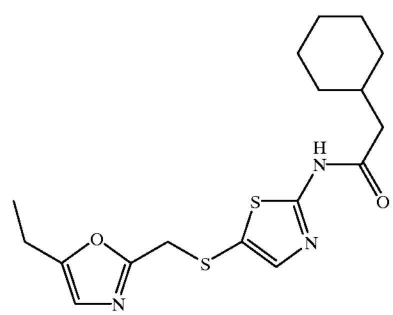 | C17H23N3O2S2 | 366 |
| 73 | 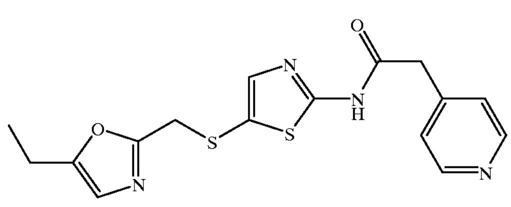 | C16H16N4O2S2 | 475 |

TABLE 1-continued
| Example | Structure | Molecular Formula | (M + H)+ |
| --- | --- | --- | --- |
| 74 | 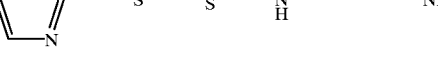 | C12H16N4O2S2 | 427 |
| 75 | 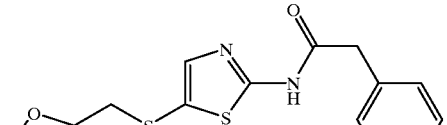 | C18H19N3O3S2 | 390 |
| 76 | 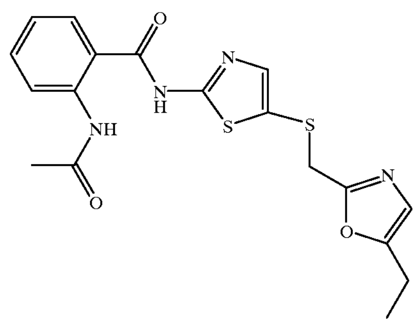 | C18H18N4O3S2 | 403 |
| 77 | 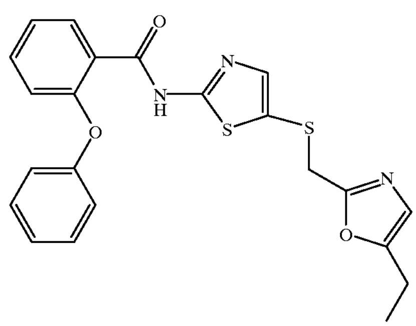 | C22H19N3O3S2 | 438 |
| 78 | 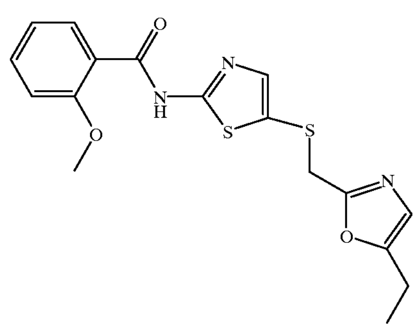 | C17H17N3O3S2 | 376 |

TABLE 1-continued

| Example | Structure | Molecular Formula | (M + H)+ |
| --- | --- | --- | --- |
| 79 | 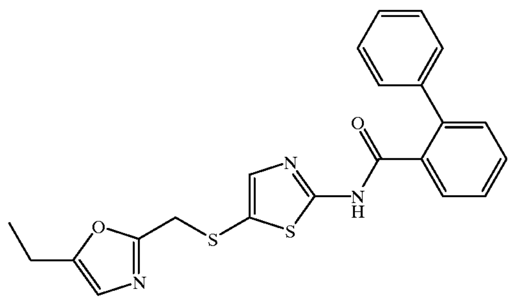 | C22H19N3O2S2 | 422 |
| 80 | 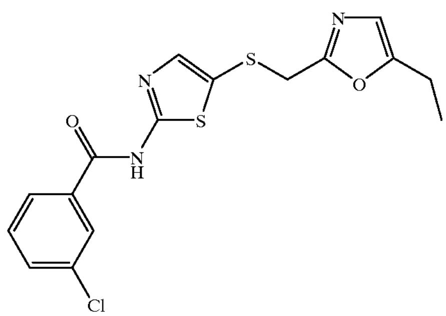 | C16H14ClN3O2S2 | 380 |
| 81 | 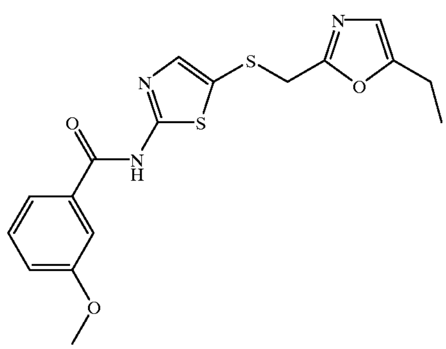 | C17H17N3O3S2 | 376 |
| 82 | 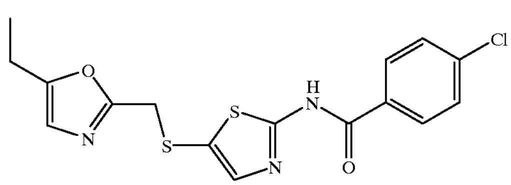 | C16H14ClN3O2S2 | 380 |
| 83 | 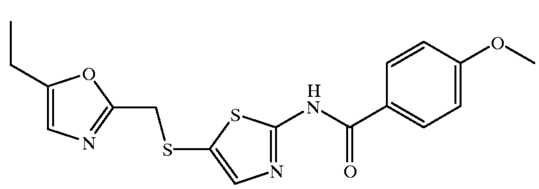 | C17H17N3O3S2 | 376 |

TABLE 1-continued

| Example | Structure | Molecular Formula | (M + H)+ |
| --- | --- | --- | --- |
| 84 | 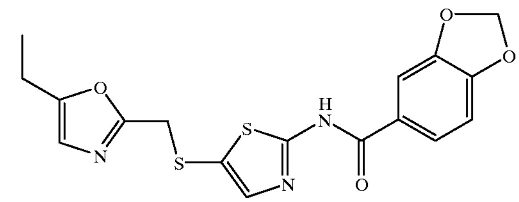 | C17H15N3O4S2 | 390 |
| 85 | 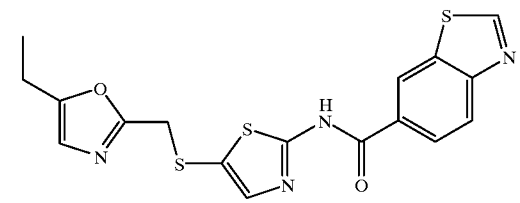 | C17H14N4O2S3 | 403 |
| 86 | 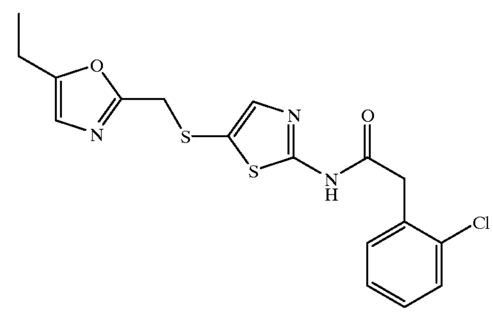 | C17H16ClN3O2S2 | 394 |
| 87 | 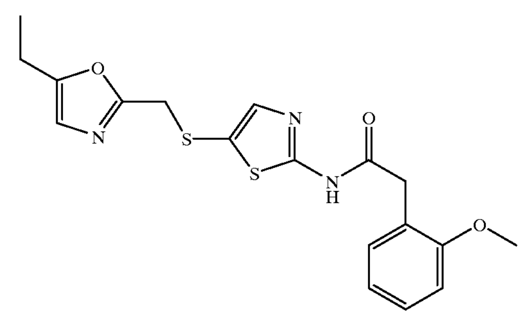 | C18H19N3O3S2 | 390 |
| 88 | 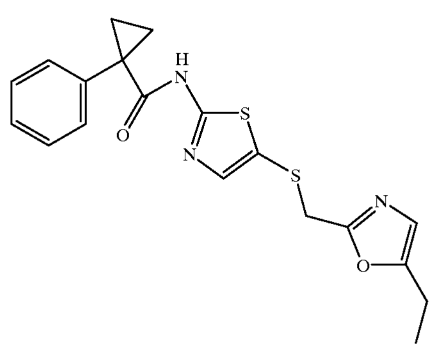 | C19H19N3O2S2 | 386 |

TABLE 1-continued
| Example | Structure | Molecular Formula | (M + H)+ |
|---|---|---|---|
| 89 | 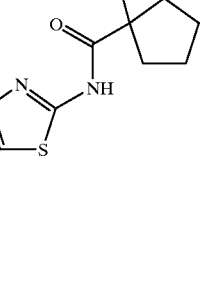 | C21H23N3O2S2 | 414 |
| 90 | 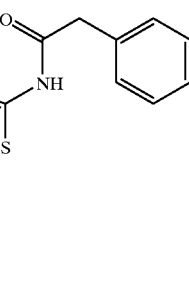 | C17H16ClN3O2S2 | 394 |
| 91 | 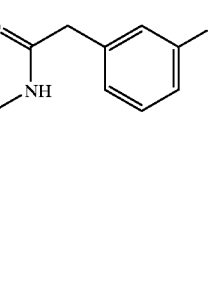 | C18H19N3O3S2 | 390 |
| 92 | 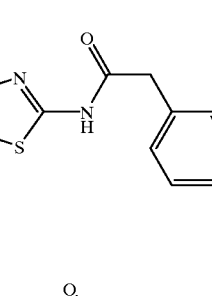 | C17H16ClN3O2S2 | 394 |
| 93 | 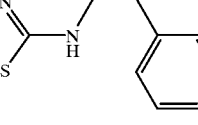 | C18H17N3O4S2 | 404 |

TABLE 1-continued
| Example | Structure | Molecular Formula | (M + H)+ |
|---|---|---|---|
| 94 | 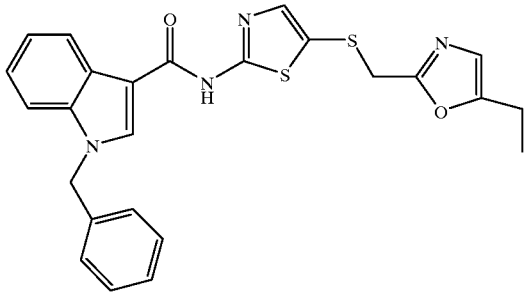 | C25H22N4O2S2 | 589 |
| 95 | 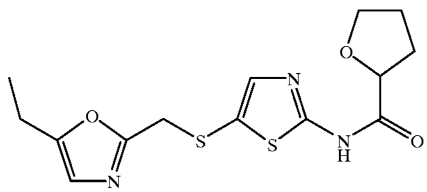 | C14H17N3O3S2 | 340 |
| 96 | 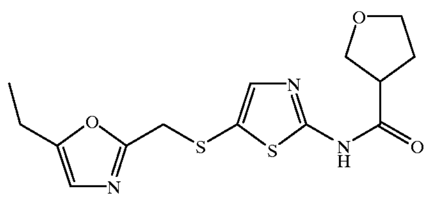 | C14H17N3O3S2 | 340 |
| 97 | 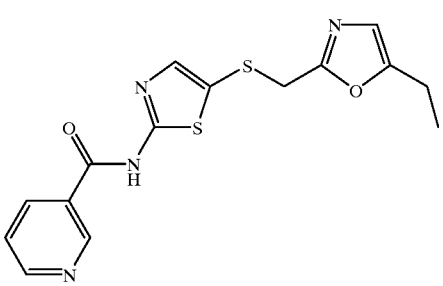 | C15H14N4O2S2 | 461 |
| 98 | 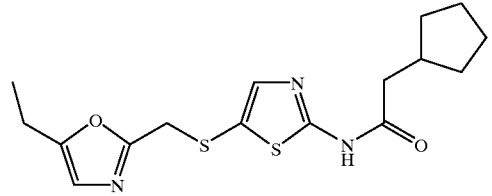 | C16H21N3O2S2 | 352 |

TABLE 1-continued

| Example | Structure | Molecular Formula | (M + H)+ |
| --- | --- | --- | --- |
| 99 | 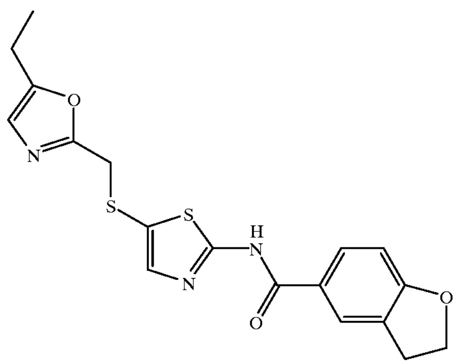 | C18H17N3O3S2 | 388 |
| 100 | 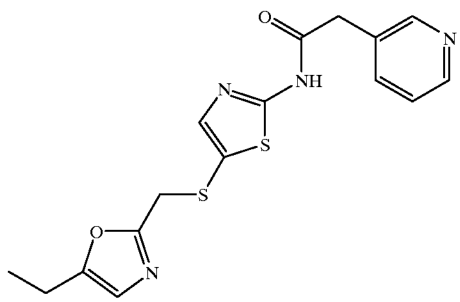 | C16H16N4O2S2 | 475 |
| 101 | 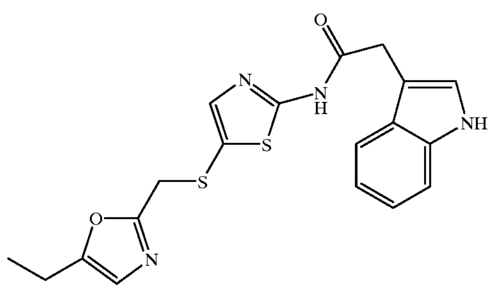 | C19H18N4O2S2 | 513 |
| 102 | 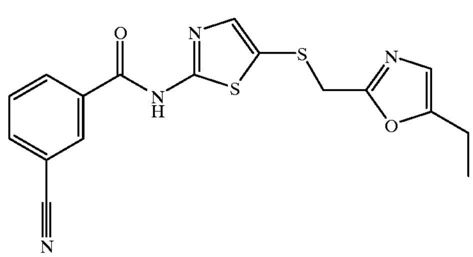 | C17H14N4O2S2 | 371 |
| 103 | 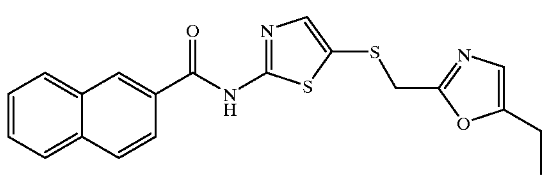 | C20H17N3O2S2 | 396 |

TABLE 1-continued

| Example | Structure | Molecular Formula | (M + H)+ |
|---|---|---|---|
| 104 | 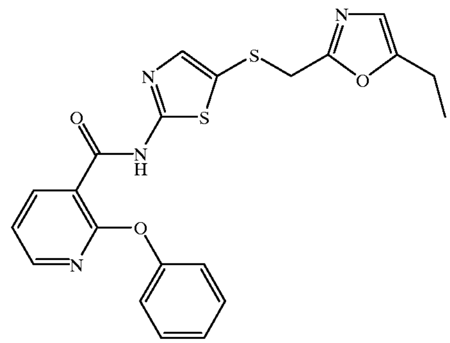 | C21H18N4O3S2 | 553 |
| 105 | 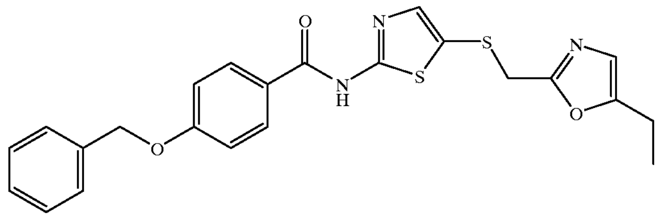 | C23H21N3O3S2 | 452 |
| 106 | 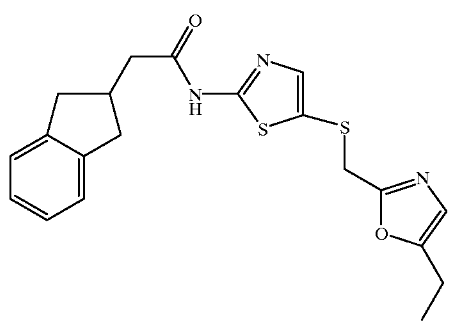 | C20H21N3O2S2 | 400 |
| 107 | 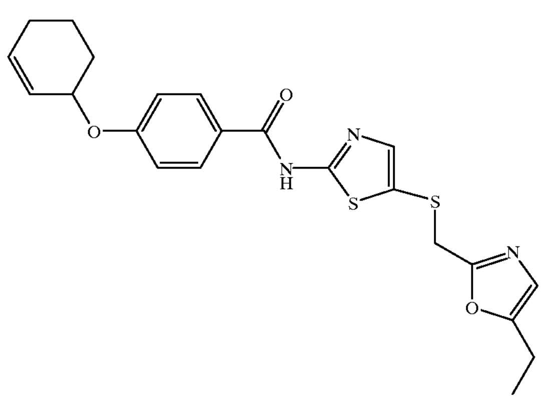 | C22H23N3O3S2 | 442 |

TABLE 1-continued

| Example | Structure | Molecular Formula | (M + H)+ |
|---|---|---|---|
| 108 | 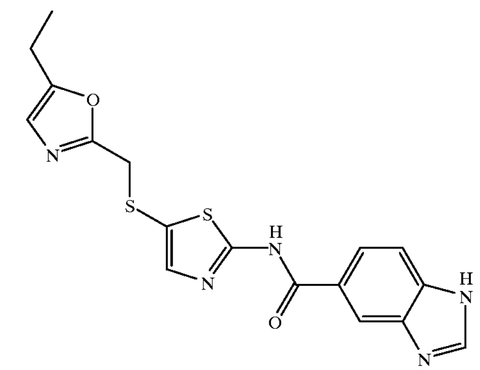 | C17H15N5O2S2 | 500 |
| 109 | 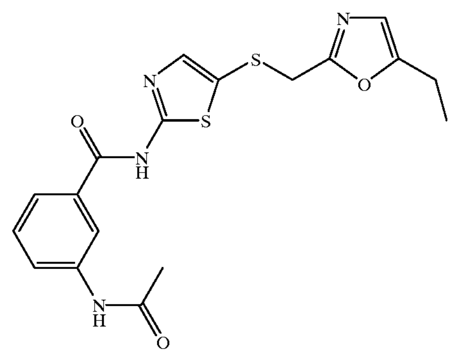 | C18H18N4O3S2 | 403 |
| 110 | 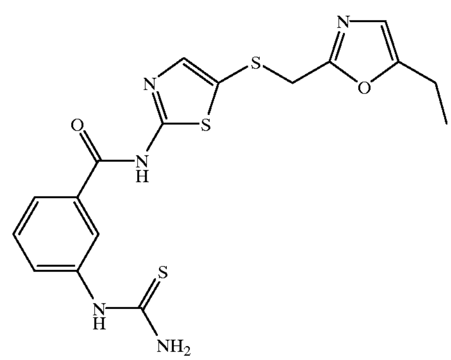 | C17H17N5O2S3 | 420 |
| 111 | 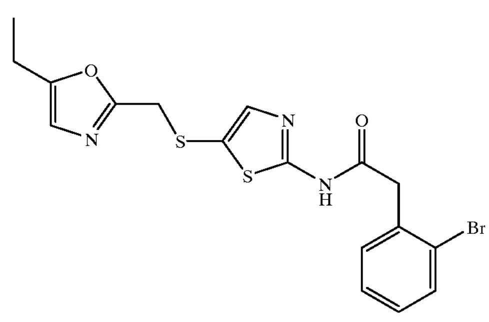 | C17H16BrN3O2S2 | 439 |

TABLE 1-continued

| Example | Structure | Molecular Formula | (M + H)+ |
|---|---|---|---|
| 112 | 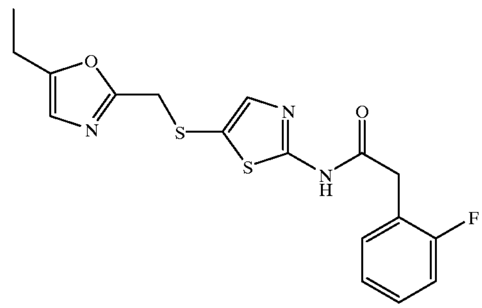 | C17H16FN3O2S2 | 378 |
| 113 | 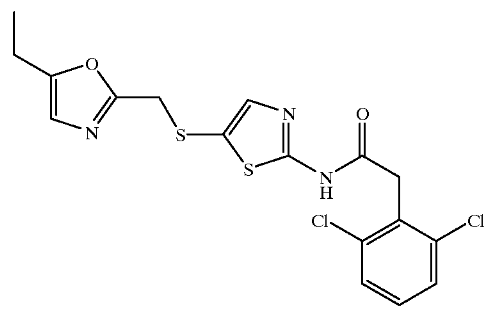 | C17H15Cl2N3O2S2 | 429 |
| 114 | 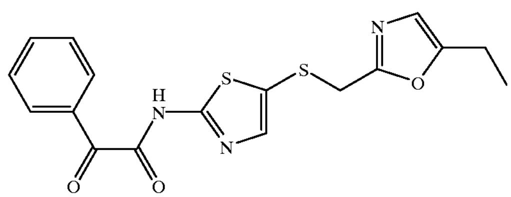 | C17H15N3O3S2 | 374 |
| 115 | 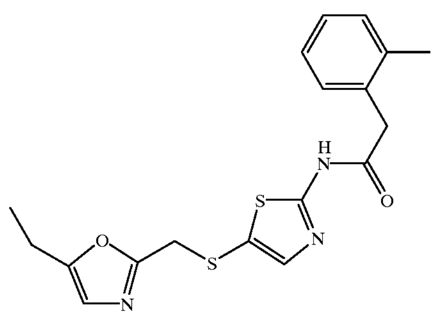 | C18H19N3O2S2 | 374 |
| 116 | 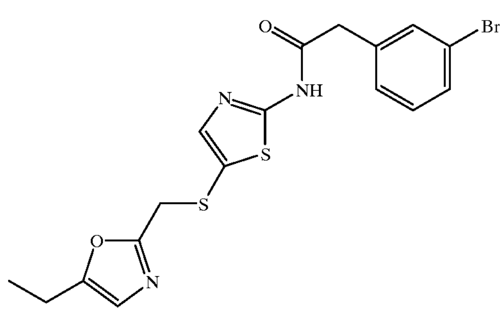 | C17H16BrN3O2S2 | 439 |

TABLE 1-continued

| Example | Structure | Molecular Formula | (M + H)+ |
|---|---|---|---|
| 117 | 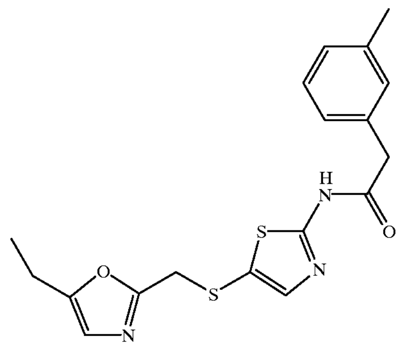 | C18H19N3O2S2 | 374 |
| 118 | 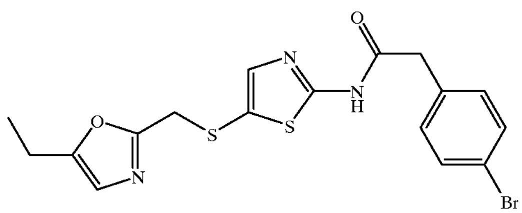 | C17H16BrN3O2S2 | 439 |
| 119 | 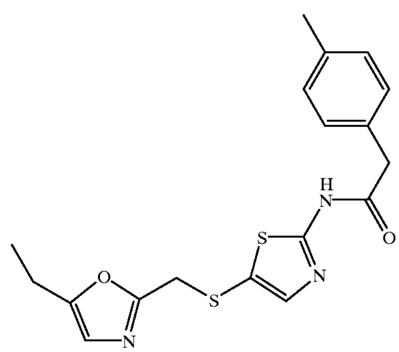 | C18H19N3O2S2 | 374 |
| 120 | 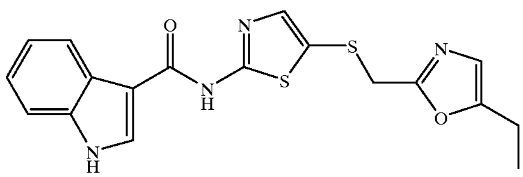 | C18H16N4O2S2 | 499 |
| 121 | 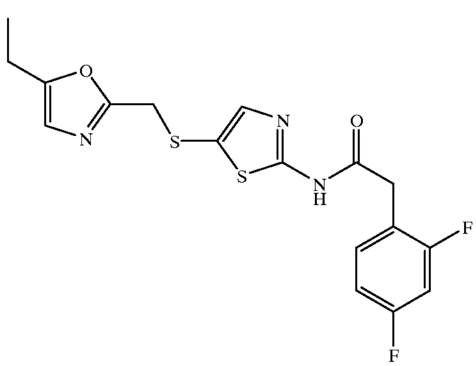 | C17H15F2N3O2S2 | 396 |

TABLE 1-continued

| Example | Structure | Molecular Formula | (M + H)+ |
|---|---|---|---|
| 122 | 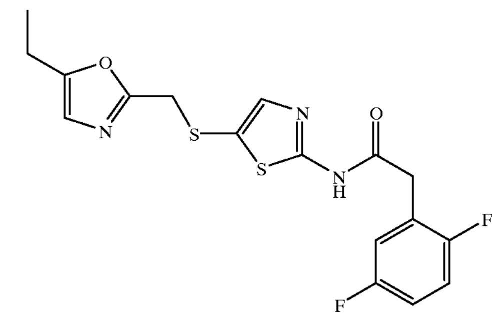 | C17H15F2N3O2S2 | 396 |
| 123 | 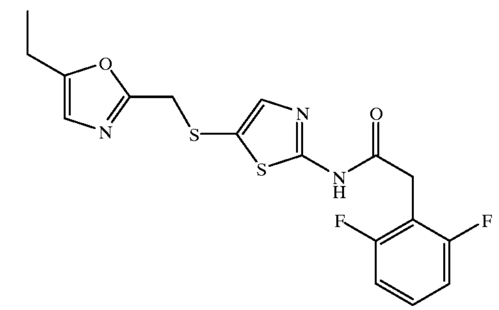 | C17H15F2N3O2S2 | 396 |
| 124 | 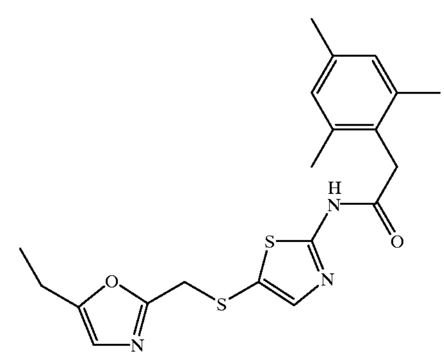 | C20H23N3O2S2 | 402 |
| 125 | 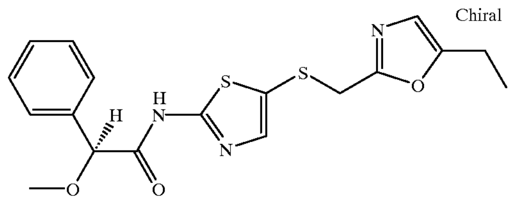 | C18H19N3O3S2 | 390 |
| 126 | 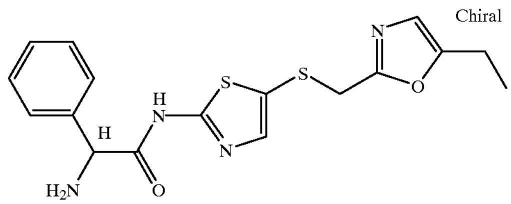 | C17H18N4O2S2 | 489 |

TABLE 1-continued
| Example | Structure | Molecular Formula | (M + H)+ |
|---|---|---|---|
| 127 | 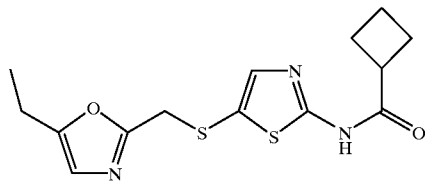 | C14H17N3O2S2 | 324 |
| 128 | 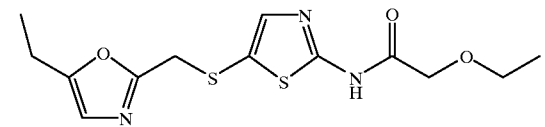 | C13H17N3O3S2 | 328 |
| 129 | 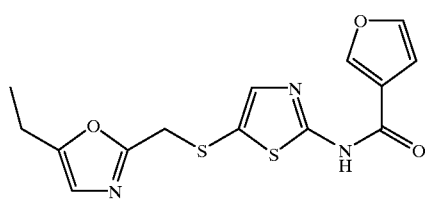 | C14H13N3O3S2 | 336 |
| 130 | 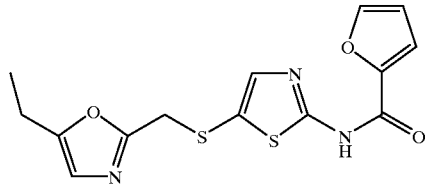 | C14H13N3O3S2 | 336 |
| 131 | 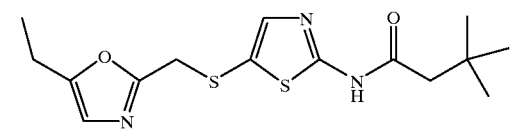 | C15H21N3O2S2 | 340 |
| 132 | 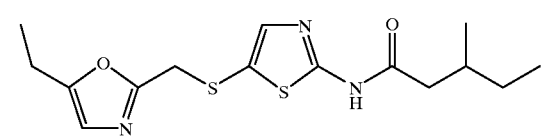 | C15H21N3O2S2 | 340 |
| 133 | 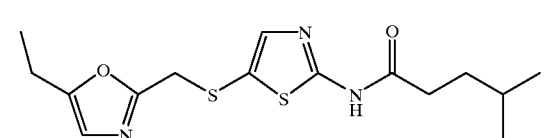 | C15H21N3O2S2 | 340 |
| 134 | 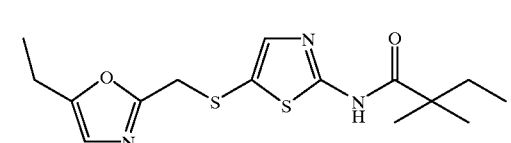 | C15H21N3O2S2 | 340 |

TABLE 1-continued

| Example | Structure | Molecular Formula | (M + H)+ |
|---|---|---|---|
| 135 | 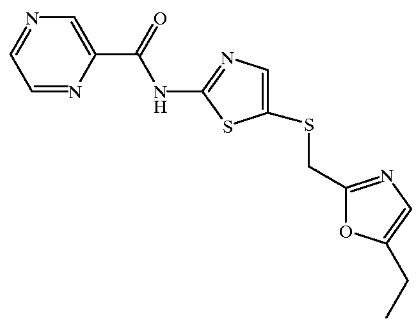 | C14H13N5O2S2 | 348 |
| 136 | 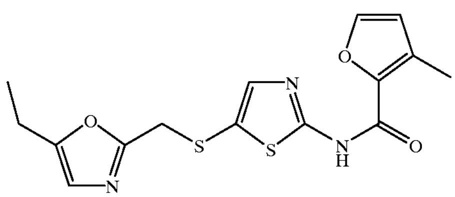 | C15H15N3O3S2 | 350 |
| 137 | 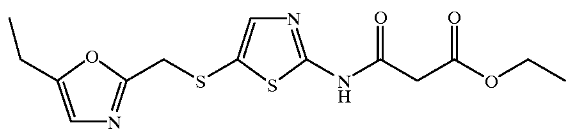 | C14H17N3O4S2 | 356 |
| 138 | 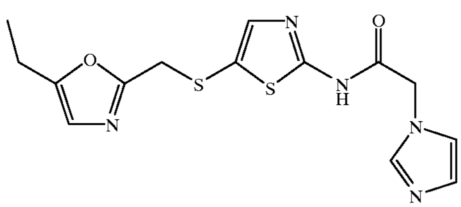 | C14H15N5O2S2 | 464 |
| 139 | 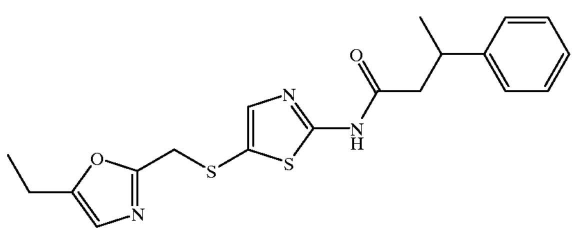 | C19H21N3O2S2 | 388 |
| 140 | 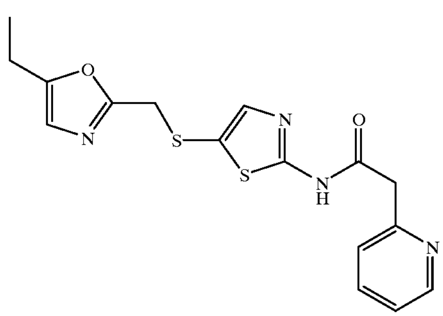 | C16H16N4O2S2 | 475 |

TABLE 1-continued

| Example | Structure | Molecular Formula | (M + H)+ |
|---|---|---|---|
| 141 | 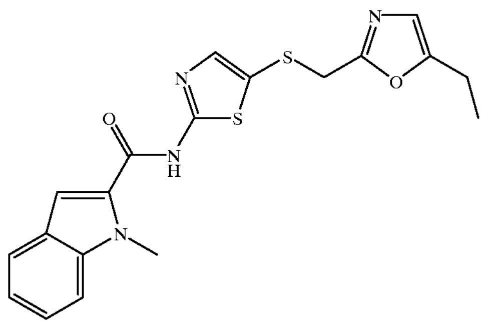 | C19H18N4O2S2 | 513 |
| 142 | 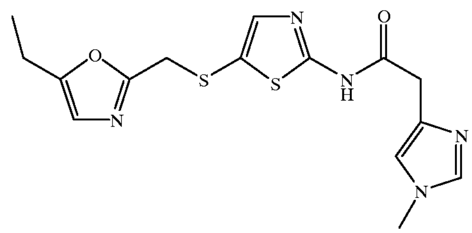 | C15H17N5O2S2 | 478 |
| 143 | 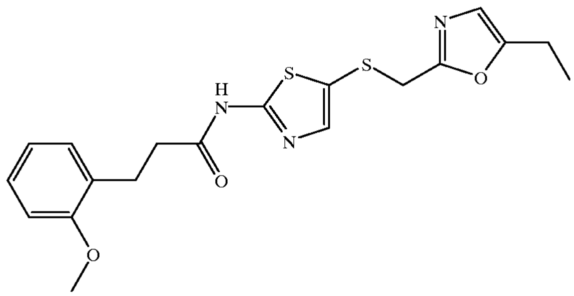 | C19H21N3O3S2 | 404 |
| 144 | 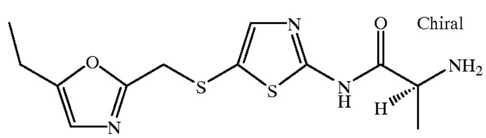 | C12H16N4O2S2 | 427 |
| 145 | 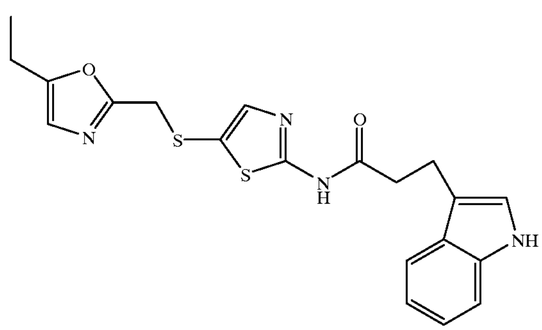 | C20H20N4O2S2 | 527 |
| 146 | 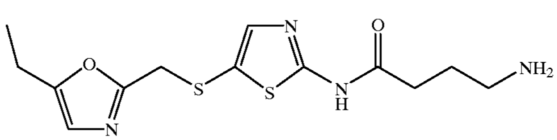 | C13H18N4O2S2 | 441 |

TABLE 1-continued
| Example | Structure | Molecular Formula | (M + H)+ |
| --- | --- | --- | --- |
| 147 | 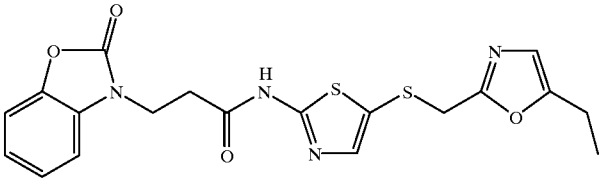 | C19H18N4O4S2 | 431 |
| 148 | 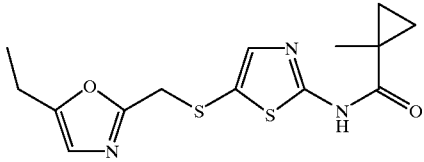 | C14H17N3O2S2 | 324 |
| 149 | 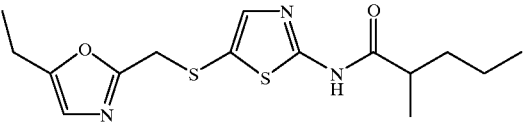 | C15H21N3O2S2 | 340 |
| 150 | 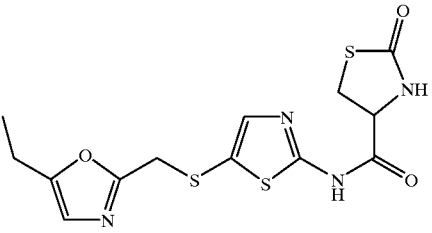 | C13H14N4O3S3 | 371 |
| 151 | 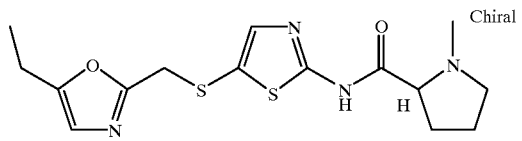 | C15H20N4O2S2 | 467 |
| 152 | 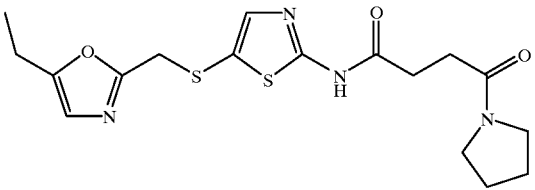 | C17H22N4O3S2 | 395 |
| 153 | 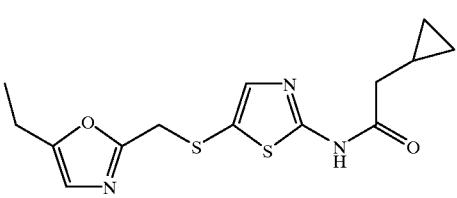 | C14H17N3O2S2 | 324 |

TABLE 1-continued

| Example | Structure | Molecular Formula | (M + H)+ |
|---|---|---|---|
| 154 | 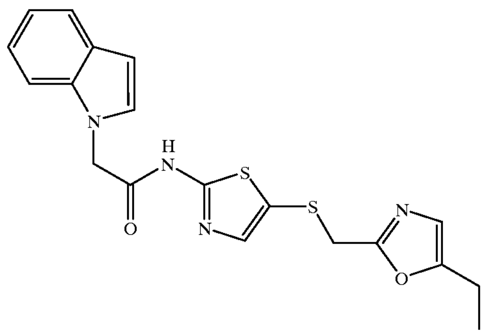 | C19H18N4O2S2 | 513 |
| 155 | 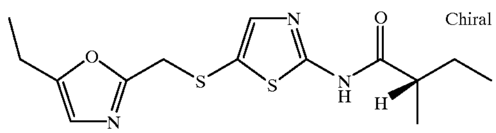 | C14H19N3O2S2 | 326 |
| 156 | 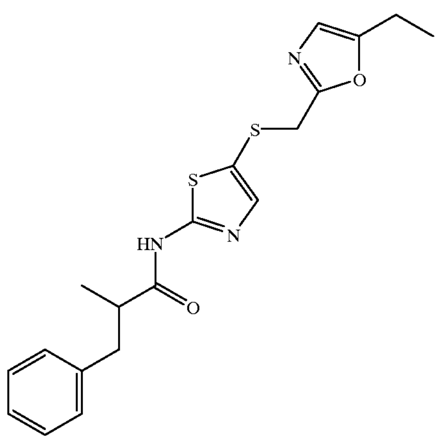 | C19H21N3O2S2 | 388 |
| 157 | 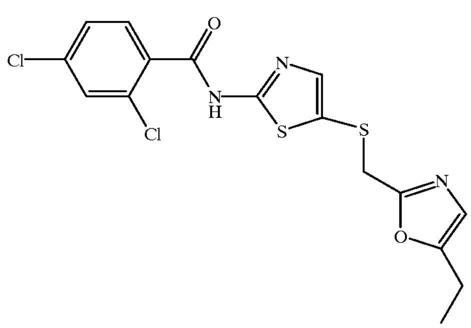 | C16H13Cl2N3O2S2 | 415 |
| 158 | 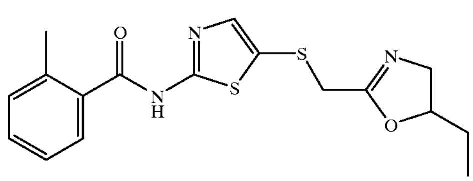 | C17H17N3O2S2 | 360 |

TABLE 1-continued

| Example | Structure | Molecular Formula | (M + H)+ |
|---------|-----------|-------------------|----------|
| 159 | 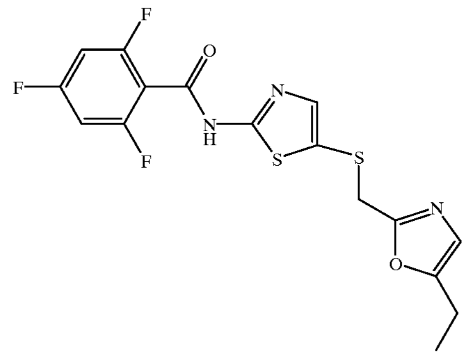 | C16H12F3N3O2S2 | 400 |
| 160 | 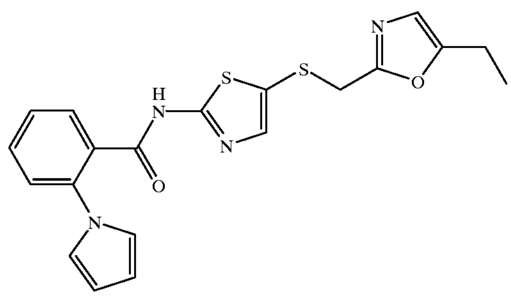 | C20H18N4O2S2 | 525 |
| 161 | 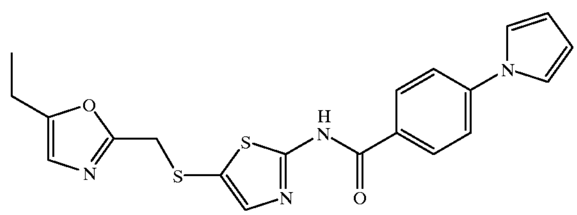 | C20H18N4O2S2 | 525 |
| 162 | 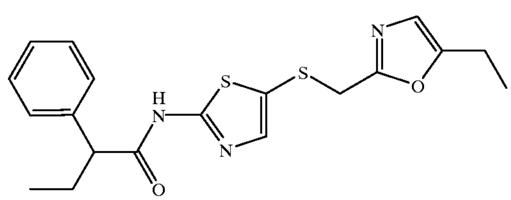 | C19H21N3O2S2 | 388 |
| 163 | 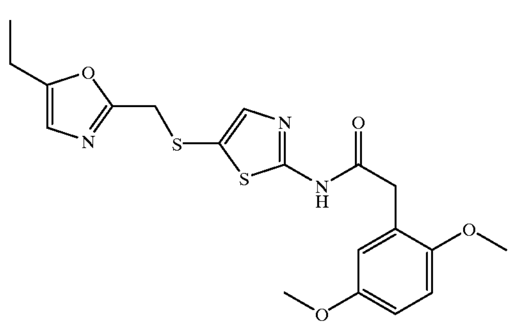 | C19H21N3O4S2 | 420 |

TABLE 1-continued

| Example | Structure | Molecular Formula | (M + H)+ |
|---|---|---|---|
| 164 | 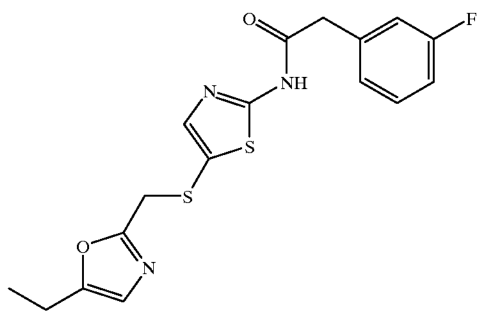 | C17H16FN3O2S2 | 378 |
| 165 | 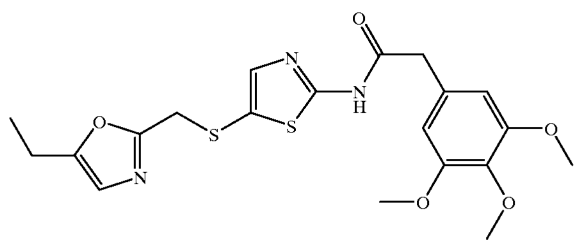 | C20H23N3O5S2 | 450 |
| 166 | 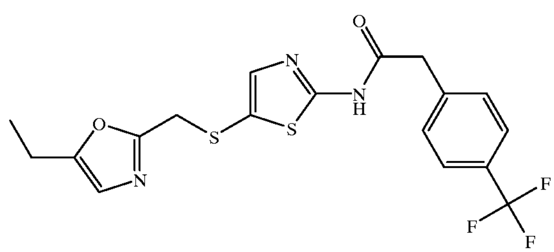 | C18H16F3N3O2S2 | 428 |
| 167 | 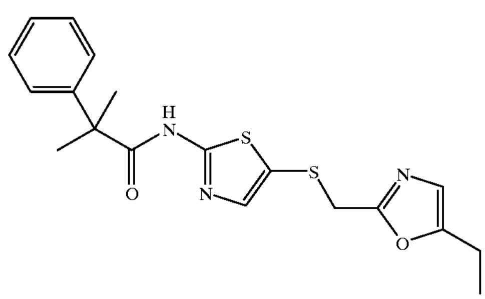 | C19H21N3O2S2 | 388 |
| 168 | 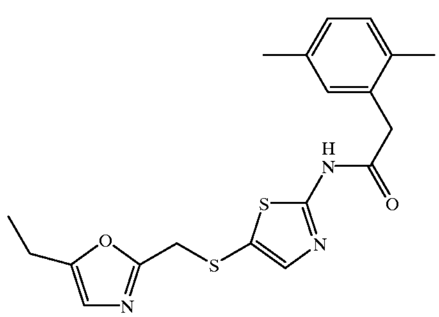 | C19H21N3O2S2 | 388 |

TABLE 1-continued

| Example | Structure | Molecular Formula | (M + H)+ |
|---|---|---|---|
| 169 | 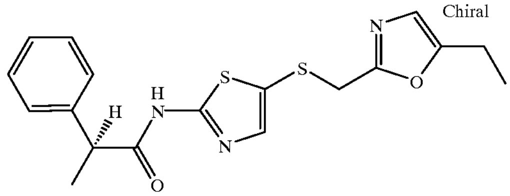 | C18H19N3O2S2 | 374 |
| 170 | 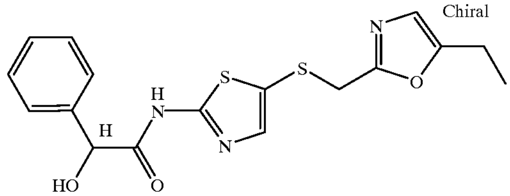 | C17H17N3O3S2 | 376 |
| 171 | 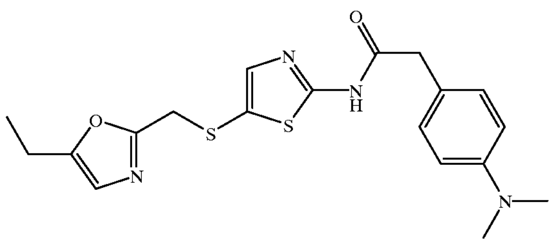 | C19H22N4O2S2 | 517 |
| 172 | 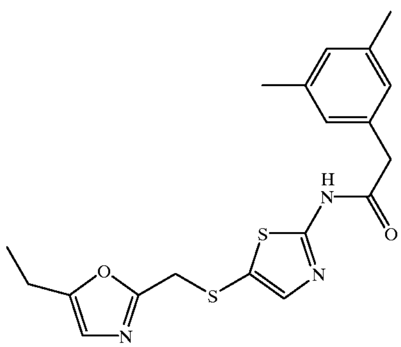 | C19H21N3O2S2 | 388 |
| 173 | 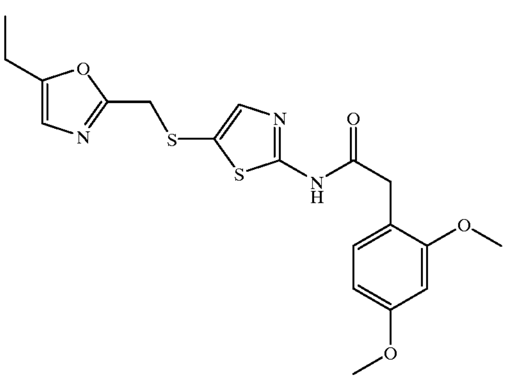 | C19H21N3O4S2 | 420 |
| 174 | 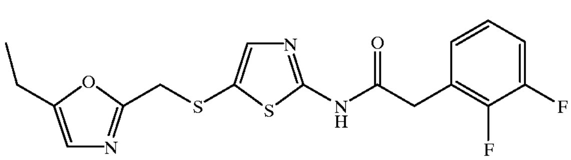 | C17H15F2N3O2S2 | 396 |

TABLE 1-continued

| Example | Structure | Molecular Formula | (M + H)+ |
|---|---|---|---|
| 175 | 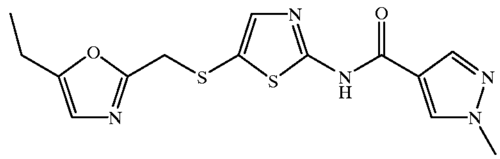 | C14H15N5O2S2 | 350 |
| 176 | 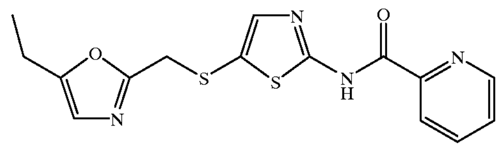 | C15H14N3O2S2 | 461 |
| 177 | 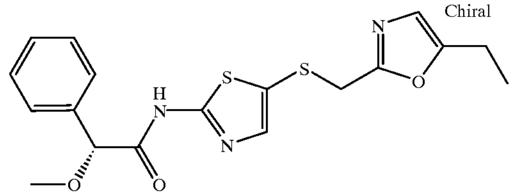 | C18H19N3O3S2 | 390 |
| 178 | 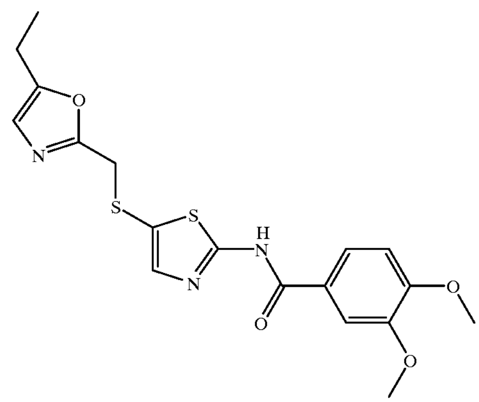 | C18H19N3O4S2 | 406 |
| 179 | 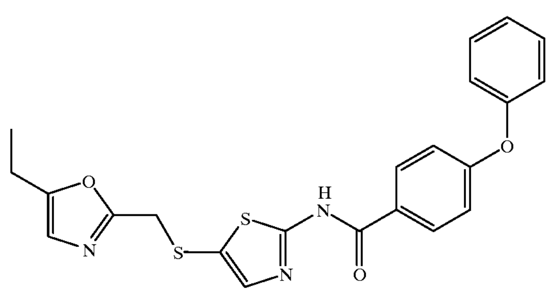 | C22H19N3O3S2 | 438 |

TABLE 1-continued

| Example | Structure | Molecular Formula | (M + H)+ |
| --- | --- | --- | --- |
| 180 | 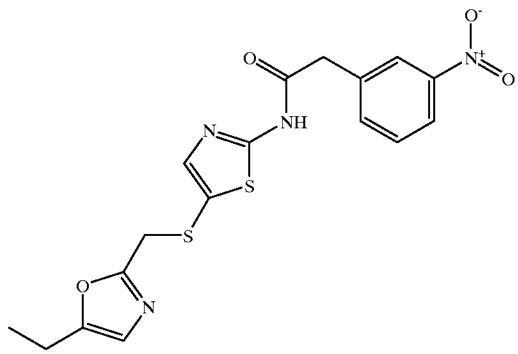 | C17H16N4O4S2 | 405 |
| 181 | 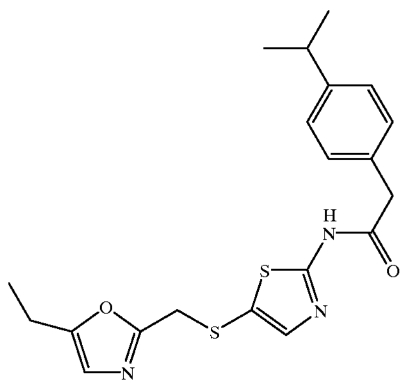 | C20H23N3O2S2 | 402 |
| 182 | 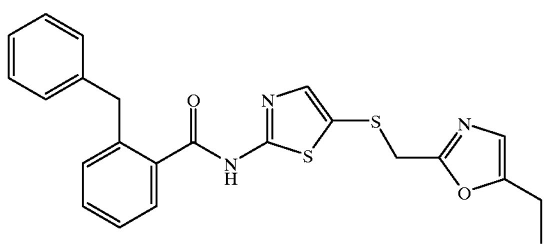 | C23H21N3O2S2 | 436 |
| 183 | 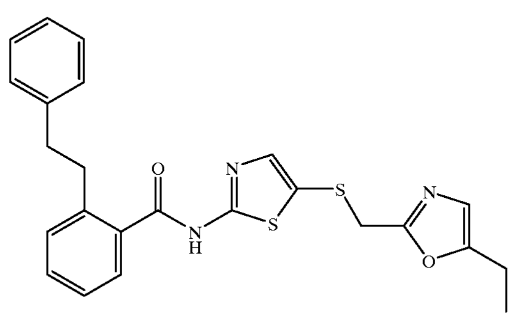 | C24H23N3O2S2 | 450 |

TABLE 1-continued
| Example | Structure | Molecular Formula | (M + H)+ |
|---|---|---|---|
| 184 | 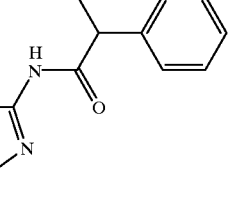 | C23H21N3O2S2 | 436 |
| 185 | 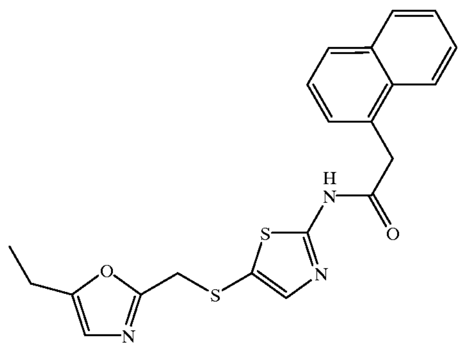 | C21H19N3O2S2 | 410 |
| 186 | 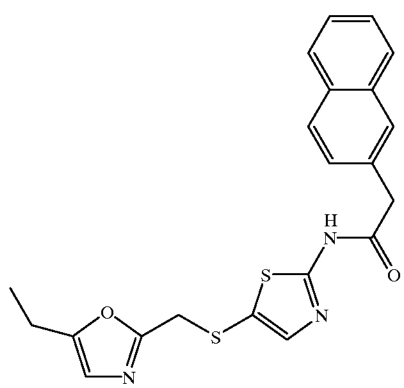 | C21H19N3O2S2 | 410 |
| 187 | 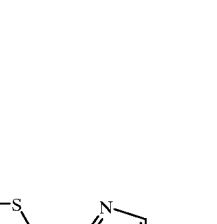 | C17H15Cl2N3O2S2 | 429 |

TABLE 1-continued
| Example | Structure | Molecular Formula | (M + H)+ |
|---|---|---|---|
| 188 | 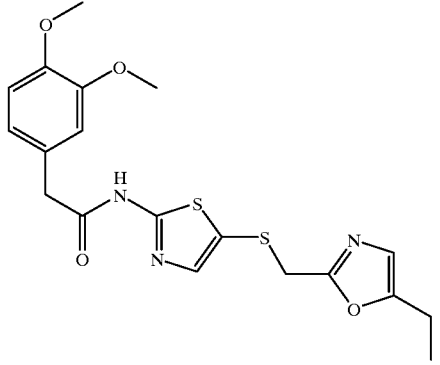 | C19H21N3O4S2 | 420 |
| 189 | 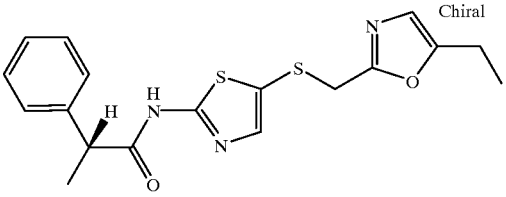 Chiral | C18H19N3O2S2 | 374 |
| 190 | 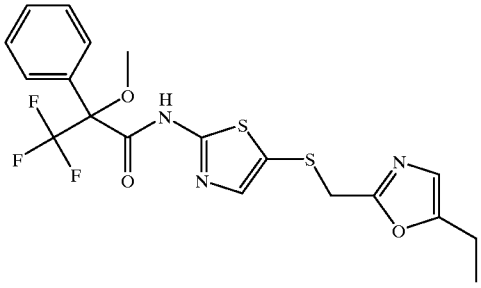 | C19H18F3N3O3S2 | 458 |
| 191 | 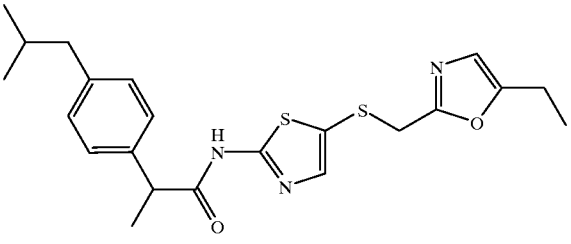 | C22H27N3O2S2 | 430 |
| 192 | 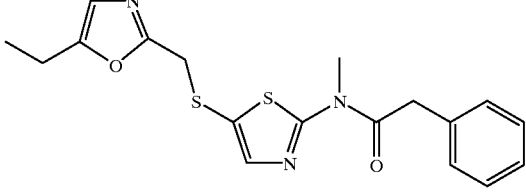 | C18H19N3O2S2 | 374 |

TABLE 1-continued

| Example | Structure | Molecular Formula | (M + H)+ |
|---|---|---|---|
| 193 | 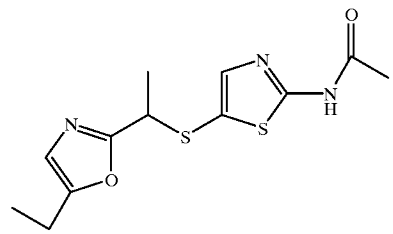 | C12H15N3O2S2 | 298 |
| 194 | 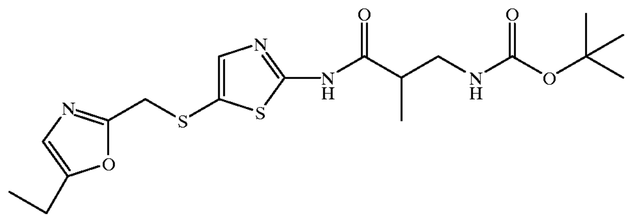 | C18H26N4O4S2 | 427 |
| 195 | 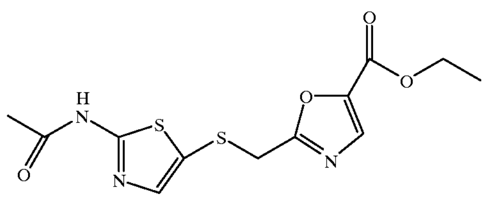 | C12H13N3O4S2 | 328 |
| 196 | 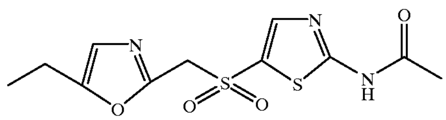 | C11H13N3O4S2 | 316 |
| 197 | 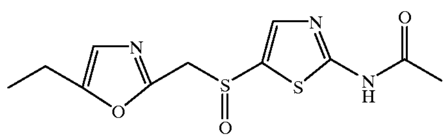 | C11H13N3O3S2 | 300 |
| 198 | 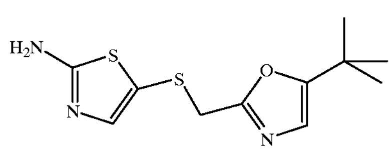 | C11H15N3OS2 | 270 |
| 199 | 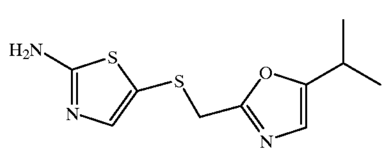 | C10H13N3OS2 | 256 |

TABLE 1-continued

| Example | Structure | Molecular Formula | (M + H)+ |
|---|---|---|---|
| 200 | 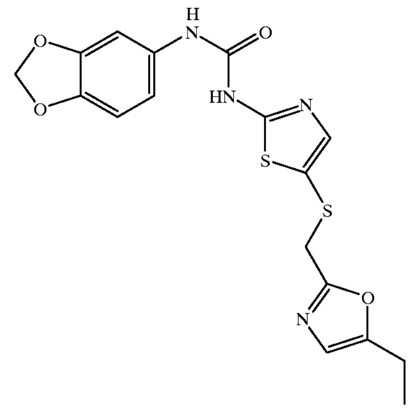 | C17H16N4O4S2 | 405 |
| 201 | 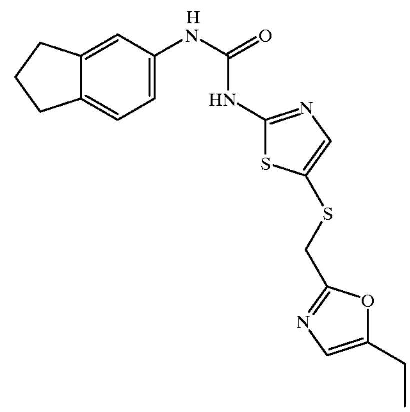 | C19H20N4O2S2 | 401 |
| 202 | 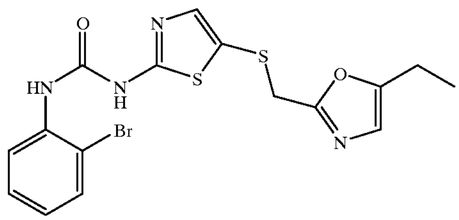 | C16H15BrN4O2S2 | 440 |
| 203 | 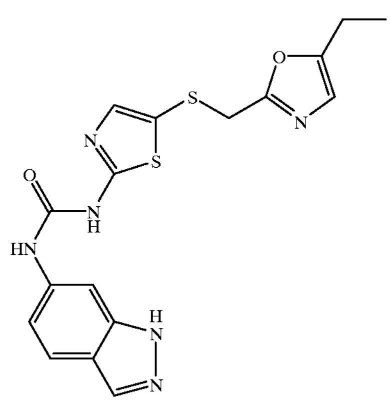 | C17H16N6O2S2 | 515 |

TABLE 1-continued

| Example | Structure | Molecular Formula | (M + H)+ |
|---|---|---|---|
| 204 | 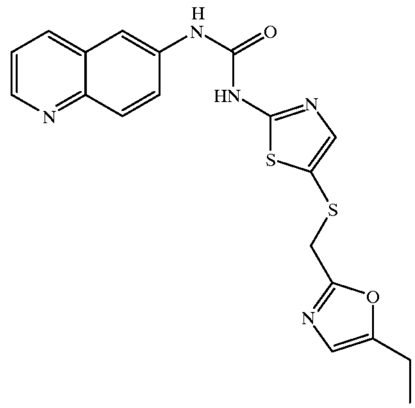 | C19H17N5O2S2 | 526 |
| 205 | 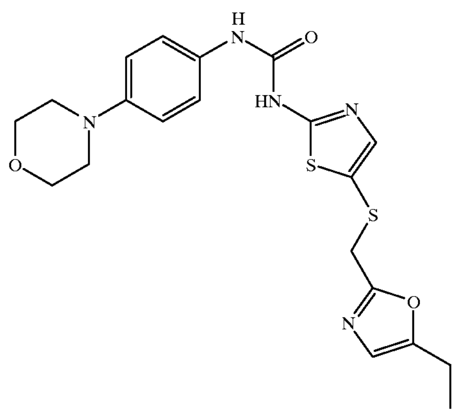 | C20H23N5O3S2 | 560 |
| 206 | 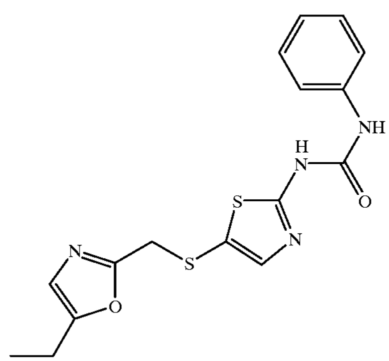 | C16H16N4O2S2 | 361 |
| 207 | 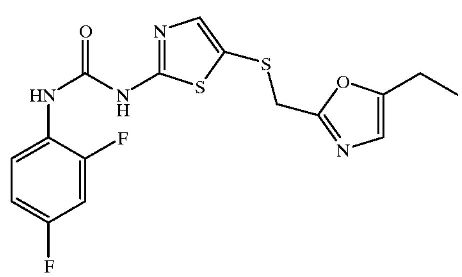 | C16H14F2N4O2S2 | 397 |

TABLE 1-continued
| Example | Structure | Molecular Formula | (M + H)+ |
|---|---|---|---|
| 208 | 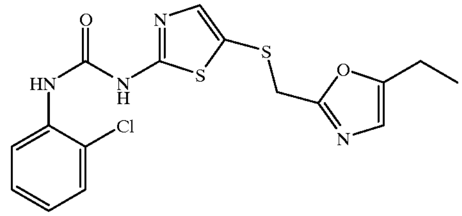 | C16H15ClN4O2S2 | 395 |
| 209 | 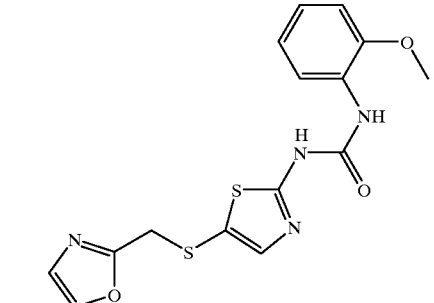 | C17H18N4O3S2 | 391 |
| 210 | 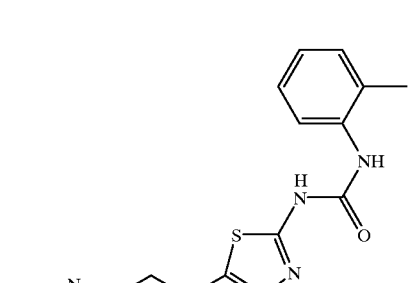 | C17H18N4O2S2 | 375 |
| 211 | 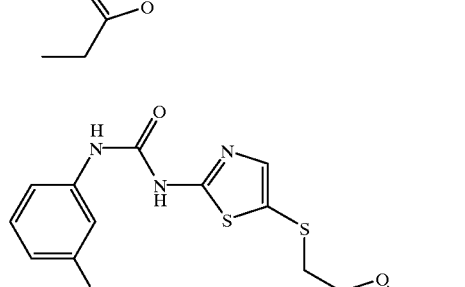 | C16H15BrN4O2S2 | 440 |
| 212 | 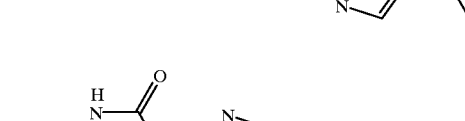 | C16H15ClN4O2S2 | 395 |

TABLE 1-continued

| Example | Structure | Molecular Formula | (M + H)+ |
|---|---|---|---|
| 213 | 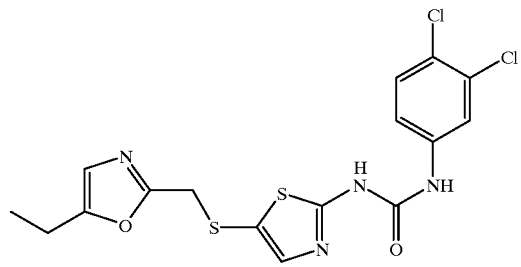 | C16H14Cl2N4O2S2 | 430 |
| 214 | 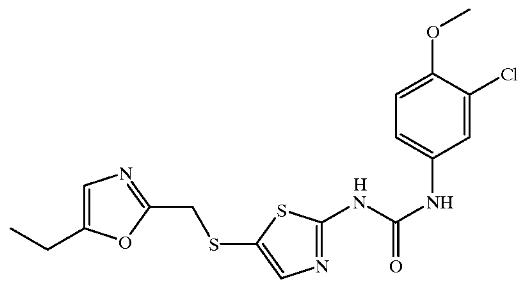 | C17H17ClN4O3S2 | 425 |
| 215 | 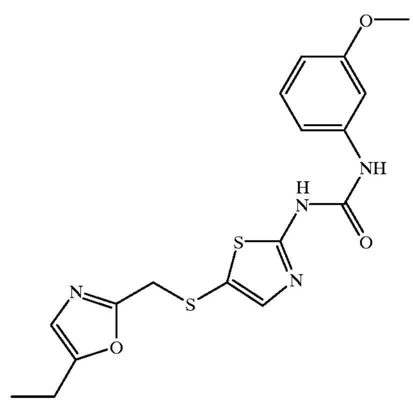 | C17H18N4O3S2 | 391 |
| 216 | 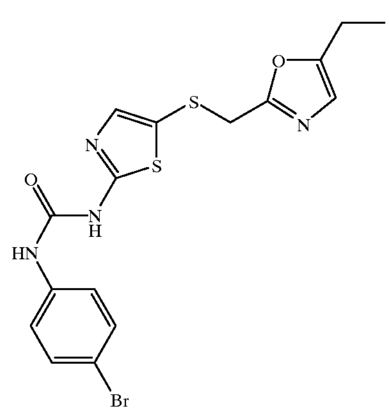 | C16H15BrN4O2S2 | 440 |

TABLE 1-continued

| Example | Structure | Molecular Formula | (M + H)+ |
|---|---|---|---|
| 217 | 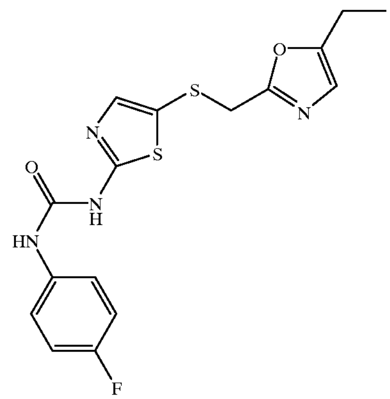 | C16H15FN4O2S2 | 379 |
| 218 | 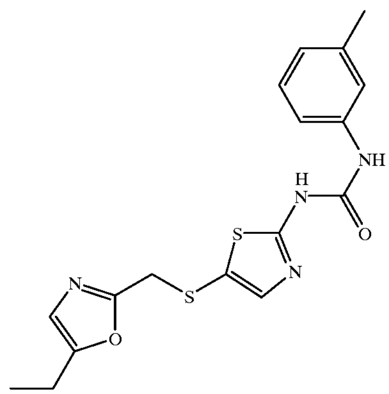 | C17H18N4O2S2 | 375 |
| 219 | 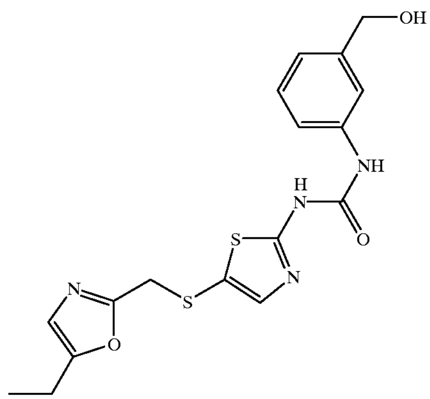 | C17H18N4O3S2 | 391 |

TABLE 1-continued

| Example | Structure | Molecular Formula | (M + H)+ |
|---|---|---|---|
| 220 | 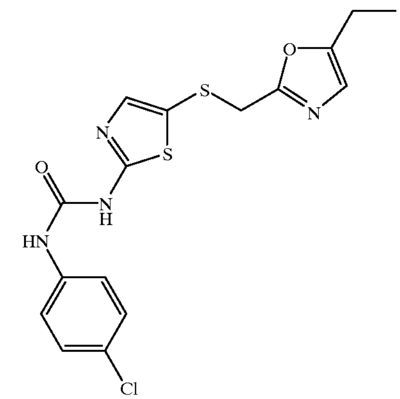 | C16H15ClN4O2S2 | 395 |
| 221 | 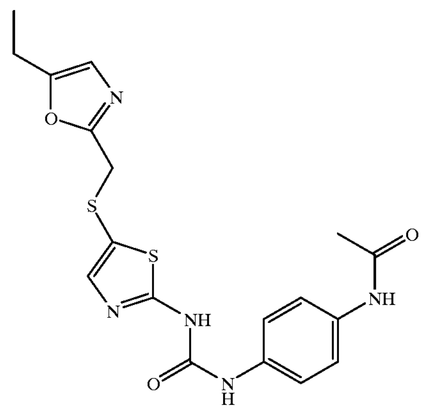 | C18H19N5O3S2 | 418 |
| 222 | 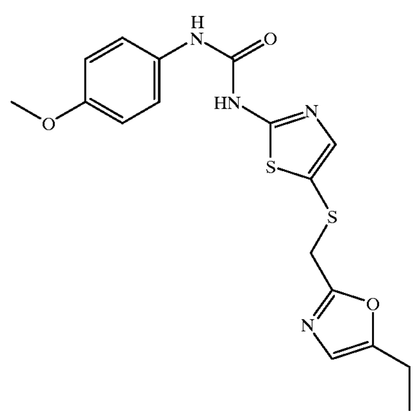 | C17H18N4O3S2 | 391 |

TABLE 1-continued
| Example | Structure | Molecular Formula | (M + H)+ |
|---|---|---|---|
| 223 | 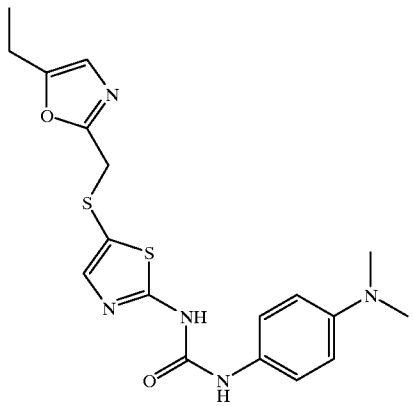 | C18H21N5O2S2 | 518 |
| 224 | 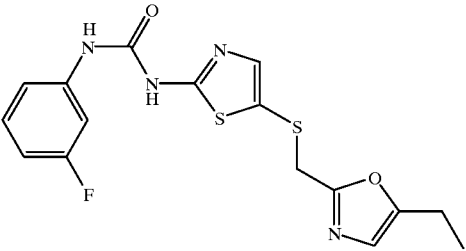 | C16H15FN4O2S2 | 379 |
| 225 | 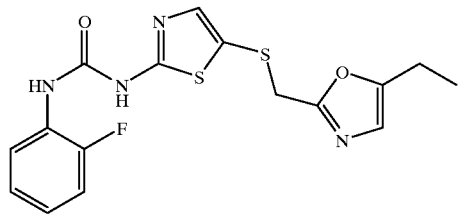 | C16H15FN4O2S2 | 379 |
| 226 | 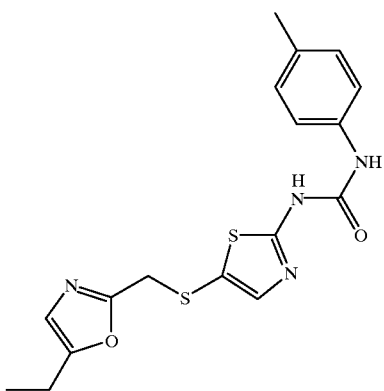 | C17H18N4O2S2 | 375 |

TABLE 1-continued
| Example | Structure | Molecular Formula | (M + H)+ |
|---|---|---|---|
| 227 | 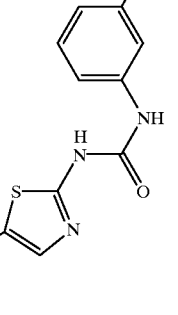 | C17H17N5O3S2 | 404 |
| 228 | 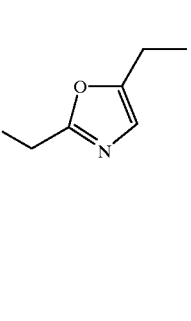 | C17H15N5O2S3 | 418 |
| 229 | 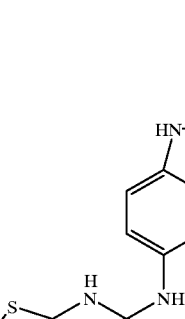 | C17H16N6O2S2 | 401 |
| 230 | 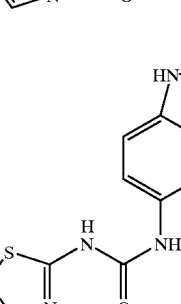 | C16H15N7O2S2 | 402 |

TABLE 1-continued
| Example | Structure | Molecular Formula | (M + H)+ |
|---|---|---|---|
| 231 | 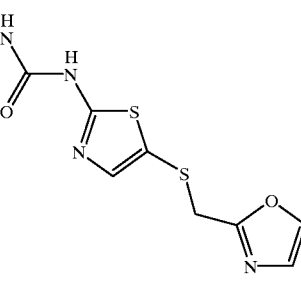 | C16H17N5O2S2 | 490 |
| 232 | 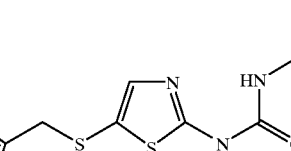 | C15H20N4O2S2 | 353 |
| 233 | 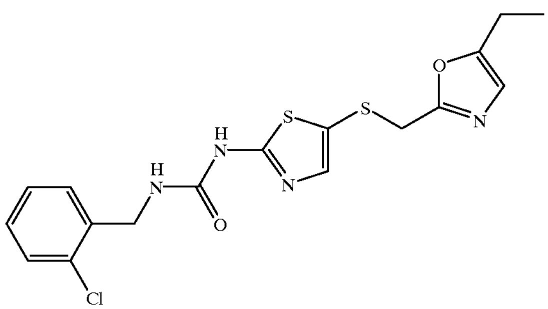 | C17H17ClN4O2S2 | 409 |
| 234 | 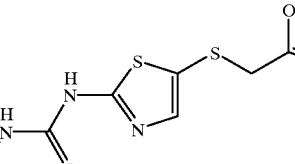 | C17H19N5O2S2 | 504 |
| 235 | 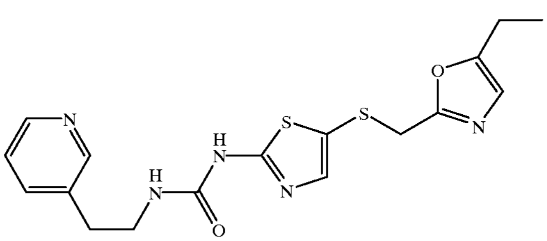 | C17H19N5O2S2 | 504 |

TABLE 1-continued

| Example | Structure | Molecular Formula | (M + H)+ |
|---|---|---|---|
| 236 | 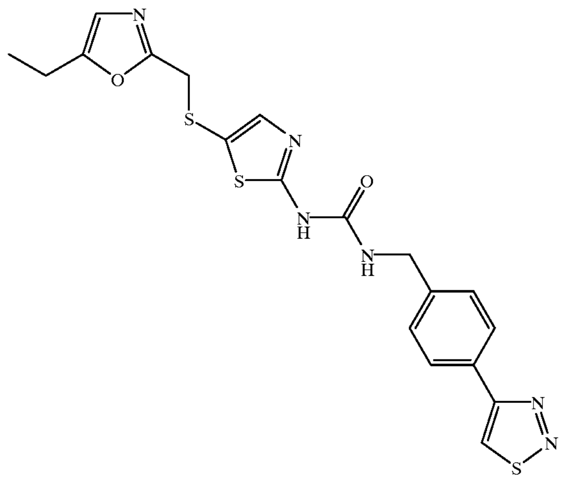 | C19H18N6O2S3 | 459 |
| 237 | 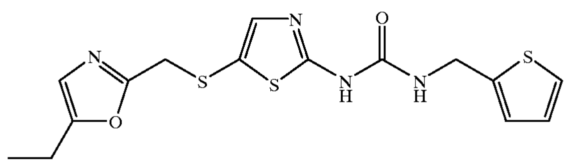 | C15H16N4O2S3 | 381 |
| 238 | 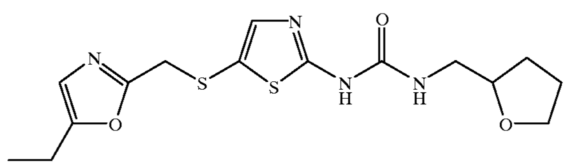 | C15H20N4O3S2 | 369 |
| 239 | 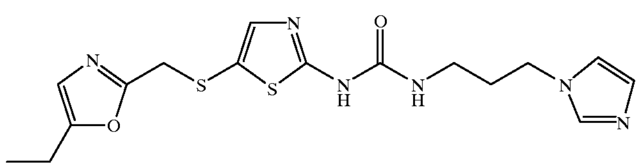 | C16H20N6O2S2 | 507 |
| 240 | 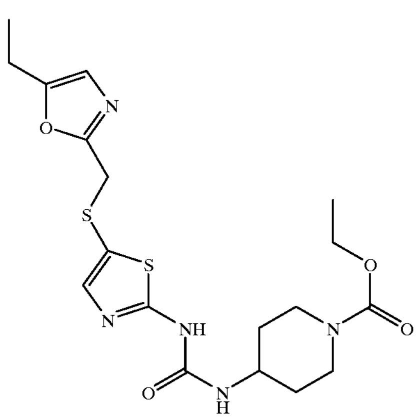 | C18H25N5O4S2 | 440 |

TABLE 1-continued

| Example | Structure | Molecular Formula | (M + H)+ |
|---|---|---|---|
| 241 | 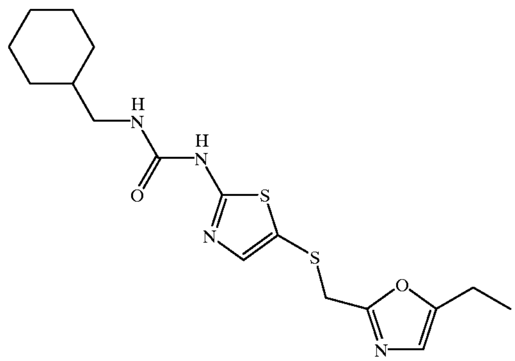 | C17H24N4O2S2 | 381 |
| 242 | 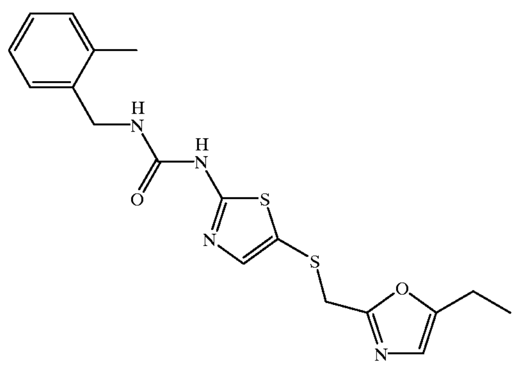 | C18H20N4O2S2 | 389 |
| 243 | 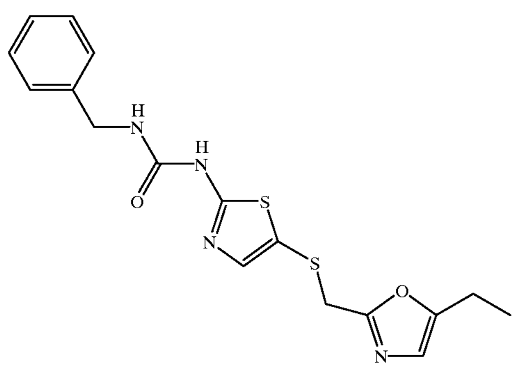 | C17H18N4O2S2 | 375 |
| 244 | 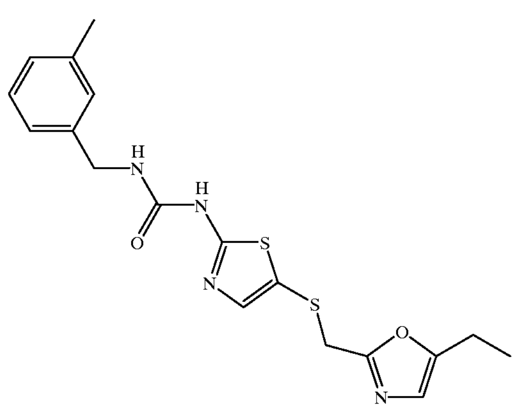 | C18H20N4O2S2 | 389 |

TABLE 1-continued

| Example | Structure | Molecular Formula | (M + H)+ |
|---|---|---|---|
| 245 | 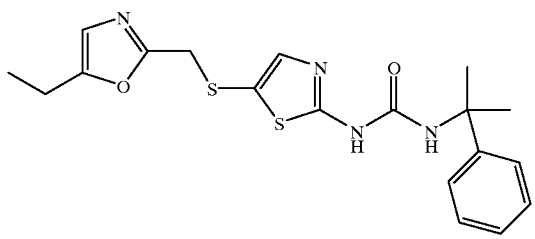 | C19H22N4O2S2 | 403 |
| 246 | 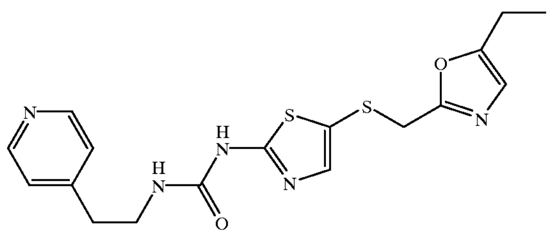 | C17H19N5O2S2 | 504 |
| 247 | 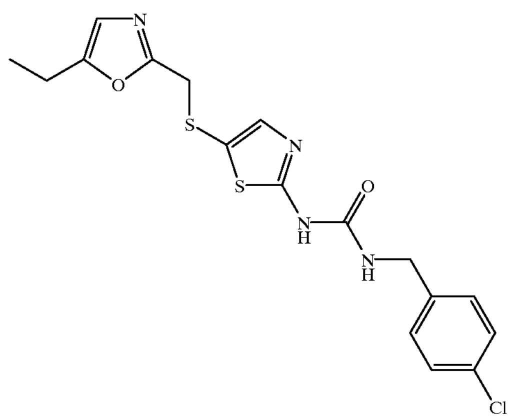 | C17H17ClN4O2S2 | 409 |
| 248 | 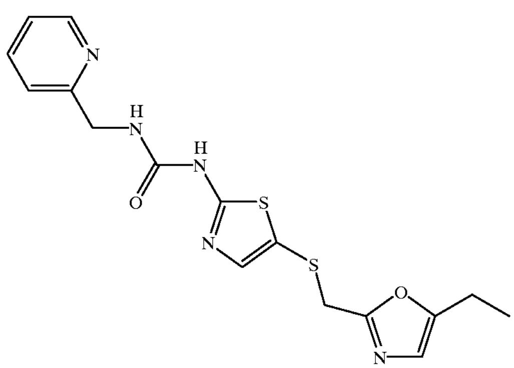 | C16H17N5O2S2 | 490 |
| 249 | 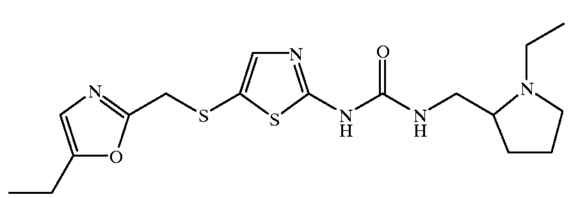 | C17H25N5O2S2 | 510 |

TABLE 1-continued
| Example | Structure | Molecular Formula | (M + H)+ |
|---|---|---|---|
| 250 | 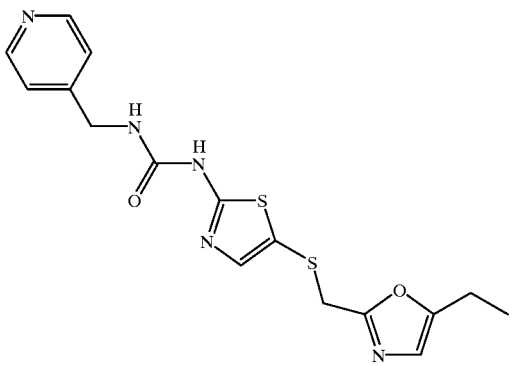 | C16H17N5O2S2 | 490 |
| 251 | 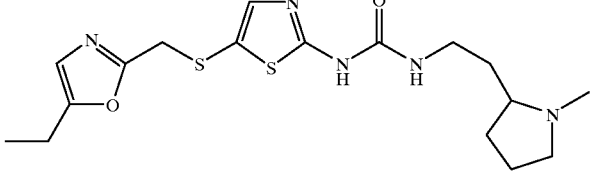 | C17H25N5O2S2 | 510 |
| 252 | 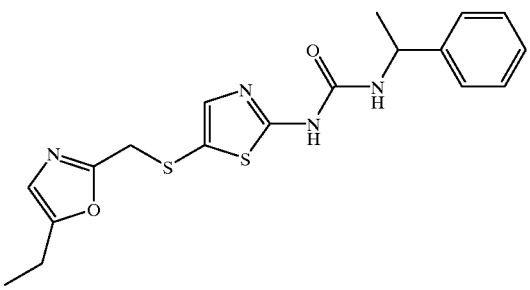 | C18H20N4O2S2 | 389 |
| 253 | 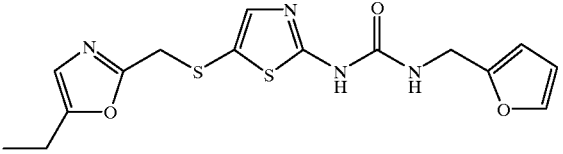 | C15H16N4O3S2 | 365 |
| 254 | 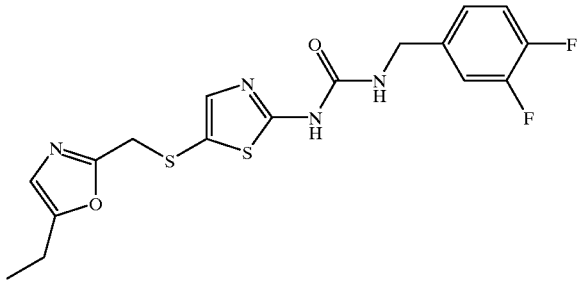 | C17H16F2N4O2S2 | 411 |
| 255 | 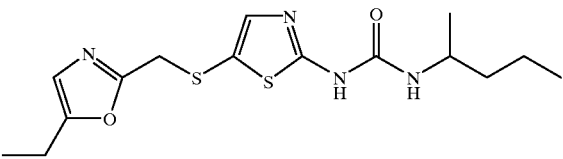 | C15H22N4O2S2 | 355 |

TABLE 1-continued
| Example | Structure | Molecular Formula | (M + H)+ |
|---|---|---|---|
| 256 | 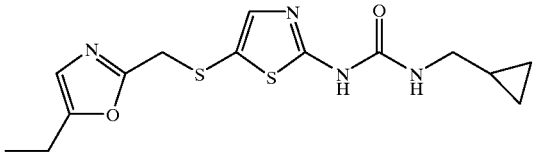 | C14H18N4O2S2 | 339 |
| 257 | 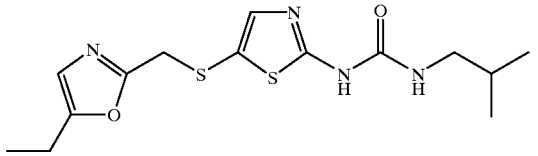 | C14H20N4O2S2 | 341 |
| 258 | 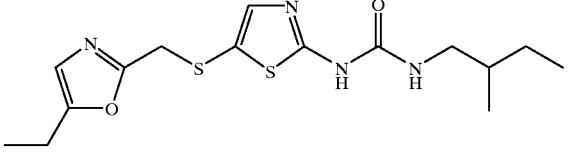 | C15H22N4O2S2 | 355 |
| 259 | 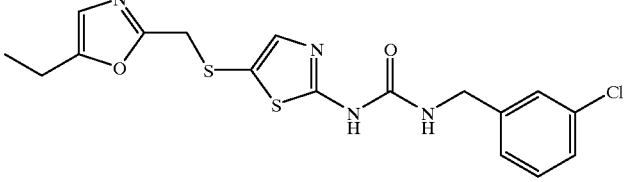 | C17H17ClN4O2S2 | 409 |
| 260 | 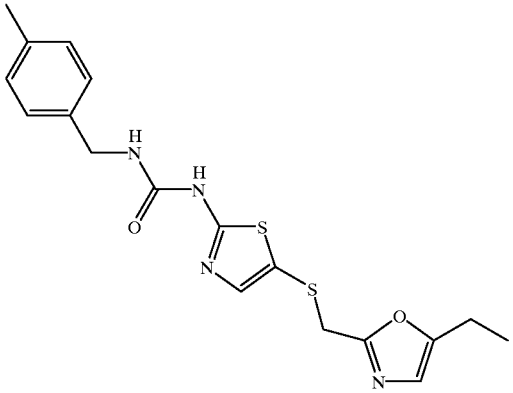 | C18H20N4O2S2 | 389 |

TABLE 1-continued
| Example | Structure | Molecular Formula | (M + H)+ |
|---|---|---|---|
| 261 | 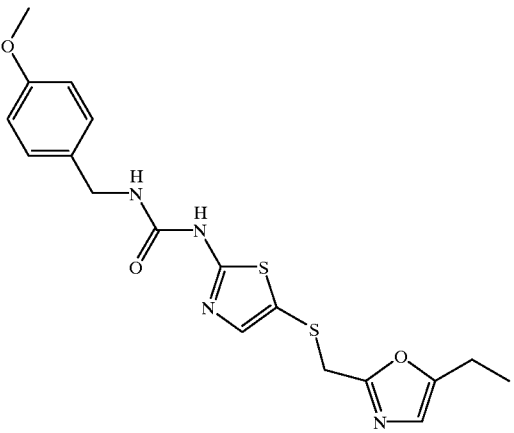 | C18H20N4O3S2 | 405 |
| 262 | 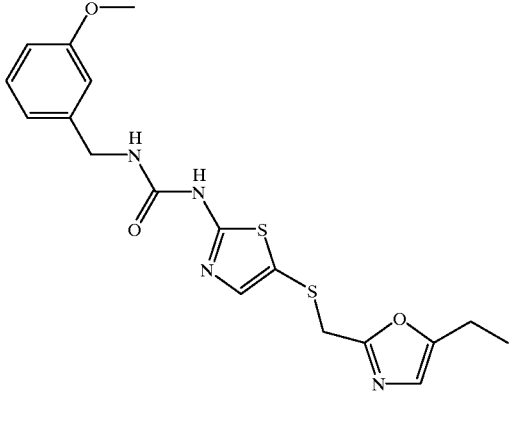 | C18H20N4O3S2 | 405 |
| 263 | 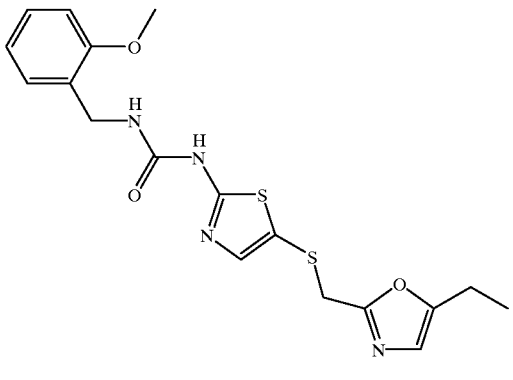 | C18H20N4O3S2 | 405 |
| 264 | 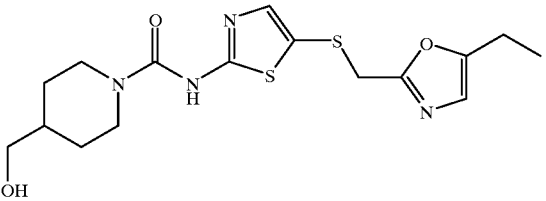 | C16H22N4O3S2 | 341 |

TABLE 1-continued
| Example | Structure | Molecular Formula | (M + H)+ |
|---|---|---|---|
| 265 | 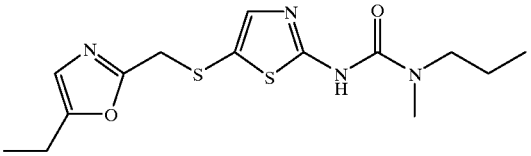 | C14H20N4O2S2 | 512 |
| 266 | 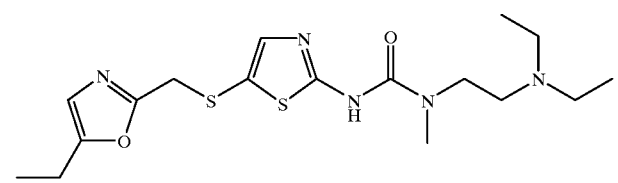 | C17H27N5O2S2 | 353 |
| 267 | 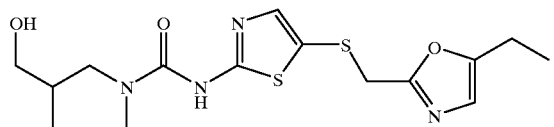 | C16H22N4O3S2 | 425 |
| 268 | 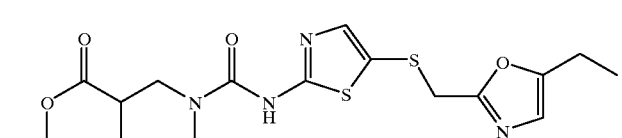 | C18H24N4O4S2 | 401 |
| 269 | 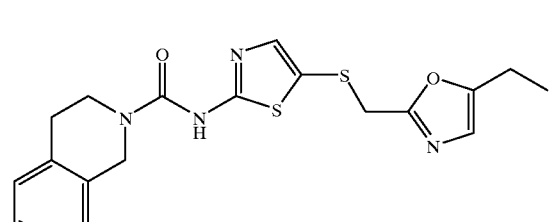 | C19H20N4O2S2 | 383 |
| 270 | 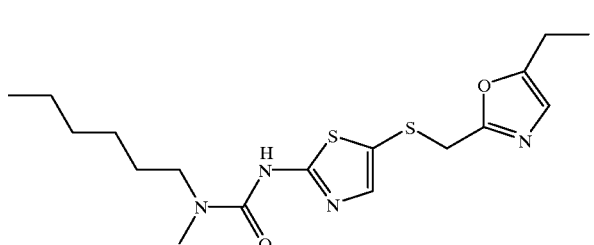 | C17H26N4O2S2 | 355 |
| 271 | 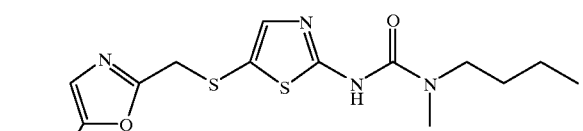 | C15H22N4O2S2 | 433 |

TABLE 1-continued

| Example | Structure | Molecular Formula | (M + H)+ |
|---|---|---|---|
| 272 | 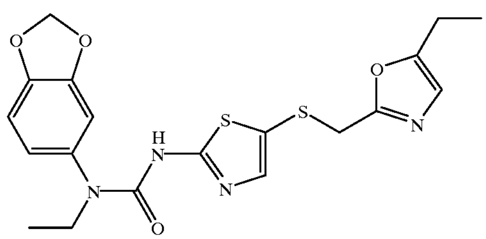 | C19H20N4O4S2 | 512 |
| 273 | 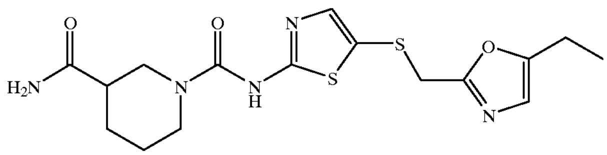 | C16H21N5O3S2 | 353 |
| 274 | 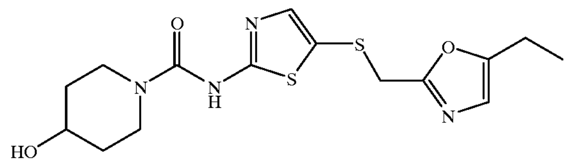 | C15H20N4O3S2 | 367 |
| 275 | 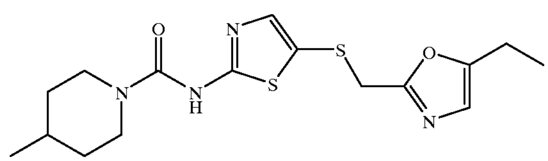 | C16H22N4O2S2 | 389 |
| 276 | 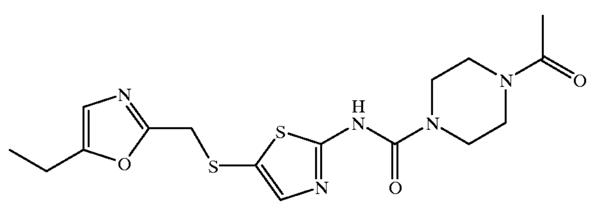 | C16H21N5O3S2 | 425 |
| 277 | 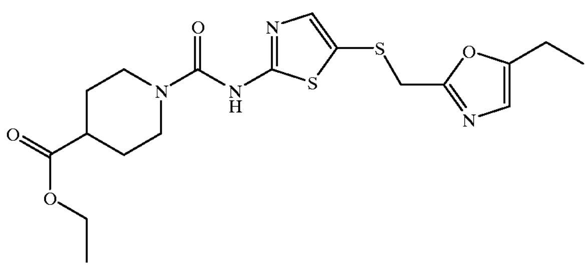 | C18H24N4O4S2 | 369 |
| 278 | 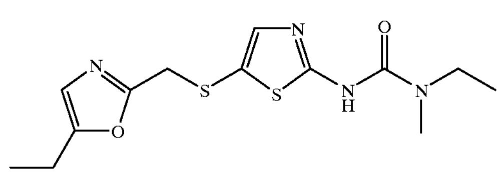 | C13H18N4O2S2 | 465 |

TABLE 1-continued

| Example | Structure | Molecular Formula | (M + H)+ |
|---|---|---|---|
| 279 | 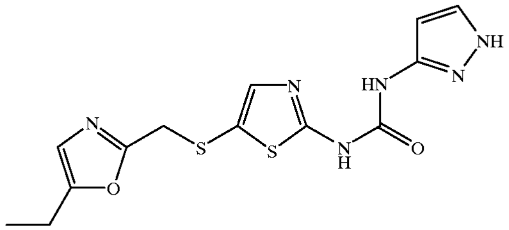 | C13H14N6O2S2 | 493 |
| 280 | 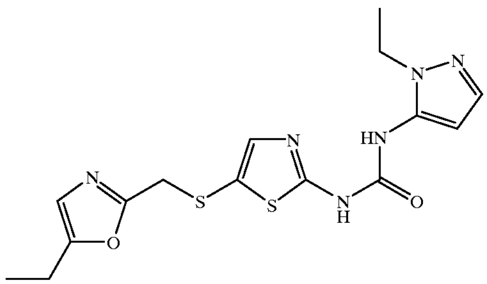 | C15H18N6O2S2 | 466 |
| 281 | 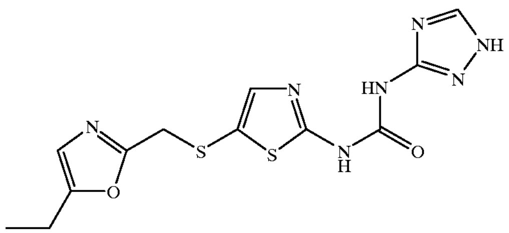 | C12H13N7O2S2 | 366 |
| 282 | 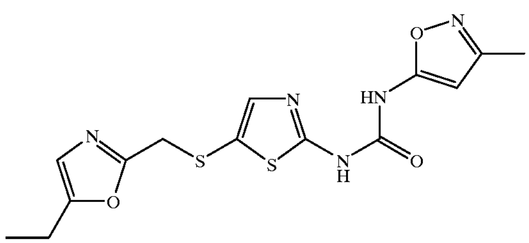 | C14H15N5O3S2 | 366 |
| 283 | 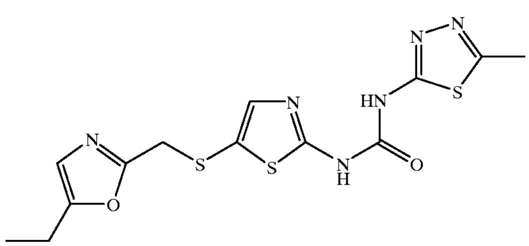 | C13H14N6O2S3 | 409 |
| 284 | 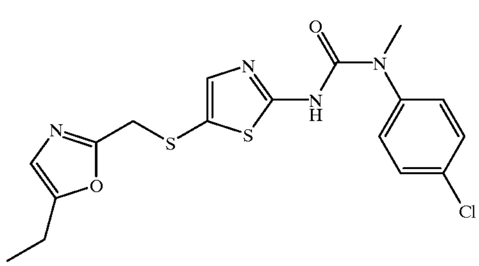 | C17H17ClN4O2S2 | 387 |

TABLE 1-continued
| Example | Structure | Molecular Formula | (M + H)+ |
|---|---|---|---|
| 285 | 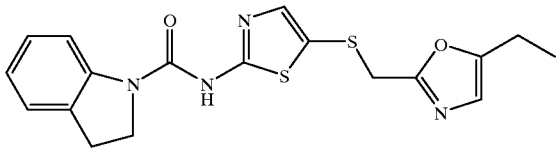 | C18H18N4O2S2 | 375 |
| 286 | 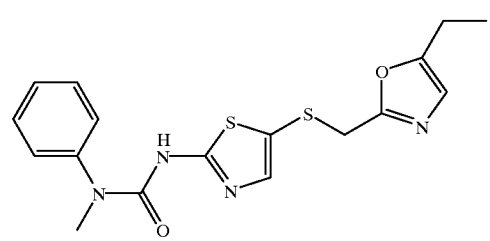 | C17H18N4O2S2 | 405 |
| 287 | 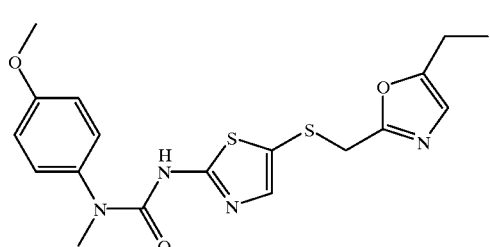 | C18H20N4O3S2 | 389 |
| 288 | 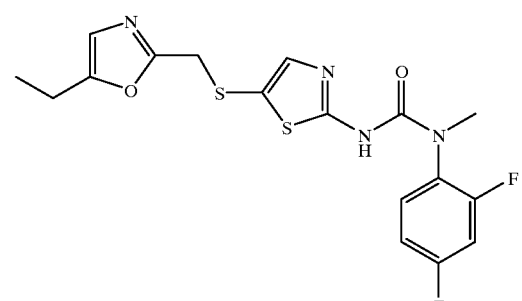 | C17H16F2N4O2S2 | 490 |
| 289 | 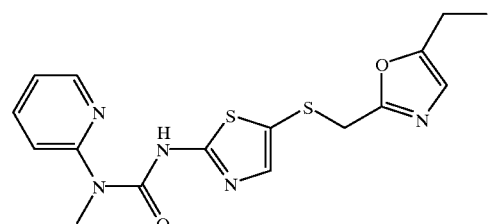 | C16H17N5O2S2 | 476 |

TABLE 1-continued

| Example | Structure | Molecular Formula | (M + H)+ |
|---|---|---|---|
| 290 | 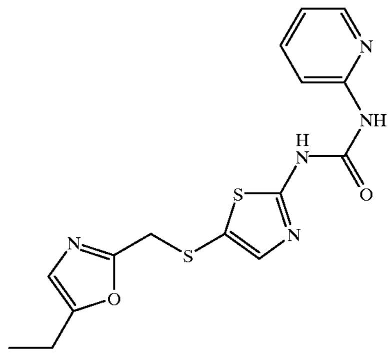 | C15H15N5O2S2 | 510 |
| 291 | 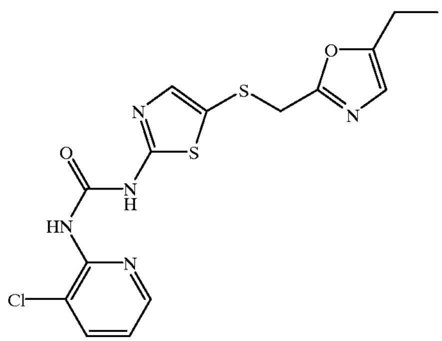 | C15H14ClN5O2S2 | 490 |
| 292 | 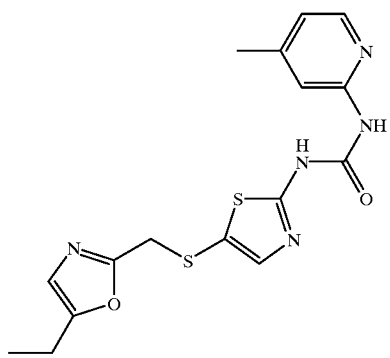 | C16H17N5O2S2 | 490 |
| 293 | 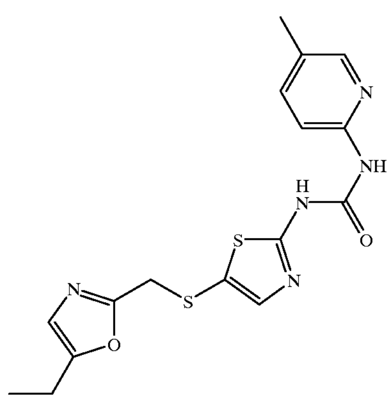 | C16H17N5O2S2 | 476 |

TABLE 1-continued

| Example | Structure | Molecular Formula | (M + H)+ |
|---|---|---|---|
| 294 | 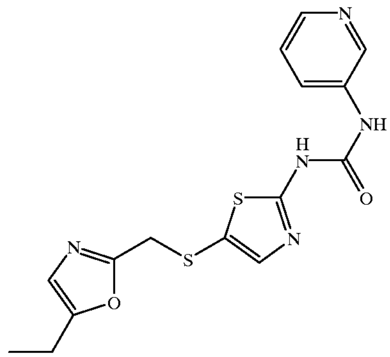 | C15H15N5O2S2 | 526 |
| 295 | 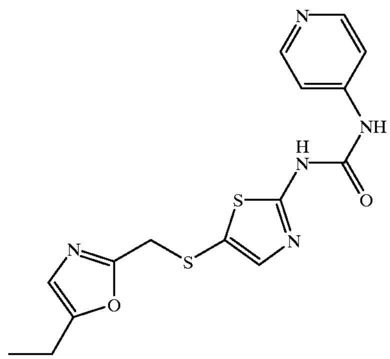 | C15H15N5O2S2 | 540 |
| 296 | 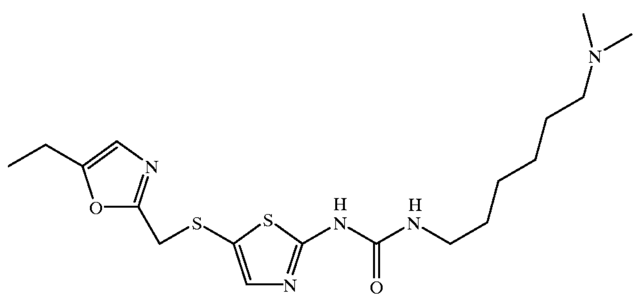 | C18H29N5O2S2 | 526 |
| 297 | 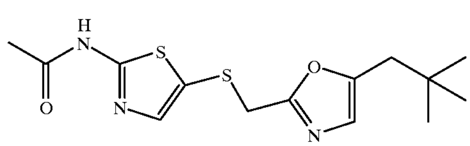 | C14H19N3O2S2 | 326 |
| 298 | 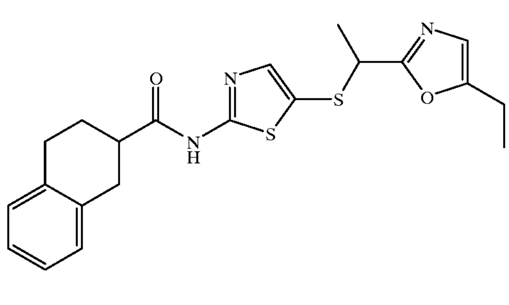 | C21H23N3O2S2 | 414 |

TABLE 1-continued
| Example | Structure | Molecular Formula | (M + H)+ |
|---|---|---|---|
| 299 | 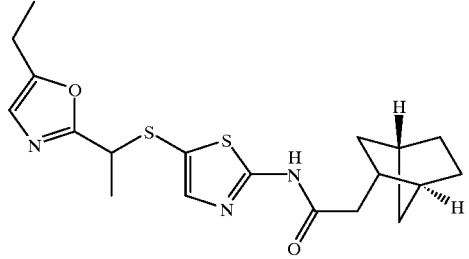 | C19H25N3O2S2 | 392 |
| 300 | 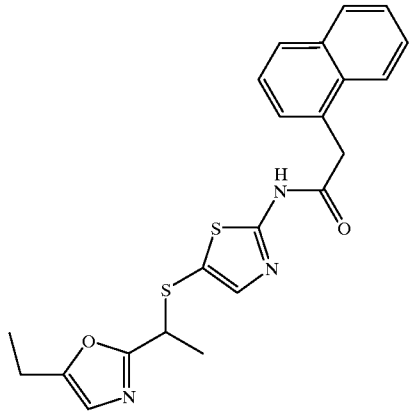 | C22H21N3O2S2 | 424 |
| 301 | 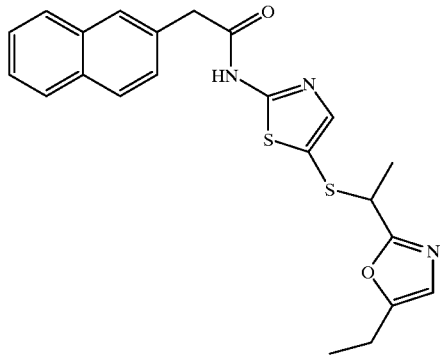 | C22H21N3O2S2 | 424 |
| 302 | 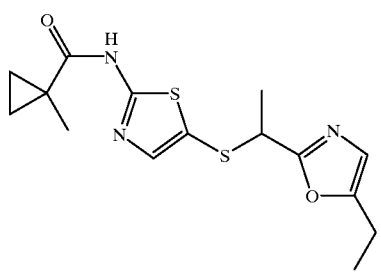 | C15H19N3O2S2 | 338 |

TABLE 1-continued

| Example | Structure | Molecular Formula | (M + H)+ |
|---|---|---|---|
| 303 | 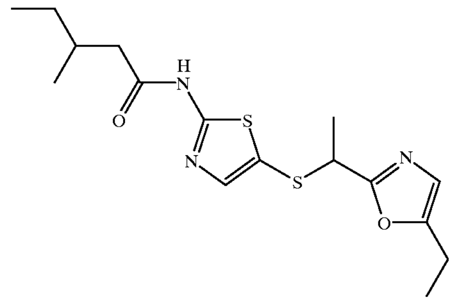 | C16H23N3O2S2 | 354 |
| 304 | 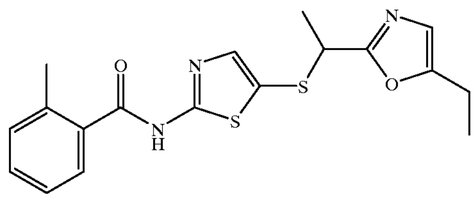 | C18H19N3O2S2 | 374 |
| 305 | 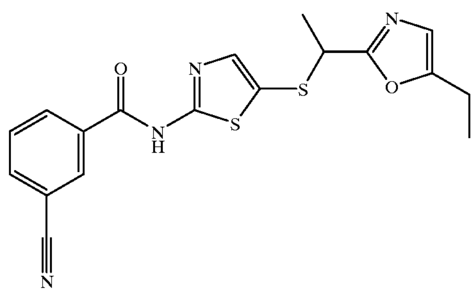 | C18H16N4O2S2 | 385 |
| 306 | 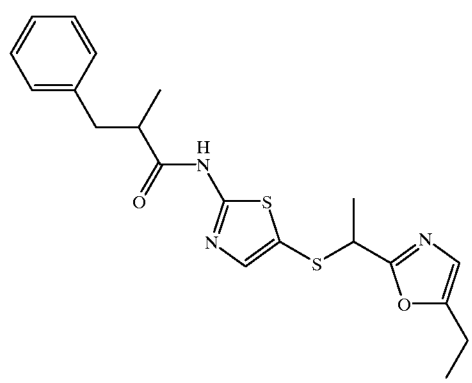 | C20H23N3O2S2 | 402 |
| 307 | 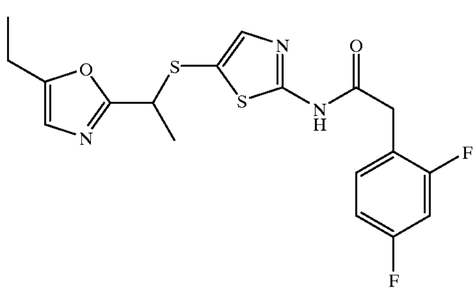 | C18H17F2N3O2S2 | 410 |

TABLE 1-continued

| Example | Structure | Molecular Formula | (M + H)+ |
|---|---|---|---|
| 308 | 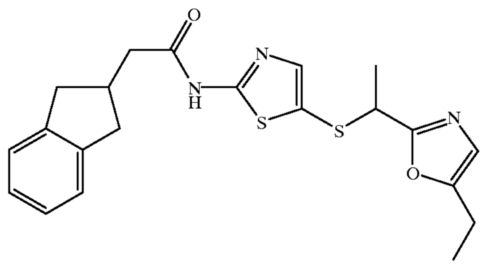 | C21H23N3O2S2 | 414 |
| 309 | 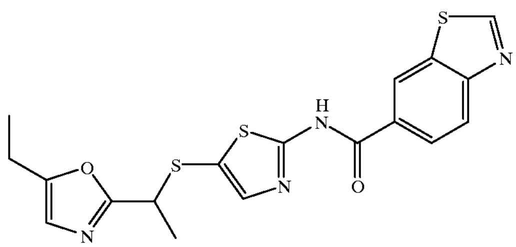 | C18H16N4O2S3 | 417 |
| 310 | 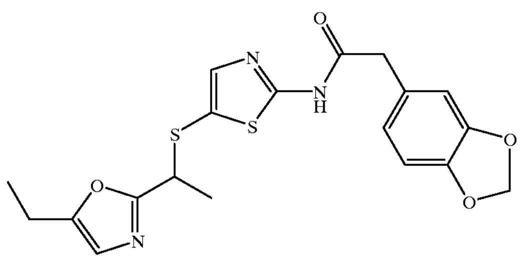 | C19H19N3O4S2 | 418 |
| 311 | 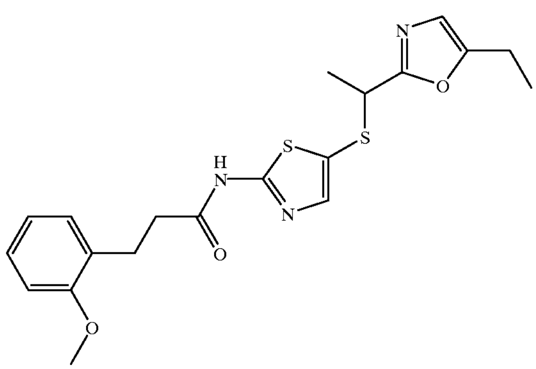 | C20H23N3O3S2 | 418 |
| 312 | 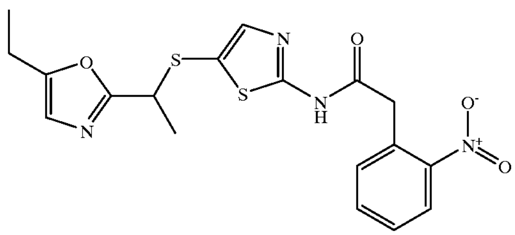 | C18H18N4O4S2 | 419 |

TABLE 1-continued

| Example | Structure | Molecular Formula | (M + H)+ |
|---|---|---|---|
| 313 | 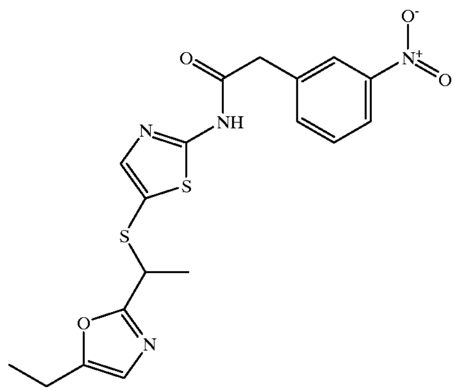 | C18H18N4O4S2 | 419 |
| 314 | 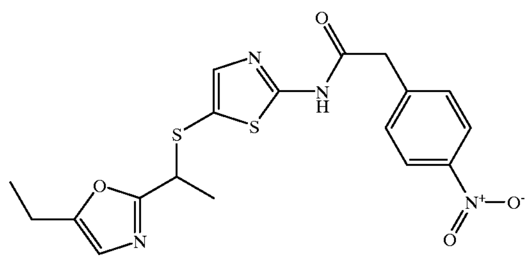 | C18H18N4O4S2 | 419 |
| 315 | 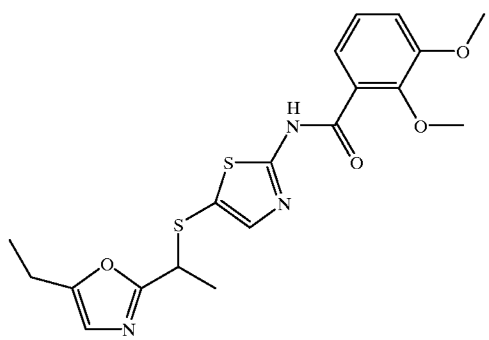 | C19H21N3O4S2 | 420 |
| 316 | 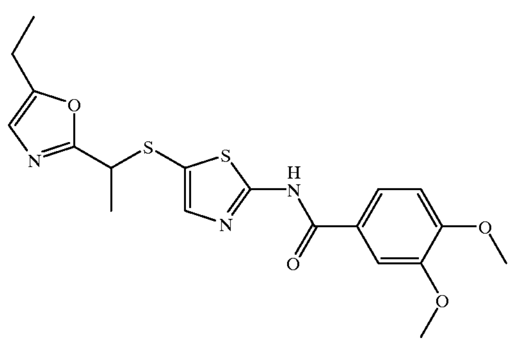 | C19H21N3O4S2 | 420 |

TABLE 1-continued

| Example | Structure | Molecular Formula | (M + H)+ |
| --- | --- | --- | --- |
| 317 | 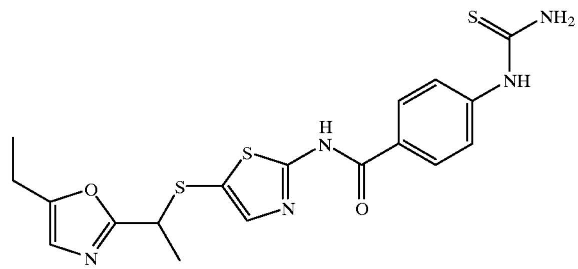 | C18H19N5O2S3 | 434 |
| 318 | 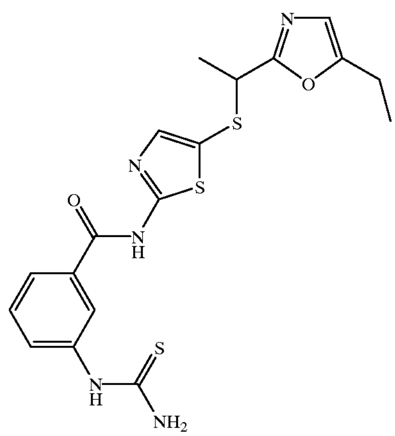 | C18H19N5O2S3 | 434 |
| 319 | 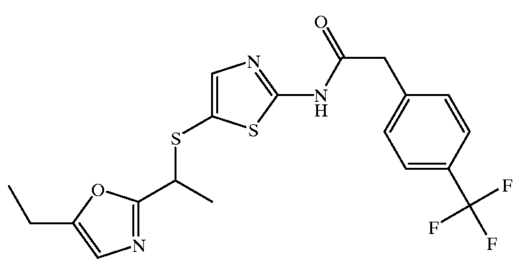 | C19H18F3N3O2S2 | 442 |
| 320 | 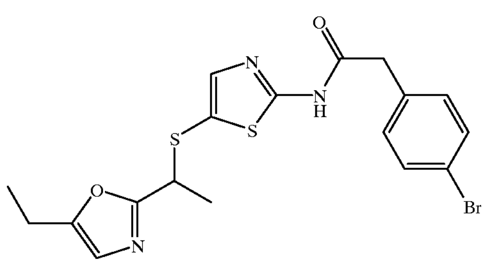 | C18H18BrN3O2S2 | 453 |
| 321 | 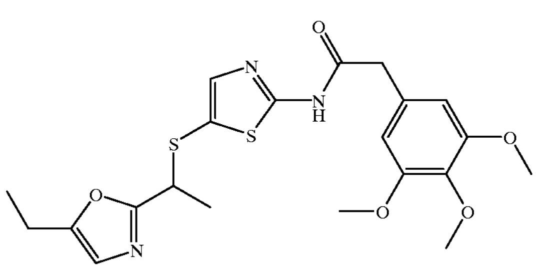 | C21H25N3O5S2 | 464 |

TABLE 1-continued
| Example | Structure | Molecular Formula | (M + H)+ |
|---|---|---|---|
| 322 | 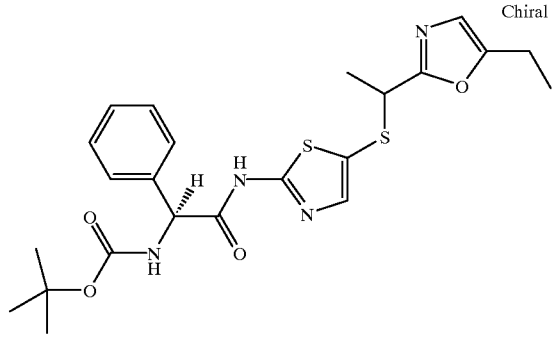 Chiral | C23H28N4O4S2 | 489 |
| 323 | 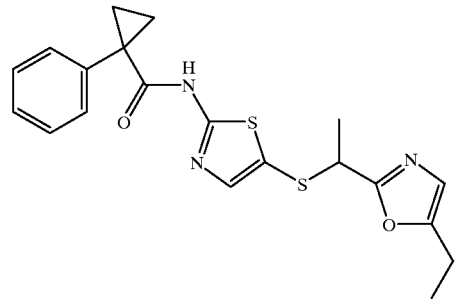 | C20H21N3O2S2 | 400 |
| 324 | 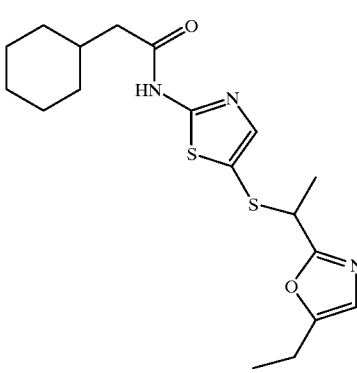 | C18H25N3O2S2 | 380 |
| 325 | 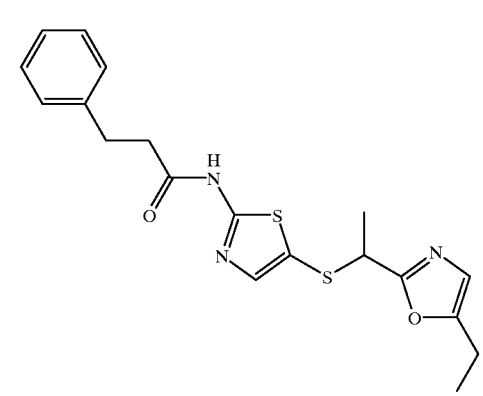 | C19H21N3O2S2 | 388 |

6,040,321
147
148
TABLE 1-continued
| Example | Structure | Molecular Formula | (M + H)+ |
|---|---|---|---|
| 326 | 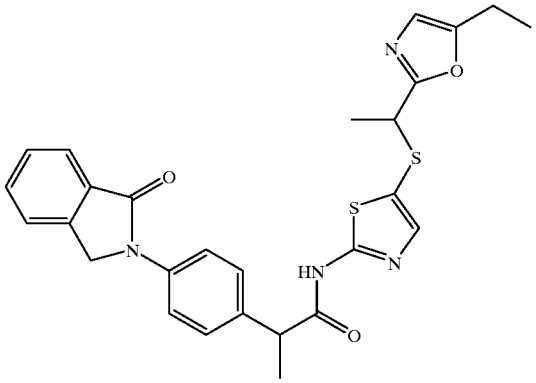 | C27H26N4O3S2 | 519 |
| 327 | 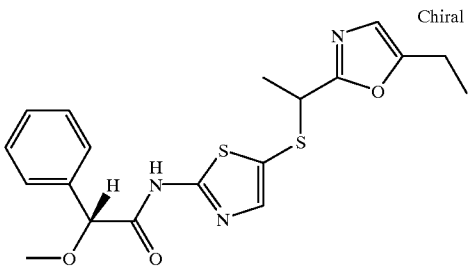 Chiral | C19H21N3O3S2 | 404 |
| 328 | 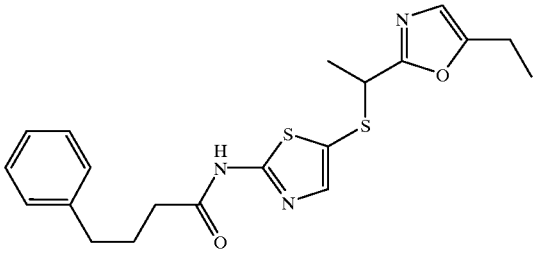 | C20H23N3O2S2 | 402 |
| 329 | 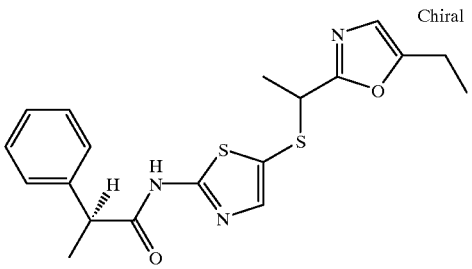 Chiral | C19H21N3O2S2 | 388 |
| 330 | 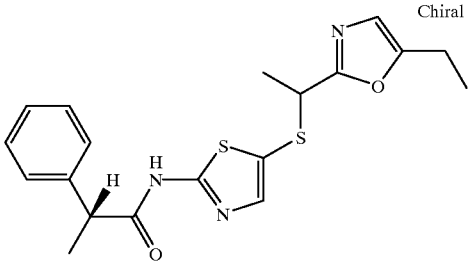 Chiral | C19H21N3O2S2 | 388 |

TABLE 1-continued
| Example | Structure | Molecular Formula | (M + H)+ |
| --- | --- | --- | --- |
| 331 | 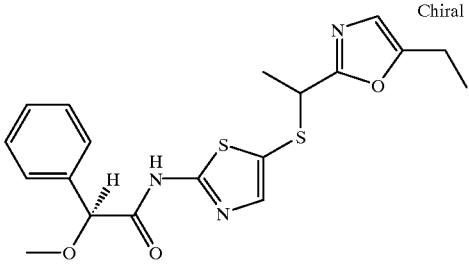 | C19H21N3O3S2 | 404 |
| 332 | 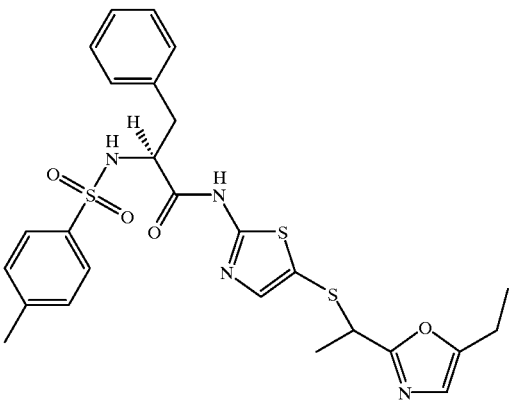 | C26H28N4O4S3 | 557 |
| 333 | 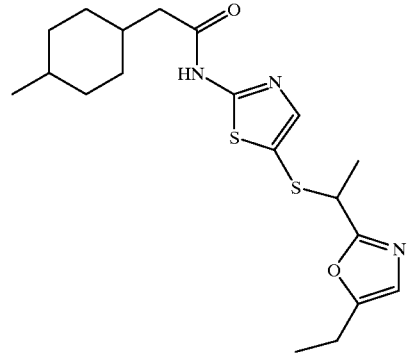 | C19H27N3O2S2 | 394 |
| 334 | 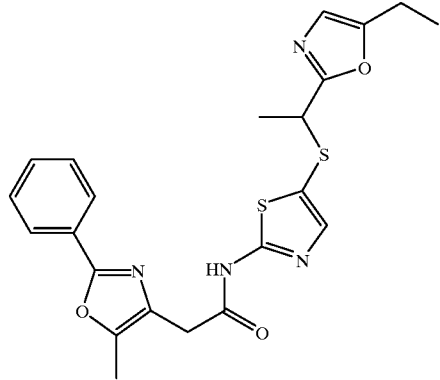 | C22H22N4O3S2 | 455 |

TABLE 1-continued
| Example | Structure | Molecular Formula | (M + H)+ |
|---|---|---|---|
| 335 | 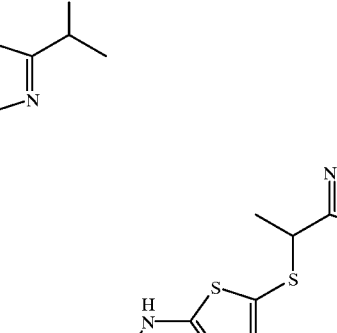 | C22H25N3O4S2 | 460 |
| 336 | 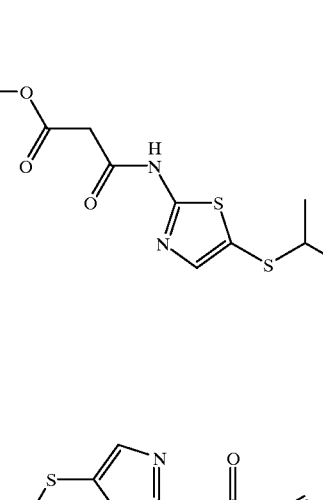 | C20H21N3O3S2 | 416 |
| 337 | 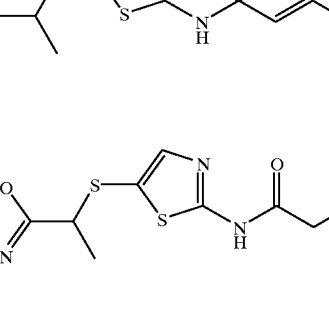 | C15H19N3O4S2 | 370 |
| 338 | 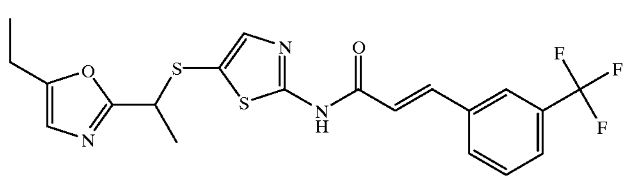 | C20H18F3N3O2S2 | 454 |
| 339 | 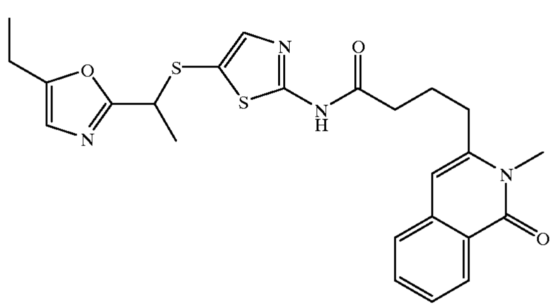 | C24H26N4O3S2 | 483 |

TABLE 1-continued

| Example | Structure | Molecular Formula | (M + H)+ |
|---|---|---|---|
| 340 | 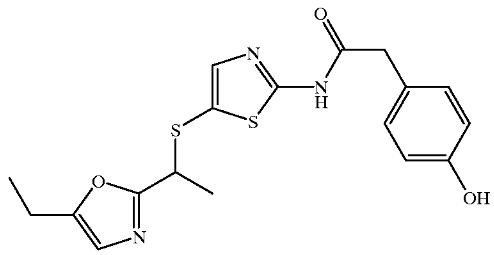 | C18H19N3O3S2 | 390 |
| 341 | 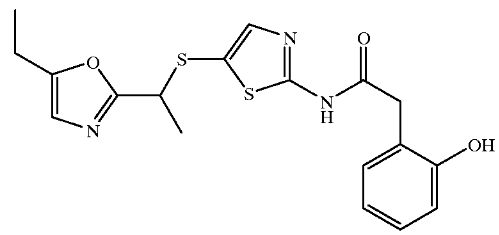 | C18H19N3O3S2 | 390 |
| 342 | 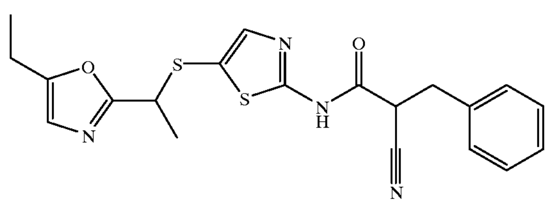 | C20H20N4O2S2 | 413 |
| 343 | 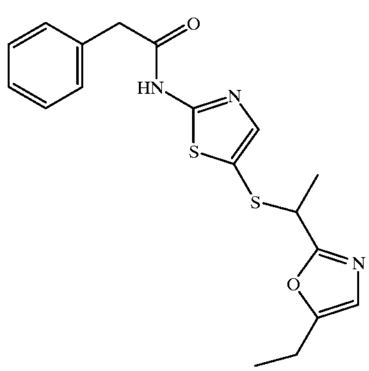 | C18H19N3O2S2 | 374 |
| 344 | 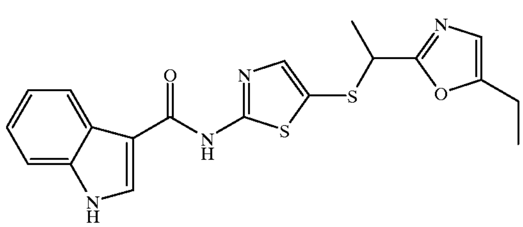 | C19H18N4O2S2 | 399 |

TABLE 1-continued
| Example | Structure | Molecular Formula | (M + H)+ |
|---|---|---|---|
| 345 | 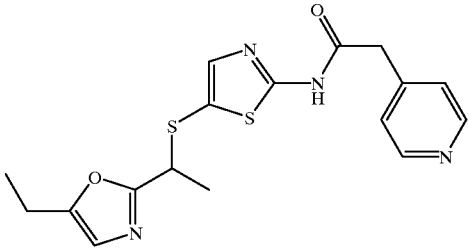 | C17H18N4O2S2 | 489 |
| 346 | 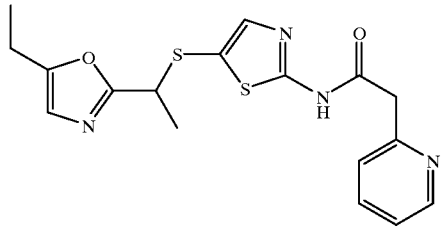 | C17H18N4O2S2 | 489 |
| 347 | 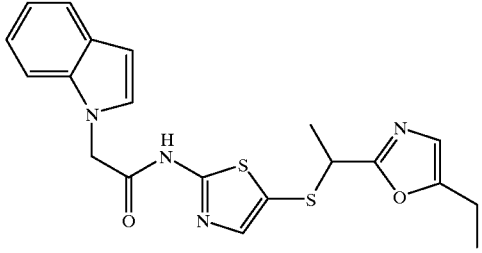 | C20H20N4O2S2 | 413 |
| 348 | 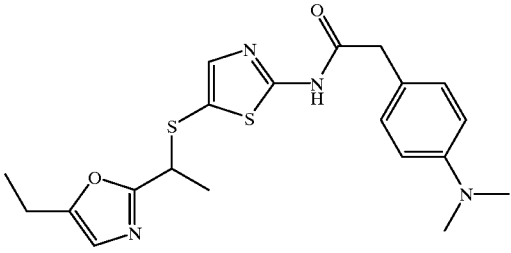 | C20H24N4O2S2 | 531 |
| 349 | 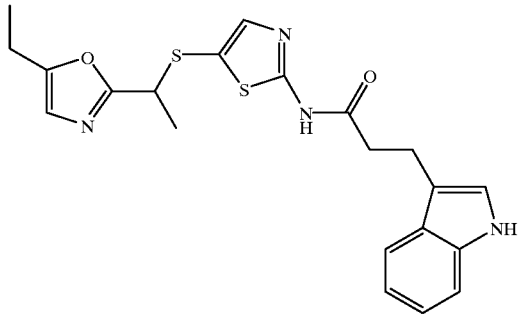 | C21H22N4O2S2 | 427 |

TABLE 1-continued

| Example | Structure | Molecular Formula | (M + H)+ |
| --- | --- | --- | --- |
| 350 | 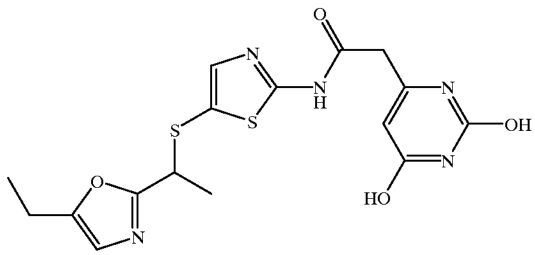 | C16H17N5O4S2 | 408 |
| 351 | 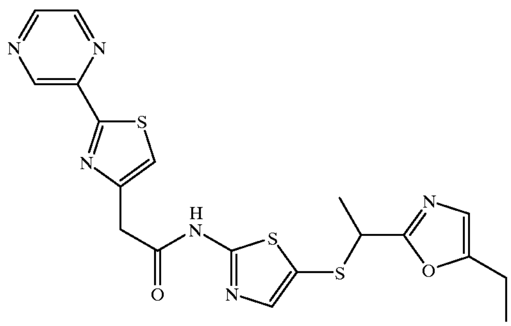 | C19H18N6O2S3 | 687 |
| 352 | 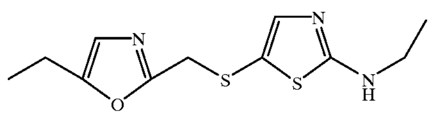 | C11H15N3OS2 | 270 |
| 353 | 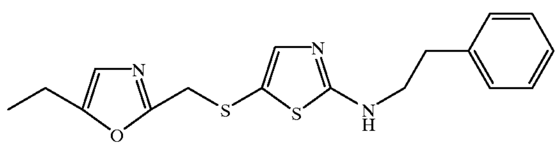 | C17H19N3OS2 | 346 |
| 354 | 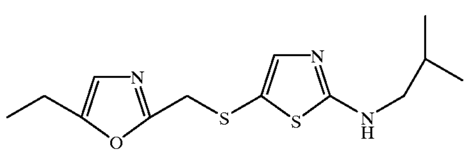 | C13H19N3OS2 | 298 |
| 355 | 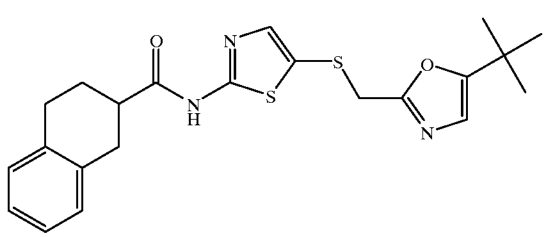 | C22H25N3O2S2 | 428 |

TABLE 1-continued
| Example | Structure | Molecular Formula | (M + H)+ |
|---|---|---|---|
| 356 | 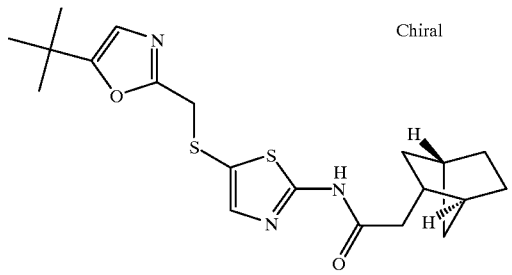 Chiral | C20H27N3O2S2 | 406 |
| 357 | 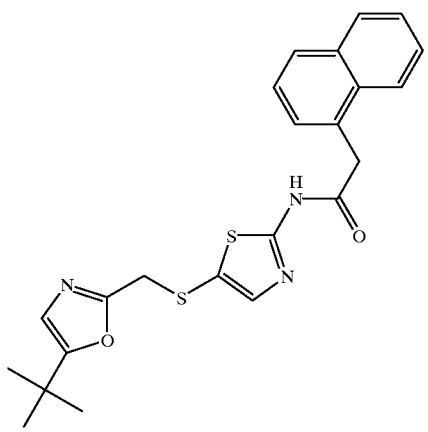 | C23H23N3O2S2 | 438 |
| 358 | 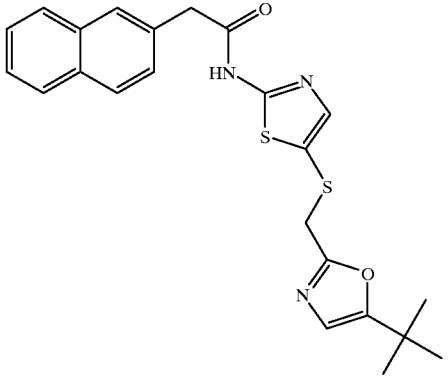 | C23H23N3O2S2 | 438 |
| 359 | 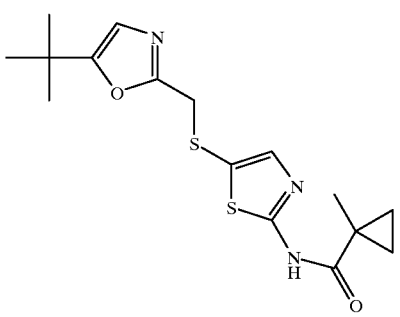 | C16H21N3O2S2 | 352 |

TABLE 1-continued
| Example | Structure | Molecular Formula | (M + H)+ |
|---|---|---|---|
| 360 | 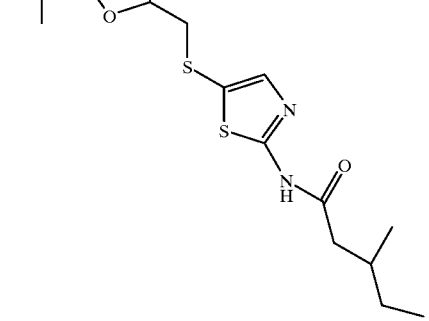 | C17H25N3O2S2 | 368 |
| 361 | 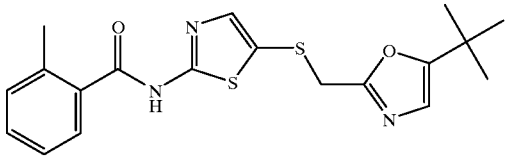 | C19H21N3O2S2 | 388 |
| 362 | 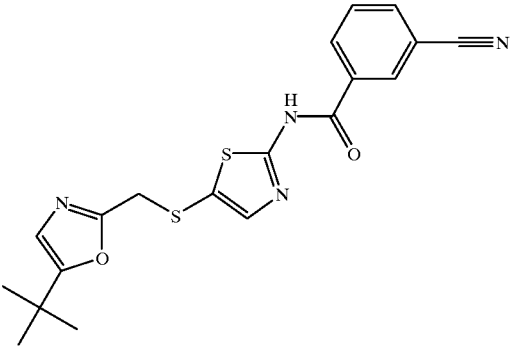 | C19H18N4O2S2 | 399 |
| 363 | 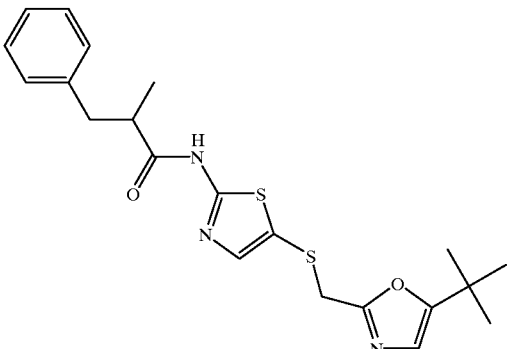 | C21H25N3O2S2 | 416 |

TABLE 1-continued

| Example | Structure | Molecular Formula | (M + H)+ |
| --- | --- | --- | --- |
| 364 | 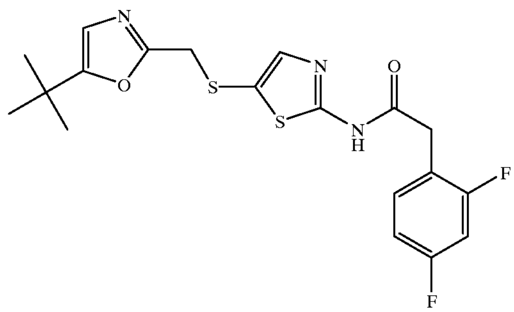 | C19H19F2N3O2S2 | 424 |
| 365 | 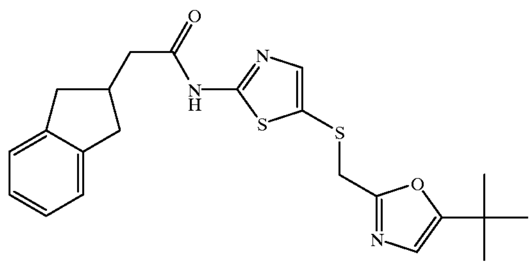 | C22H25N3O2S2 | 428 |
| 366 | 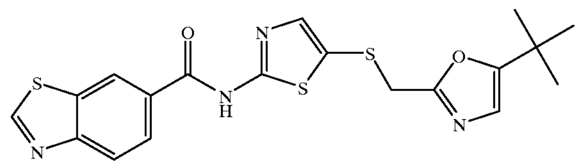 | C19H18N4O2S3 | 431 |
| 367 | 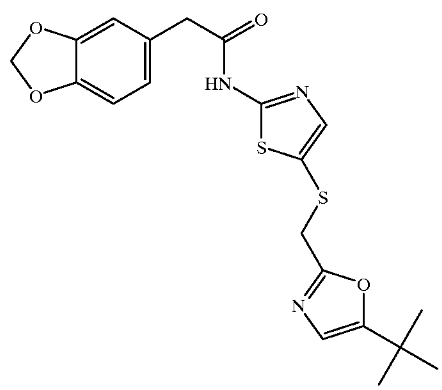 | C20H21N3O4S2 | 432 |
| 368 | 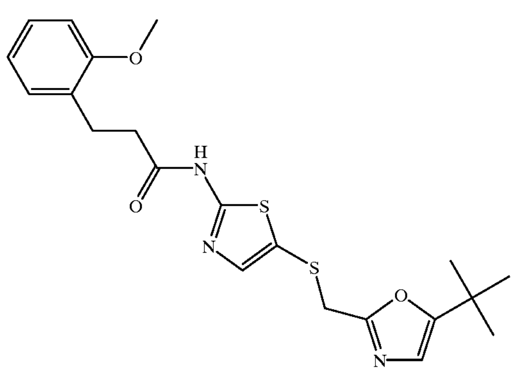 | C21H25N3O3S2 | 432 |

TABLE 1-continued

| Example | Structure | Molecular Formula | (M + H)+ |
|---|---|---|---|
| 369 | 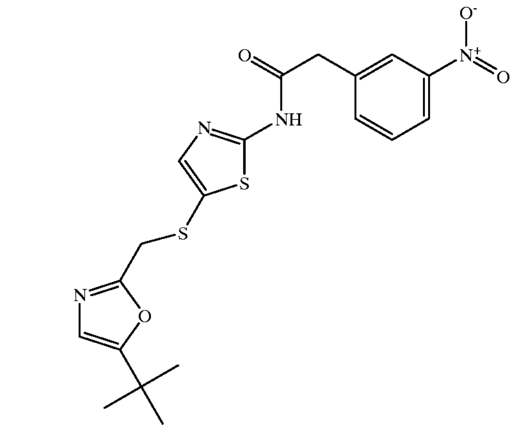 | C19H20N4O4S2 | 433 |
| 370 | 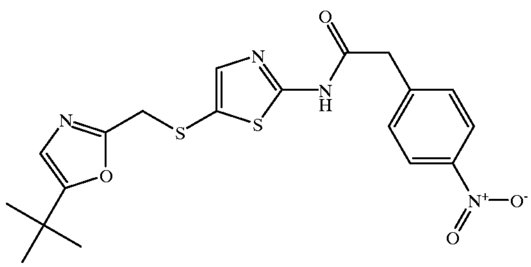 | C19H20N4O4S2 | 433 |
| 371 | 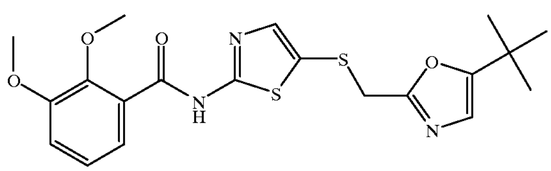 | C20H23N3O4S2 | 434 |
| 372 | 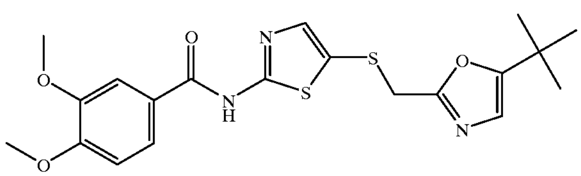 | C20H23N3O4S2 | 434 |
| 373 | 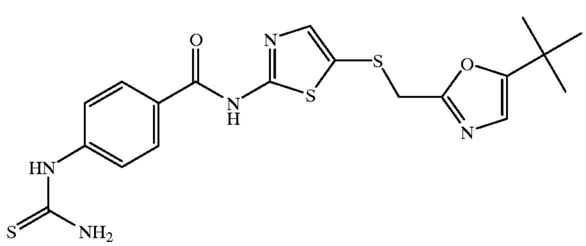 | C19H21N5O2S3 | 448 |
| 374 | 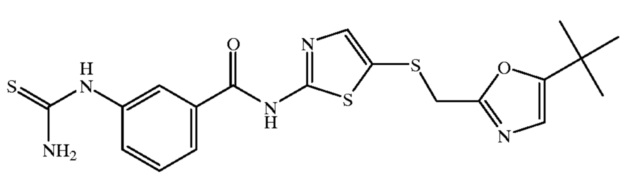 | C19H21N5O2S3 | 448 |

TABLE 1-continued
| Example | Structure | Molecular Formula | (M + H)+ |
| --- | --- | --- | --- |
| 375 | 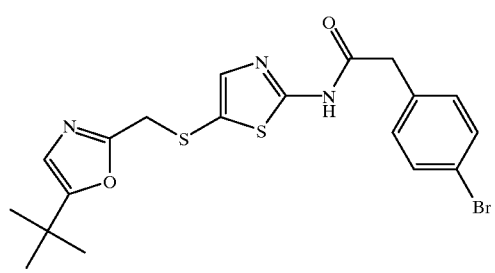 | C19H20BrN3O2S2 | 467 |
| 376 | 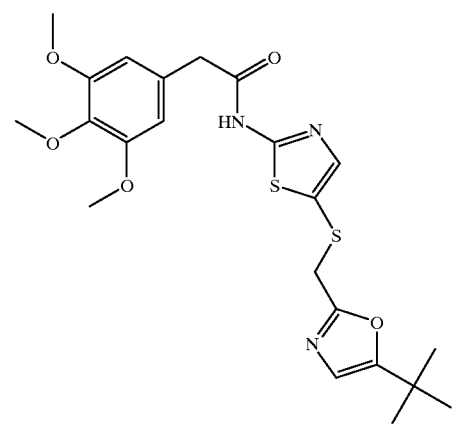 | C22H27N3O5S2 | 478 |
| 377 | 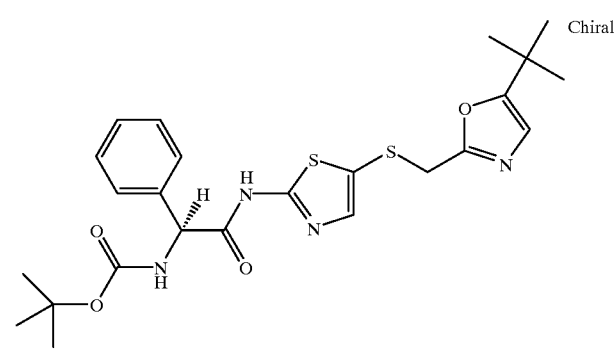 Chiral | C24H30N4O4S2 | 503 |
| 378 | 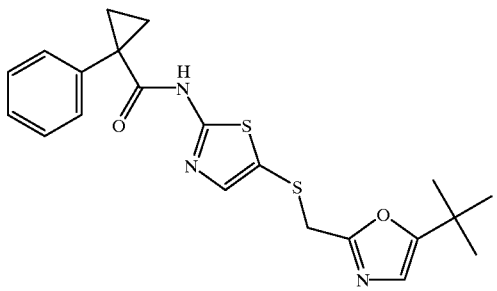 | C21H23N3O2S2 | 414 |

TABLE 1-continued
| Example | Structure | Molecular Formula | (M + H)+ |
|---|---|---|---|
| 379 | 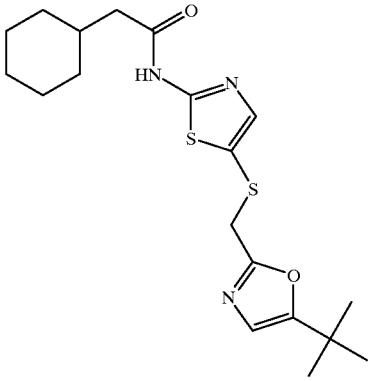 | C19H27N3O2S2 | 394 |
| 380 | 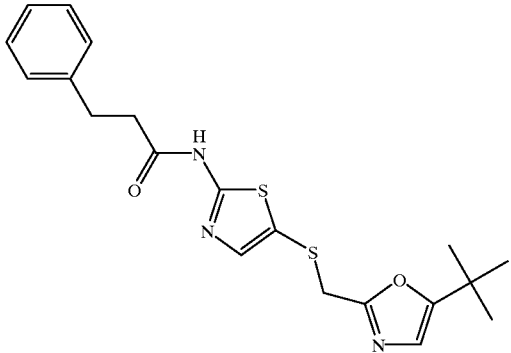 | C20H23N3O2S2 | 402 |
| 381 | 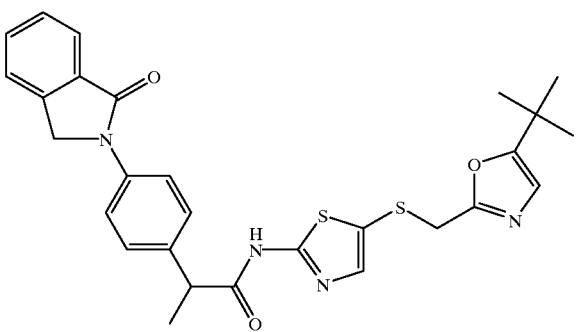 | C28H28N4O3S2 | 533 |
| 382 | 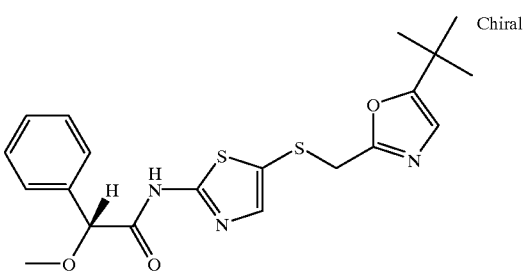 Chiral | C20H23N3O3S2 | 418 |

TABLE 1-continued

| Example | Structure | Molecular Formula | (M + H)+ |
|---|---|---|---|
| 383 | 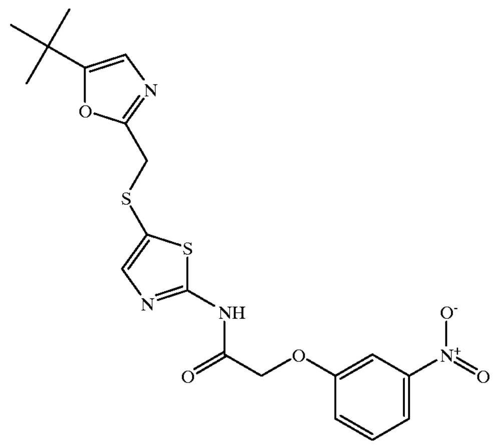 | C19H20N4O5S2 | 449 |
| 384 | 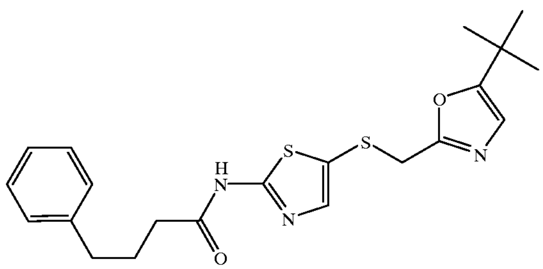 | C21H25N3O2S2 | 416 |
| 385 | 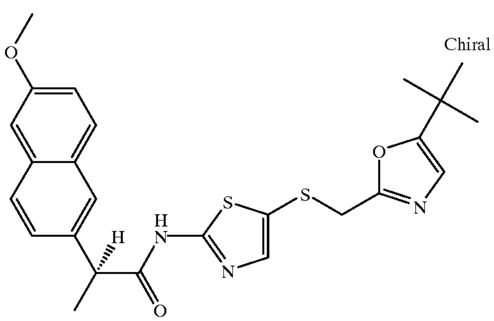 | C25H27N3O3S2 | 482 |
| 386 | 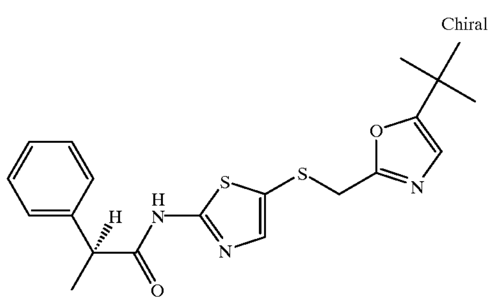 | C20H23N3O2S2 | 402 |

TABLE 1-continued
| Example | Structure | Molecular Formula | (M + H)+ |
|---|---|---|---|
| 387 | 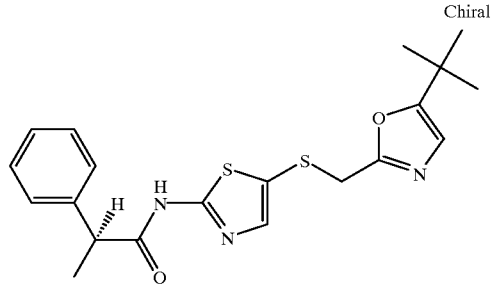 | C20H23N3O2S2 | 402 |
| 388 | 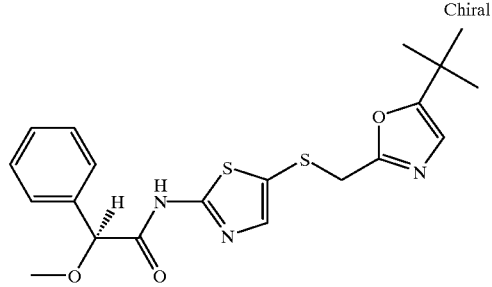 | C20H23N3O3S2 | 418 |
| 389 | 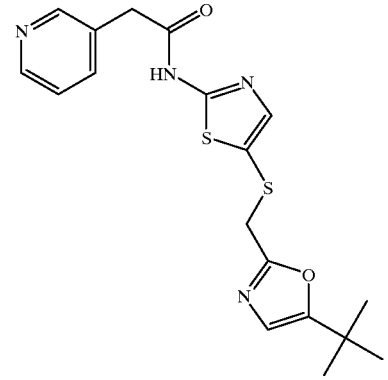 | C18H20N4O2S2 | 503 |
| 390 | 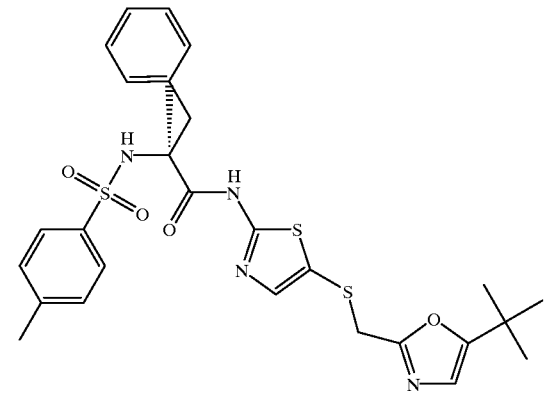 | C27H30N4O4S3 | 571 |

TABLE 1-continued

| Example | Structure | Molecular Formula | (M + H)+ |
|---|---|---|---|
| 391 | 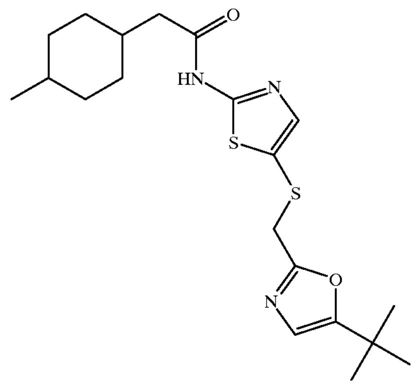 | C20H29N3O2S2 | 408 |
| 392 | 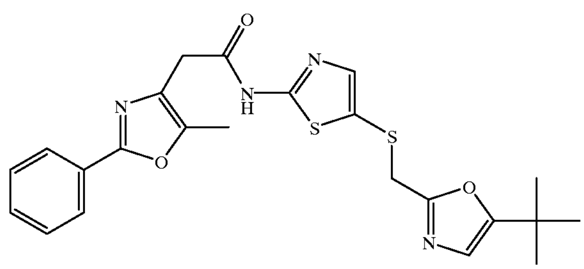 | C23H24N4O3S2 | 469 |
| 393 | 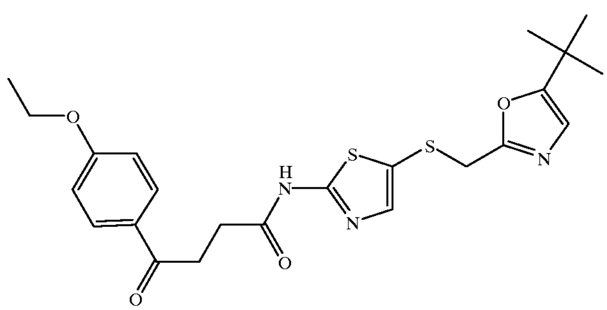 | C23H27N3O4S2 | 474 |
| 394 | 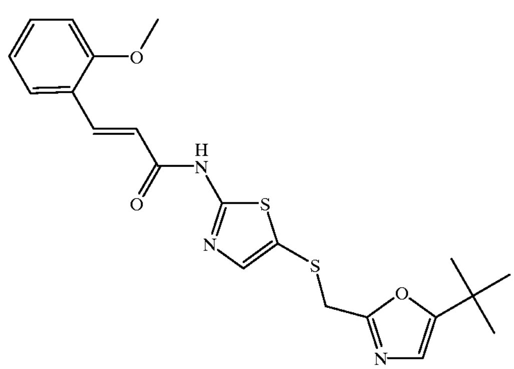 | C21H23N3O3S2 | 430 |

TABLE 1-continued

| Example | Structure | Molecular Formula | (M + H)+ |
|---|---|---|---|
| 395 | 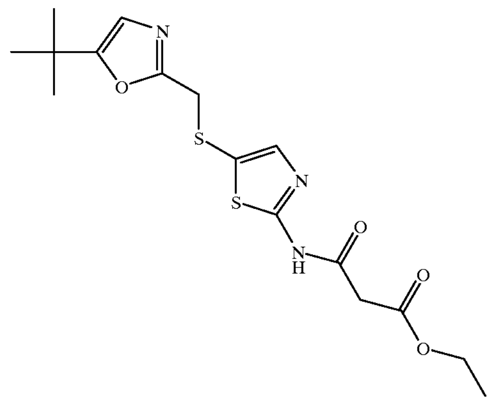 | C16H21N3O4S2 | 384 |
| 396 | 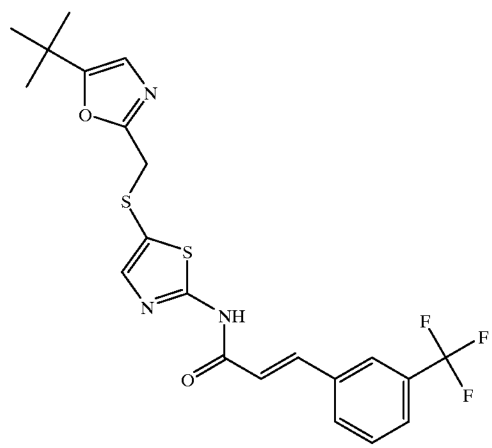 | C21H20F3N3O2S2 | 468 |
| 397 | 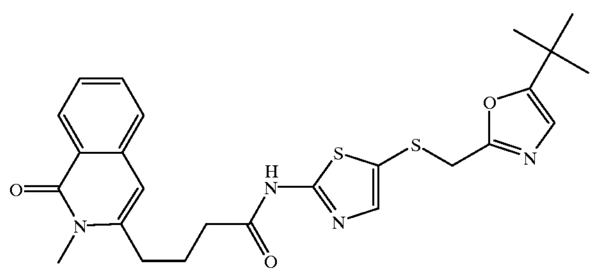 | C25H28N4O3S2 | 497 |
| 398 | 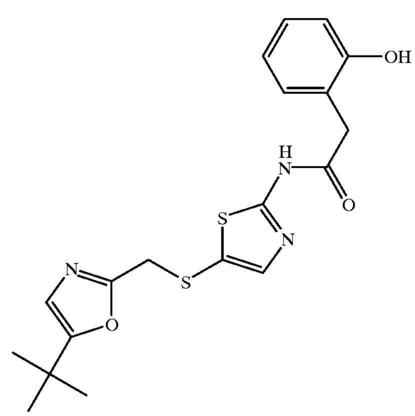 | C19H21N3O3S2 | 404 |

TABLE 1-continued

| Example | Structure | Molecular Formula | (M + H)+ |
|---|---|---|---|
| 399 | 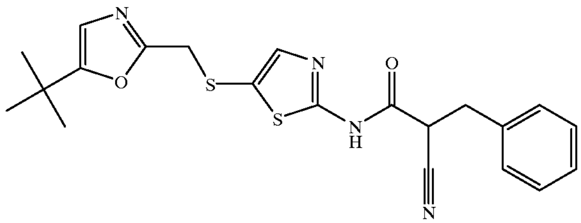 | C21H22N4O2S2 | 427 |
| 400 | 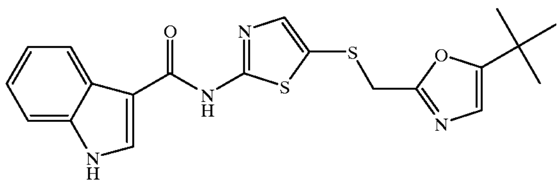 | C20H20N4O2S2 | 413 |
| 401 | 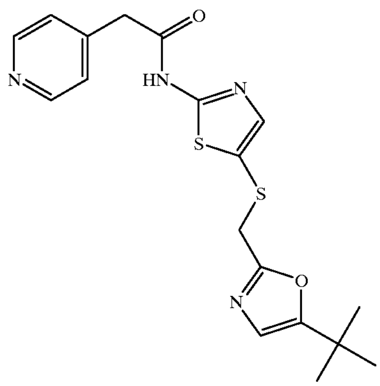 | C18H20N4O2S2 | 503 |
| 402 | 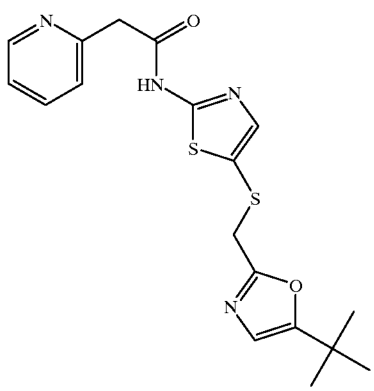 | C18H20N4O2S2 | 503 |
| 403 | 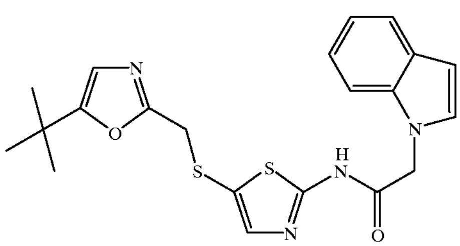 | C21H22N4O2S2 | 427 |

TABLE 1-continued

| Example | Structure | Molecular Formula | (M + H)+ |
|---|---|---|---|
| 404 | 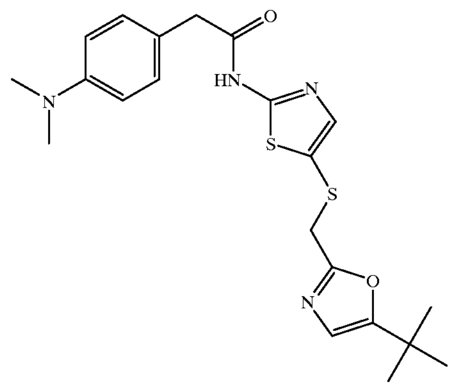 | C21H26N4O2S2 | 545 |
| 405 | 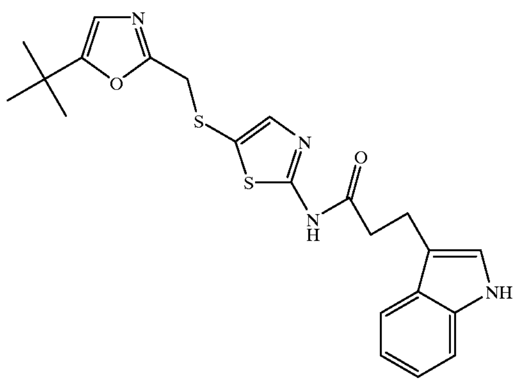 | C22H24N4O2S2 | 441 |
| 406 | 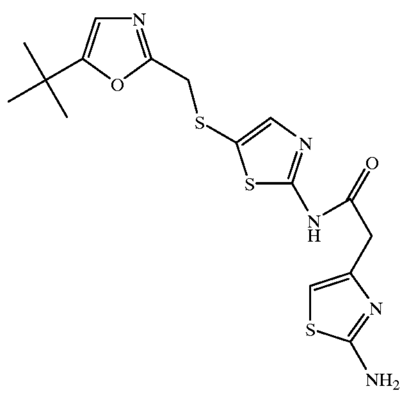 | C16H19N5O2S3 | 524 |
| 407 | 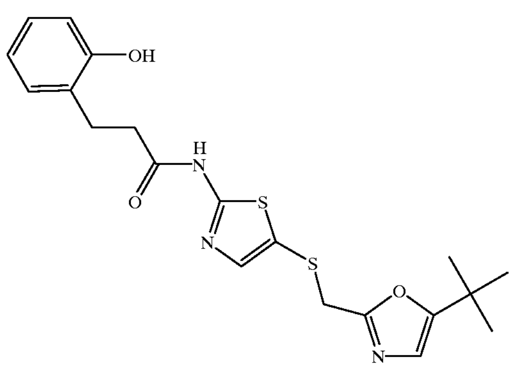 | C20H23N3O3S2 | 418 |

TABLE 1-continued

| Example | Structure | Molecular Formula | (M + H)+ |
|---|---|---|---|
| 408 | 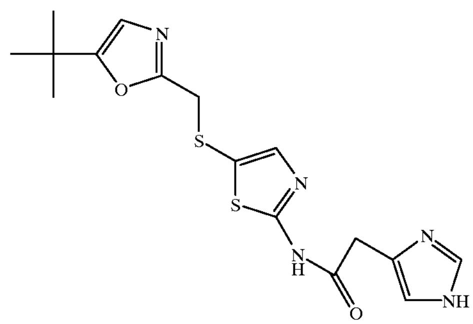 | C16H19N5O2S2 | 492 |
| 409 | 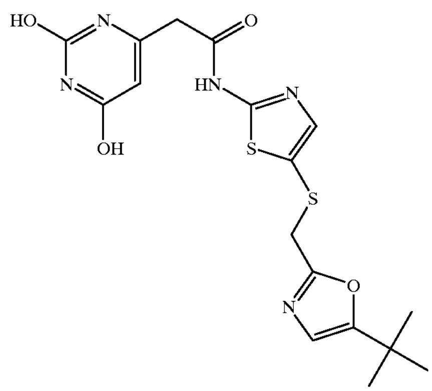 | C17H19N5O4S2 | 422 |
| 410 | 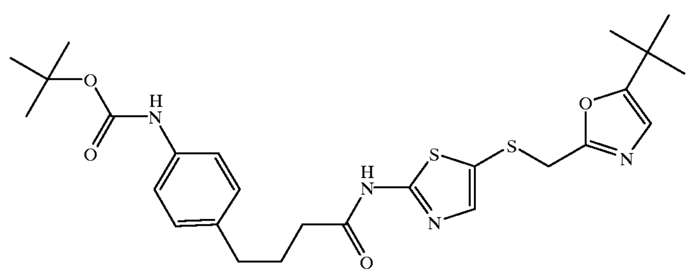 | C26H34N4O4S2 | 531 |
| 411 | 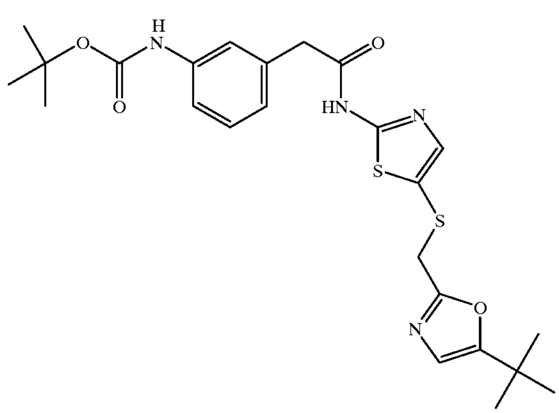 | C24H30N4O4S2 | 503 |

TABLE 1-continued
| Example | Structure | Molecular Formula | (M + H)+ |
|---|---|---|---|
| 412 | 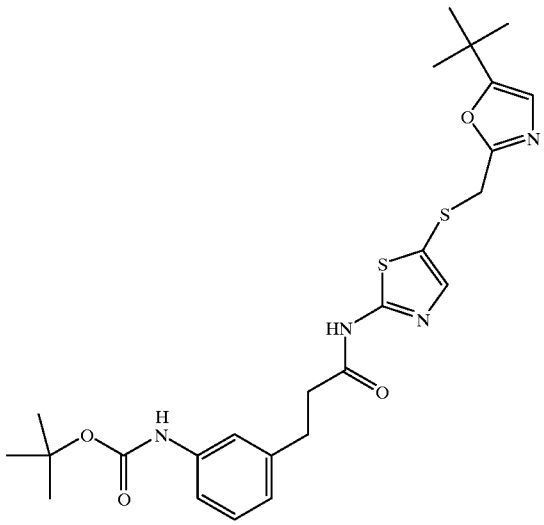 | C25H32N4O4S2 | 517 |
| 413 | 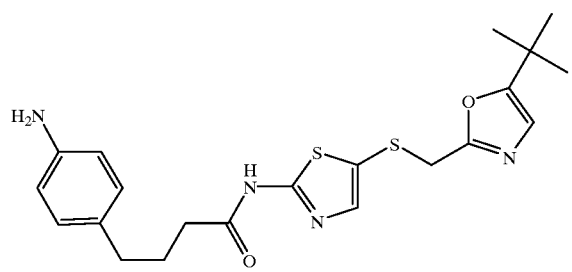 | C21H26N4O2S2 | 545 |
| 414 | 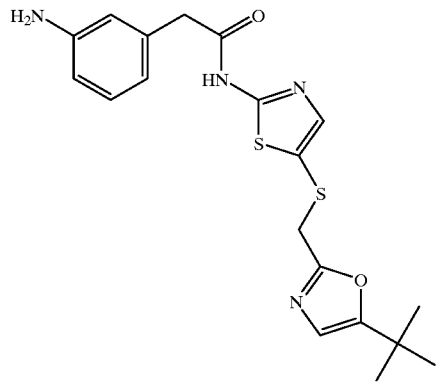 | C19H22N4O2S2 | 517 |

TABLE 1-continued
| Example | Structure | Molecular Formula | (M + H)+ |
| --- | --- | --- | --- |
| 415 | 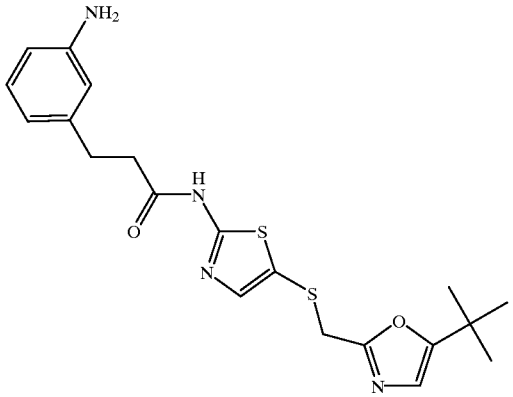 | C20H24N4O2S2 | 531 |
| 416 | 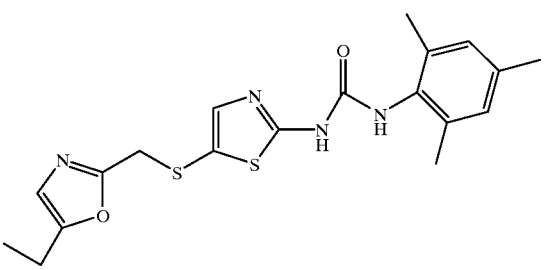 | C19H22N4O2S2 | 403 |
| 417 | 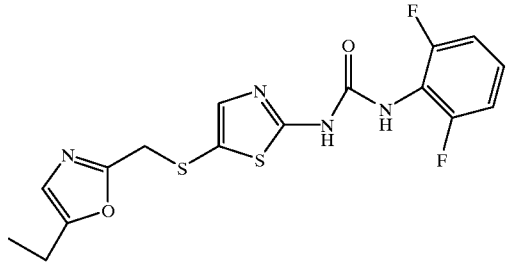 | C16H14F2N4O2S2 | 397 |
| 418 | 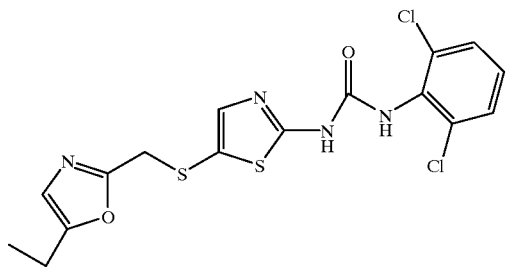 | C16H14Cl2N4O2S2 | 430 |
| 419 | 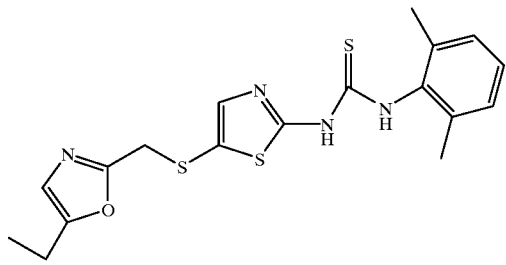 | C18H20N4OS3 | 405 |

TABLE 1-continued
| Example | Structure | Molecular Formula | (M + H)+ |
| --- | --- | --- | --- |
| 420 | 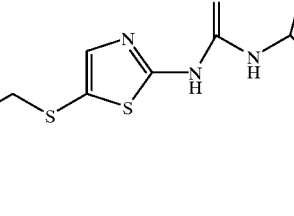 | C16H14Cl2N4OS3 | 446 |
| 421 | 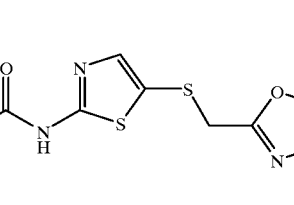 | C21H23N3O2S2 | 414 |
| 422 |  Chiral | C19H25N3O2S2 | 392 |
| 423 | 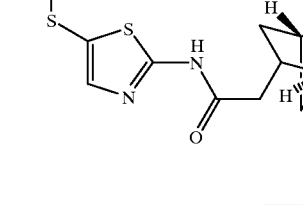 | C22H21N3O2S2 | 424 |

TABLE 1-continued

| Example | Structure | Molecular Formula | (M + H)+ |
|---|---|---|---|
| 424 | 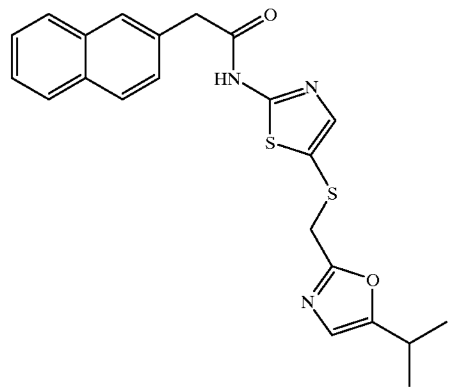 | C22H21N3O2S2 | 424 |
| 425 | 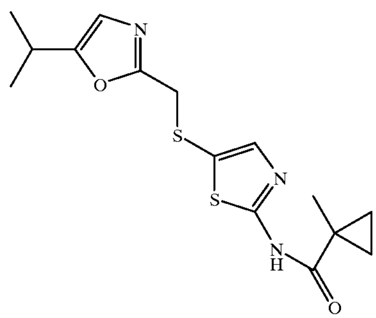 | C15H19N3O2S2 | 338 |
| 426 | 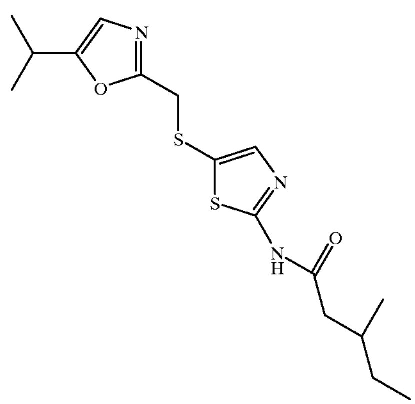 | C16H23N3O2S2 | 354 |
| 427 | 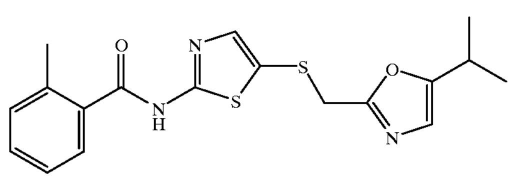 | C18H19N3O2S2 | 374 |

TABLE 1-continued

| Example | Structure | Molecular Formula | (M + H)+ |
|---|---|---|---|
| 428 | 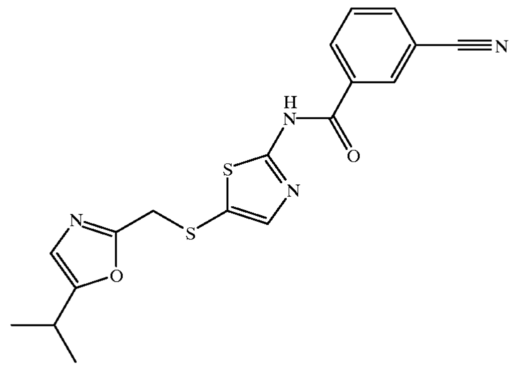 | C18H16N4O2S2 | 385 |
| 429 | 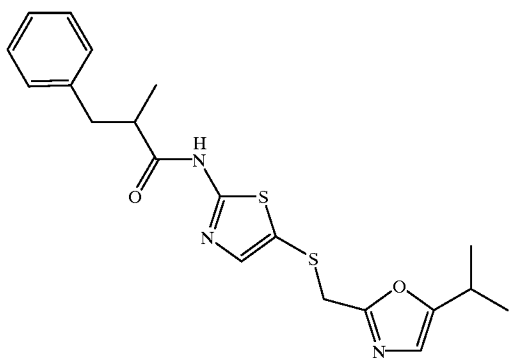 | C20H23N3O2S2 | 402 |
| 430 | 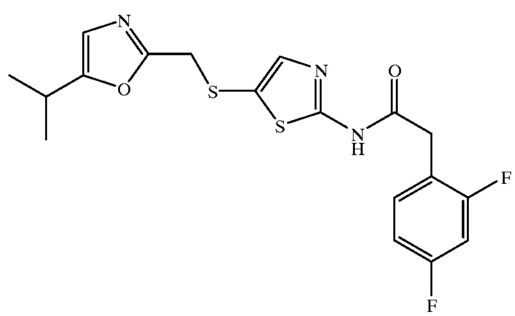 | C18H17F2N3O2S2 | 410 |
| 431 | 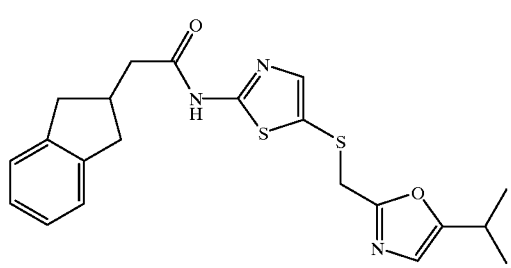 | C21H23N3O2S2 | 414 |
| 432 | 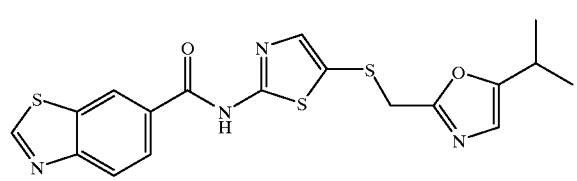 | C18H16N4O2S3 | 417 |

TABLE 1-continued

| Example | Structure | Molecular Formula | (M + H)+ |
|---|---|---|---|
| 433 | 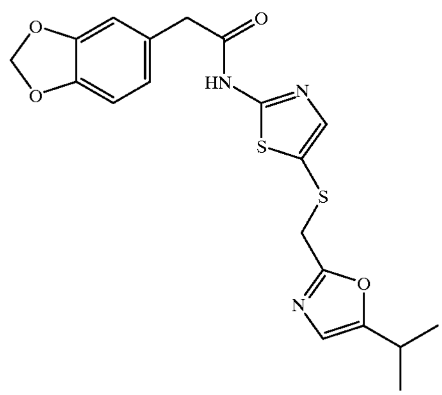 | C19H19N3O4S2 | 418 |
| 434 | 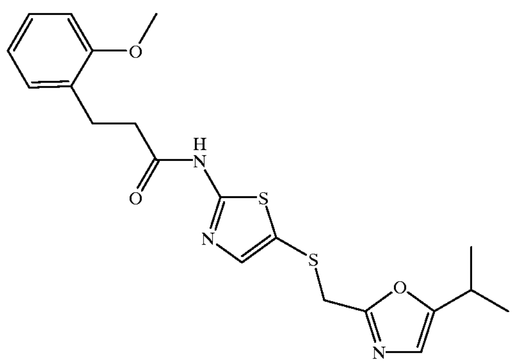 | C20H23N3O3S2 | 418 |
| 435 | 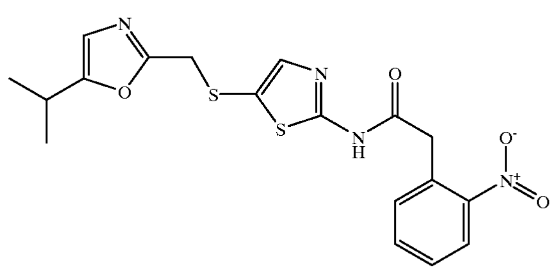 | C18H18N4O4S2 | 419 |
| 436 | 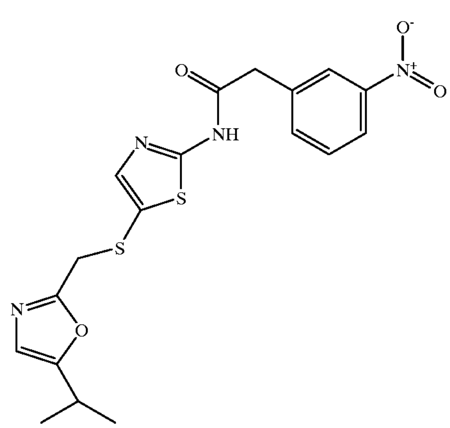 | C18H18N4O4S2 | 419 |

TABLE 1-continued
| Example | Structure | Molecular Formula | (M + H)+ |
| --- | --- | --- | --- |
| 437 | 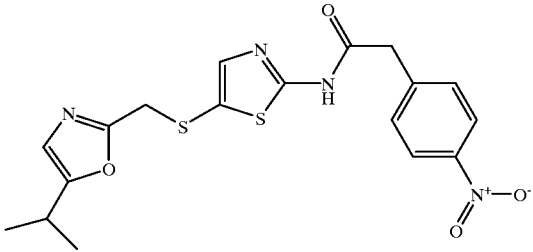 | C18H18N4O4S2 | 419 |
| 438 | 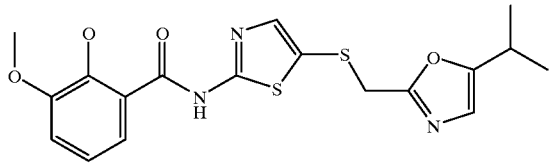 | C19H21N3O4S2 | 420 |
| 439 | 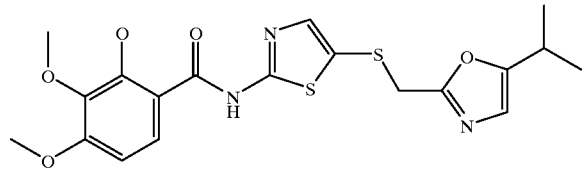 | C19H21N3O4S2 | 420 |
| 440 | 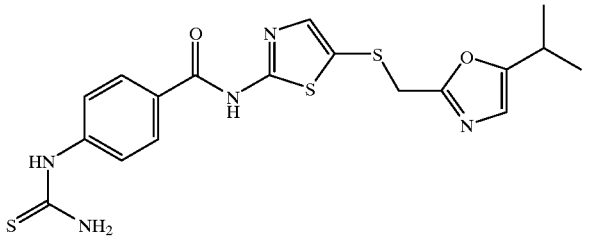 | C18H19N5O2S3 | 434 |
| 441 | 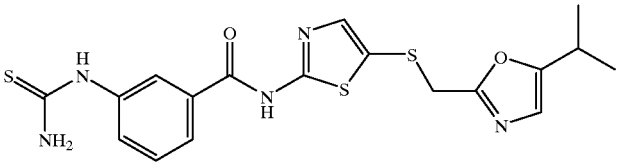 | C18H19N5O2S3 | 434 |
| 442 | 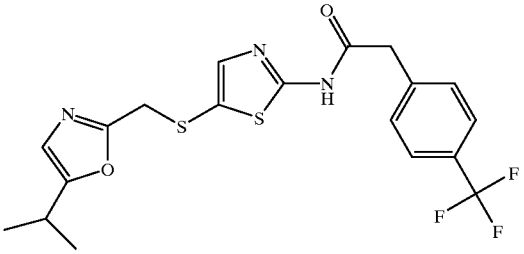 | C19H18F3N3O2S2 | 442 |

TABLE 1-continued
| Example | Structure | Molecular Formula | (M + H)+ |
|---|---|---|---|
| 443 | 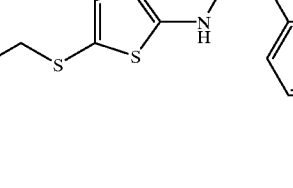 | C18H18BrN3O2S2 | 453 |
| 444 | 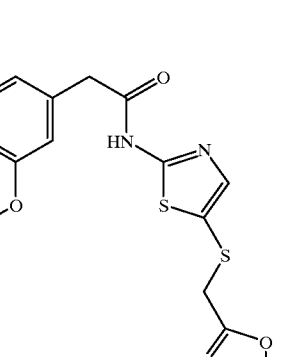 | C21H25N3O5S2 | 464 |
| 445 | 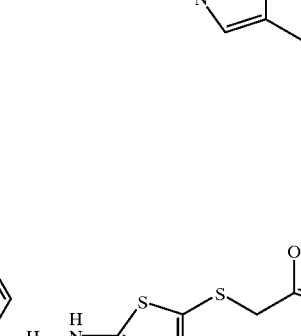 Chiral | C23H28N4O4S2 | 489 |
| 446 | 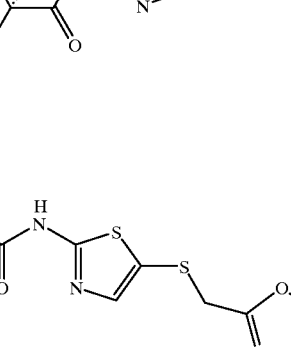 | C20H21N3O2S2 | 400 |

TABLE 1-continued

| Example | Structure | Molecular Formula | (M + H)+ |
|---|---|---|---|
| 447 | 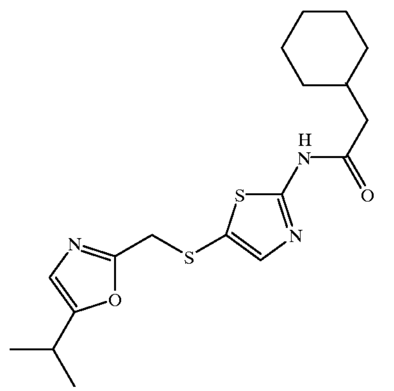 | C18H25N3O2S2 | 380 |
| 448 | 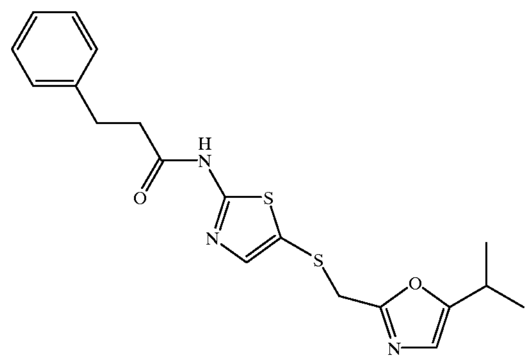 | C19H21N3O2S2 | 388 |
| 449 | 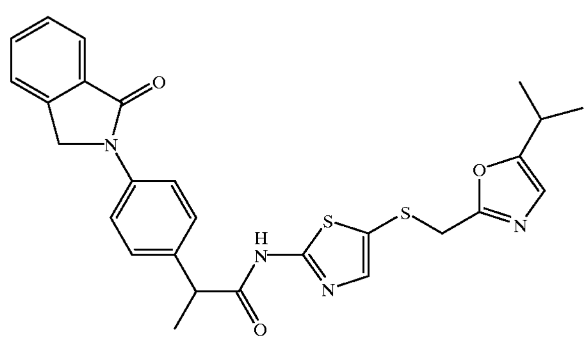 | C27H26N4O3S2 | 519 |
| 450 | Chiral | C19H21N3O3S2 | 404 |

TABLE 1-continued

| Example | Structure | Molecular Formula | (M + H)+ |
|---|---|---|---|
| 451 | 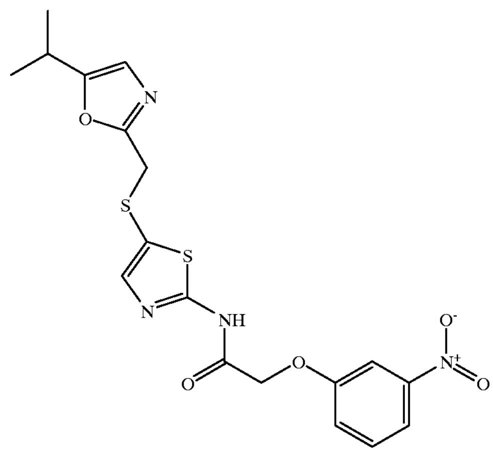 | C18H18N4O5S2 | 435 |
| 452 | 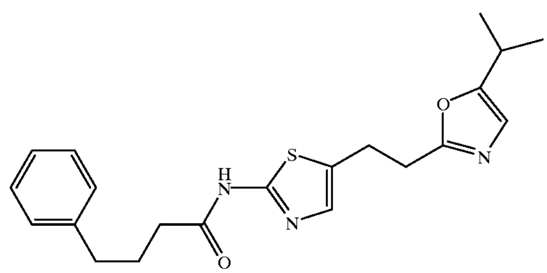 | C20H23N3O2S2 | 402 |
| 453 | 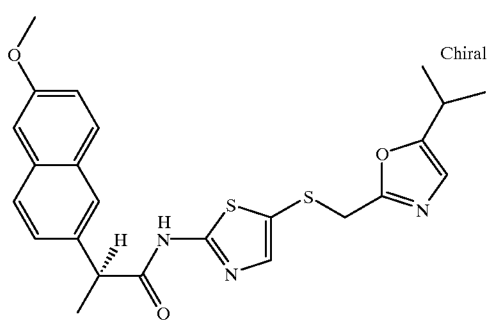 | C24H25N3O3S2 | 468 |
| 454 | 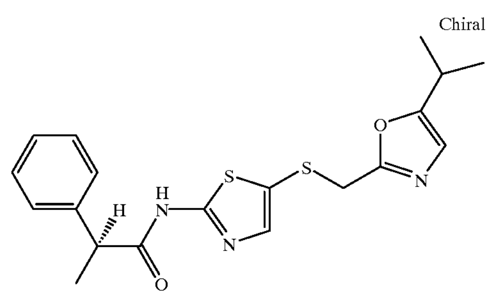 | C19H21N3O2S2 | 388 |

TABLE 1-continued
| Example | Structure | Molecular Formula | (M + H)+ |
|---|---|---|---|
| 455 | 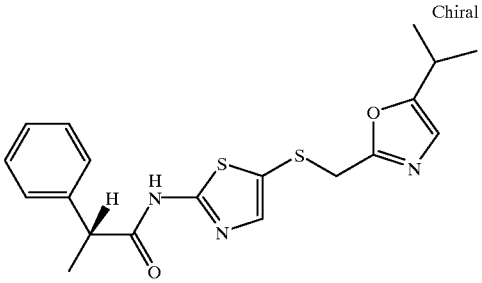 Chiral | C19H21N3O2S2 | 388 |
| 456 | 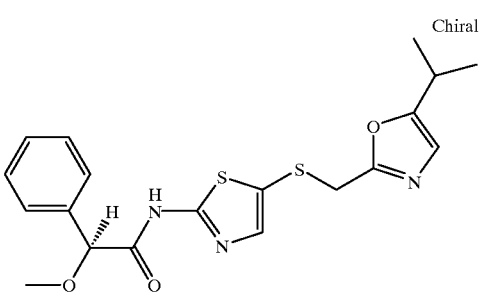 Chiral | C19H21N3O3S2 | 404 |
| 457 | 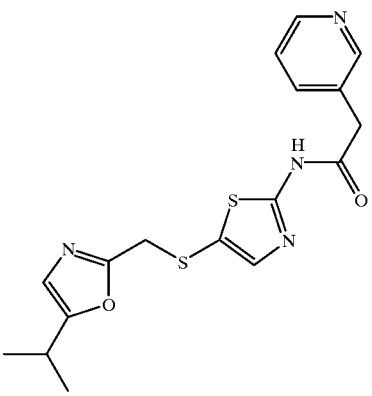 | C17H18N4O2S2 | 489 |
| 458 | 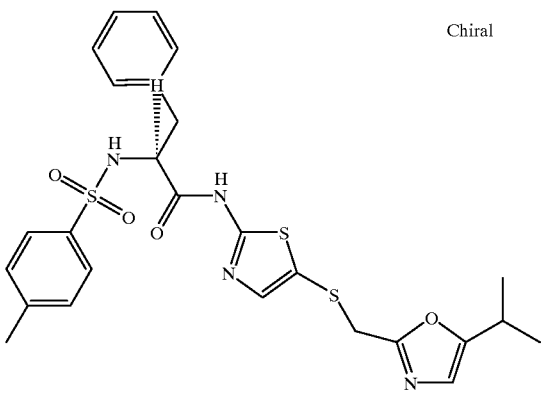 Chiral | C26H28N4O4S3 | 557 |

6,040,321
TABLE 1-continued
| Example | Structure | Molecular Formula | (M + H)+ |
|---|---|---|---|
| 459 | 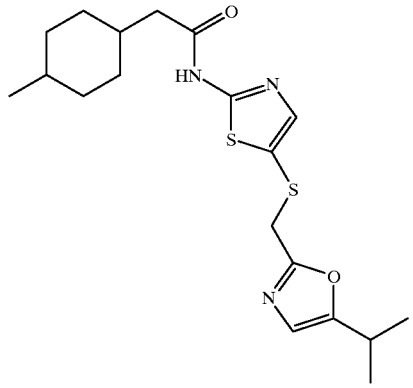 | C19H27N3O2S2 | 394 |
| 460 | 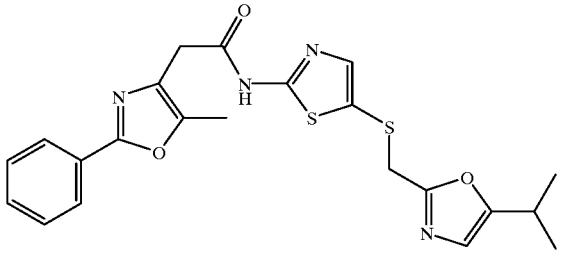 | C22H22N4O3S2 | 455 |
| 461 | 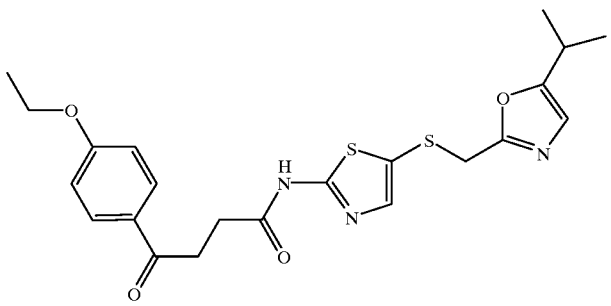 | C22H25N3O4S2 | 460 |
| 462 | 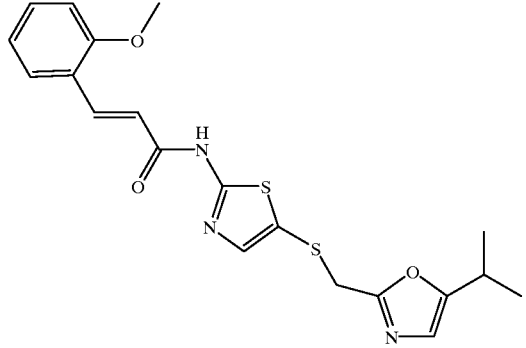 | C20H21N3O3S2 | 416 |

TABLE 1-continued

| Example | Structure | Molecular Formula | (M + H)+ |
|---|---|---|---|
| 463 | 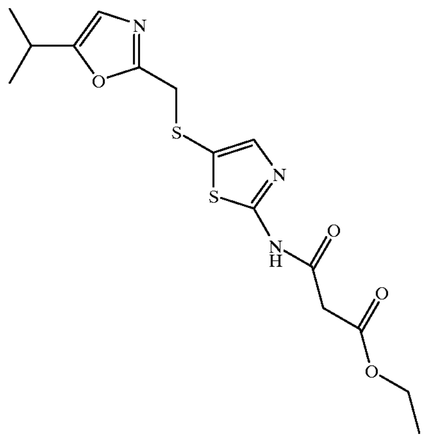 | C15H19N3O4S2 | 370 |
| 464 | 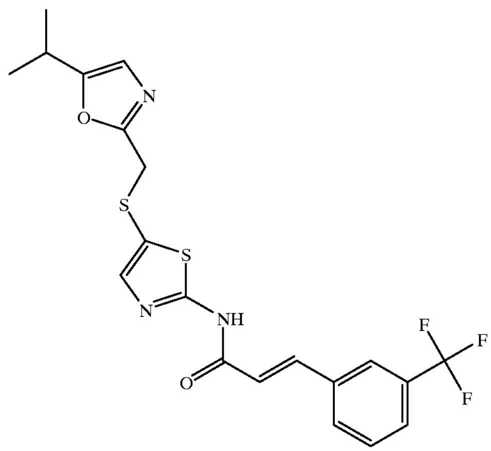 | C20H18F3N3O2S2 | 454 |
| 465 | 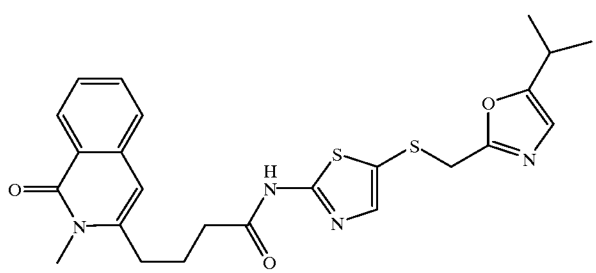 | C24H26N4O3S2 | 483 |
| 466 | 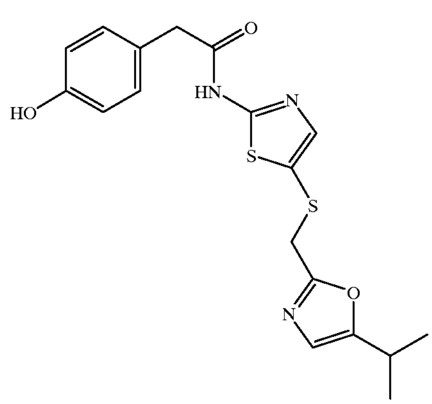 | C18H19N3O3S2 | 390 |

TABLE 1-continued

| Example | Structure | Molecular Formula | (M + H)+ |
| --- | --- | --- | --- |
| 467 | 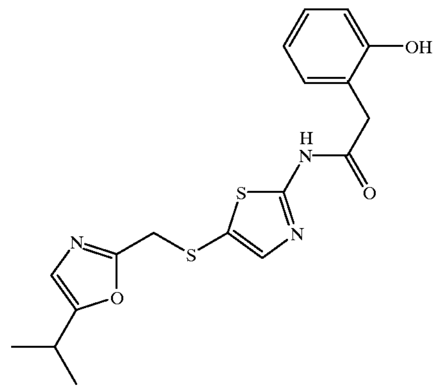 | C18H19N3O3S2 | 390 |
| 468 | 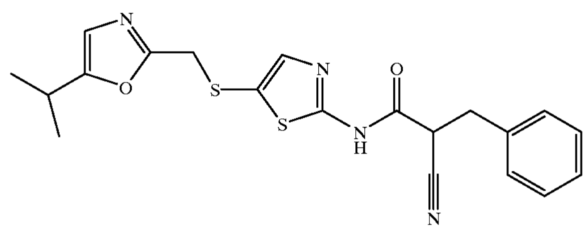 | C20H20N4O2S2 | 413 |
| 469 | 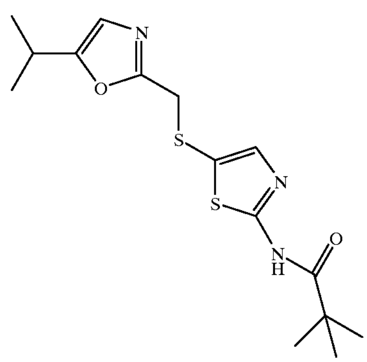 | C15H21N3O2S2 | 340 |
| 470 | 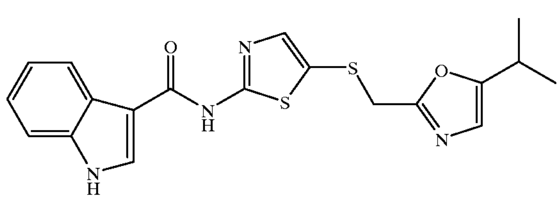 | C19H18N4O2S2 | 399 |

TABLE 1-continued

| Example | Structure | Molecular Formula | (M + H)+ |
|---|---|---|---|
| 471 | 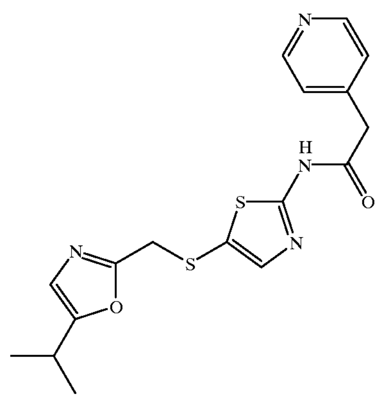 | C17H18N4O2S2 | 489 |
| 472 | 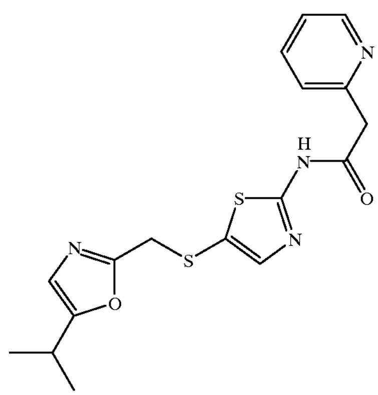 | C17H18N4O2S2 | 489 |
| 473 | 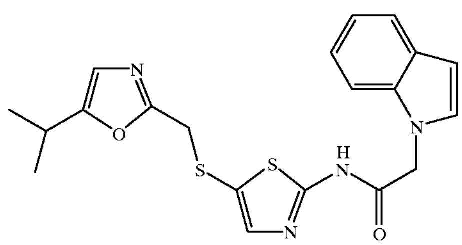 | C20H20N4O2S2 | 413 |
| 474 | 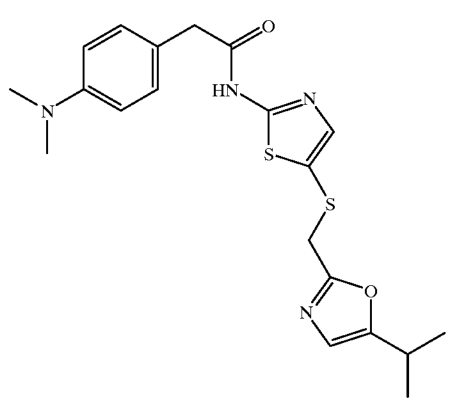 | C20H24N4O2S2 | 531 |

TABLE 1-continued

| Example | Structure | Molecular Formula | (M + H)+ |
| --- | --- | --- | --- |
| 475 | 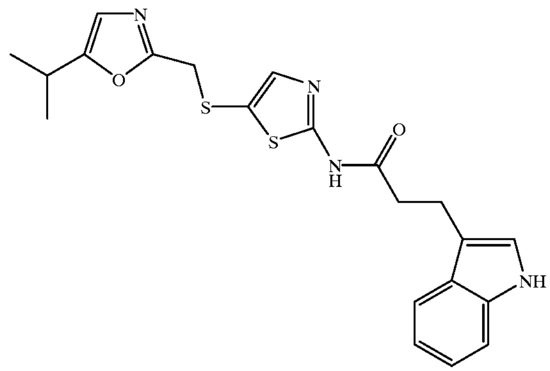 | C21H22N4O2S2 | 427 |
| 476 | 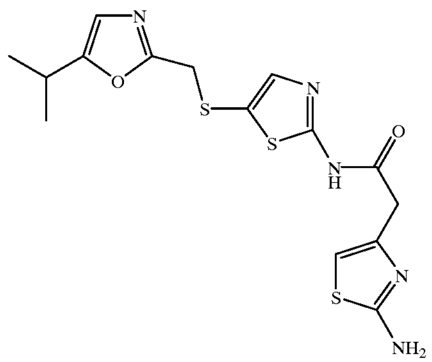 | C15H17N5O2S3 | 510 |
| 477 | 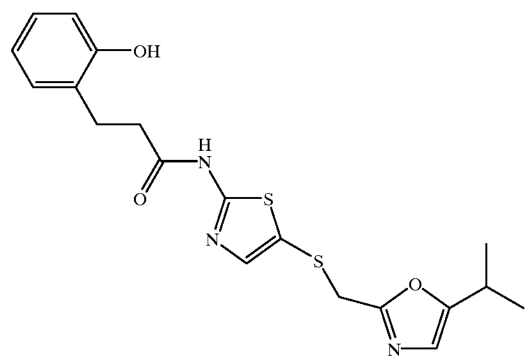 | C19H21N3O3S2 | 404 |
| 478 | 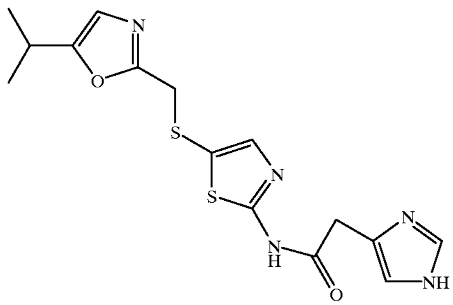 | C15H17N5O2S2 | 478 |

TABLE 1-continued

| Example | Structure | Molecular Formula | (M + H)+ |
|---|---|---|---|
| 479 | 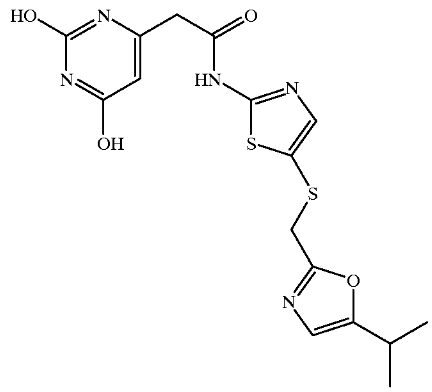 | C16H17N5O4S2 | 408 |
| 480 | 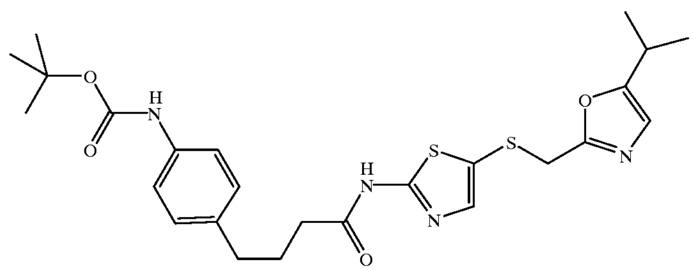 | C25H32N4O4S2 | 517 |
| 481 | 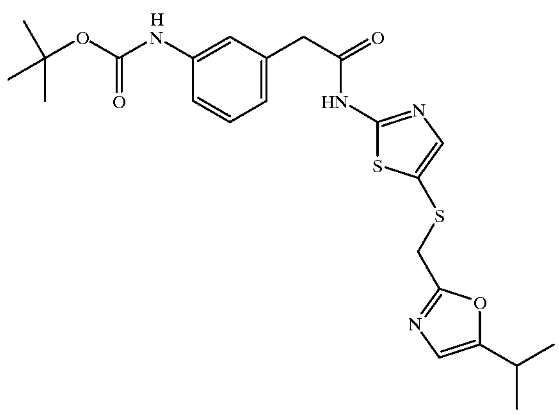 | C23H28N4O4S2 | 489 |
| 482 | 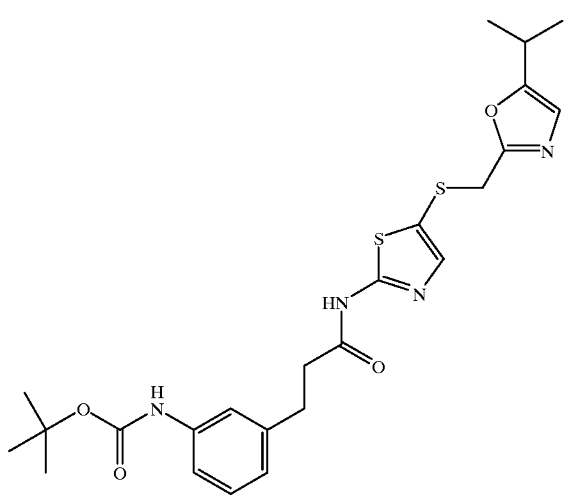 | C24H30N4O4S2 | 503 |

TABLE 1-continued

| Example | Structure | Molecular Formula | (M + H)+ |
|---|---|---|---|
| 483 | 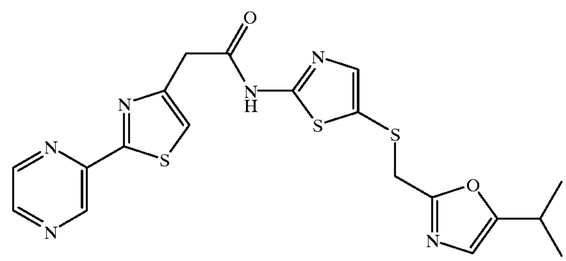 | C19H18N6O2S3 | 459 |
| 484 | 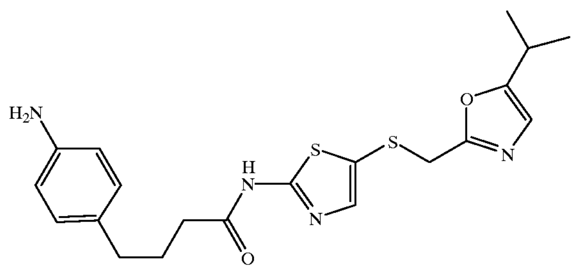 | C20H24N4O2S2 | 531 |
| 485 | 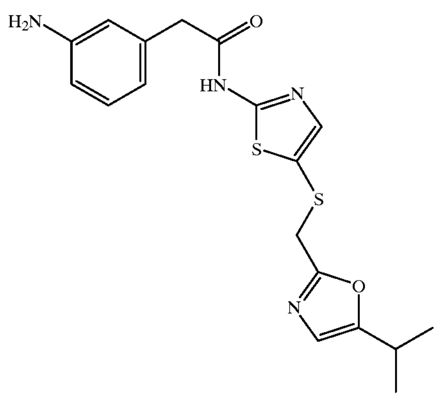 | C18H20N4O2S2 | 503 |
| 486 | 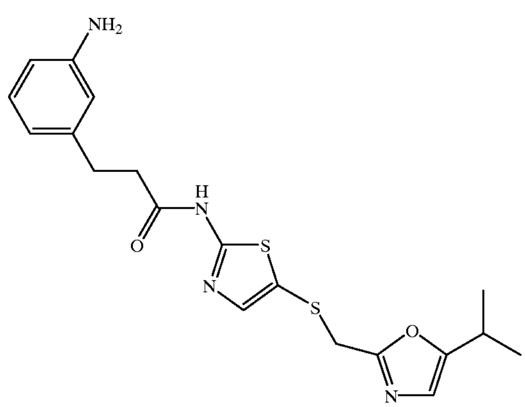 | C19H22N4O2S2 | 517 |

TABLE 1-continued

| Example | Structure | Molecular Formula | (M + H)+ |
|---|---|---|---|
| 487 | 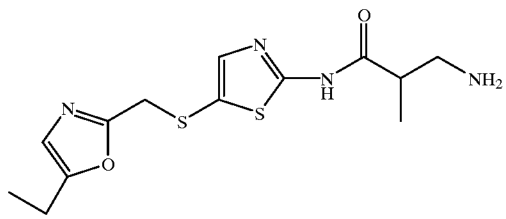 | C13H18N4O2S2 | 363 |
| 488 | 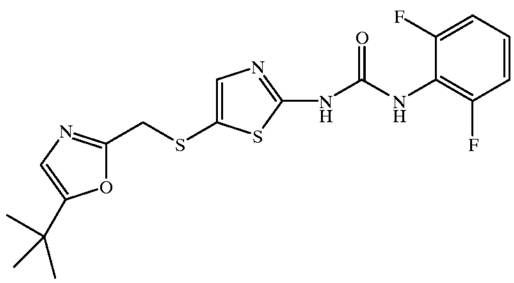 | C18H18F2N4O2S2 | 425 |
| 489 | 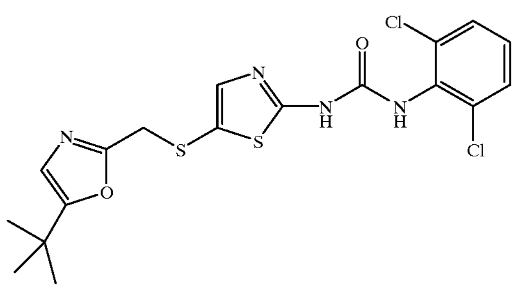 | C18H18Cl2N4O2S2 | 458 |
| 490 | 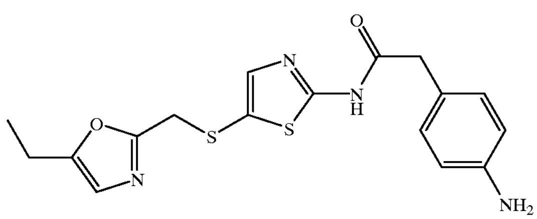 | C17H18N4O2S2 | 489 |
| 491 | 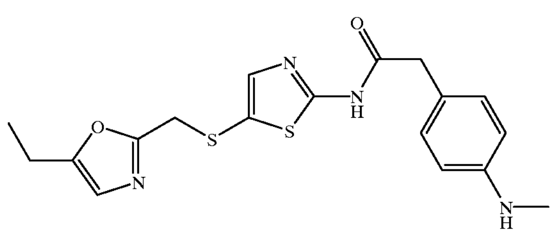 | C18H20N4O2S2 | 389 |
| 492 | 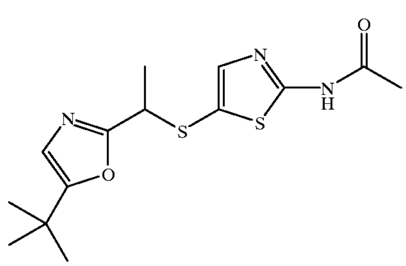 | C14H19N3O2S2 | 326 |

TABLE 1-continued

| Example | Structure | Molecular Formula | (M + H)+ |
|---------|-----------|-------------------|----------|
| 493 | 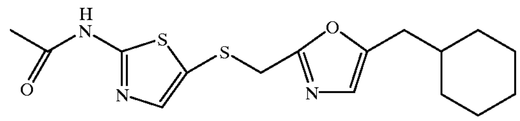 | C16H21N3O2S2 | 352 |
| 494 | 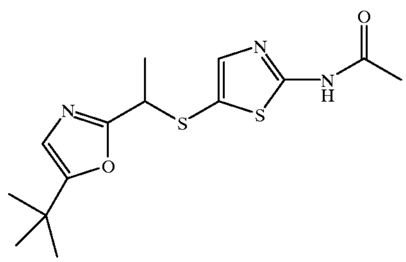 | C14H19N3O2S2 | 326 |
| 495 | 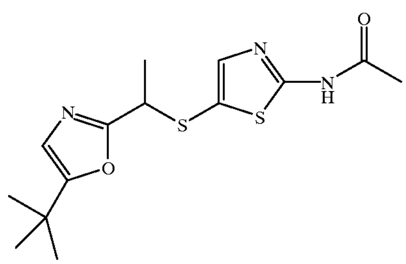 | C14H19N3O2S2 | 326 |
| 496 | 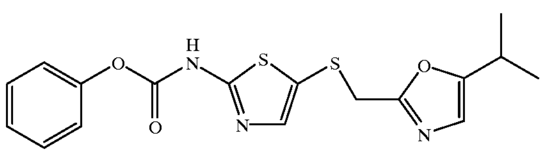 | C17H17N3O3S2 | 376 |
| 497 | 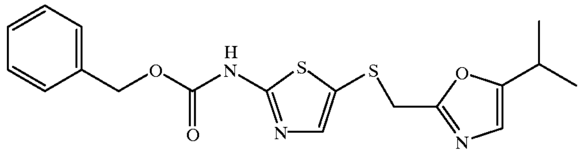 | C18H19N3O3S2 | 390 |
| 498 | 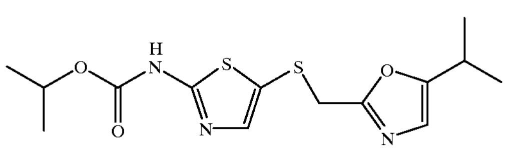 | C14H19N3O3S2 | 342 |
| 499 | 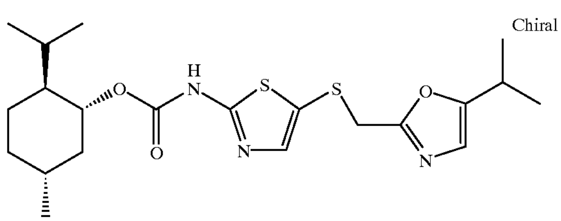 | C21H31N3O3S2 | 438 |

TABLE 1-continued

| Example | Structure | Molecular Formula | (M + H)+ |
|---|---|---|---|
| 500 | 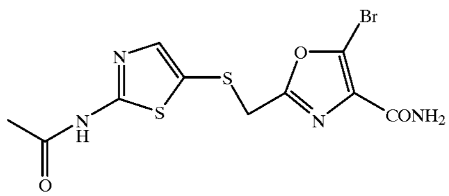 | C10H9BrN4O3S2 | 378 |
| 501 | 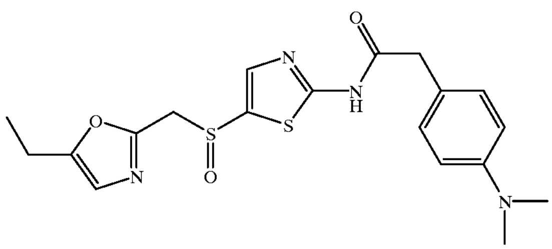 | C19H22N4O3S2 | 419 |
| 502 | 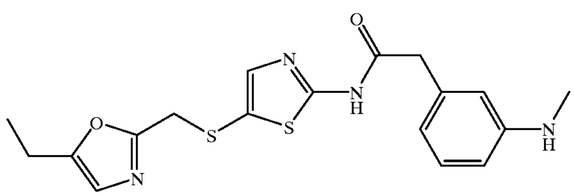 | C18H20N4O2S2 | 389 |
| 503 | 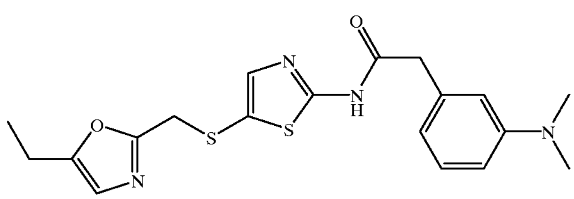 | C19H22N4O2S2 | 403 |
| 504 | 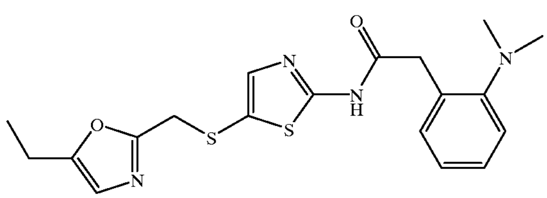 | C19H22N4O2S2 | 403 |
| 505 | 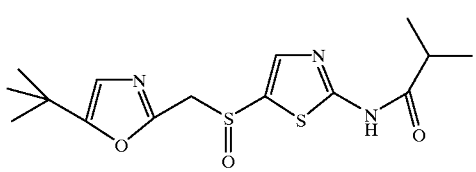 | C15H21N3O3S2 | 356 |
| 506 | 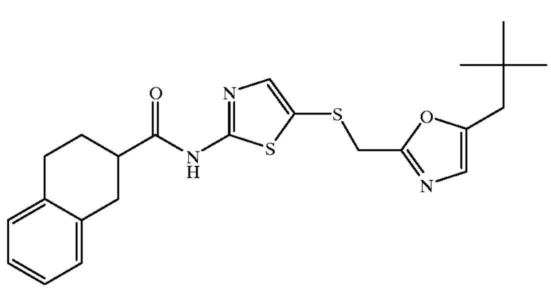 | C23H27N3O2S2 | 442 |

TABLE 1-continued
| Example | Structure | Molecular Formula | (M + H)+ |
| --- | --- | --- | --- |
| 507 | 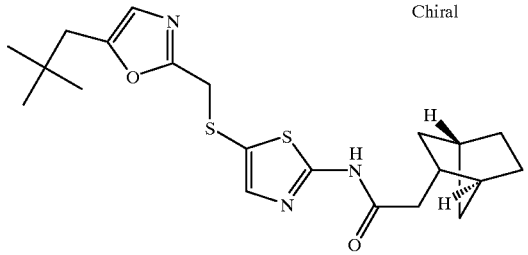 Chiral | C21H29N3O2S2 | 420 |
| 508 | 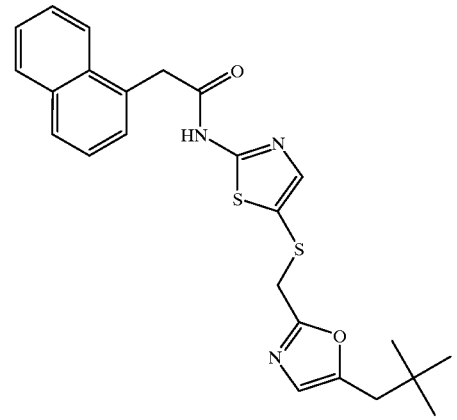 | C24H25N3O2S2 | 452 |
| 509 | 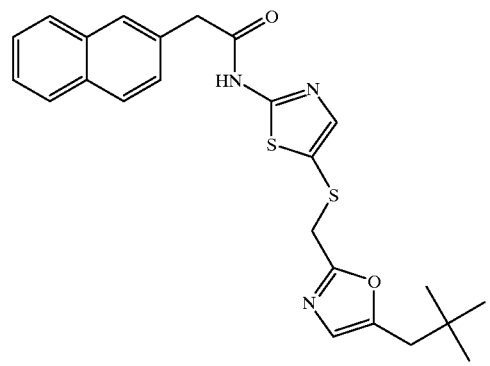 | C24H25N3O2S2 | 452 |
| 510 | 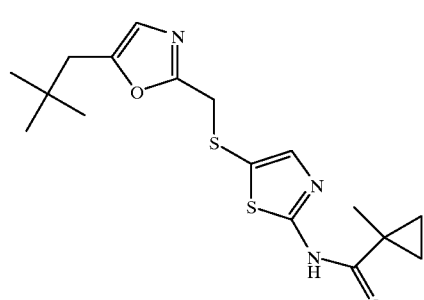 | C17H23N3O2S2 | 366 |

TABLE 1-continued
| Example | Structure | Molecular Formula | (M + H)+ |
|---|---|---|---|
| 511 | 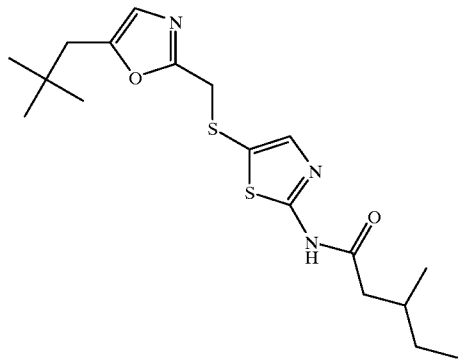 | C18H27N3O2S2 | 382 |
| 512 | 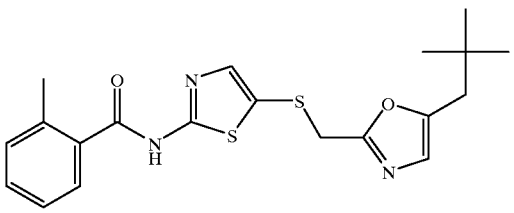 | C20H23N3O2S2 | 402 |
| 513 | 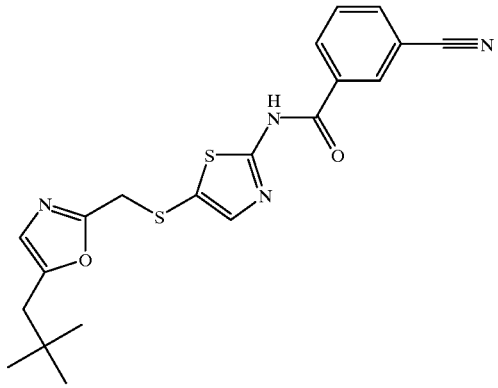 | C20H20N4O2S2 | 413 |
| 514 | 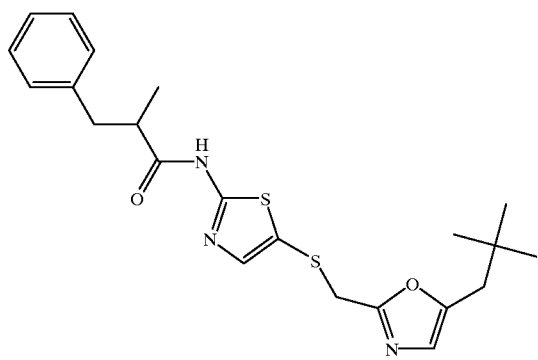 | C22H27N3O2S2 | 430 |

TABLE 1-continued
| Example | Structure | Molecular Formula | (M + H)+ |
|---|---|---|---|
| 515 | 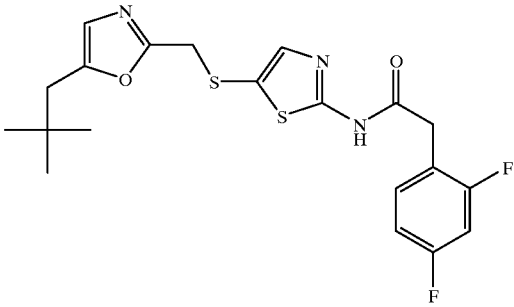 | C20H21F2N3O2S2 | 438 |
| 516 | 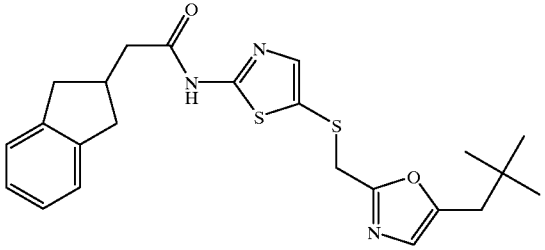 | C23H27N3O2S2 | 442 |
| 517 | 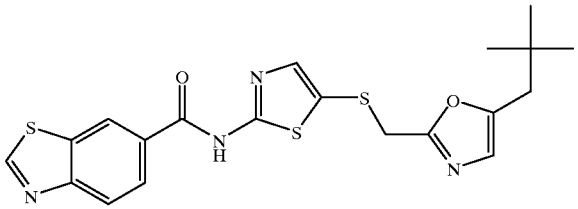 | C20H20N4O2S3 | 445 |
| 518 | 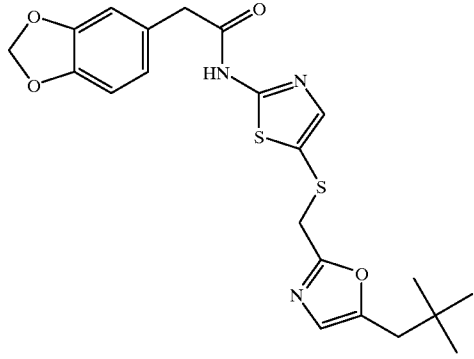 | C21H23N3O4S2 | 446 |
| 519 | 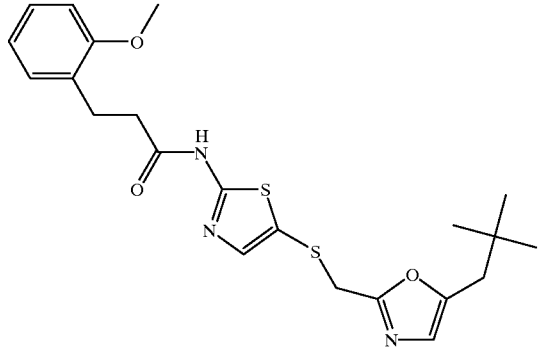 | C22H27N3O3S2 | 446 |

TABLE 1-continued
| Example | Structure | Molecular Formula | (M + H)+ |
|---|---|---|---|
| 520 | 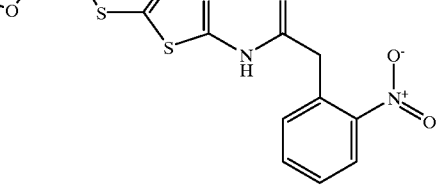 | C20H22N4O4S2 | 447 |
| 521 | 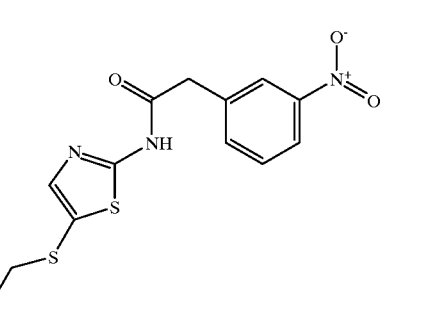 | C20H22N4O4S2 | 447 |
| 522 | 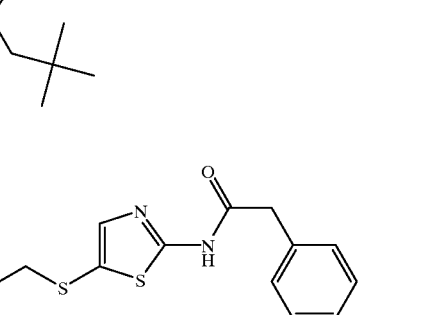 | C20H22N4O4S2 | 447 |
| 523 | 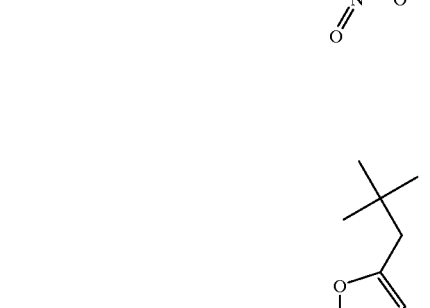 | C21H25N3O3S2 | 432 |

TABLE 1-continued

| Example | Structure | Molecular Formula | (M + H)+ |
|---|---|---|---|
| 524 | 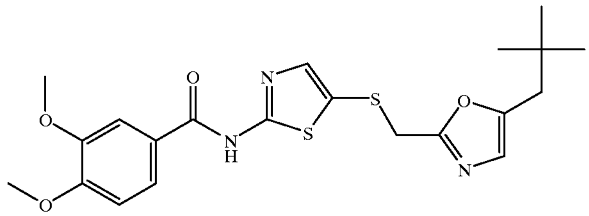 | C21H25N3O4S2 | 448 |
| 525 | 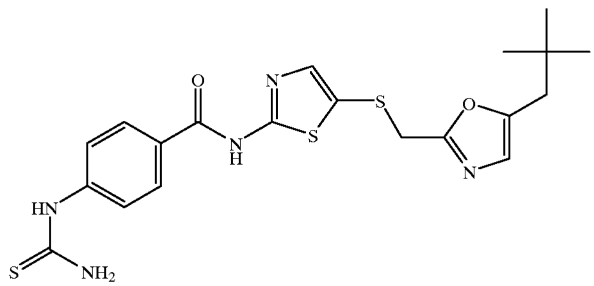 | C20H23N5O2S3 | 462 |
| 526 | 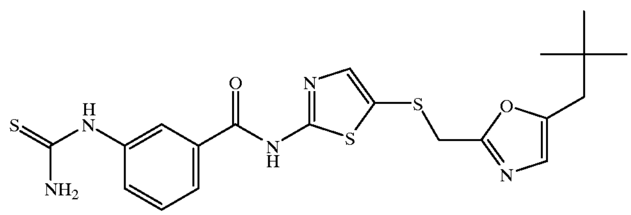 | C20H23N5O2S3 | 462 |
| 527 | 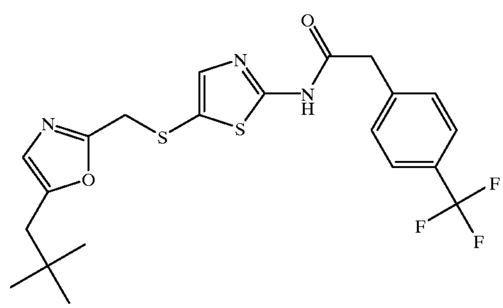 | C21H22F3N3O2S2 | 470 |
| 528 | 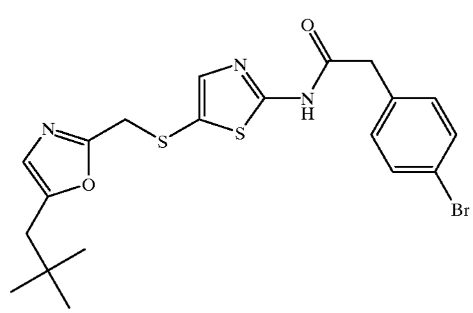 | C20H22BrN3O2S2 | 481 |

TABLE 1-continued
| Example | Structure | Molecular Formula | (M + H)+ |
|---|---|---|---|
| 529 | 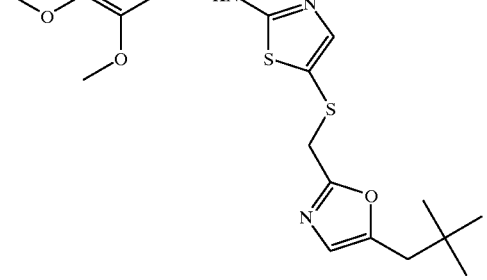 | C23H29N3O5S2 | 492 |
| 530 | 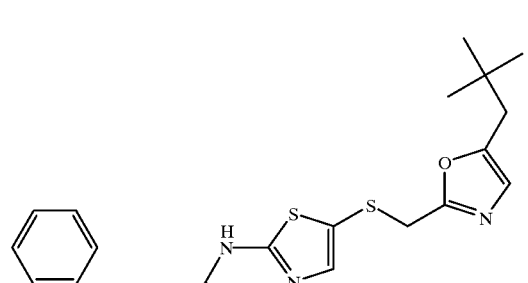 | C21H24N4O3S2 | 445 |
| 531 | 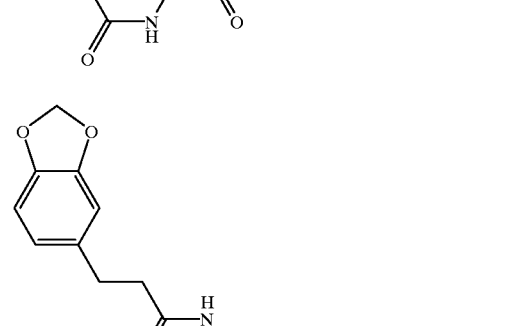 | C22H25N3O4S2 | 460 |
| 532 | 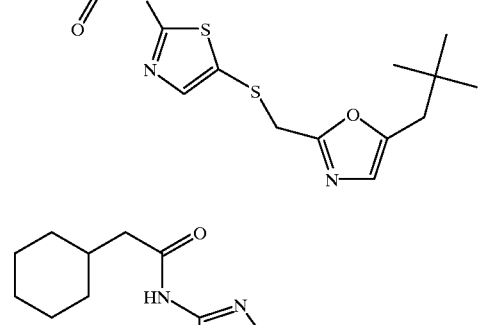 | C20H29N3O2S2 | 408 |

TABLE 1-continued

| Example | Structure | Molecular Formula | (M + H)+ |
|---|---|---|---|
| 533 | 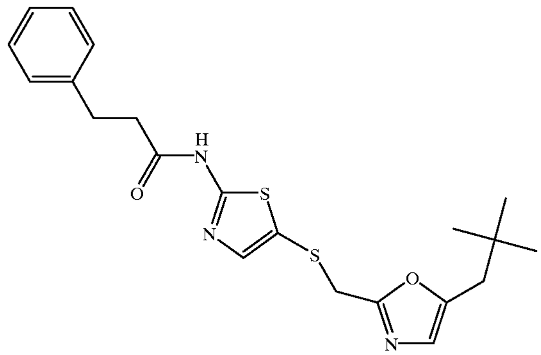 | C21H25N3O2S2 | 416 |
| 534 | 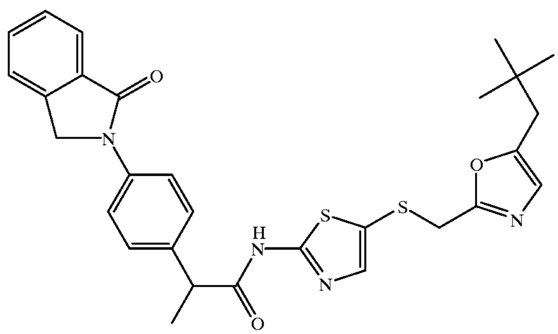 | C29H30N4O3S2 | 547 |
| 535 | 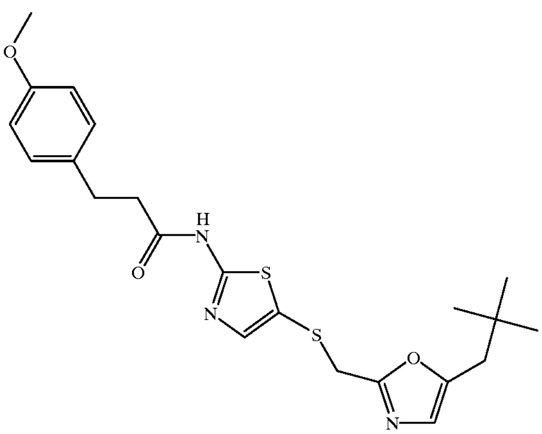 | C22H27N3O3S2 | 446 |
| 536 | 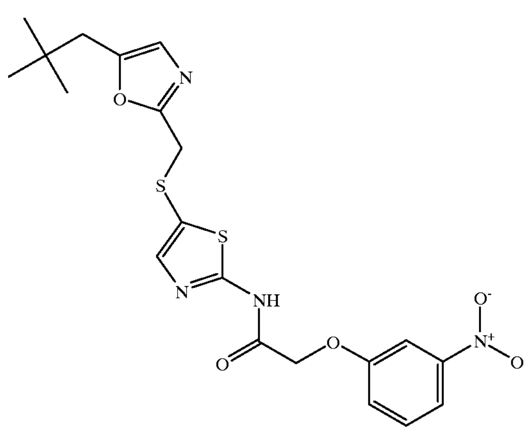 | C20H22N4O5S2 | 463 |

TABLE 1-continued
| Example | Structure | Molecular Formula | (M + H)+ |
|---|---|---|---|
| 537 | 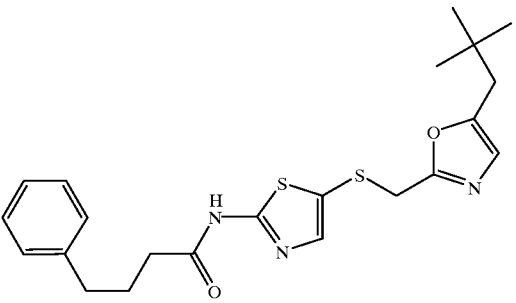 | C22H27N3O2S2 | 430 |
| 538 | Chiral 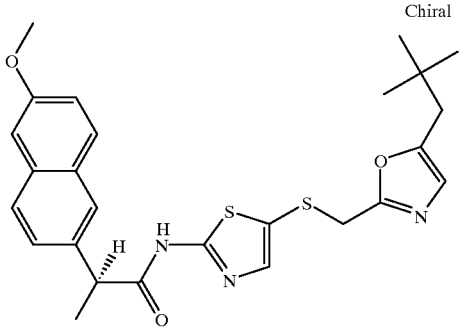 | C26H29N3O3S2 | 496 |
| 539 | Chiral 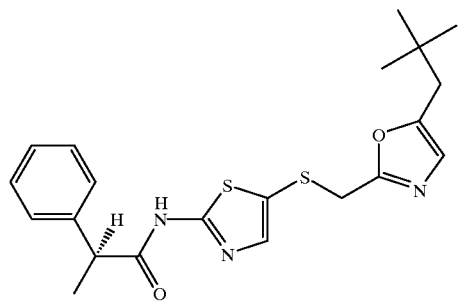 | C21H25N3O2S2 | 416 |
| 540 | 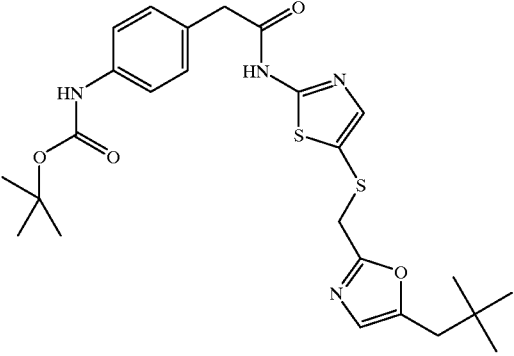 | C25H32N4O4S2 | 517 |

TABLE 1-continued
| Example | Structure | Molecular Formula | (M + H)+ |
|---|---|---|---|
| 541 | 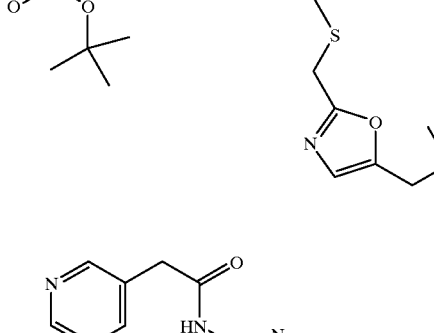 | C26H34N4O4S2 | 531 |
| 542 | 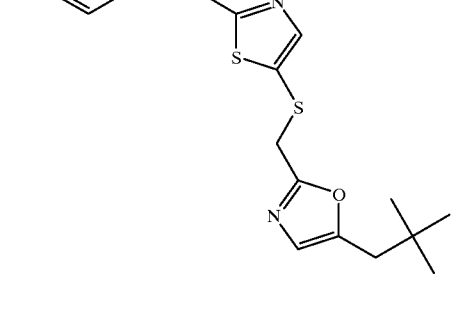 | C19H22N4O2S2 | 517 |
| 543 | 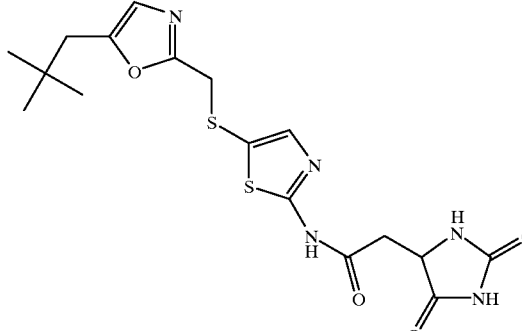 | C17H21N5O4S2 | 424 |
| 544 | 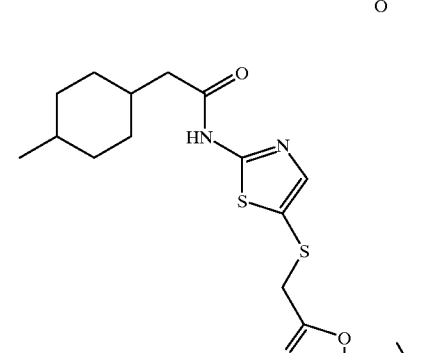 | C21H31N3O2S2 | 422 |

TABLE 1-continued
| Example | Structure | Molecular Formula | (M + H)+ |
|---|---|---|---|
| 545 | 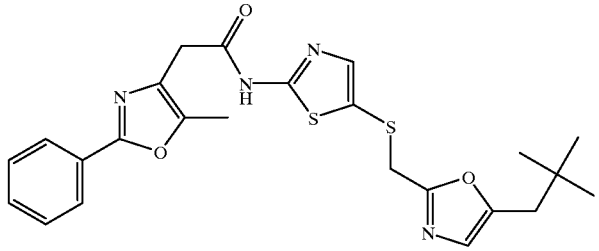 | C24H26N4O3S2 | 483 |
| 546 | 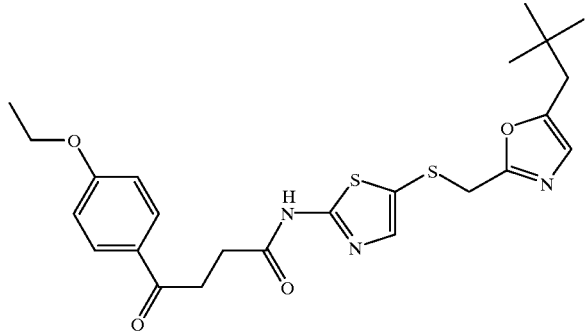 | C24H29N3O4S2 | 488 |
| 547 | 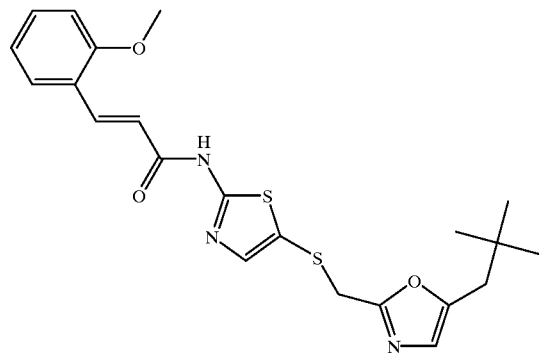 | C22H25N3O3S2 | 444 |
| 548 | 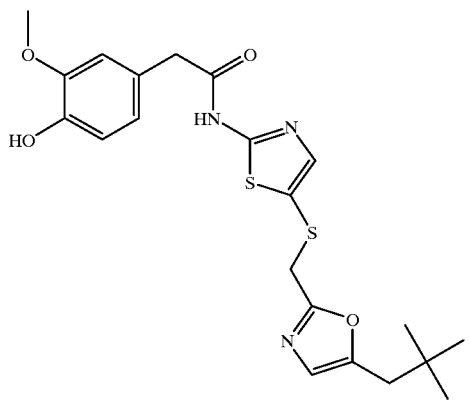 | C21H25N3O4S2 | 448 |

TABLE 1-continued

| Example | Structure | Molecular Formula | (M + H)+ |
|---|---|---|---|
| 549 | 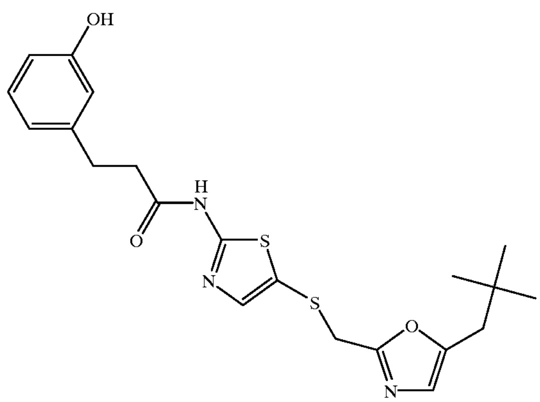 | C21H25N3O3S2 | 432 |
| 550 | 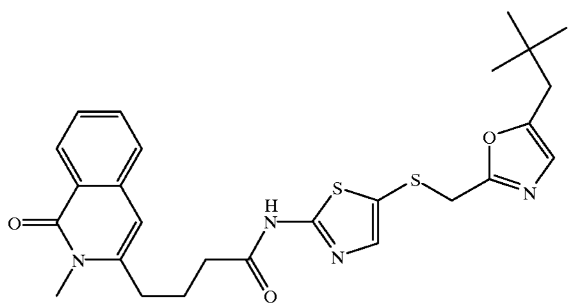 | C26H30N4O3S2 | 511 |
| 551 | 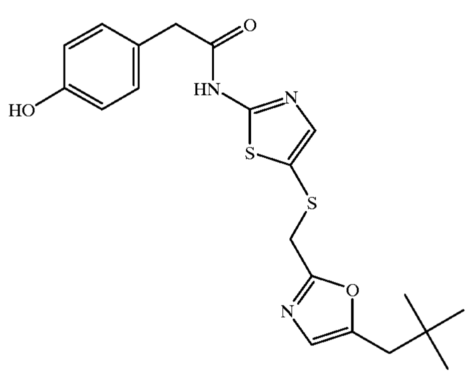 | C20H23N3O3S2 | 418 |
| 552 | 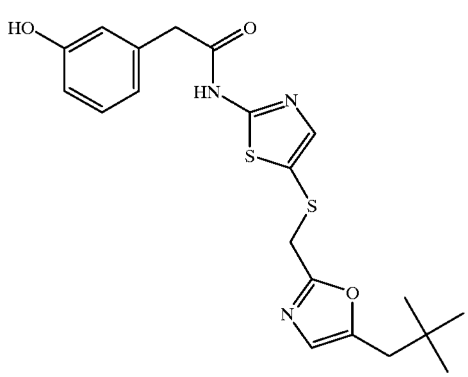 | C20H23N3O3S2 | 418 |

TABLE 1-continued

| Example | Structure | Molecular Formula | (M + H)+ |
|---|---|---|---|
| 553 | 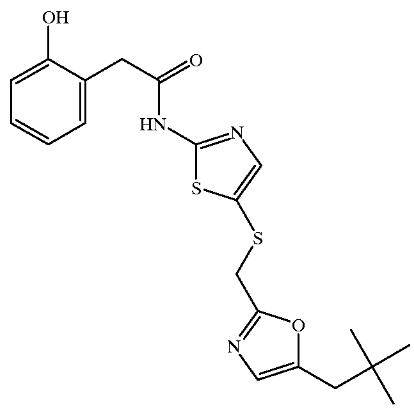 | C20H23N3O3S2 | 418 |
| 554 | 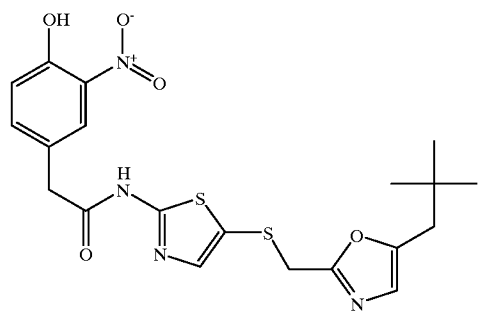 | C20H22N4O5S2 | 463 |
| 555 | 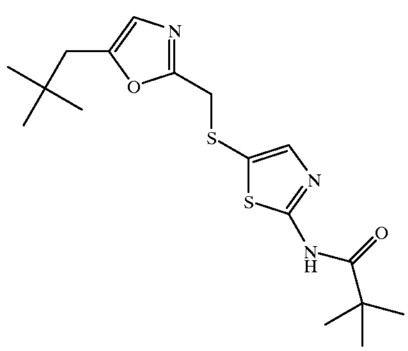 | C17H25N3O2S2 | 368 |
| 556 | 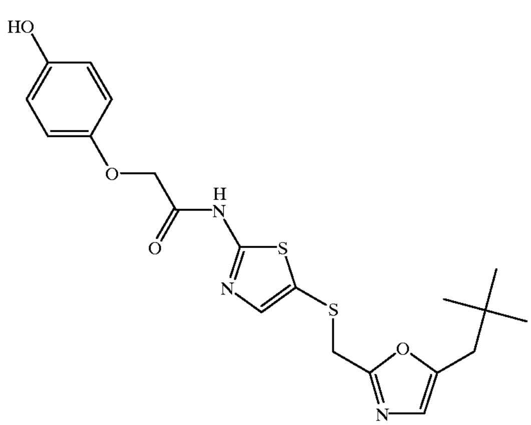 | C20H23N3O4S2 | 434 |

TABLE 1-continued

| Example | Structure | Molecular Formula | (M + H)+ |
|---|---|---|---|
| 557 | 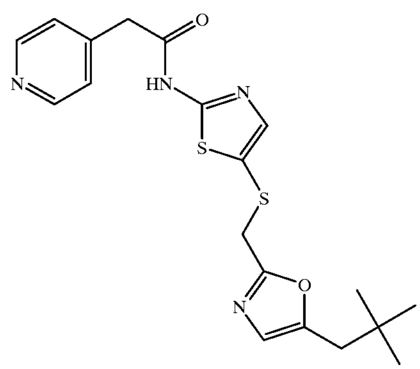 | C19H22N4O2S2 | 517 |
| 558 | 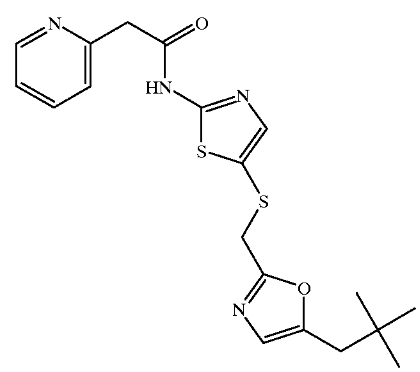 | C19H22N4O2S2 | 517 |
| 559 | 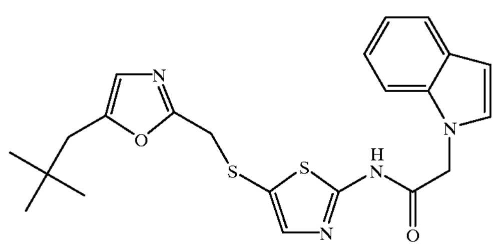 | C22H24N4O2S2 | 441 |
| 560 | 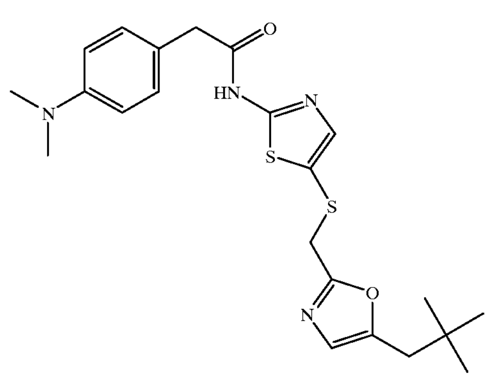 | C22H28N4O2S2 | 559 |

TABLE 1-continued
| Example | Structure | Molecular Formula | (M + H)+ |
|---|---|---|---|
| 561 | 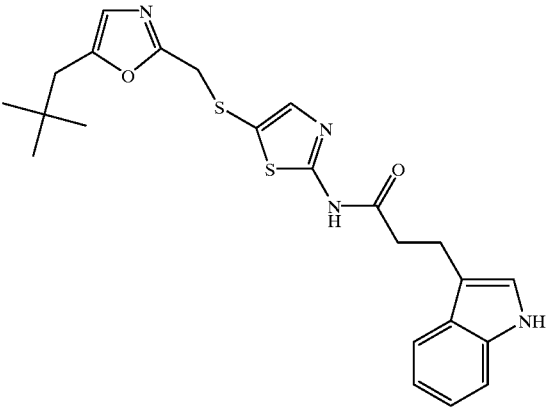 | C23H26N4O2S2 | 569 |
| 562 | 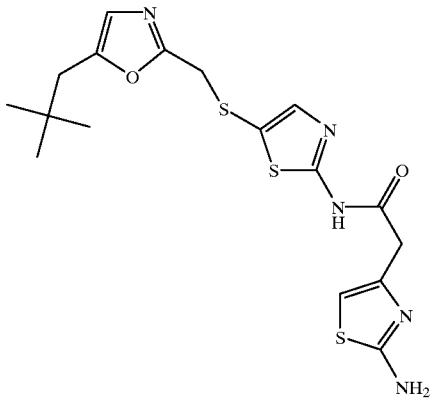 | C17H21N5O2S3 | 538 |
| 563 | 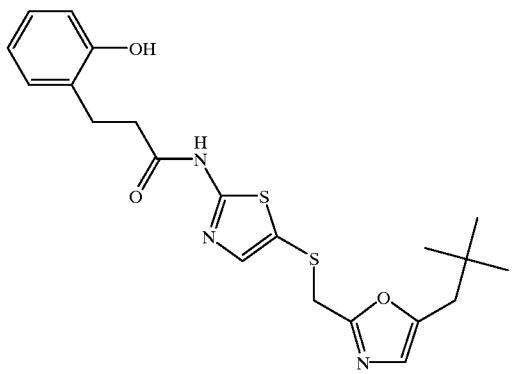 | C21H25N3O3S2 | 432 |
| 564 | 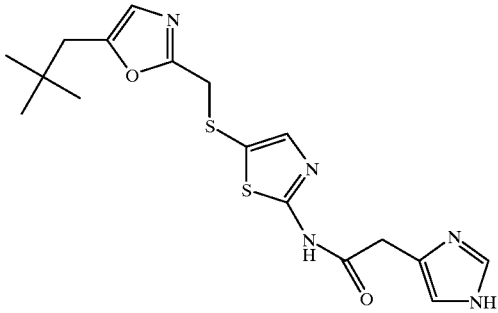 | C17H21N5O2S2 | 506 |

TABLE 1-continued

| Example | Structure | Molecular Formula | (M + H)+ |
|---|---|---|---|
| 565 | 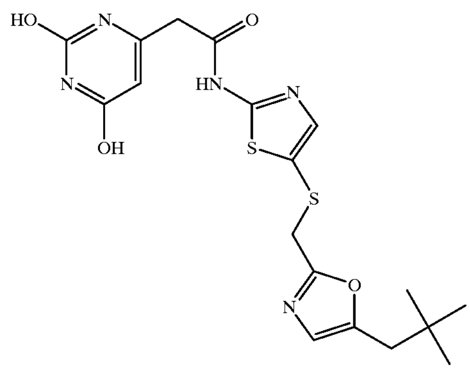 | C18H21N5O4S2 | 436 |
| 566 | 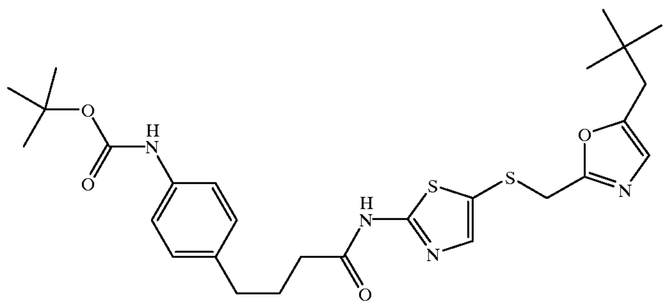 | C27H36N4O4S2 | 545 |
| 567 | 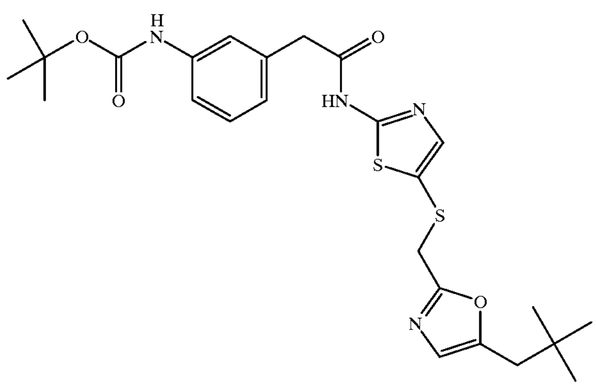 | C25H32N4O4S2 | 517 |

TABLE 1-continued
| Example | Structure | Molecular Formula | (M + H)+ |
|---|---|---|---|
| 568 | 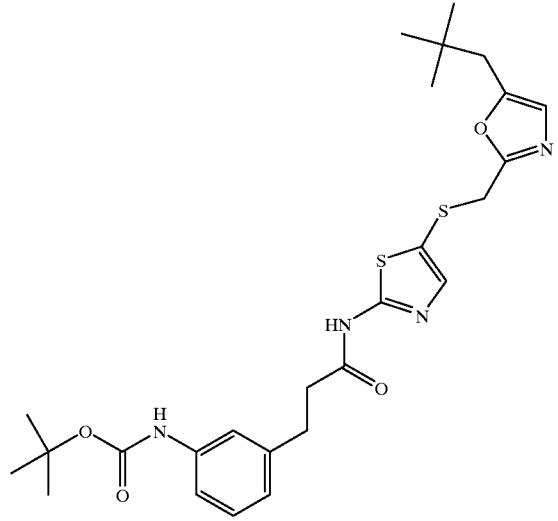 | C26H34N4O4S2 | 531 |
| 569 | 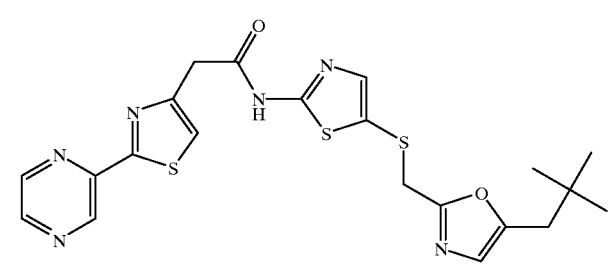 | C21H22N6O2S3 | 487 |
| 570 | 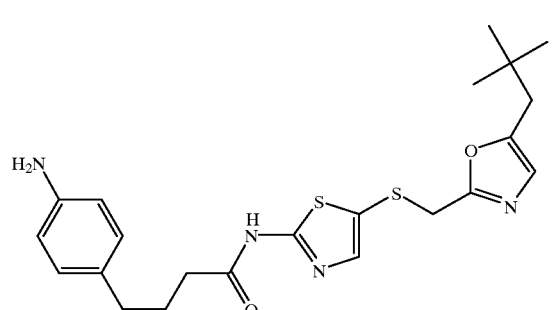 | C22H28N4O2S2 | 559 |
| 571 | 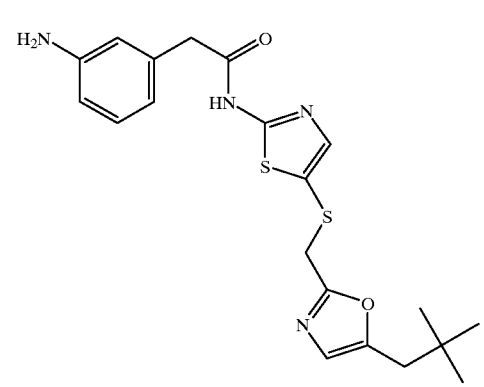 | C20H24N4O2S2 | 531 |

TABLE 1-continued

| Example | Structure | Molecular Formula | (M + H)+ |
| --- | --- | --- | --- |
| 572 | 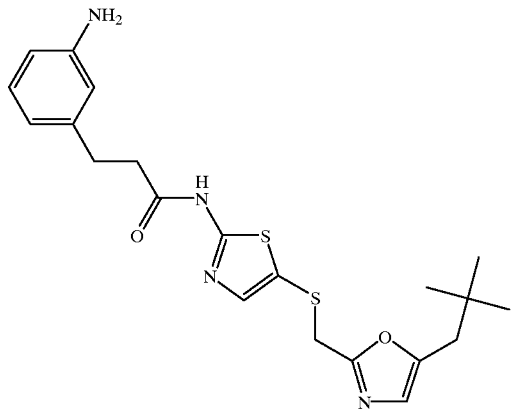 | C21H26N4O2S2 | 545 |
| 573 | 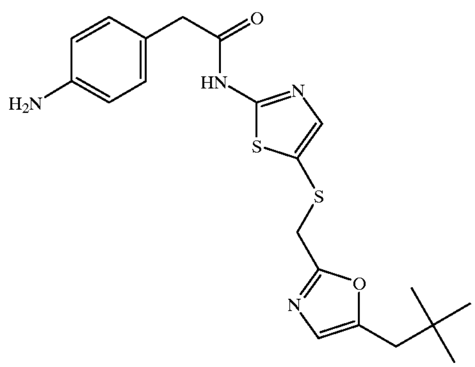 | C20H24N4O2S2 | 531 |
| 574 | 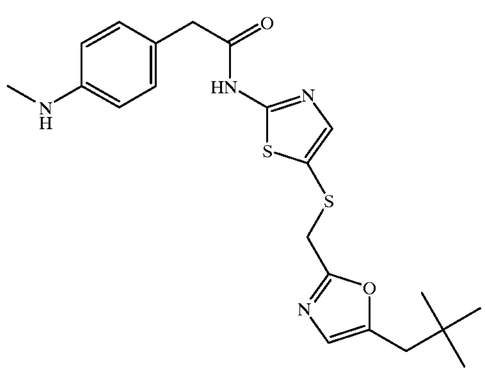 | C21H26N4O2S2 | 545 |
| 575 | 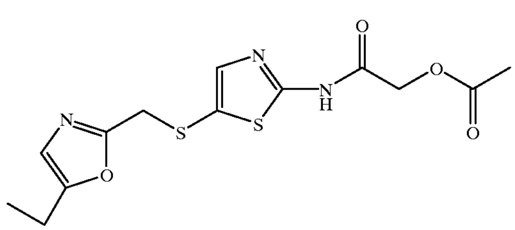 | C13H15N3O4S2 | 342 |

TABLE 1-continued
| Example | Structure | Molecular Formula | (M + H)+ |
|---|---|---|---|
| 576 | 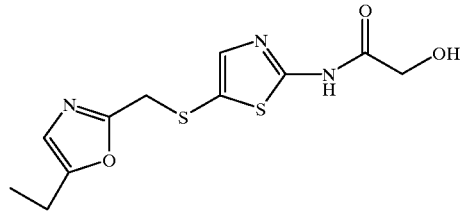 | C11H13N3O3S2 | 300 |
| 577 | 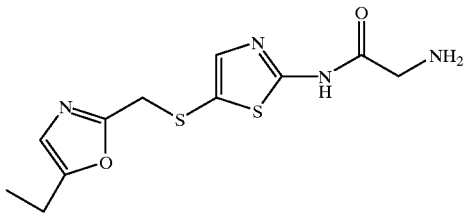 | C11H14N4O2S2 | 413 |
| 578 | 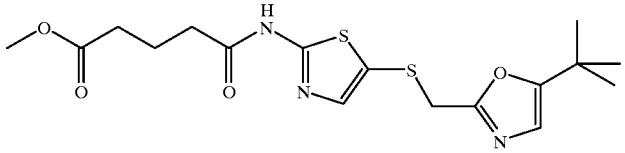 | C17H23N3O4S2 | 398 |
| 579 | 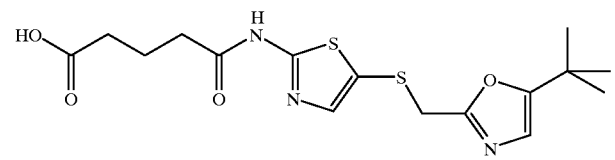 | C16H21N3O4S2 | 384 |
| 580 | 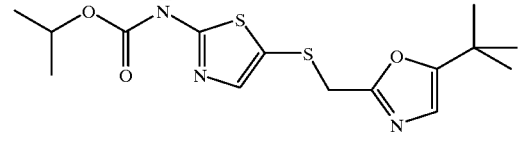 | C15H21N3O3S2 | 356 |
| 581 | 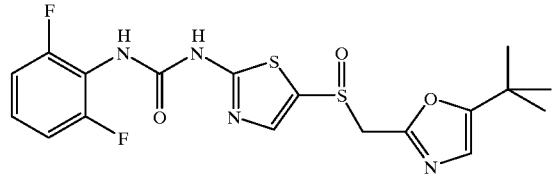 | C18H18F2N4O3S2 | 441 |
| 582 | 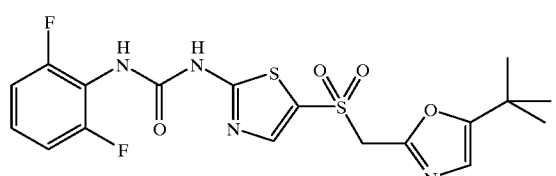 | C18H18F2N4O4S2 | 457 |
| 583 | 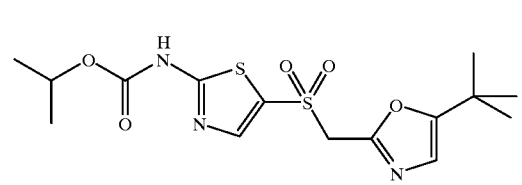 | C15H21N3O5S2 | 388 |

TABLE 1-continued

| Example | Structure | Molecular Formula | (M + H)+ |
|---|---|---|---|
| 584 | 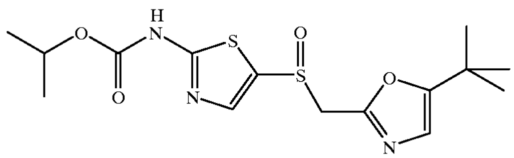 | C15H21N3O4S2 | 372 |
| 585 | 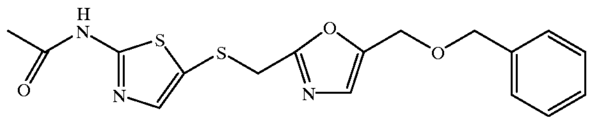 | C17H17N3O3S2 | 376 |
| 586 | 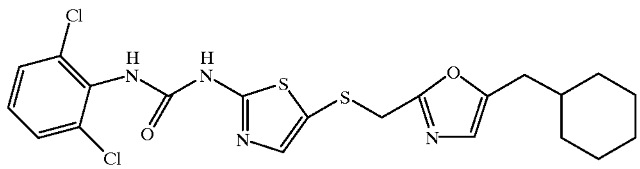 | C21H22Cl2N4O2S2 | 498 |
| 587 | 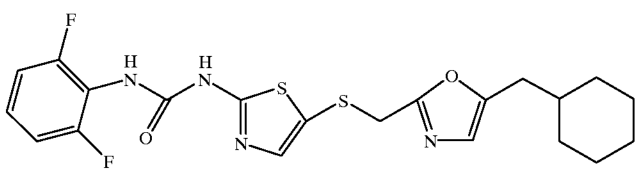 | C21H22F2N4O2S2 | 465 |
| 588 | 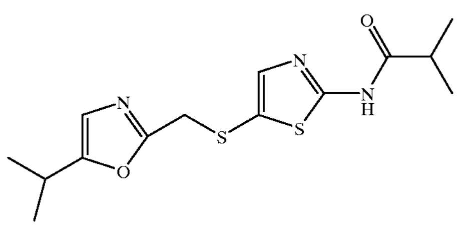 | C14H19N3O2S2 | 326 |
| 589 | 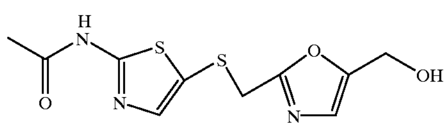 | C10H11N3O3S2 | 286 |
| 590 | 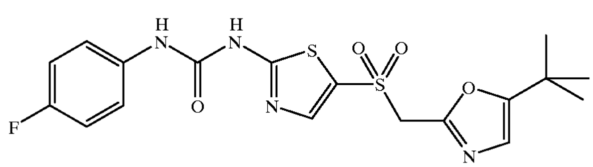 | C18H19FN4O4S2 | 439 |
| 591 | 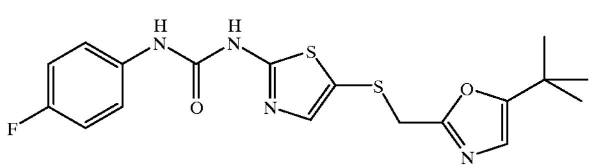 | C18H19FN4O2S2 | 407 |
| 592 | 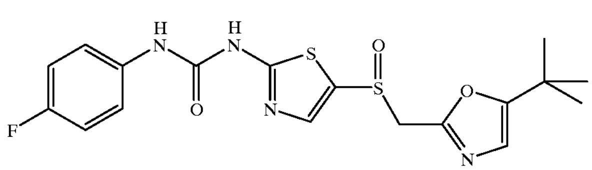 | C18H19FN4O3S2 | 423 |

TABLE 1-continued
| Example | Structure | Molecular Formula | (M + H)+ |
|---|---|---|---|
| 593 | 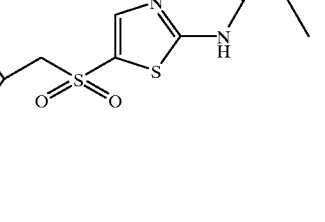 | C15H21N3O4S2 | 372 |
| 594 | 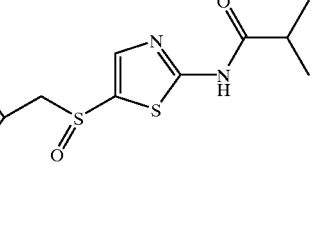 | C14H19N3O3S2 | 342 |
| 595 | 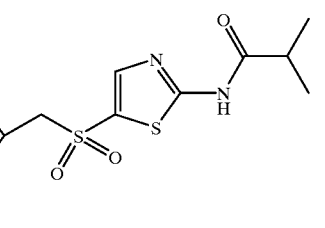 | C14H19N3O4S2 | 358 |
| 596 | 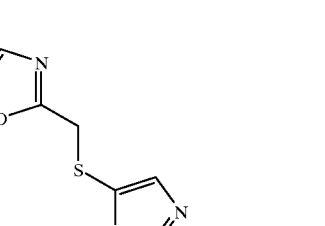 | C14H20N4O2S2 | 341 |
| 597 | 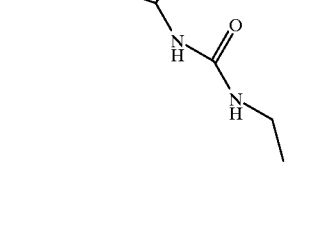 | C18H19FN4O2S2 | 407 |

TABLE 1-continued

| Example | Structure | Molecular Formula | (M + H)+ |
|---|---|---|---|
| 598 | 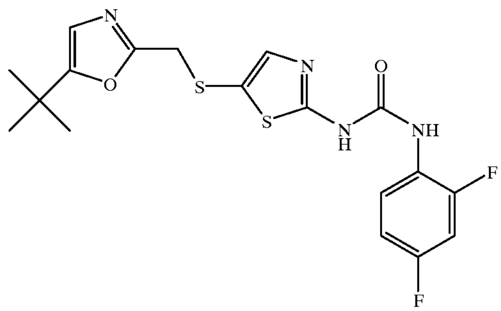 | C18H18F2N4O2S2 | 425 |
| 599 | 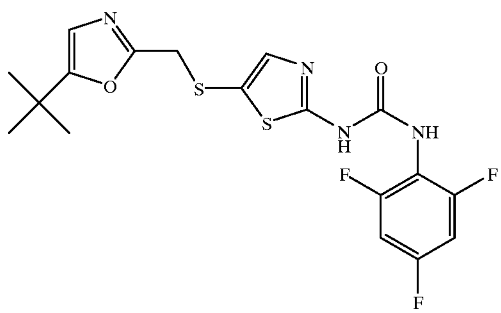 | C18H17F3N4O2S2 | 443 |
| 600 | 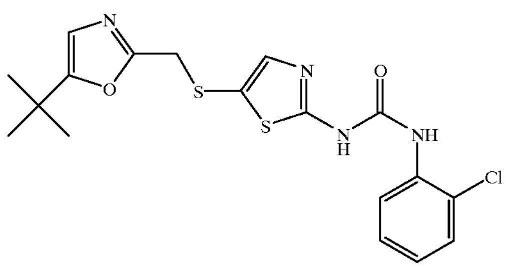 | C18H19ClN4O2S2 | 423 |
| 601 | 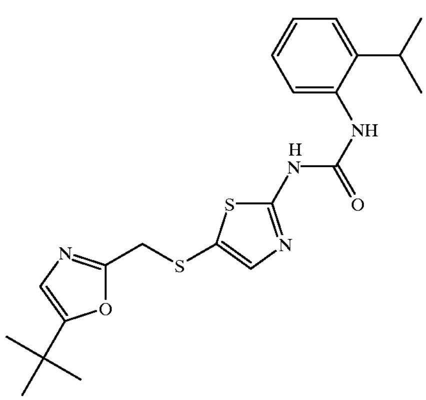 | C21H26N4O2S2 | 431 |

TABLE 1-continued

| Example | Structure | Molecular Formula | (M + H)+ |
|---|---|---|---|
| 602 | 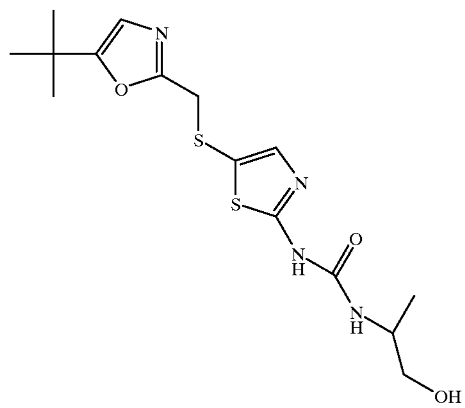 | C15H22N4O3S2 | 371 |
| 603 | 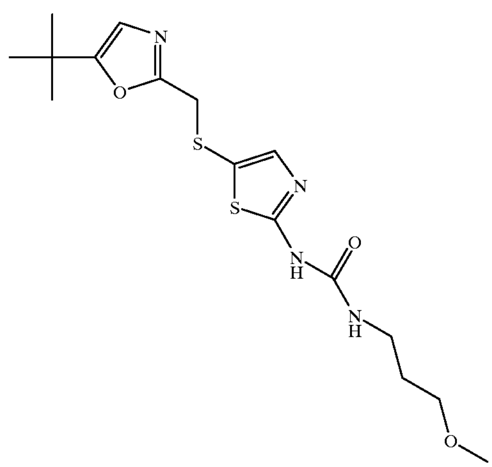 | C16H24N4O3S2 | 385 |
| 604 | 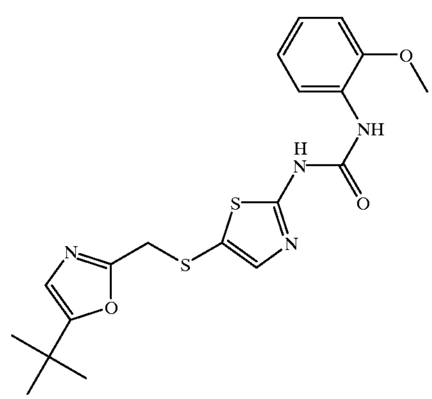 | C19H22N4O3S2 | 419 |

TABLE 1-continued
| Example | Structure | Molecular Formula | (M + H)+ |
|---|---|---|---|
| 605 | 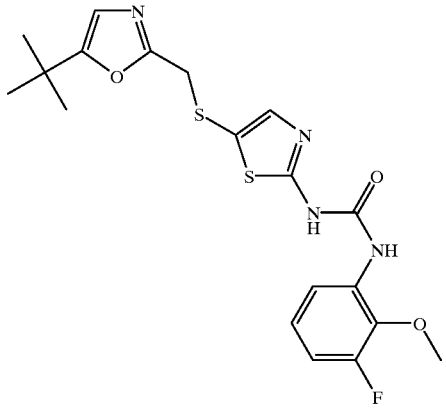 | C19H21FN4O3S2 | 437 |
| 606 | 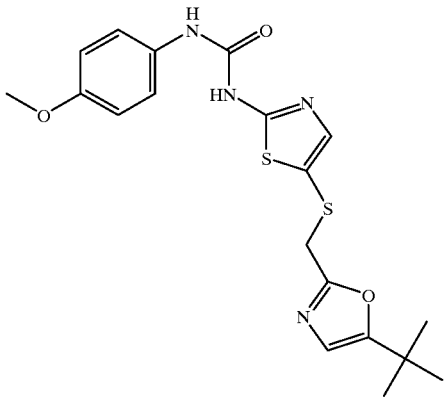 | C19H22N4O3S2 | 419 |
| 607 | 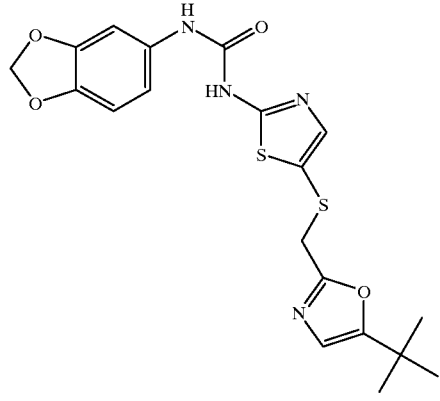 | C19H20N4O4S2 | 433 |

TABLE 1-continued
| Example | Structure | Molecular Formula | (M + H)+ |
|---|---|---|---|
| 608 | 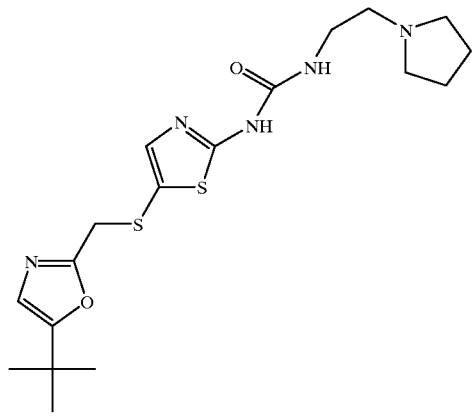 | C18H27N5O2S2 | 524 |
| 609 | 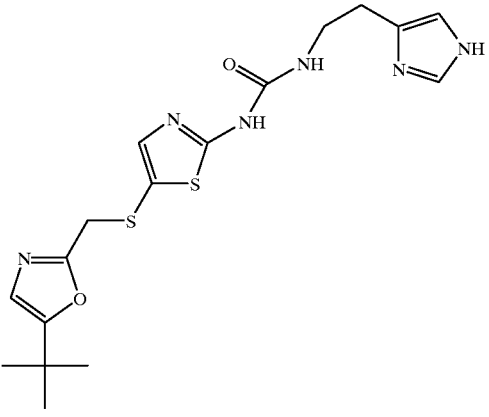 | C17H22N6O2S2 | 521 |
| 610 | 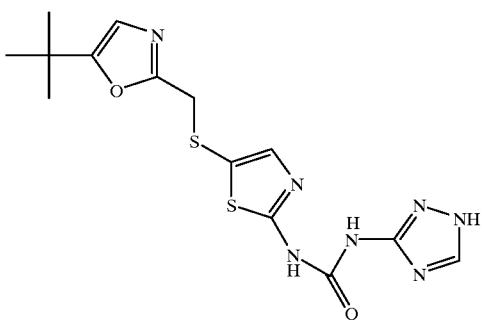 | C14H17N7O2S2 | 494 |

TABLE 1-continued
| Example | Structure | Molecular Formula | (M + H)+ |
|---|---|---|---|
| 611 | 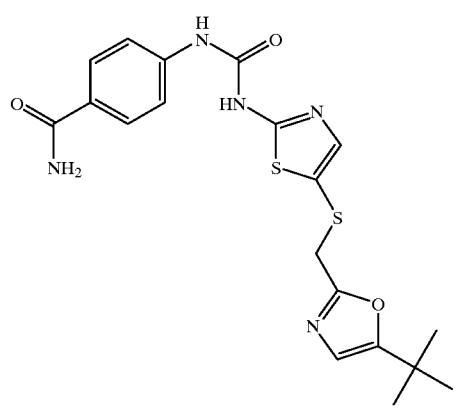 | C19H21N5O3S2 | 432 |
| 612 | 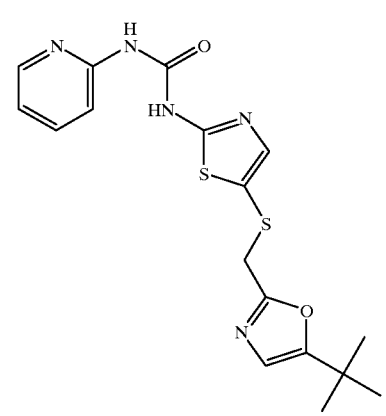 | C17H19N5O2S2 | 504 |
| 613 | 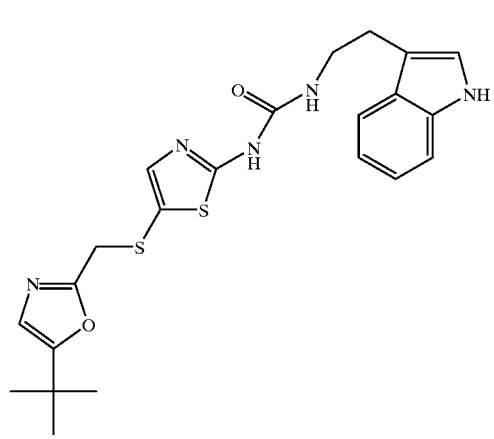 | C22H25N5O2S2 | 456 |

TABLE 1-continued

| Example | Structure | Molecular Formula | (M + H)+ |
| --- | --- | --- | --- |
| 614 | 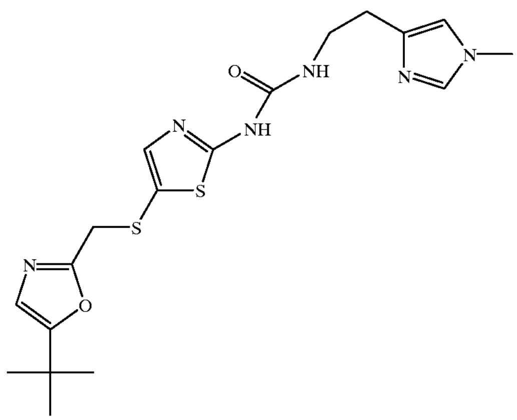 | C18H24N6O2S2 | 535 |
| 615 | 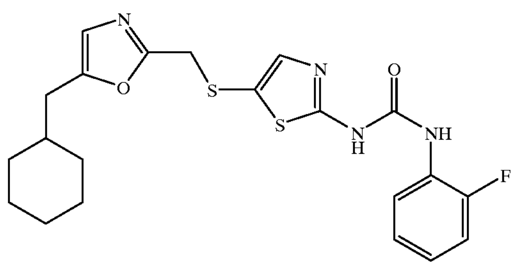 | C21H23FN4O2S2 | 447 |
| 616 | 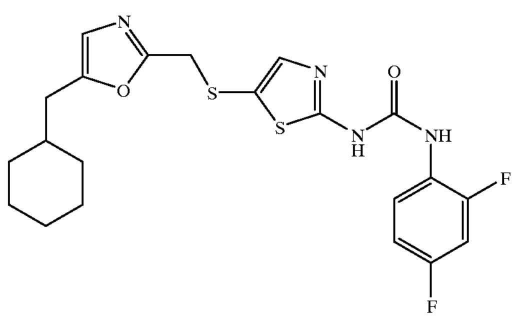 | C21H22F2N4O2S2 | 465 |
| 617 | 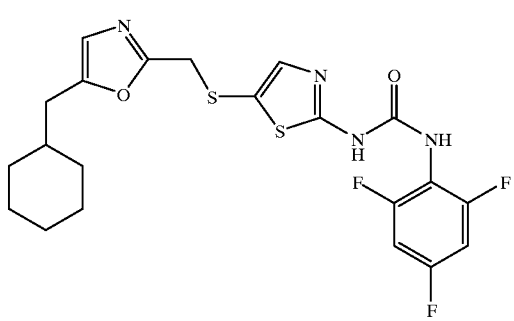 | C21H21F3N4O2S2 | 483 |

TABLE 1-continued

| Example | Structure | Molecular Formula | (M + H)+ |
|---|---|---|---|
| 618 | 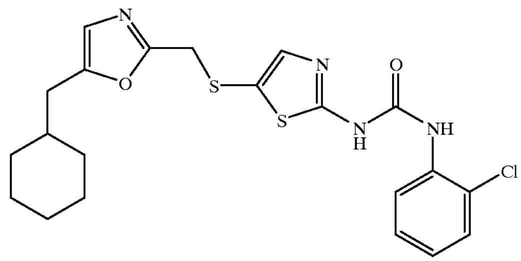 | C21H23ClN4O2S2 | 464 |
| 619 | 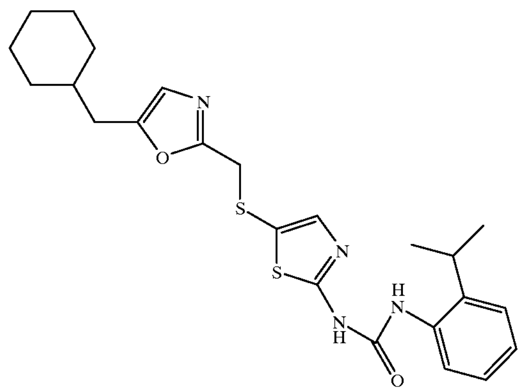 | C24H30N4O2S2 | 471 |
| 620 | 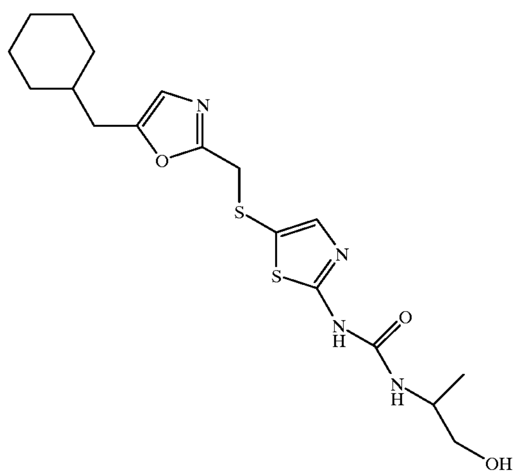 | C18H26N4O3S2 | 411 |

TABLE 1-continued
| Example | Structure | Molecular Formula | (M + H)+ |
|---|---|---|---|
| 621 | 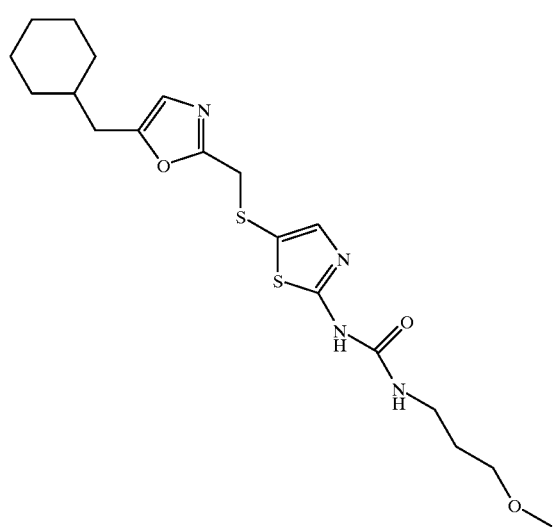 | C19H28N4O3S2 | 425 |
| 622 | 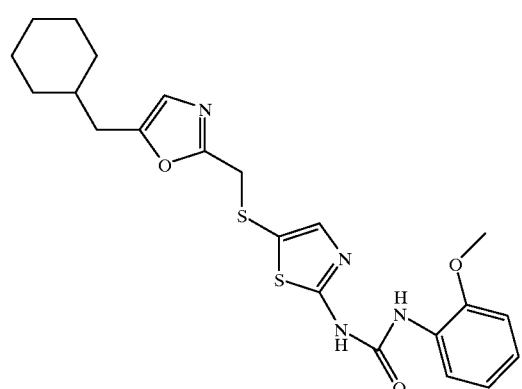 | C22H26N4O3S2 | 459 |
| 623 | 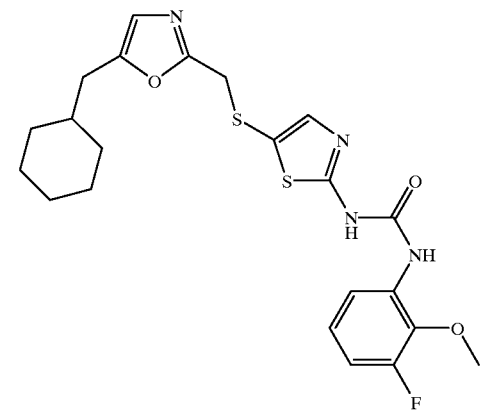 | C22H25FN4O3S2 | 477 |

TABLE 1-continued

| Example | Structure | Molecular Formula | (M + H)+ |
|---|---|---|---|
| 624 | 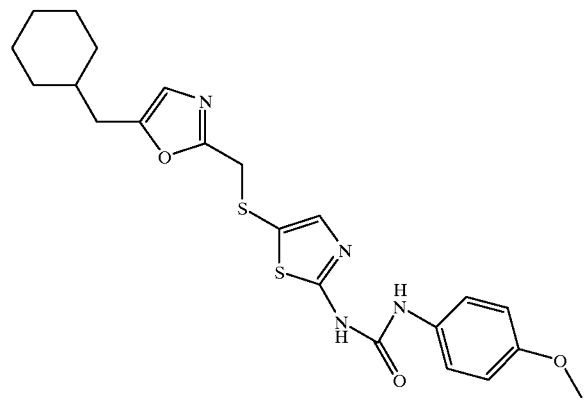 | C22H26N4O3S2 | 459 |
| 625 | 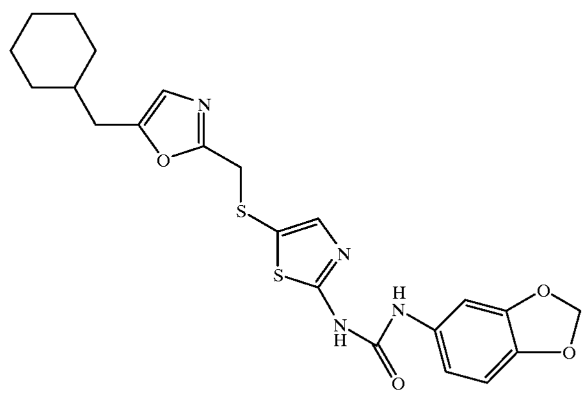 | C22H24N4O4S2 | 473 |
| 626 | 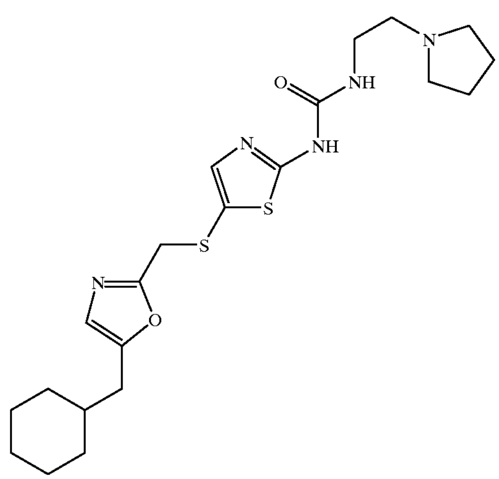 | C21H31N5O2S2 | 564 |

TABLE 1-continued
| Example | Structure | Molecular Formula | (M + H)+ |
|---|---|---|---|
| 627 | 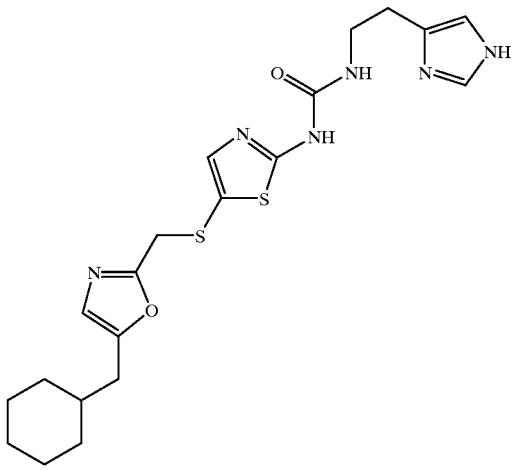 | C20H26N6O2S2 | 561 |
| 628 | 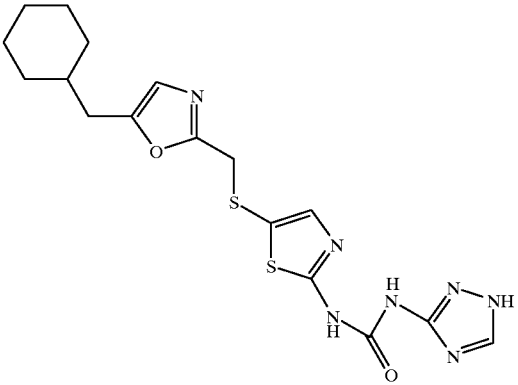 | C17H21N7O2S2 | 534 |
| 629 | 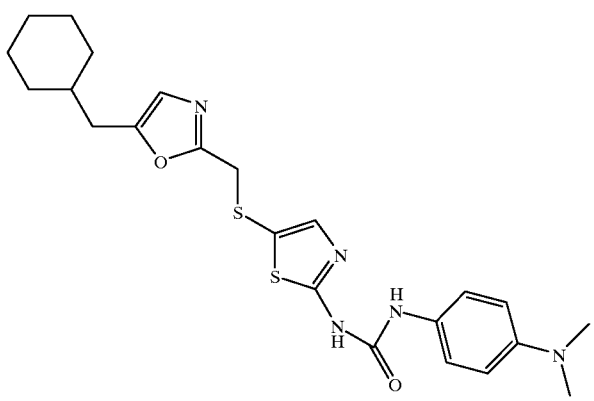 | C23H29N5O2S2 | 586 |

TABLE 1-continued
| Example | Structure | Molecular Formula | (M + H)+ |
|---|---|---|---|
| 630 | 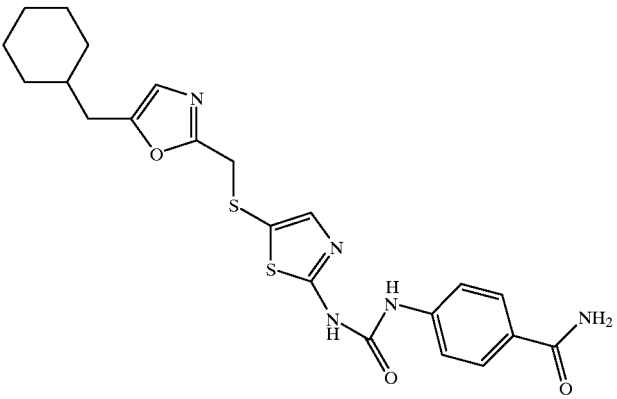 | C22H25N5O3S2 | 472 |
| 631 | 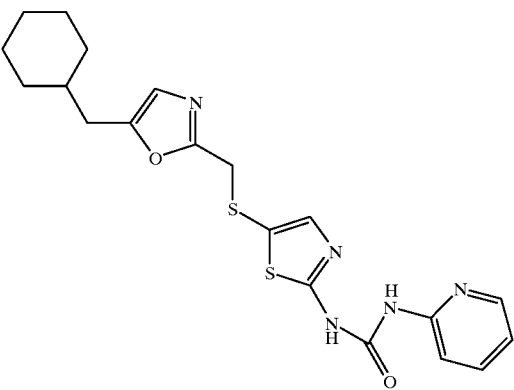 | C20H23N5O2S2 | 544 |
| 632 | 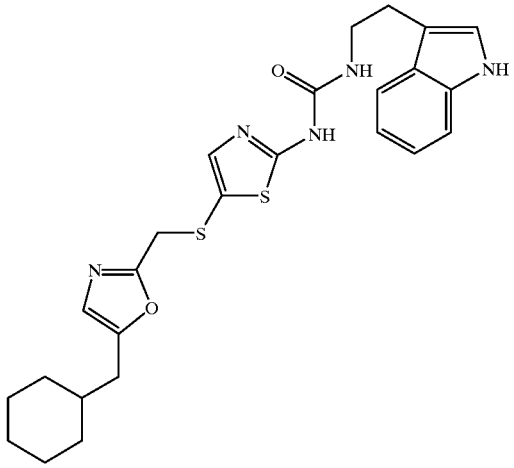 | C25H29N5O2S2 | 496 |

TABLE 1-continued

| Example | Structure | Molecular Formula | (M + H)+ |
|---|---|---|---|
| 633 | 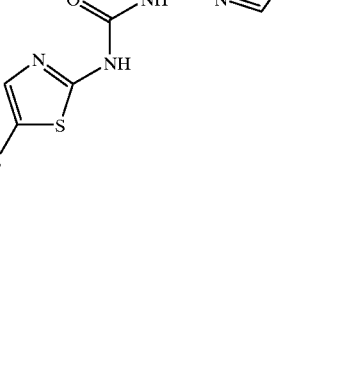 | C21H28N6O2S2 | 575 |
| 634 | 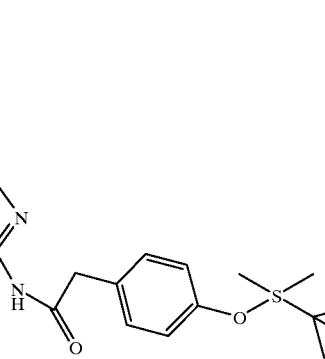 | C24H33N3O3S2Si | 504 |
| 635 | 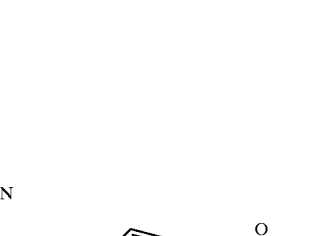 | C23H28N4O4S2 | 489 |

Example 636

Preparation of N-[5-[[(5-t-Butyl-2-oxazolyl)methyl]thio]-2-thiazolyl]-N'-cyano-N''-(2,6-difluorophenyl)guanidine.

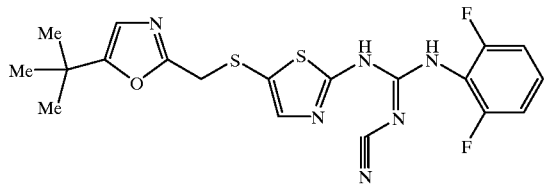

A solution of 100 mg of N-[5-[[(5-t-Butyl-2-oxazolyl)methyl]thio]-2-aminothiazole and 68 mg of 2,6-difluorophenyl isothiocyanate was heated at 65° C. for 16 hours under argon. The solution was evaporated to dryness and the residue purified by flash chromatography to give 91 mg of the intermediate thiourea.

To a solution of 30 mg of N-[5-[[(5-t-Butyl-2-oxazolyl)methyl]thio]-2-thiazolyl]-N''-(2,6-difluorophenyl)thiourea, 52 mg of ethyl-3(3-dimethylamino)propyl carbodiimide hydrochloride and 48 μL of diisopropylethylamine in 0.5 mL methylene chloride was added a solution of 29 mg of cyanamide in 0.1 mL tetrahydrofuran. After stirring for 1 hr, the solvent was removed and the crude material purified by HPLC to give 8 mg of Example 636 compound.

MS: (M+H)+ 449+

$^1$H NMR (400 MHz, CDCl$_3$): d 1.27 (9 H, s), 4.19 (2 H, s), 6.69 (1 H, s), 7.03 (2 H, m), 7.35 (1 H, m), 8.74 (1 H, s).

Example 637

Preparation of
N-[5-[[(5-isopropyl-2-oxazolyl)fluoromethyl]thio]-2-thiazolyl acetimide.

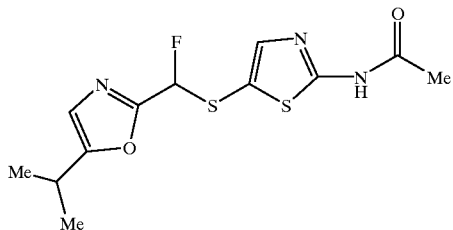

To a stirred mixture of 2-acetamido-5-thiazole thiol acetate (141 mg) in 3 mL of dry THF under argon was added 1 N t-BuOK in THF (0.72 mL). This mixture was stirred at room temperature for 25 min, and a solution of 5-isopropyl-(2-(chlorofluoromethyl))oxazole (116 mg) in 2 mL of dry THF was added. The reaction mixture was stirred at 60° C. for 18 hr, diluted with 150 mL of EtOAc and washed with saturated $NH_4Cl$ solution (2×25 mL), saturated $NaHCO_3$ solution (1×25 mL) and brine (1×25 mL). The organic layer was dried ($MgSO_4$), filtered and concentrated in vacuo to give Example 637 compound.

MS: (M+H)+316 HPLC retention time 3.52 min. (Column: YMC ODS S05 4.6×50 mm column, 0% to 100% B gradient in 4 min. Solvent A: 10% $CH_3OH$/90% $H_2O$/0.2% $H_3PO_4$; Solvent B: 90% $CH_3OH$/10% $H_2O$/0.2% $H_3PO_4$; UV: 220 nM).

What is claimed is:

1. A compound of the formula

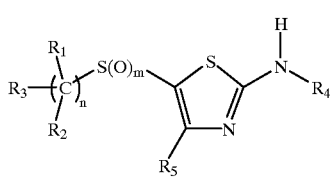

(I)

and pharmaceutically acceptable salts thereof wherein:
$R_1$ and $R_2$ are independently hydrogen, fluorine or alkyl;
$R_3$ is aryl or heteroaryl;
$R_4$ is alkyl, cycloalkyl, aryl, cycloalkylalkyl, arylalkyl, heteroaryl, heteroarylalkyl, heterocycloalkyl, heterocycloalkylalkyl; or
CO-alkyl, CO-cycloalkyl, CO-aryl, CO-alkyl-cycloalkyl, CO-alkyl-aryl,
CO-heteroaryl, CO-alkyl-heteroaryl, CO-heterocycloalkyl,
CO-alkyl-heterocycloalkyl; or
CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or
COO-alkyl, COO-cycloalkyl, COO-aryl, COO-alkyl-cycloalkyl,
COO-alkyl-aryl, COO-heteroaryl, COO-alkyl-heteroaryl,
COO heterocycloalkyl, COO-alkyl-heterocycloalkyl; or
$SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or
C(NCN)NH-alkyl, C(NCN)NH-cycloalkyl, C(NCN)NH-aryl,
C(NCNNH)-alkyl-cycloalkyl, C(NCN)NH-alkyl-aryl,
C(NCN)NH-heteroaryl, C(NCN)NH-alkyl-heteroaryl,
C(NCN)NH-heterocycloalkyl, C(NCN)NH-alkyl-heterocylcoalkyl; or
$C(NNO_2)$NH-alkyl, $C(NNO_2)$NH-cycloalkyl, $C(NNO_2)$NH-aryl,
$C(NNO_2)$NH-alkyl-cycloalkyl, $C(NNO_2)$NH-alkyl-aryl,
$C(NNO_2)$NH-heteroaryl, $C(NNO_2)$NH-alkyl-heteroaryl,
$C(NNO_2)$NH-heterocyloalkyl, $C(NNO_2)$NH-alkyl-heterocycloalkyl; or
C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or
C(NH)NHCO-alkyl, C(NH)NHCO-cycloalkyl, C(NH)NHCO-aryl,
C(NH)NHCO-alkyl-cycloalkyl, C(NH)NHCO-alkyl-aryl,
C(NH)NHCO-heteroaryl, C(NH)NHCO-alkyl-heteroaryl,
C(NH)NHCO-heterocylcloalkyl,
C(NH)NHCO-alkyl-heterocycloalkyl; or
$C(NOR_6)$NH-alkyl, $C(NOR_6)$NH-cycloalkyl, $C(NOR_6)$NH-aryl,
$C(NOR_6)$NH-alkyl-cycloalkyl, $C(NOR_6)$NH-alkyl-aryl,
$C(NOR_6)$NH-heteroaryl, $C(NOR_6)$NH-alkyl-heteroaryl,
$C(NOR_6)$NH-heterocylcoalkyl, $C(NOR_6)$NH-alkyl-heterocycloalkyl;
$R_5$ is hydrogen or alkyl;
$R_6$ is hydrogen, alkyl, cycloalkyl, aryl, cycloalkylakyl, arylalkyl, heteroaryl, heteroarylalkyl, heterocycloalkyl or heterocycloalkylalkyl;
m is an integer of 0 to 2; and
n is an integer of 1 to 3.

2. The compounds as recited in claim 1, wherein
$R_1$ and $R_2$ are independently hydrogen, fluorine or alkyl;

$R_3$ is 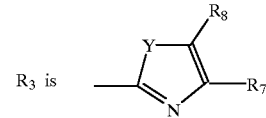

wherein Y is oxygen, sulfur or $NR_9$
$R_3$ is alkyl, cycloalkyl, aryl, cyoloalkylalkyl, arylalkyl, heteroaryl, heteroarylalkyl, heterocycloalkyl, heterocycloalkylalkyl, or
CO-alkyl, CO-cycloalkyl, CO-aryl, CO-alkyl-cycloalkyl, CO-alkyl-aryl,
CO-heteroaryl, CO-alkyl-heteroaryl, CO-heterocycloalkyl,
CO-alkyl-heterocycloalkyl; or
CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or
COO-alkyl, COO-cycloalkyl, COO-aryl, COO-alkyl-cycloalkyl, COO-alkyl-aryl, COO-heteroaryl, COO-alkyl-heteroaryl,
COO-heterocycloalkyl, COO-alkyl-heterocycloalkyl; or SO₂-cycloalkyl, SO₂-aryl, SO₂-alkyl-cycloalkyl, SO₂-alkyl-aryl,
SO₂-heteroaryl, SO₂-alkyl-heteroaryl, SO₂-heterocycloalkyl,
SO₂-alkyl-heterocycloalkyl; or C(NCN)NH-alkyl, C(NCN)NH-cycloalkyl, C(NCN)NH-aryl,
C(NCNNH)-alkyl-cycloalkyl, C(NCN)NH-alkyl-aryl,
C(NCN)NH-heteroaryl, C(NCN)NH-alkyl-heteroaryl,
C(NCN)N H-heterocycloalkyl, C(NCN)NH-alkyl-heterocylcoalkyl; or C(NNO₂)NH-alkyl, C(NNO₂)NH-cycloalkyl, C(NNO₂)NH-aryl,
C(NNO₂)NH-alkyl-cycloalkyl, C(NNO₂)NH-alkyl-aryl,
C(NNO₂)NH-heteroaryl, C(NNO₂)NH-alkyl-heteroaryl,
C(NNO₂)NH-heterocyloalkyl, C(NNO₂) NH-alkyl-heterocycloalkyl; or C(NH)NH-alkyl, C(NH)NH-cycloalkyl, C(NH)NH-aryl,
C(NH)NH-alkyl-cycloalkyl, C(NH)NH-alkyl-aryl,
C(NH)NH-heteroaryl, C(NH)NH-alkyl-heteroaryl,
C(NH)NH-heterocycloalkyl, C(NH)NH-alkyl-heterocycloalkyl; or C(NH)NHCO-alkyl, C(NH)NHCO-cycloalkyl, C(NH)NHCO-aryi,
C(NH)NHCO-alkyl-cycloalkyl, C(NH) NHC alkyl-aryl,
C(NH)NHCO-heteroaryl, C(NH)NHCO-alkyl-heteroaryl,
C(NH)NHCO-heterocylcloalkyl,
C(NH)NHCO-alkyl-heterocycloalkyl; or C(NOR₆)NH-alkyl, C(NOR₆)NH-cycloalkyl, C(NOR₆)NH-aryl,
C(NOR₆)NH-alkyl-cycloalkyl, C(NOR₆)NH-alkyl-aryl,
C(NOR₆)NH-heteroaryl, C(NOR₆)NH-alkyl-heteroaryl,
C(NOR₆)NH-heterocylcoalkyl, C(NOR₆)NH-alkyl-heterocycloalkyl;

$R_5$ is hydrogen or alkyl:

$R_6$ is hydrogen, alkyl, cycloalkyl, aryl, cycloalkylakyl, arylalkyl, heteroaryl, heteroarylalkyl, heterocycloalkyl or heterocycloalkylalkyl;

$R_7$ and $R_8$ are independently hydrogern, alkyl, substituted alkyl, cycloalkyl, aryl, substituted aryl, cycloalkylalkyl, arylalkyl, heteroaryl, substituted heteroaryl, heteroarylalkyl, heterocycloalkyl, heterocycloalkyalkyl;

$R_8$ is hydrogen, alkyl, cycloalkyl, aryl, akylcycloalkyl, arylalkyl, heteroaryl, heteroarylalkyl, heterocycloalkyl or heterocycloalkylalkyl;

m is an integer of 0 to 2; and n is an inteaer of 1 to 3.

3. The compounds as recited in claim 1, wherein
$R_1$ and $R_2$ are independently hydrogen, fluorine or alkyl;

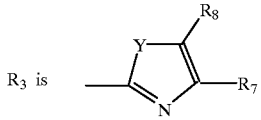

$R_3$ is wherein Y is oxygen;
$R_4$ is alkyl, cycloalkyl, aryl, cycloalkylalkyl, arylalkyl, heteroaryl, heteroarylalkyl, heterocycloalkyl, heterocycloalkylalkyl; or
CO-alkyl, CO-cycloalkyl, CO-aryl, CO-alkyl-cycloalkyl, CO-alkyl-aryl,
CO-heteroaryl, CO-alkyl-heteroaryl, CO-heterocycloalkyl,
CO-alkyl-heterocycloalkyl; or
CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or
COO-alkyl, COO-cycloalkyl, COO-aryl, COO-alkyl-cycloalkyl,
COO-alkyl-aryl, CO-heteroaryl, COO-alkyl-heteroaryl,
COO-heterocycloalkyl, COO-alkyl-heterocycloalkyl; or
SO₂-cycloalkyl, SO₃-aryl, SO₂-alkyl-cycloalkyl, SO₂-alkyl-aryl,
SO₂-heteroaryl, SO₂-alkyl-heteroaryl, SO₂-heterocycloalkyl,
SO₂-alkyl-heterocycloalkyl; or
C(NCN)NH-alkyl, C(NCN)NH-cycloalkyl, C(NCN)NH-aryl,
C(NCNNH)-alkyl-cycloalkyl, C(NCN)NH-alkyl-aryl,
C(NCN)NH-heteroaryl, C(NCN)NH-alkyl-heteroaryl,
C(NCN)NH-heterocycloalkyl, C(NCN)NH-akyl-heterocylcoalkyl; or
C(NNO₂)NH-alkyl, C(NNO₂)NH-cycloalkyl, C(NNO₂)NH-aryl,
C(NNO₂)NH-alkyl-cycloalkyl, C(NNO₂)NH-alkyl-aryl,
C(NNO₂)NH-heteroaryl, C(NNO₂)NH-alkyl-heteroaryl,
C(NNO₂)NH-heterocyloalkyl, C(NNO₂)NH-alkyl-heterocycloalkyl; or
C(NH)NH-alkyl, C(NH)NH-cycloalkyl, C(NH)NH-ayrl,
C(NH)NH-alkyl-cycloalkyl, C(NH)NH-alkyl-aryl,
C(NH)NH-heteroaryl, C(NR)NH-alkyl-heteroaryl,
C(NH)NH-heterocycloalkyl, C(NH)NH-alkyl-heterocycloalkyl; or
C(NH)NHCO-alkyl, C(NH)NHCO-cycloalkyl, C(NNOH)NHCO-aryl,
C(NH)NHCO-alkyl-cycloalkyl, C(NH)NHCO alkyl-aryl;
C(NH)NHCO-heteroaryl, C(NH)NHCO-alkyl-heteroaryl,
C(NH)NHCO-heterocylcloalkyl,
C(NH)NHCO-alkyl-heterocycloalkyl; or
C(NOR₆)NH-alkyl, C(NOR₂)NH-cycloalkyl, C(NOR₆)NH-aryl,
C(NOR₅)NH-alkyl-cycloalkyl, C(NOR₅)NH-alkyl-aryl,
C(NOR₅)NH-heteroaryl, C(NOR₅)NH-alkyl-heteroaryl, C(NOR₆)NH-heterocylcoalkyl, C(NOR₅)NH-alkyl-heterocycloalkyl;

R₅ is hydrogen;

R₅ is hydrogen, alkyl, cycloalkyl, aryl, cyclolkylakyl, arylalkyl, heteroaryl, heteroarylalkyl, heterocycloalkyl or heterocycloalkylalkyl;

R₇ and R₅ are independently hydrogen, alkyl, substituted alkyl, cycloalkyl, aryl, subsituted aryl, cycloal kylakyl, arylalkyl, heteroaryl, substituted heteroaryl, heteroarylalkyl, heterocycloalkyl, heterocycloalkyalkyl;

m is an integer of 0 to 2; and n is an integer of 1 to 3.

4. The compounds as recited in claim 1, wherein

R₁ and R₂ are independently hydrogen, fluorine or alkyl;

R₃ is 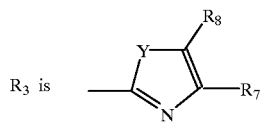

wherein Y is sulfur;

R₆ is alkyl, cycloalkyl, aryl, oycloalkylalkyl, arylalkyl, heteroaryl, heteroarylalkyl, heterocycloalkyl, heterocycloalkylalkyl, or CO-alkyl, CO-cycloalkyl, CO-aryl, CO-alkyl-cycloalkyl, CO-alkyl-aryl,
CO-heteroaryl, CO-alkyl-heteroaryl, CO-heterocycloalkyl,
CO-alkyl-heterocycloalkyl; or CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl: or COO-alkyl, COO-cycloalkyl, COO-aryl, COO-alkyl-cycloalkyl,
COO-alkyl-aryl, COO-heteroaryl, COO-alkyl-heteroaryl,
COO-heterocycloalkyl, COO-alkyl-heterocycloalkyl; or SO₂-cycloalkyl, SO₂-aryl, SO₂-alkyl-cyloalkyl, SO₂-alkyl-aryl,
SO₂-heteroaryl, SO₂-alkyl-heteroaryl, SO₂-heterocycloalkyl,
SO₂-alkyl-heterocycloalkyl; or C(NCN)NH-alkyl, C(NCN)NH-cycloalkyl, C(NCN)OH-aryl,
C(NCNNH)-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocylcoalkyl; or C(NNO₂)NH-alkyl, C(NNO₂)NH-cycloalkyl, C(NNO₂)NH-aryl,
C(NNO₂)NH-alkyl-cycloalkyl, C(NNO₂)NH-alkyl-aryl,
C(NNO₂)NH-heteroaryl, C(NNO₂)NH-alkyl-heteroaryl,
C(NNO₂)NH-heterocyloalkyl, C(NNO)NH-alkyl-heterocycloalkyl; or C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl,
C(NH)NHCO-alkyl-cycloalkyl, C(NH)NHCO-alkyl-aryl,
C(NH)NHCO-heteroaryl, C(NH)NHCO-alkyl-heteroaryl,
C(NH)NHCO-heterocylcoalkyl,
C(NH)NHCO-alkyl-heterocycloalkyl; or C(NOR₆)NH-alkyl, C(NOR₆)NH-cycloalkyl, C(NOR₆)NH-aryl,
C(NOR₆)NH-alkylcycloalkyl, C(NOR₆)NH-alkyl-aryl,
C(NOR₆)NH-heteroaryl, C(NOR₆)NH-alkyl-heteroaryl,
C(NOR₆)NH-heterocylcoalkyl, C(NOR₆)NH-alkyl-heterocycloalkyl;

R₆ is hydrogen;

R₆ is hydrogen, alkyl, cycloalkyl, aryl, cycloalkylakyl, arylalkyl, heteroaryl, heteroarylalkyl, heterocycloalkyl or heterocycloalkylalkyl;

R₇ and R₈ are independently hydrogen, alkyl, substituted alkyl, cycloalkyl, aryl, substituted aryl, cycloalkylalkyl, arylalkyl, heteroaryl, substituted heteroaryl, heteroarylalkyl, heterocycloalkyl, heterocycloalkyalkyl;

m is an integer of 0 to 2; and n is an integer of 1 to 3.

5. The compounds as recited in claim 1, wherein

R₁ and R₂ are independently hydrogen, fluorine or alkyl;

R₃ is 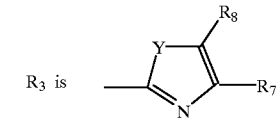

wherein Y is NR₉;

R₄ is alkyl, cycloalkyl, aryl, cycloalkylalkyl, arylalkyl, heteroaryl, heteroarylalkyl, heterocycloalkyl, heterocycloalkylalkyl; or CO-alkyl, CO-cycloalkyl, CO-aryl, CO-alkyl-cycloalkyl, CO-alkyl-aryl,
CO-heteroaryl, CO-alkyl-heteroaryl, CO-heterocycloalkyl,
CO-alkyl-heterocycloalkyl; or CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or COO-alkyl, COO-cycloalkyl, COO-aryl, COO-alkyl-cycloalkyl,
COO-alkyl-aryl, COO-heteroaryl, COO-alkyl-heteroaryl,
COO-heterocycloalkyl, COO-alkyl-heterocycloalkyl; or SO₂-cycloalkyl, SO₂-aryl, SO₂-alkyl-cycloalkyl, SO₂-alkyl-aryl,
SO₂-heteroaryl, SO₂-alkyl-heteroaryl, SO₂-heterocycloalkyl,
SO₂-alkyl-heterocycloalkyl; or C(NCN)NH-alkyl, C(NCN)NH-cycloalkyl, C(NCN)NH-aryl,
C(NCNNH)-alkyl-cycloalkyl, C(NCN)NH-alkyl-aryl,
C(NCN)NH-heteroaryl, C(NCN)NH-alkyl-heteroaryl,
C(NCN)NH-heterocycloalkyl, C(NCN)NH-alkyl-heterocylcoalkyl; or C(NNO₂)NH-alkyl, C(NNO₂)NH-cycloalkyl, C(NNO₂)NH-aryl,
  C(NNO₂)NH-alkyl-cycloalkyl, C(NNO₃)NH-alkyl-aryl,
  C(NNO₂)NH-heteroaryl, C(NNO₂)NH-alkylheteroaryl,
  C(NNO₂)NH-heterocyloalkyl, C(NNO₂)NH-alkyl-heterocycloalkyl; or
C(NH)NH-alkyl, C(NH)NH-cycloalkyl, C(NH)NH-aryl,
  C(NH)NH-alkyl-cycloalkyl, C(NH)NH-alkyl-aryl,
  C(NH)NH-heteroaryl, C(NH)NH-alkyl-heteroaryl,
  C(NH)NH-heterocycloalkyl, C(NH)NH-alkyl-heterocycloakyl; or
C(NH)NHCO-alkyl, C(NH)NHCO-cycloalkyl, C(NH)NHCO-aryl,
  C(NH)NHCO-alkyl-cycloalkyl, C(NH)NHCO-alkyl-aryl,
  C(NH)NHCO-heteroaryl, C(NH)NHCO-alkyl-heteroaryl,
  C(NH)NHCO-heterocylcloalkyl,
  C(NH)NHCO-alkyl-heterocycloalkyl; or
C(NOR₈)NH-alkyl, C(NOR₆)NH-cycloalkyl, C(NOR₆)NH-aryl,
  C(NOR₆)NH-alkyl-cycloalkyl, C(NOR₅)NH-alkyl-aryl,
  C(NOR₆)NH-heteroaryl, C(NOR₆)NH-alkyl-heteroaryl,
  C(NOR₆)NH-heterocylcoalkyl, C(NOR₆)NH-alkyl-heterocycloalkyl;

$R_5$ is hydrogen, $R_5$ is hydrogen, alkyl, cycloalkyl, aryl, cycloalkylakyl, arylalkyl, heteroaryl, heteroarylalkyl, heterocycloalkyl or heterocycloalkylalkyl;

$R_7$ and $R_8$ are independently hydrogen, alkyl, substituted alkyl, cycloalkyl, aryl, subsituted aryl, cycloalkylalkyl, arylalkyl, heteroaryl, substituted heteroaryl, heteroarylalkyl, heterocycloalkyl, heterocycloalkylalkyl;

$R_9$ is hydrogen, alkyl cycloalkyl, aryl, cycloalkylakyl, arylalkyl, heteroaryl, heteroarylalkyl, heterocycloalkyl or heterocycloalkylalkyl;

m is an integer of 0 to 2; and n is an integer of 1 to 3.

6. The compounds as recited in claim 1, wherein $R_1$ and $R_2$ are independently hydrogen, fluorine or alkyl;

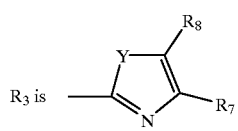

wherein Y is oxygen;

$R_4$ is CO-alkyl, CO-alkyl-aryl, CO-cycloalkyl, CO-alkyl-heteroaryl, CO-alkyl-heteroalkyl, CO-alkyl-heterocycloalkyl, CONH-alkyl, CONH-alkyl-aryl, CONH-cycloalkyl, or CONH-alkyl-heterocycloalkyl;

$R_5$ is hydrogen; and $R_7$ and $R_8$ are hydrogen;

m is the integer 0; and n is the integer 1.

7. The compounds as recited in claim 1, wherein $R_1$ and $R_2$ are independently hydrogen, fluorine or alkyl;

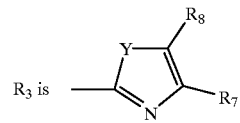

wherein Y is oxygen;

$R_4$ is CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl, or CONH-alkyl-heterocycloalkyl;

$R_5$ is hydrogen;

$R_7$ and $R_8$ are alkyl;

m is the integer 0; and n is the integer 1.

8. The compounds as recited in claim 1, wherein $R_1$ and $R_2$ are independently hydrogen, fluorine or alkyl;

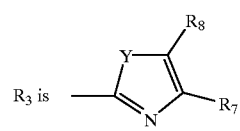

wherein Y is oxygen;

$R_4$ is CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl, or CONH-alkyl-heterocycloalkyl;

$R_5$ is hydrogen;

$R_7$ is hydrogen;

$R_8$ is alkyl;

m is the integer 0; and n is the integer 1.

9. The compounds as recited in claim 1, wherein $R_1$ and $R_2$ are independently hydrogen, fluorine or alkyl;

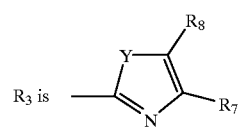

wherein Y is oxygen;

$R_4$ is CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl, or CONH-alkyl-heterocycloalkyl;

$R_5$ is hydrogen;

$R_7$ is alkyl;

$R_8$ is hydrogen;

m is the integer 0; and n is the integer 1.

10. The compounds as recited in claim 1, wherein $R_1$ and $R_2$ are independently hydrogen, fluorine or alkyl;

$R_3$ is 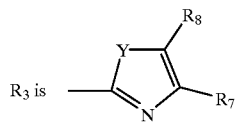

wherein Y is sulfur;

$R_4$ is CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl, or CONH-alkyl-heterocycloalkyl;

$R_5$ is hydrogen;

$R_7$ is hydrogen;

$R_8$ is alkyl;

m is the integer 0; and n is the integer 1.

11. The compounds as recited in claim 1, wherein $R_1$ and $R_2$ are independently hydrogen, fluorine or alkyl;

$R_3$ is 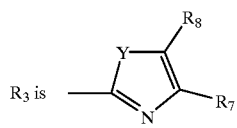

wherein Y is sulfur;

$R_4$ is CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl, or CONH-alkyl-heterocycloalkyl;

$R_5$ is hydrogen;

$R_7$ is alkyl;

$R_8$ is hydrogen;

m is the integer 0; and n is the integer 1.

12. The compounds as recited in claim 1, wherein $R_1$ and $R_2$ are independently hydrogen, fluorine or alkyl;

$R_3$ is 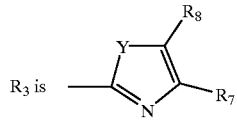

wherein Y is $NR_9$;

$R_4$ is CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl, or CONH-alkyl-heterocycloalkyl;

$R_5$ is hydrogen;

$R_7$ is hydrogen;

$R_8$ is alkyl;

$R_9$ is hydrogen, alkyl, cycloalkyl, aryl, alkyl-cycloalkyl, alkyl-aryl, heteroaryl, alkyl-heteroaryl, heterocycloalkyl, or alkyl-heterocycloalkyl;

m is the integer 0; and n is the integer 1.

13. The compounds as recited in claim 1, wherein $R_1$ and $R_2$ are independently hydrogen, fluorine or alkyl;

$R_3$ is 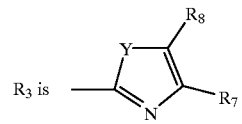

wherein Y is $NR_9$;

$R_4$ is CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl, or CONH-alkyl-heterocycloalkyl;

$R_5$ is hydrogen;

$R_7$ is alkyl;

$R_8$ is hydrogen;

$R_9$ is alkyl;

m is the integer 0; and n is the integer 1.

14. The compounds as recited in claim 1, wherein $R_1$ and $R_2$ are independently hydrogen, fluorine or alkyl;

$R_3$ is 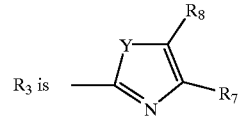

wherein X is $NR_9$;

$R_4$ is CO-alkyl, CO-alkyl-aryl, CO-cycloalkyl, CO-alkyl-heteroaryl, CO-alkyl-heteroalkyl, CO-alkyl-heterocycloalkyl, CONH-alkyl, CONH-alkyl-aryl, CONH-cycloalkyl, or CONH-alkyl-heterocycloalkyl;

$R_5$ is hydrogen;

$R_7$ is alkyl;

$R_8$ is hydrogen;

$R_9$ is hydrogen;

m is the integer 0 n is the integer 1.

15. The compound as recited in claim 1, which is

N-[5-[[5-Ethyl-2-oxazolyl)methyl]thio]-2-thiazoly] acetamide;

N-[5-[[5-Ethyl-2-oxazolyl)methyl]thio]-2-thiazolyl] benzamide;

N-[5-[[5-Ethyl-2-oxazolyl)methyl]thio]-2-thiazolyl] benzenesulfonamide;

N-[5-[[(4,5-Dimethyl-2-oxazolyl)methyl]thio]-2-thiazolyl]acetamide;

N-[5-[[(5-t-Butyl-2-oxazolyl)methyl]thio]-2-thiazolyl] acetamide;

N-[5-[[5-t-Butyl-2-oxazolyl)methyl]thio]-2-thiazolyl] trimethylacetamide;

N-[5-[[(4-Ethyl-2-oxazolyl)methyl]thio]-2-thiazolyl] acetamide; or a pharmaceutically acceptable salt thereof.

16. A pharmaceutical composition comprising a compound of claim 1 and a pharmaceutically acceptable carrier.

17. A pharmaceutical composition comprising a compound of claim 1, in combination with a pharmaceutically acceptable carrier, and an anti-cancer agent formulated as a fixed dose.

18. A pharmaceutical composition according to claim 16, comprising a compound of claim 1 in combination with a pharmaceutically acceptable carrier, with an anticancer treatment or anticancer agent administered in sequence.

19. The pharmaceutical composition according to claim 18, wherein said combination comprising said compound of claim 1 and said pharmaceutically acceptable carrier, is administered prior to administration of said anticancer treatment or anticancer agent.

20. The pharmaceutical composition according to claim 18, wherein said combination comprising said compound of claim 1 and said pharmaceutically acceptable carrier, is administered after administration of said anticancer treatment or anticancer agent.

21. A method of inhibiting protein kinases which comprises administering to a mammalian specie in need thereof an effective protein kinase inhibiting amount of a compound of claim 1.

22. A method of inhibiting cyclin dependent kinases which comprises administering to a mammalian specie in need thereof an effective cyclin dependent kinase inhibiting amount of a compound of claim 1.

23. A method of inhibiting cdc2 (cdk1) which comprises administering to a mammalian specie in need thereof an effective cdc2 inhibiting amount of a compound of claim 1.

24. A method of inhibiting cdk2 which comprises administering to a mammalian specie in need thereof an effective cdk2 inhibiting amount of a compound of claim 1.

25. A method of inhibiting cdk3 which comprises administering to a mammalian specie in need thereof an effective cdk3 inhibiting amount of a compound of claim 1.

26. A method of inhibiting cdk4 which comprises administering to a mammalian specie in need thereof an effective cdk4 inhibiting amount of a compound of claim 1.

27. A method of inhibiting cdk5 which comprises administering to a mammalian specie in need thereof an effective cdk5 inhibiting amount of a compound of claim 1.

28. A method of inhibiting cdk6 which comprises administering to a mammalian specie in need thereof an effective cdk6 inhibiting amount of a compound of claim 1.

29. A method of inhibiting cdk7 which comprises administering to a mammalian specie in need thereof an effective cdk7 inhibiting amount of a compound of claim 1.

30. A method of inhibiting cdk8 which comprises administering to a mammalian specie in need thereof an effective cdk8 inhibiting amount of a compound of claim 1.

31. A method for treating proliferative diseases comprising administering to a mammalian specie in need thereof a therapeutically effective amount of a composition of claim 16.

32. A method for treating cancer comprising administering to a mammalian specie in need thereof a therapeutically effective amount of a composition of claim 16.

33. A method for treating inflammation, inflamatory bowel disease, or transplantation rejection, comprising administering to a mammalian specie in need thereof a therapeutically effective amount of a composition of claim 16.

34. A method for treating arthritis comprising administering to a mammalian specie in need thereof a therapeutically effective amount of a composition of claim 16.

35. A method for treating infection by HIV, or for treating and preventing the development of AIDS, comprising administering to a mammalian specie in need thereof a therapeutically effective amount of a composition of claim 16.

36. A method for treating viral infections, comprising administering to a mammalian specie in need thereof a therapeutically effective amount of a composition of claim 16.

37. A method for treating fungal infections, comprising administering to a mammalian specie in need thereof a therapeutically effective amount of a composition of claim 16.

38. A method for preventing the development of cancer or tumor relapse, comprising administering to a mammalian specie in need thereof a therapeutically effective amount of a composition of claim 16.

39. A method for treating neurodegenerative disease, comprising administering to a mammalian specie in need thereof a therapeutically effective amount of a composition of claim 16.

40. A method for treating proliferative diseases comprising administering to a mammalian specie in need thereof a therapeutically effective amount of a composition of claim 17.

41. A method for treating cancer comprising administering to a mammalian specie in need thereof a therapeutically effective amount of a composition of claim 17.

42. A method for preventing the development of cancer or tumor relapse, comprising administering to a mammalian specie in need thereof a therapeutically effective amount of a composition of claim 17.

43. A method for treating proliferative diseases comprising administering to a mammalian specie in need thereof a therapeutically effective amount of a composition of claim 18.

44. A method for treating cancer comprising administering to a mammalian specie in need thereof a therapeutically effective amount of a composition of claim 18.

45. A method for preventing the development of cancer or tumor relapse, comprising administering to a mammalian specie in need thereof a therapeutically effective amount of a composition of claim 18.

* * * * *

UNITED STATES PATENT AND TRADEMARK OFFICE
CERTIFICATE OF CORRECTION

| | | |
|---|---|---|
| PATENT NO. | : 6,040,321 | Page 1 of 1 |
| DATED | : March 21, 2000 | |
| INVENTOR(S) | : Kim et al. | |

It is certified that error appears in the above-identified patent and that said Letters Patent is hereby corrected as shown below:

<u>Column 292,</u>
Line 54, delete "$R_3$ is alkyl," and insert -- $R_4$ is alkyl, -- therefor.

<u>Column 295,</u>
Line 25, delete "$R_6$ is alkyl," and insert -- $R_4$ is alkyl, -- therefor.

<u>Column 296,</u>
Line 16, delete "$R_6$ is hydrogen;" and insert -- $R_5$ is hydrogen; -- therefor.

<u>Column 297,</u>
Line 32, delete "$R_5$ is hydrogen," and insert -- $R_6$ is hydrogen, -- therefor.

Signed and Sealed this

Eighth Day of July, 2003

JAMES E. ROGAN
*Director of the United States Patent and Trademark Office*